(12) United States Patent
Walsh et al.

(10) Patent No.: US 10,041,044 B2
(45) Date of Patent: Aug. 7, 2018

(54) AGE-ASSOCIATED CLONAL HEMATOPOIESIS ACCELERATES CARDIO-METABOLIC DISEASE DEVELOPMENT

(71) Applicant: TRUSTEES OF BOSTON UNIVERSITY, Boston, MA (US)

(72) Inventors: Kenneth Walsh, Carlisle, MA (US); Jose Fuster, Brighton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/662,546

(22) Filed: Jul. 28, 2017

(65) Prior Publication Data
US 2018/0030412 A1 Feb. 1, 2018

Related U.S. Application Data

(60) Provisional application No. 62/368,338, filed on Jul. 29, 2016.

(51) Int. Cl.
| | |
|---|---|
| *A61K 39/395* | (2006.01) |
| *C12N 5/0789* | (2010.01) |
| *C07K 16/24* | (2006.01) |
| *A61K 35/12* | (2015.01) |
| *A61K 39/00* | (2006.01) |

(52) U.S. Cl.
CPC .......... *C12N 5/0647* (2013.01); *A61K 39/395* (2013.01); *C07K 16/244* (2013.01); *A61K 2035/124* (2013.01); *A61K 2039/505* (2013.01); *C07K 2317/24* (2013.01); *C07K 2317/54* (2013.01); *C07K 2317/55* (2013.01)

(58) Field of Classification Search
CPC .................................................. A61K 39/395
See application file for complete search history.

(56) References Cited

U.S. PATENT DOCUMENTS

| | | | |
|---|---|---|---|
| 4,935,343 A | 6/1990 | Allison | |
| 5,075,222 A | 12/1991 | Hannum | |
| 5,180,812 A | 1/1993 | Dower | |
| 5,319,071 A | 6/1994 | Dower | |
| 5,464,937 A | 11/1995 | Sims | |
| 5,488,032 A | 1/1996 | Dower | |
| 5,492,888 A | 2/1996 | Dower | |

FOREIGN PATENT DOCUMENTS

| | | |
|---|---|---|
| DE | 4219626 A1 | 12/1993 |
| EP | 0220063 A | 4/1987 |
| EP | 0364778 A1 | 4/1990 |
| EP | 0267911 B1 | 5/1993 |
| EP | 0623674 A1 | 11/1994 |
| FR | 2706772 A1 | 12/1994 |
| WO | 1990/006371 A1 | 6/1990 |
| WO | 1991/008285 A1 | 6/1991 |
| WO | 1991/017184 A1 | 11/1991 |
| WO | 1992/016221 A1 | 10/1992 |
| WO | 1993/021946 A1 | 11/1993 |
| WO | 1994/002627 A1 | 2/1994 |
| WO | 1994/006457 A1 | 3/1994 |
| WO | 1994/020517 A1 | 9/1994 |
| WO | 1994/021235 A1 | 9/1994 |
| WO | 1994/021275 A1 | 9/1994 |
| WO | 1995/001997 A1 | 1/1995 |
| WO | 1996/022793 A1 | 8/1996 |
| WO | 1996/023067 A1 | 8/1996 |
| WO | 1997/028828 A1 | 8/1997 |
| WO | 2016/086197 A1 | 6/2016 |
| WO | 2016/090077 A2 | 6/2016 |
| WO | 2016/110818 A2 | 7/2016 |
| WO | 2016/179035 A1 | 11/2016 |
| WO | 2017/049166 A1 | 3/2017 |

OTHER PUBLICATIONS

Akosah et al., "Preventing myocardial infarction in the young adult in the first place: how do the National Cholesterol Education Panel III guidelines perform?", J Am Coll Cardiol 41(9) 1475-1479 (2003).
Belsky et al., "Quantification of biological aging in young adults", Proc Natl Acad Sci USA 112(30) E4104-E4110 (2015).
Busque et al., "Recurrent somatic TET2 mutations in normal elderly individuals with clonal hematopoiesis", Nat Genet 44(11) 1179-1181 (2012).
Coll et al., "A small-molecule inhibitor of the NLRP3 inflammasome for the treatment of inflammatory diseases", Nat Med 21(3) 248-288 (2015).
Fernandez-Friera et al., "Prevalence, Vascular Distribution, and Multiterritorial Extent of Subclinical Atherosclerosis in a Middle-Aged Cohort: The PESA (Progression of Early Subclinical Atherosclerosis) Study", Circulation 131(24) 2104-2113 (2015).
Genovese et al., "Clonal hematopoiesis and blood-cancer risk inferred from blood DNA sequence", N Engl J Med 371(26) 2477-2487 (2014).
Jaiswal et al., "Age-related clonal hematopoiesis associated with adverse outcomes", N Engl J Med 371(26) 2488-2498 (2014).
Khot et al., "Prevalence of conventional risk factors in patients with coronary heart disease", JAMA 290(7) 898-904 (2003).
Laclaustra et al., "Femoral and Carotid Subclinical Atherosclerosis Association With Risk Factors and Coronary Calcium: The AWHS Study", J Am Coll Cardiol 67(11) 1263-1274 (2016).
McKerrell et al., "Leukemia-associated somatic mutations drive distinct patterns of age-related clonal hemopoiesis", Cell Rep 10(8) 1239-1245 (2015).

(Continued)

*Primary Examiner* — Prema Mertz
(74) *Attorney, Agent, or Firm* — Nixon Peabody LLP; Ronald I. Eisenstein; Srividya Subramanian

(57) ABSTRACT

As demonstrated herein, a preferential and progressive expansion of a subset of hematopoietic cells bearing somatic mutations in TET2 leads to pro-inflammatory IL-1β signaling at multiple levels, including increased IL-1β transcription, increased NLRP3 inflammasome-mediated IL-1β secretion, and increased IL-1-Receptor 1-mediated IL-1β signaling. Accordingly, provided herein are compositions, methods, and assays for modulating TET2 mutation-mediated IL-1β (interleukin-1β) proinflammatory activity, particularly when caused by somatic mutations in TET2.

16 Claims, 49 Drawing Sheets
(28 of 49 Drawing Sheet(s) Filed in Color)

(56) References Cited

OTHER PUBLICATIONS

Shao et al., NLRP3 inflammasome and its inhibitors: a review, Front Pharmacol 6: 262 (2015).
Shemesh et al., "Interleukin-1 receptor type-1 in non-hematopoietic cells is the target for the pro-atherogenic effects of interleukin-1 in apoE-deficient mice", Atherosclerosis 222(2) 329-336 (2012).
Xie et al., "Age-related mutations associated with clonal hematopoietic expansion and malignancies", Nat Med 20(12) 1472-1478 (2014).
Delhommeau et al., "Mutation in TET2 in myeloid cancers." New England Journal of Medicine 360(22):2289-2301 (2009).

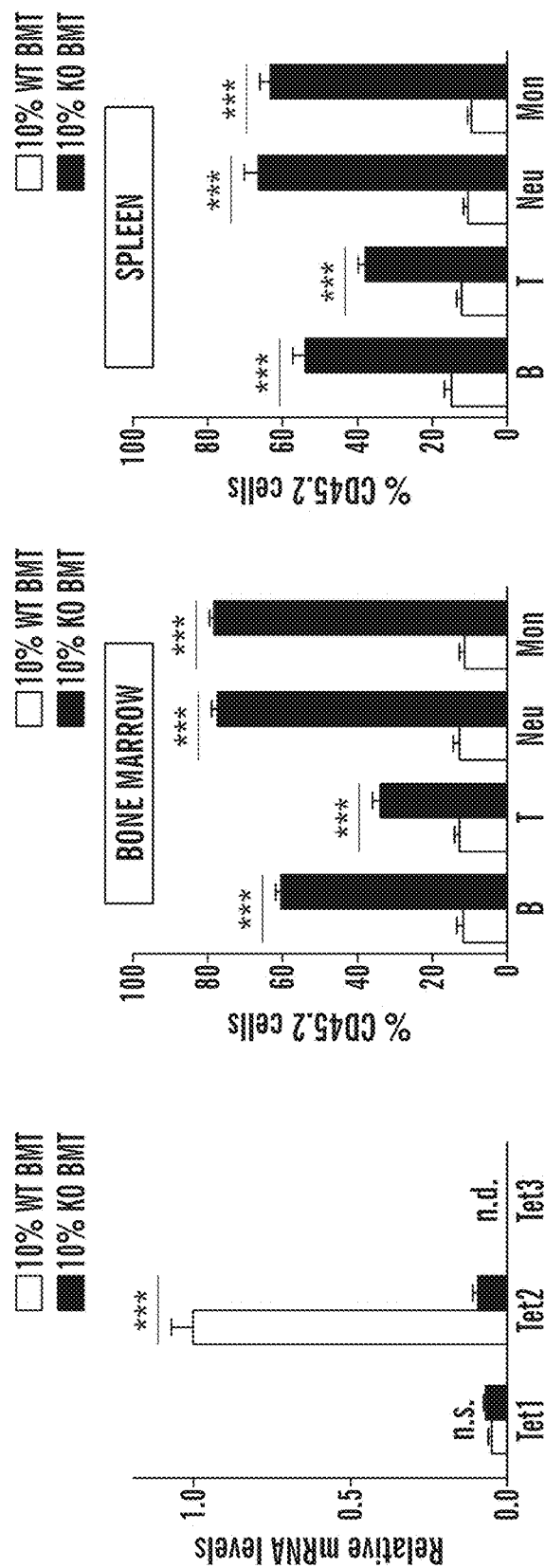

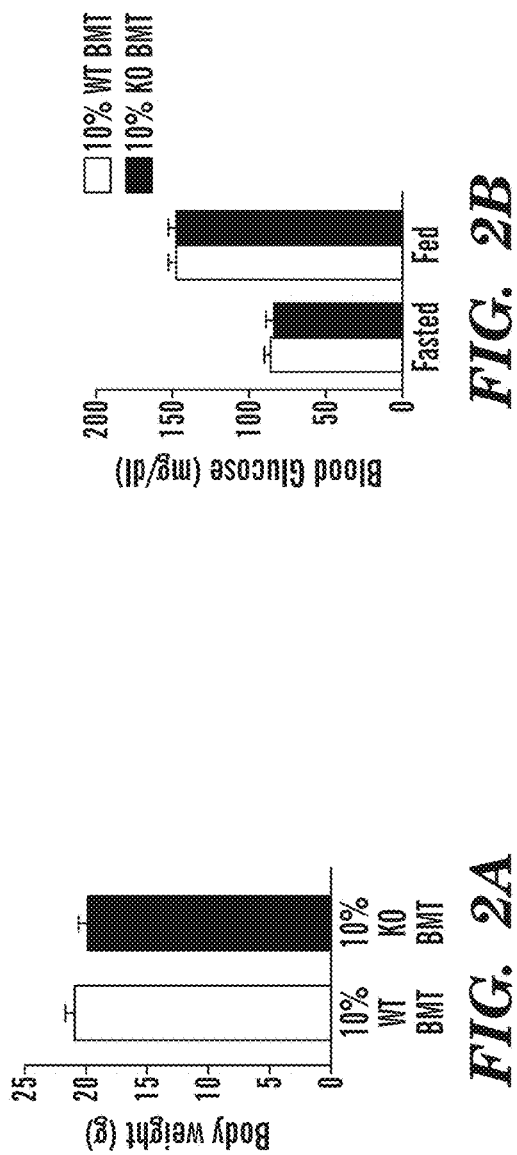
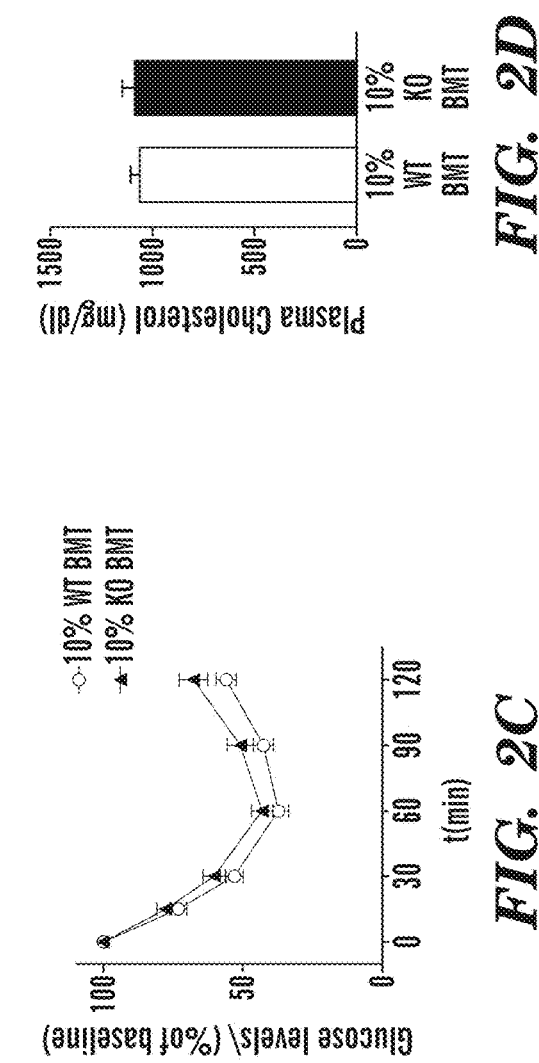

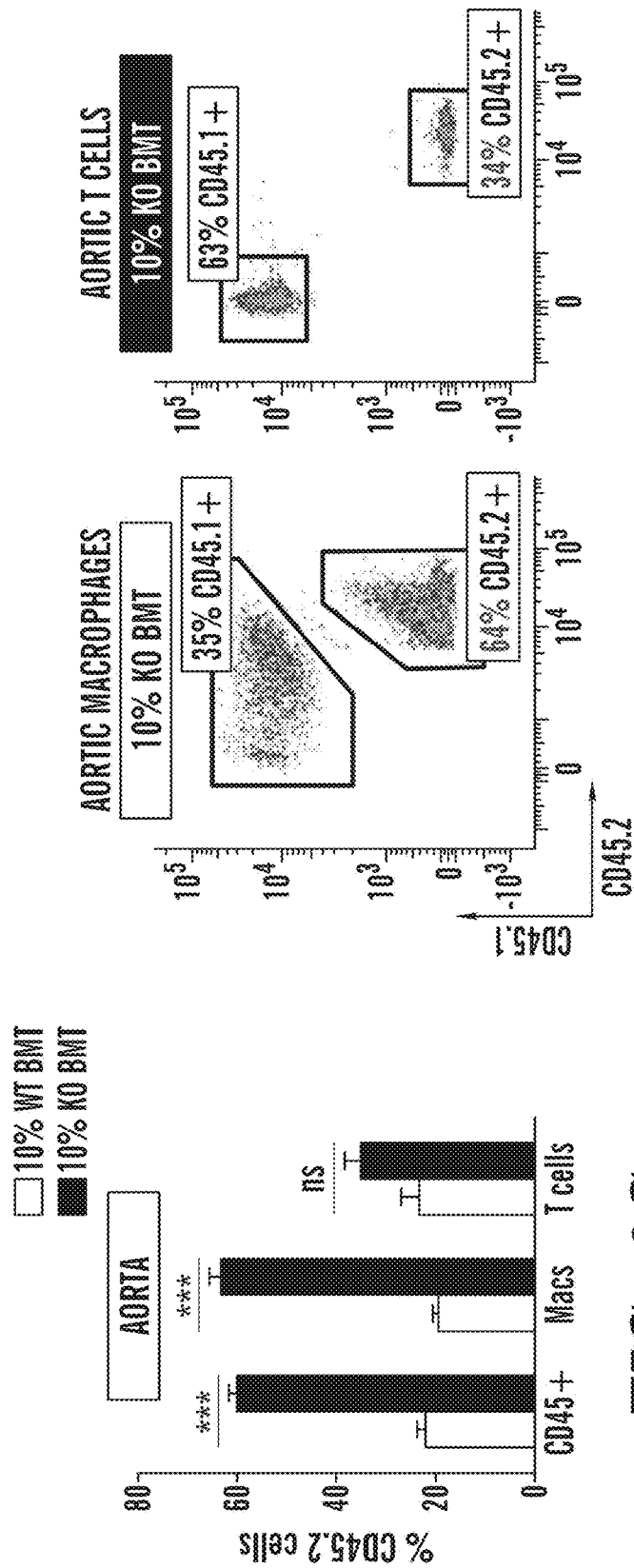

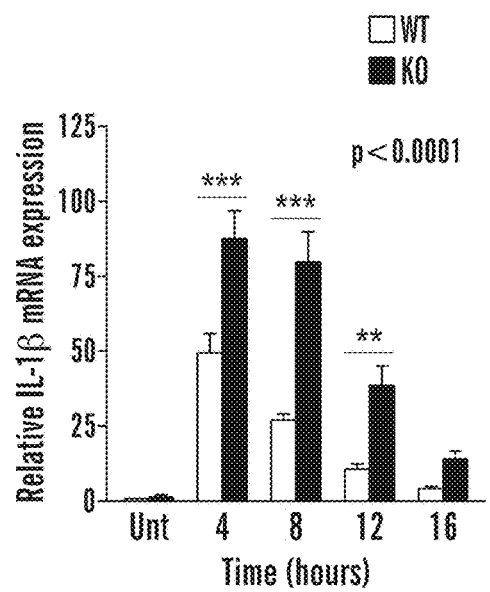
*FIG. 4A*
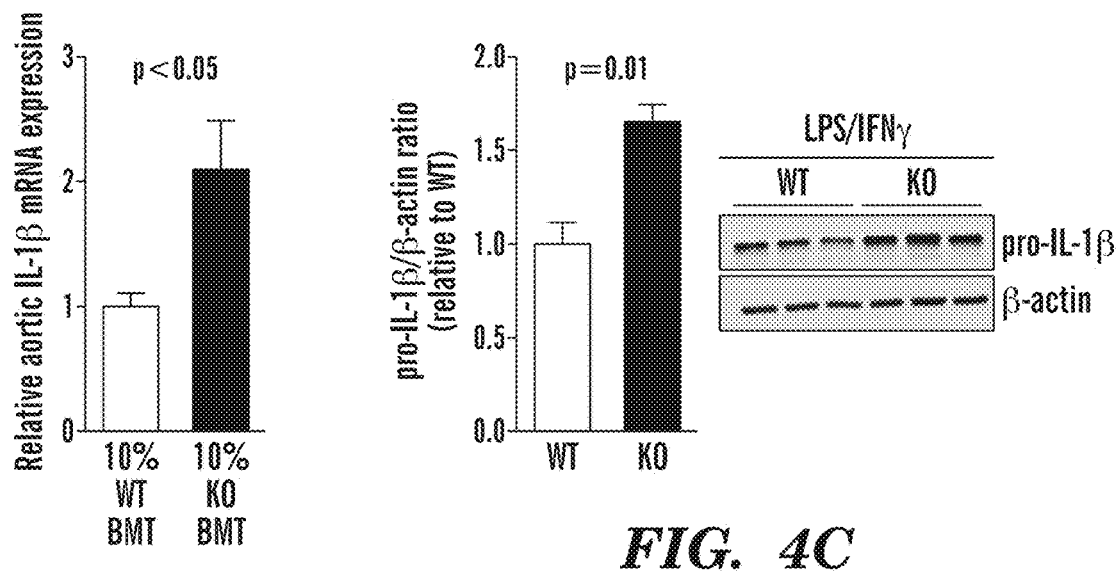
*FIG. 4B*
*FIG. 4C*

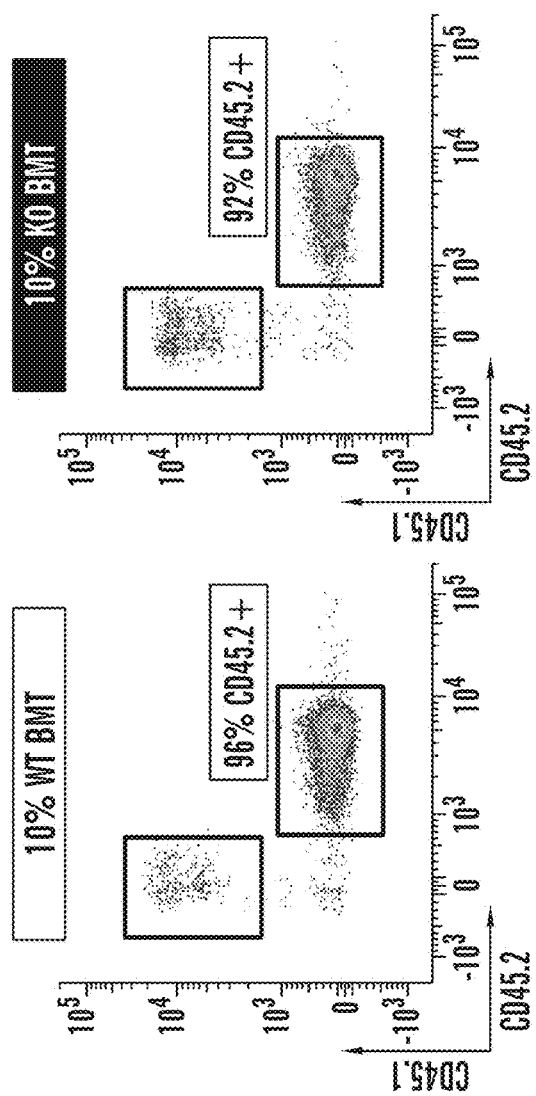
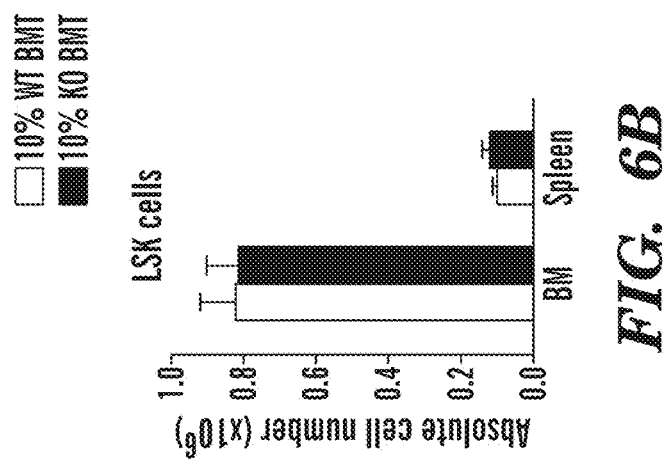
FIG. 6A
FIG. 6B

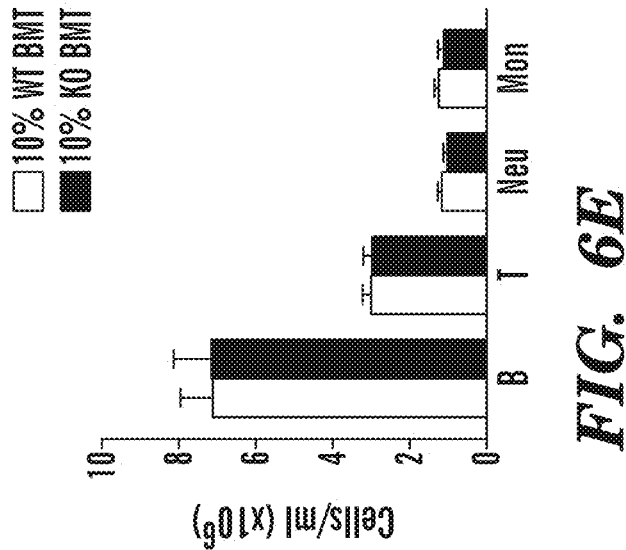
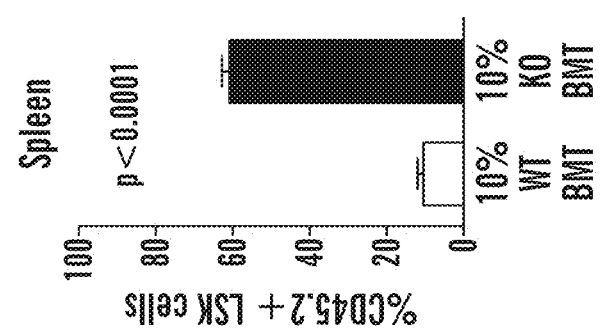
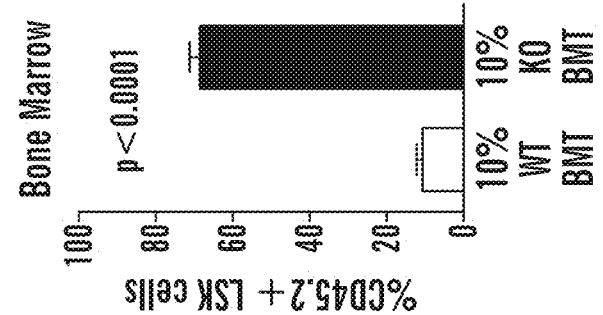

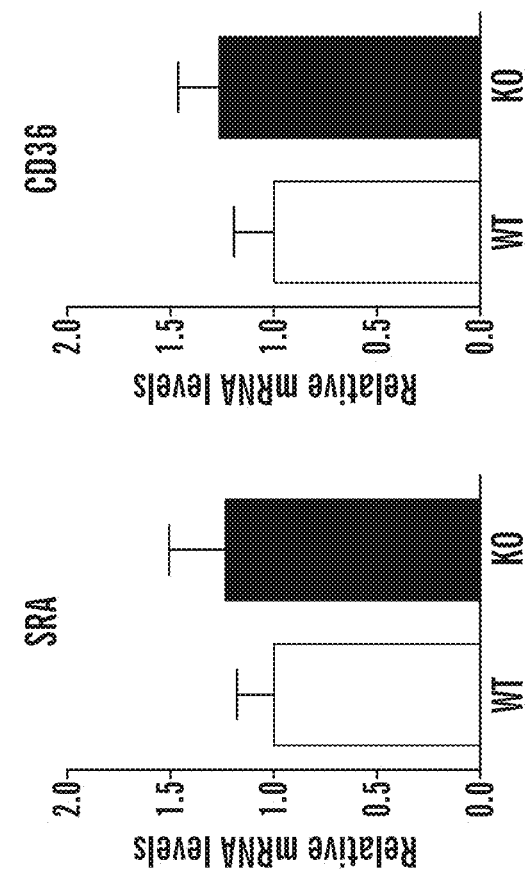
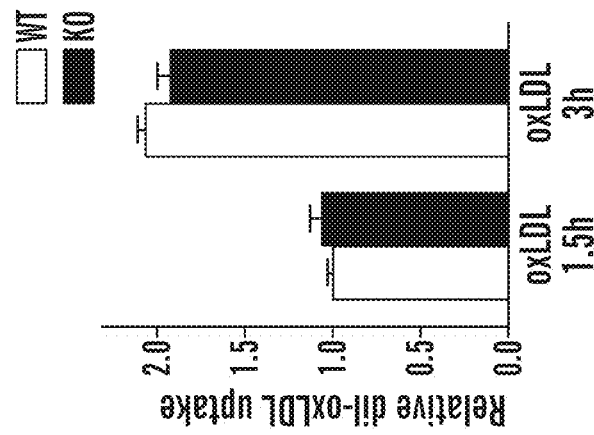
FIG. 10D
FIG. 10C

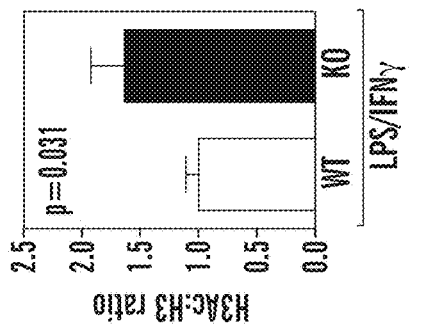
FIG. 14A
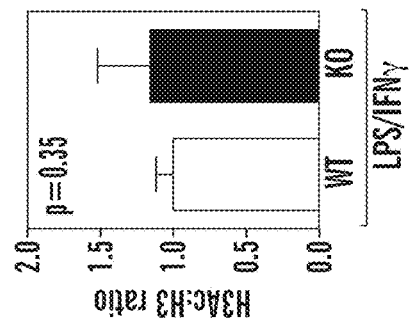
FIG. 14B
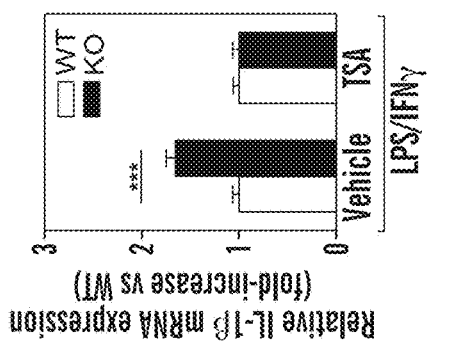
FIG. 14C
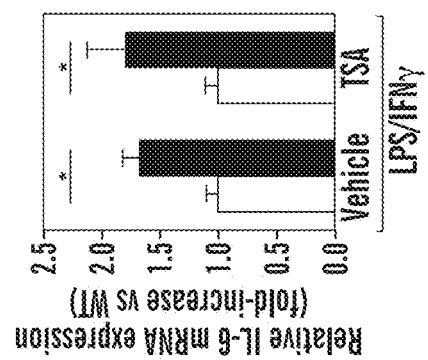
FIG. 14D
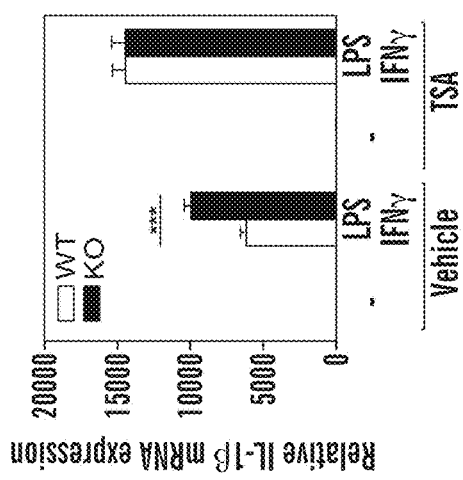
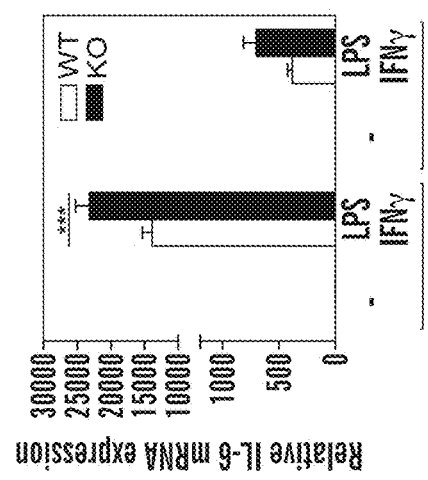

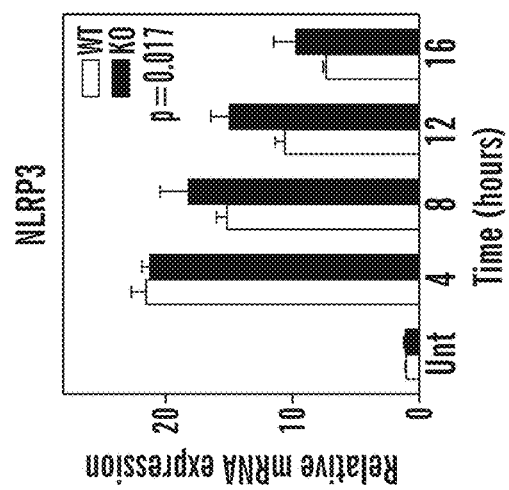
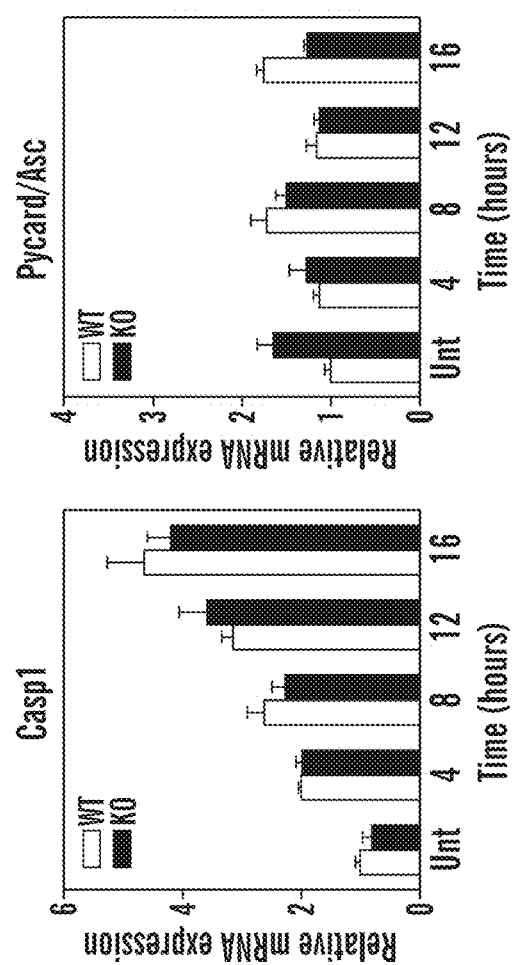
FIG. 15A
FIG. 15B

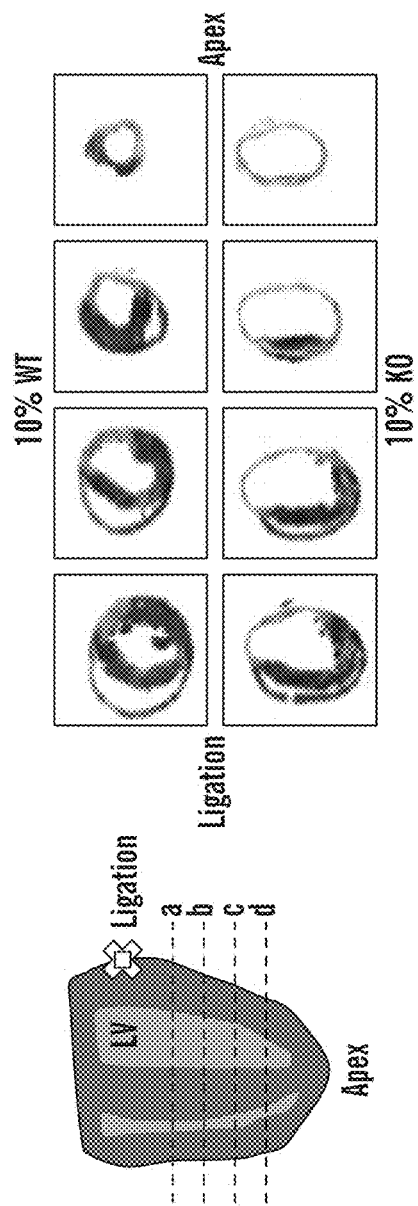
FIG. 19D
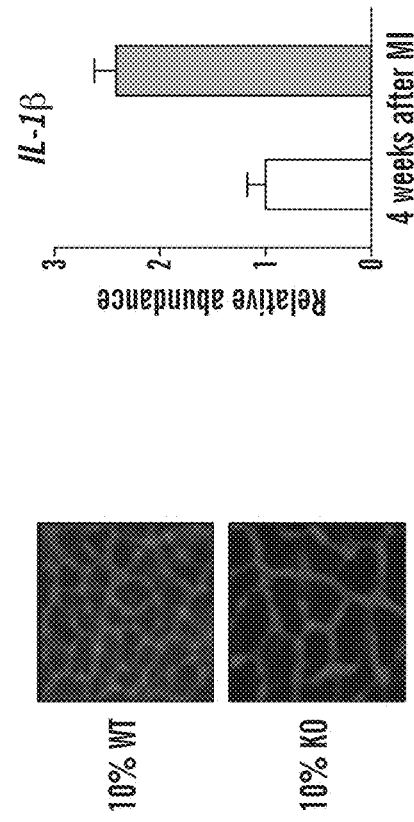
FIG. 19F
FIG. 19E

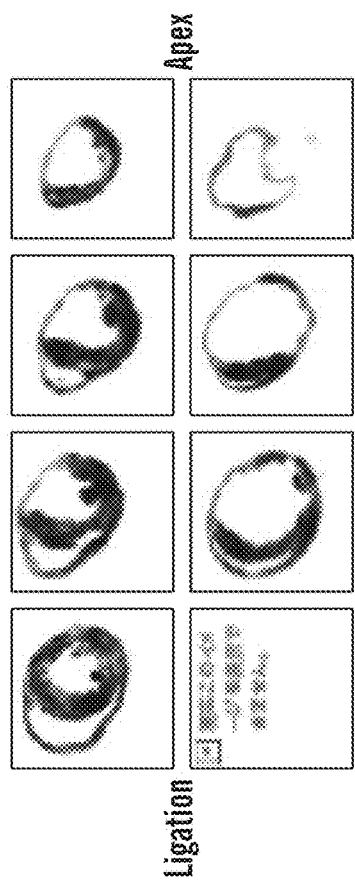
FIG. 20D
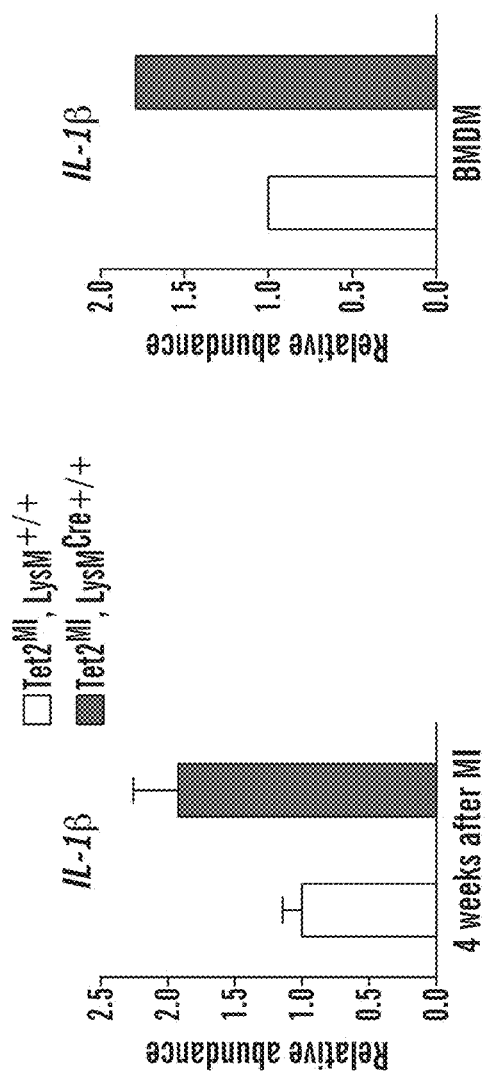
FIG. 20F
FIG. 20E

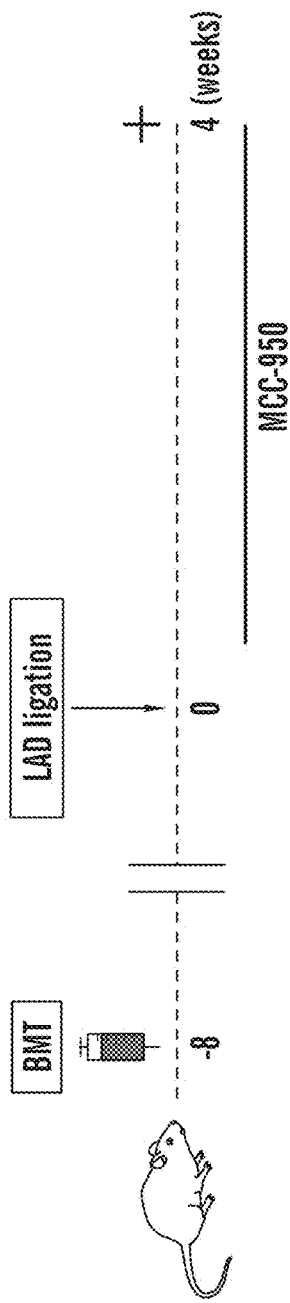
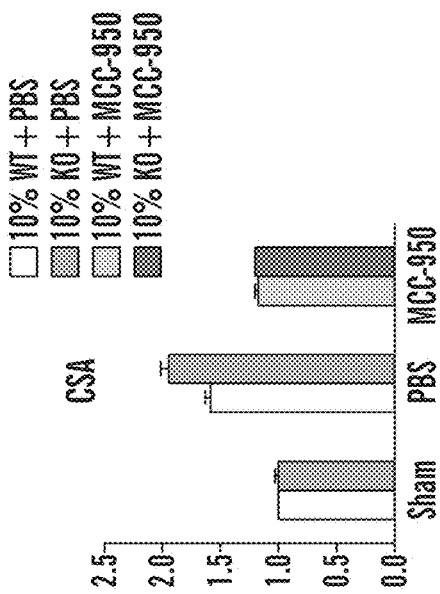
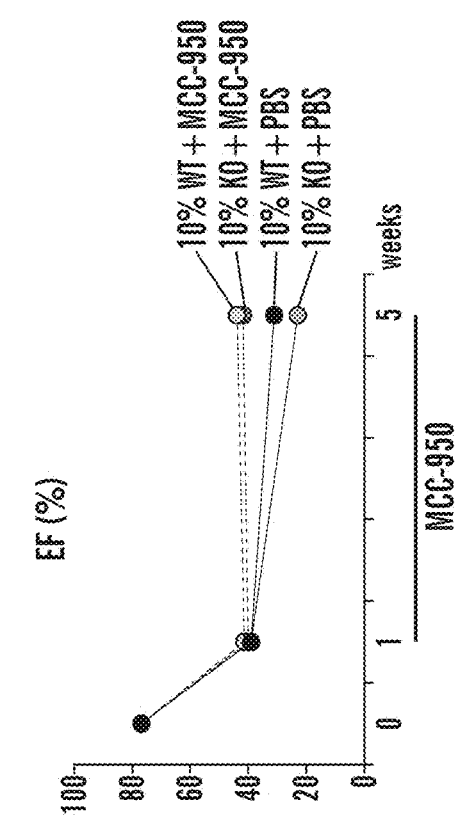
FIG. 21A
FIG. 21B
FIG. 21C

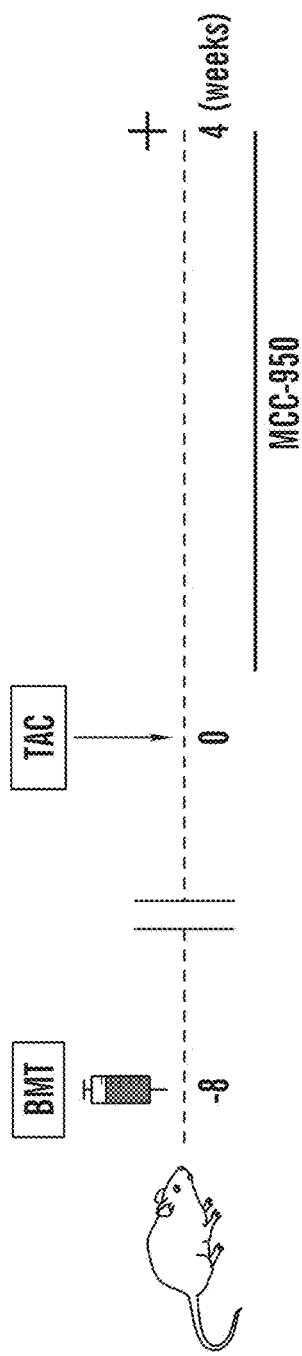
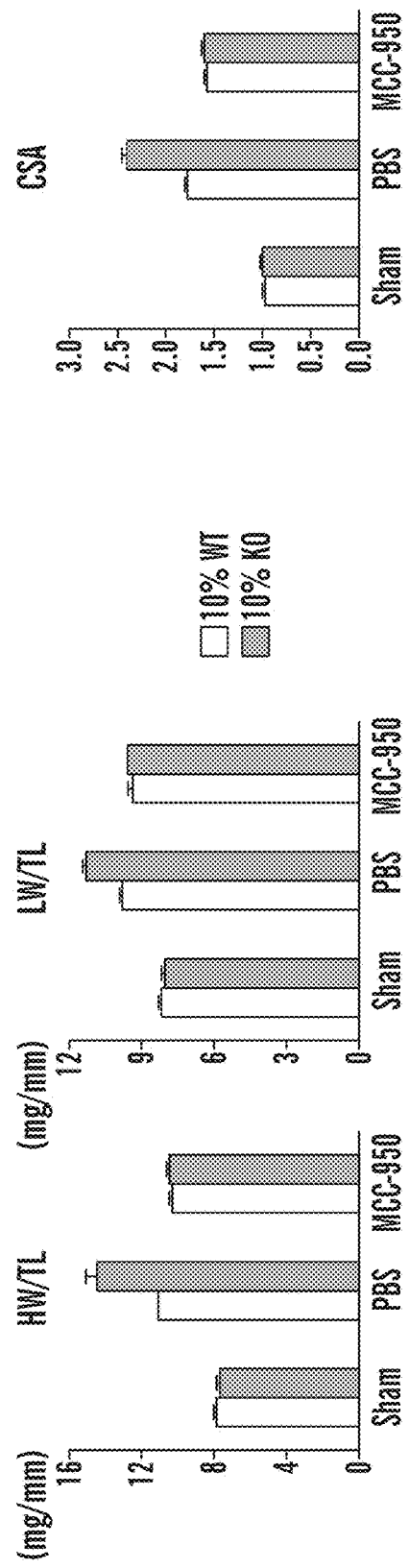
FIG. 22A
FIG. 22B
FIG. 22C

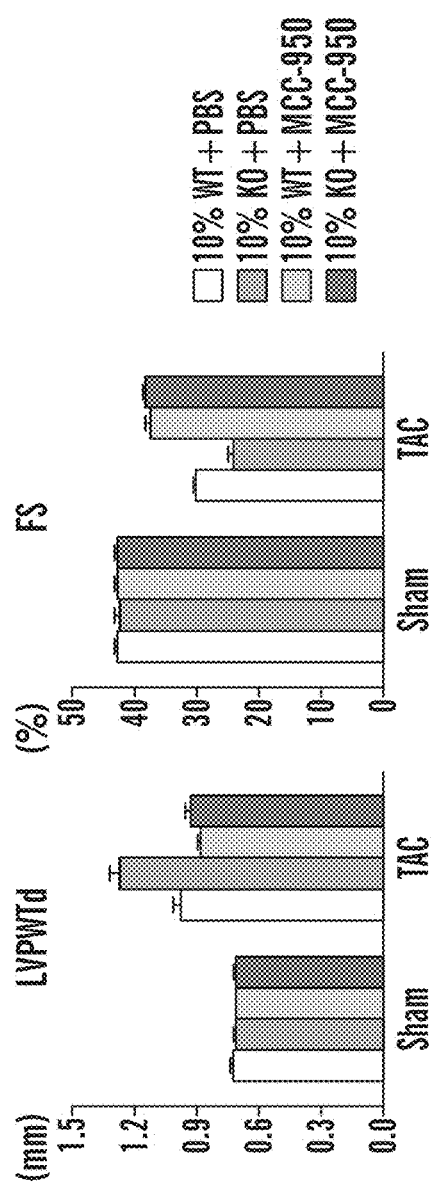
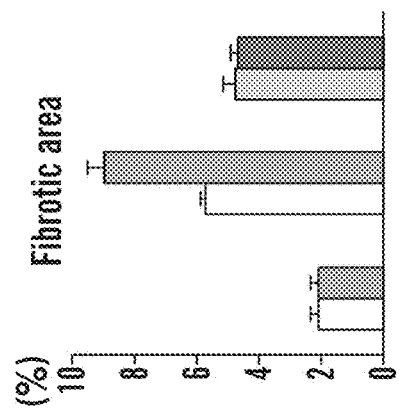
FIG. 22D
FIG. 22E

SEQUENCE LISTING

```
<160> NUMBER OF SEQ ID NOS: 61

<210> SEQ ID NO 1
<211> LENGTH: 140929
<212> TYPE: DNA
<213> ORGANISM: Homo sapiens

<400> SEQUENCE: 1
agtattgtta ctcctgcccc atcccagacc tccttaatca gaatctccaa aaggcctgcg      60
ggggtagagg agggtaacct agtcatgcat attttttcaaa agctccctaa attagatttt     120
gttttcccaa ttgaaaggtt tggtgctatc ccattctgag cattttatta atatcaccaa     180
agacccatgt ccgattaatg atttcagtag atggcgctct ttccacctgc cagcttcctt     240
gcttggcgga atgaacccta agccattcat aaaagtcaag ggcaggtcaa aggtgcaatt     300
cccaccaata ttgaaaacat acactagaac ttacctttgc aaaccaattg ttagtcggtt     360
aagacacacg ttaaagtggt ggtggggaag gggtacagta tcacatttgc ttattacatg     420
aatgtaatta ttcttctgaa gagttcaaga atgtcaactc cctggcacaa aattggaaac     480
taaagaaaca gagtagaaag cagtgatttt ttttataaag tagagatttg gacaaaagag     540 gttttttaa aaatatgaga aagatatagg aaatactgat gttactgcta tacaacatac     600
tgtgtgaaaa acttatgatg gggcaaacat agatgtctgt atctgctaaa ttgggagaca     660
gcaccaggta gcctgcaaga tcatcagctt tagagtcagc taaccctgat tgagacaatt     720
cttcccgcta ttttatagca accaagttac ttagcccttaa attctcaaca agatattacc     780
tactttactt ggttataata agcattaaat taaaagagat aatgaatgta aaacaattat     840
```

```
ttcaatgctt ggtgcacagc cagtatttaa ccaataaact tacttttgga gtgctaagta    900
aatgtaggtg ctgagttttt aattttttaa gtagcaaagg ataatagaaa attaacatga    960
ggttttgaag ggaagattcc tttaccagtc agtactaata atggtgagaa aaaaattaga   1020
ggaggataag caggaaaaaa acagaaggtt agctttggta taataaaaaa ggcctaaacc   1080
ttaattcaca aaatttagat tgtaaggtg ctctctattt acaggatgtc tgaccctaag    1140
taaatcaatt aatctcatct ttaatattta tatgatggaa attacattaa ataaatcact   1200
taacctcacc tttaatattt atatgatgga aattacatta aatgccattt ttaatatgac   1260
atcattttgc atattaagtc ataatacaca taaaatgcca aaaaactata gagtcctata   1320
aaatggtgct gaggtaatta ttaatagtta aattttattg attactgaaa ttcatcaata   1380
aagttaaaaa ttattctttc aaaataaaat gagatactaa gtgagttagt aaatttggat   1440
gaggacaaaa agagtagtta ctggattgtg aagtcagaat ttatgaaaag aaaaagtatt   1500
ccctaaaatt gtaagagatt ggtattagca atatttgcaa taattgtgga ggaatttcca   1560
tgatgttgtc ccactaatga ttctaatatt cttcatttt cttttgaga cagagtcttg     1620
cactatcacc caggctggag ttcagtggta caatcatggc tcacgtggct cacagtcttg   1680
aattcctggg cttaagtgat cctcctcagt aatattcttt ctataatgcc tttgccaata   1740
cttttcagtt tatcttatat tctactttgc ccccattaaa ttagtacaca cattggatag   1800
ttcctgattt cattaattta atattatata atttgtattt tttccttaaa attttcaaat   1860
tatataaaga aaattaacc aaataaaatc agattaggaa aaagtaact agaaatcata    1920
agagattcta tcgagattct catcatatta taatccctgg gtttagacaa taattttat    1980
taataataat ttatattaat aagctaaaat attatatctc aatatgtcat ctattggaga   2040
ctgttgaaac ttagtattct gtgttaaata cgtacctaca tataatgtgc agtaatgtaa   2100
ccaaacaaaa taaataagaa agcttttaa ccgcagtgac tgctatgctg tttgatggtc    2160
aattgtcttt taagcataca gagaatcttt atcatgttat acttcagaaa catgtttttg   2220
gagatgggaa acaacaggcc atgatttat gttttttgtta aaccagtata attctttcaa    2280
agcagtgtat atcacaacta tttctctgtg ttgaagagag tatcaagttc ttaaagaaaa   2340
atgtaatccc agcactttgg gaggctgagg taggaggagc acgaggtcag gagttggaga   2400
gcagacagga gaattgcttg aatccgggag gtggaggttg cggtgagcag agatcgcgcc   2460
actcactccg tcctgggtga cagagtgaga ctccgtttca aaaaaaaaa aaaagaaaga    2520
aagaaagaac attttctatt ctgcaggtgg gaggaaatga agaatgcacc tattattttt   2580
gtgttagtac aacataaaaa aaatttgcat tgtaaagcaa actaccatca tcagctcttt   2640
aatggacagc agcagacagg aaactgcctc caccctgaga cttaaagact gagcaactga   2700
gttagatagc aggtgcgcag gccaatcaag tcaatttct aacacagagt agcatgttgt    2760
ggaacttgtt ctattagtct tttttctctg ttaaggaagc aaggatctct ctgtatggaa   2820
gcagtgctgc tatttctagt ttgaggaaaa aaatggtaaa gaatttgata attaattgtt   2880
gttaaaacag caaattatat tttaaacaca gattgtccac acctgtagga ggaggaatct   2940
caagaatgca cacaattaat aaaagctggt tctgaattac ccatacaagt gcgcactgcg   3000
ttcagtaaac aactgatttg caactatat cctttctttc ccagaaatag caggaggaag    3060
ttttttcaaat caaaaaaaaa atctaactaa aatatttat acgtgaaggc ctgcagaatt    3120
ttacttcctt ttgctgttga aaaatcacaa tagccaagag gagtaatgta ttttatttta   3180
acttttaaaa agtcatgatg gttaagggta gagtggaggt gcagagaaag aagttggcaa   3240
```

```
gaaaatgttc agggcctgtt gtaaaaccaa ctgcaaccca acatgattc caaataggta      3300
agaacaccct gttacaacag agagcagttt tcaaagaaga aatgagaggg aggtgacctg      3360
aaagatcatt tcccagttat aactaaagga acctacggat acttttatat aaacacatg      3420
ctaatataat attttccaca tattattaaa tgtaagaaga tatataatta tatacttcta      3480
tagtcagaaa caaataaact cctagaagta aatggtttgt tactgtagta gtagtaacta      3540
cctgggcact tacctagtgc tcttattaaa aactcaccac aactctgctg tcttacaggt      3600
tgttgaacag attgaaagaa accgataccg agagagttaa gtaaaatgca caaggtcaca      3660
ctggaaaaga tagagttaag agtcactcag ctctgtaaaa ctccaaagcc catgtttcaa      3720
caactctgca atactgtgca ctgtataaat gtatgttgtg gtcttgagag aactttattt      3780
cctggacttg aaaatacat cacaagccgg gcgcggtggc tcacgcctgt aatcccagca      3840
ctctgggagg tcaggagttc cagaccagcc tggccaatat ggtgaaaccc cgtctctatt      3900
aaaaatacaa aaaatagctg gcgtggtgg cgcacgcctg tagtcccagc tactccggag      3960
gctgaggcag aagaatcgct tgaacccgga aggccgaggt tgcagtgagc cgagatcgcg      4020
ccactgcact ccagcctggg tgacagagag aggctgtctc aagaaagaaa gaaaaggaaa      4080
gaaaagaaag aaagaaataa agatcacaaa gaactttcaa acagcttaga ttttaaagtg      4140
cattaacaat ttccaagacc taagtgacgc tttagtgtac agctagaaaa catgaatgt       4200
cattcccacc tgaaatgttt aagggaaaat gtactatttc cttagtttgt gcaaaatctg      4260
aaatctgagt caactttgtt tcaaaatgga ataaacaaag tttgattgga cccactaaac      4320
attcttctta gcaacaatgc gacacttgca aggagttccc tttttcacac tcttcaaaga      4380
ggaaatattc cgatttcgta aaattagggc ttcgctttta aaaaaaatta cagaccaaaa      4440
aaagtgtggt tacacaatat aactagtatt gacttaaggg tactgtgatc accatgcagt      4500
gatcccataa aagatgtgac caaaataccc acttaaaatt tgaacgtcag tcatgtaaga      4560
acatgtaaaa gatgaaggga atatttcaaa aacgactatc tgacgtaata tgatacttac      4620
tatgactcat atgggctttg ttcttcatct catcttcaaa taaaaagttg atgattagaa      4680
aaaggagcat tagaagggg aagtaacact actcggcaat agagaaaaac tccggtcaaa       4740
ggaagagcat agttacagag ctccgaatgt cagggaaaat caagcatccg tcattcggaa      4800
ttagctctgt atcggtcggt ttcttcatta cttaattgta cggggggaaa ctacttcaaa      4860
gtaagggctc ttacgagagg caacttaagc atttgaaagt gcaggtttat ttcctcctag      4920
cgagaagtag ggggtcacta gtgagaaacc tatttcaatc tgtgagacgc ccccttctac      4980
tcagcccacg tggctaaagt aaacagaagg tgggccgggg cggggagaaa cagaactcgg      5040
tcaatttccc agtttgtcgg gtcttttaaaa atacaggccc ctaaagcact aagggcatgc      5100
cctcggtgaa acaggggagc gcttctgctg aatgagatta agcgacaga aaagggaaag       5160
gagagcgcgg gcaacgggat ctaaagggag atagagacgg gggcctctga gggtaaggtg      5220
ggcgcaagcg gaggtgtggt gcggggagag gtgccagtgg gtggaggcgg gggccagagc      5280
gagggcacgt gcgggtacac tccggaggag gtgggtgcgc gcggggcgt gtgcgcggga       5340
cctcgaagtg gtggtggagt gcagaccagc aaaaagtttc aaagggaaat cttagatgtc      5400
acgtctttgt ccaggcaccc gtgccatccc aacctccac ctcgccccca accttcgcgc       5460
ttgctctgct tcttctccca ggggtggaga cccgccgagg tccccggggt cccgagggc       5520
tgcacccttc cccgcgctcg ccagccctgg ccctactcc gcgctggtcc gggcgcacca       5580
```

```
ctcccccgc gccactgcac ggcgtgaggg cagcccaggt ctccactgcg cgccccgctg    5640
tacggcccca ggtgccgccg gcctttgtgc tggacgcccg gtgcgggggg ctaattccct    5700
gggagccggg gctgagggcc ccagggcggc ggcgcaggcc ggggcggagc gggaggaggc    5760
cggggcggag caggaggagg cccgggcgga ggaggagagc cggcggtagc ggcagtggca    5820
gcggcgagag cttgggcggc cgccgccgcc tcctcgcgag cgccgcgcgc ccgggtcccg    5880
ctcgcatgca agtcacgtcc gcccctcgg cgcggccgcc ccgagacgcc ggccccgctg     5940
agtgatgaga acagacgtca aactgcctta tgaatattga tgcggaggct aggctgcttt    6000
cgtagagaag cagaaggaag caagatggct gccctttagg atttgttaga aaggagaccc    6060
gactgcaact gctggattgc tgcaaggctg agggacgaga acgaggtcag agcgcttctc    6120
ttatgccgcg aaactctccc tttcttctcc ccttcgcttt ttctcgggct tccagggact    6180
ggggagcaaa ccctgtagtg tcacccacaa ataccaagag ggaagaggga agcttcacaa    6240
attactggag cctcttcaac atggctgaca aatatagttt taattccctc tacccctttt    6300
aaacctgtag ttctgtgttc tcttctctcc tcctaatgct cgtcccctca tctcccagaa    6360
aacttacctt tgtgcctccg acgagccggt ttcccggcct tttttaatcc tcagaaaagt    6420
gatttttaaa tttgctttcc tttctaaaat agttcagctt tgggggcact acttttccct    6480
ttaatcctct tccctgttt cttcgtgta agtgaaacga gtctcccgtt tatcctgaac      6540
aacctcagag agaacactga tagggtgttt ttcgacccett ttatcagctg tagggtctgg   6600
gtctgggttt gtgtctgcct cctcctacct tcttatcccc ctttagggg ctgtacgaag     6660 tgaatgtcac agggagtgga attggagtac actgagtggg ttttttttt ccttaagtcc    6720 gcgcgttttg ttagcggcgc tgagtgaaag aggaaagaat agtttctctg gttccccaaa    6780
caagaccaga actcactttt ctcaaggtac ataagtcagc gctgggctga gccttccagc    6840
ctggggaatg tatgtaagag aatttatgga caaatctgtg tcccggcttt gtgcttctcc    6900
cgaatcagct tcgtttggtt ccttggtaag tgacaggcag acacaaaggc aggcgcaggc    6960
ccggggaggg ggcgggaggg ggtggggagc gcagcgttgg agttgcaaga ctgcaaggtc    7020
aggggcgcct aaagaaatga aacccaatcc cagcaaagaa gtgaagagca gatttataac    7080
agtcccatcc aaatttctct ttggcttctc tctttggtct ttcatctctc tgcctttctc    7140
tctgtgtctc ctctctactc tttcttctct ctctctcata cacatacaca cacacacaca    7200
cacacacacc tcactcgcat cttgctgaat cttttcactg ggactgcttg tctagttta    7260 ttaagctaat agggtttgta tggagagttt tctacctatg acataatgaa gtgtggcctg    7320
gatagactcc tggaaaggcc gaaaatgaaa tataagtgtt atttgctggt tattcccctc    7380
atgatatact tttaattaca ttgagggagt tctcccttct tcatctaatg tttaagaatt    7440
gagaaaaggc ttatttttcca gcggtaaaat ttagtgcata aaatttagtg aaatatttat    7500
atatttacgt gtctagggag tggaatacat tcatgaattt aatatctcaa atcacacatt     7560 gtgcttttc cccttcagtc agggattata atgggaaacc caaattcaaa gatattcatc     7620
aacaaatgat ccatcatagg aataagattg tatcttaagg gaagttggga ttcacagaga    7680
aaagacattg gttggtttg gtgtgatact gtgggtattg ttgcctggct aatgaaatca     7740
ttacatttgc atttaatgg aaagttgaaa tactaagggg agttatgttc ttttacatgt      7800
ttgtatgtgt gcttaataat gtttggaata gaatataaat ttaaacacaa taaatattga    7860 ttttttaaa tgttaataag cagagaacgg ttaatgaagt gttggataat caaactgaag     7920
tttagaagac aatttatagg attaaaaaat ggatagaagg aaaaacacaa taatagatat    7980
```

```
ttctccataa gtcgaatttc caaaactatt tgtcctcgat agttcacttt gtaactttct    8040
attttgatct ttgttaattt aatgtagttt gctttaatca ttgatacgtg gggttctttc    8100
acatgattac aagggagaag cattactcat ctctgtggaa tagaaacggt tcattggtta    8160
gttcttattt gccctaaaat taaaacaaaa attaggattt taccattaat gctgttcatg    8220
gtaaactatc gagaaaacta tggttaatta ttccagcaat tcagaattaa aaacaattcc    8280
ttttgctaac aaactaatat ttactttttg gggacaactt tcaaatgtt gtggtatata    8340 ctgtcttcag gctactcaac taataataga tacaacattt tccactcaat aaataagaat    8400
aactacattg gttaataatt ttgaatacaa ctatgaaggc ttgttttttc ctgtcatcaa    8460
atttagattc ttgttatttt gtgcatccta cttttatact gaaaatagct gctaattaat    8520
actgtataaa gtatttcagt gattataagg aagagatgtg tatgttagtc actttatcct    8580
ttgttggaaa agagaaatta ttttaataag tatggggtag tttacaataa aagacataac    8640
ctcagttctt tctttaccat atatgtgatc atactaccta ggtgctccaa aaattccata    8700
ggactgtctt gggttattga attttaggaa catgataatg gacaataaca agatagatag    8760
cttttcttaa ctatgacatt gttttgctta ttttcttatt gaactaatca tcaatgagaa    8820
attaagttgc agtgagagaa atcccttgct ttgtttaaat tgtcatattt gccaaactct    8880
tcttaaggct ttaattaggt ctgatgtgcc agtttatgcc agaagccgga ggaattgata    8940
tgattttgag gcagtggcac atggtcctac tagacattgg caagtgaata tcacttccag    9000
aacaagtgaa gtgcacctgc caaggagttg ttatgaaaga attccaaagt ccttattggg    9060
cactggtctt gtattaggta acaacaactg gagttaatgt tttagtttca cttgttgaag    9120
ttaaaagttc cctatcaatt cttctaagac tccaccccca aacaatgttg taagtcaaat    9180
gtcactattg aaatgtattt ccttaattac tgacctcatt aagaagccct tcttatgatt    9240
cataggcaca cctcacagaa actctatttt ccatcctgcc caaagtctga gtaggtaaat    9300
tcttatgaat tcttatgaaa ttaccttgaa ataaatatc ttcaaaagtt acggatgcta    9360
gacattgtat aatgtcaata ttttagaata tctaatattt agaaaatctt agatctactt    9420
tttatgcttt aattgcttct aatgcaagtt aaattgtttt tgttgttatt gttttaatag    9480
aatttcatag tcttatctag caatttcaaa tcgctggaaa gagtcatctt tgttatataa    9540
ataaccatgt agactgtttt aatgttattg tttcctacct tgggaacagg ctaaaacttt    9600
ggaccagctg tcagtatttg ttcatcagaa taacactttg tcaatgatta ttctaccatt    9660
gcacagtagt tcttaaggat agtaatggta ccaaagccag cagcaataga atatctccca    9720
agccaacttt acaattggag ccttcactgt gggaaagacc agttgccaag tagagctggt    9780
ggttatctgg gaaactgtgc tgaagaacac aaccacaaat gattttgcca aatatacagt    9840
atttacttgg tctagatctc caatttctat ttctactcac tgccaaaact gagtgaatac    9900
tgtgacatta ttgaaggagg ttatgcagta catctgttgg tttggtatat agtaggagag    9960
aagggttcca ggagggaaag gggaaagtca gagcatgtga atcactgtga ctacaatcca    10020
aaaagaatta tgtatgtctg ctatttccag cattatttt gtcctatatt gtacattgca    10080
gagacttgct gacttaaaat agatatataa tctttttctc aaaagaatag atatttggtt    10140
gtccattcca aataacaaat tttggatggg cgtggtgact catgcctgta atcctagcac    10200
tttgggaggc caaggtgaga gatcacttga ggccaggagt ttgaaaccac cctgggcaac    10260
acagtcaggc cccagtctct acaaaaaatt taaaaagtta gtggggcatg gtggtacatt    10320
```

```
cctgtagtcc cagctactca ggagactgag ataggaggat ggattgagct caagtgttct   10380
aacttatagt gagctctgat cacaccactg cgctccagcc caggcaagag ggagagaccc   10440
tatctcaaac agcgacaaca acaaaaccaa acaaacaaaa aagcacattc tatcagcttt   10500
gatttatgtt ttcttcattt gtaatgacat gtagttaaat gtgtcatact tcaaaaagaa   10560
gaaacagata gtaggtggat tttcaatata atatatatta gatatagata atatatattt   10620
tcaatatata atatatgtaa aaataaaattc agtgataata tcatcctacc tgcagtttta   10680
agaattcaga actcaggcca ggtgtggtgg ctcattctgg gaggggaagg caggaggatc   10740
acttgaggcc agaagttcta gaccagcctg gcaacatag tgagatacct gtctctattc   10800
aataaaaata aaaataaaaa taattcagaa ctcaatgctt tatactcact gaaagttgtt   10860
cctctaaact gacttgaaat catgttccaa ataaactgag aattaaagta agagacgagg   10920
ccggttgtgg tggctcatgc ctgtaatccc agcactttgg gacgacaagg caggtggatg   10980
acctgaggtc aggagtttga gaccagcctg gccaacatgg tgaaaccctg tctctactaa   11040
aaatacaaaa attagccggg catggtggca cacaccagta atcccagcta ctcaggaggc   11100
tgaggcccga gaatcacttg agcctgggca tggtggctca tacctataat cccagcactt   11160
tgggaggccg aggcaggtgg atcacctgac gtcaggaatt cgagaccagt ctggccaaca   11220
tggtgaaacc ccatctccac taaacataca aaattagctg ggtgtggtgg cacatgcctg   11280
tagtctcagc tattctggag gctgatacag gagaattgct tgaaccctcc cgggaggcag   11340
aggctgcggt gagccgagat ggctctgctg cactccagcc tgggcgaggc agagagactc   11400
tgcctcaaaa aaagaaaaat aataataata aataggagat gaataaattg ggataaagtg   11460
tttttgaagg acagtctagg atataaaatg aactggttgt ttgactaaaa atactacaaa   11520
tgtttctttc aaattacatt tcttttttgt ctattggaag gtaggcactg atttctatgt   11580
ctttctattc cctaatagaa cctactgttg acctctcagt caatatttaa tggatgatat   11640
agaactagtg aaaaaccatg caatttaact agaaaaaaaa agtataatct attttctttt   11700 ccttttctt tctttctttc tttctttttt tttttttttt tgagacggta tcttgctctg   11760
tcacctaggc tggagtgcag tggtgtgatc tcggctcact gcaacctctg ccttccaggt   11820
tcaagtgatt ctctttctca gcccccagag tagctgggac taggagcgtg ccccaccaca   11880
cctggctaat ttttctattt ttattagaga cagggtttca ccatgttggc caggctgatc   11940
tcgtactcct ggtctcaggt gatctgcctg cccgggtctc ccaaagtgct gggattacag   12000
gcatgagcca ctgcacctgg tctaatctat tttcaatgta taagagaaaa atagtgttaa   12060
gtgtcttggt gatggtgatg atggtaggag taatggtgtg ttttccttac atttaatttc   12120
tacaggctat ggcaattgcc ctataaaagc cacccatttt aagcacaaaa gtgaatggtt   12180
tttagtaaac ttatatggga tcatatattt ttaattgaaa tatttttga gttaattata   12240 gattcatatg ccattgtatg aaataataca gagagattcc acgtatactt gctcaatttc   12300
ccccagtggc aacactttgc aaaactataa tatcatatca catcacatgc aaaactataa   12360
tatcatatca caaccatgat actgacattg atgtggccta ctaatcttat tcagatgtcc   12420
tcagtttaac ttgtactcat ttgtgtgtgt tttgttttat accatttagt cacatgatca   12480 catatttta aaccttttt tctcaaaaca gagaagttta gcacaaaagt ttagcaattt   12540
atcaatcttg tgattgtgct gttatgccat attaaaatgt gtgtcagaat gtaagttttt   12600
gttttcttaa aagtcctttt tttgatagaa tggcctttat gttaaaaata ttttaagttg   12660
ttttgtgaca gtgtaagtcg atgtcattta attctcatca caaccctaga gataggtatt   12720
```

```
attcttatcc ctatttatga gtgaggaaac tgaagcccag tgaggttaaa taacttcctt    12780
aagttcatac agcctataca tggcttaggc ttagccagca tttgagttaa gcagtctgtc    12840
tctagtgcca aatcttttaa tcactatatt atacttcatc attatcattg atagctgtaa    12900
aagtgtataa tgtggactat gtagagaaag tcataaaagg agatttaaaa tgcatacagt    12960
tgttcacatg aaaacttgta gccaaatgtt cattacagca ttattaataa tggtaaaaaa    13020
tggaaacaac ccagatgtct atcatgtcat gagtgaataa acaaattgtg gtatatccat    13080
acagtgaaat attattaagt agtataaagg aatggattat tgataaatgc tgtcacatag    13140
gtgaatctga gaggcacaag aaaggccaca tatgatatgc tttcaatttt aagtaacgtc    13200
cagaataggc aaatctaagg agacagaaag ttggctagtt attactaggg gctagggatg    13260
ggagggaggt gactcctaat aagtatgaga tttcttttgg tgatgatgaa aatgttctat    13320
aattagatag taatgattgc ccaactcttt gaatatgctg aaacccactg aattatatgc    13380
tttaaaagga tgaatttatt gtatgtgaat tatatttcaa aaagctgttg ttataaaaat    13440
gaatgtagtt gagttatttg gtttatttta tgtcagaaaa tgtcttacat ctcatgcaaa    13500
agaaatgcag gaactatttg gattgaatga ggctaagcat atctttctag gaagatggca    13560
tcaaggagtt ttattatgcc tgtaatcctg gcactttggg aggccaaggc gggagaccag    13620
aagtttgaga ttagtctggg caacatcctc ttatagatga gaaggatact taatcactca    13680
aaagttggca ttgtgttttg tgataacaat agcctttaga gctcatatgg gaagattcaa    13740
tagatagtga taggttatat gacttggtaa agagggctta atgtataggt gcaagaaact    13800
ttctcagatg tctttagtta cctagccatt cagttcagga gatgtaaccc aagtgttaaa    13860
aggaatgtga ctgggtgcgg tggctcacac ctgtaatccc agcactttgc gaggcggaag    13920
tgggtgggtc tcttgagctc aggagttgga gacaagcctg gcaacatgg caaaacccca    13980 tccctacaaa aaatgcacaa attagctggg tgtggtggca catccctgta gttccaggta    14040
cttgtggggc tgaggcggga ggatggctcg agcctgggaa gttgaggctg cagtgagcca    14100
tgttggtgcc cccacacttc agcctgggtg acaaaatgag accctctctc tcaaaaaaaa    14160
actataaaaa ttgctgttct tgtttaaatt actacaaagt gcagtttaat ctagaaataa    14220
taacaaatta ctagatttgg ggggttatta atgtcttatc tatgtgaaaa cagaagggca    14280
atgcagggca gagaataaac ttcaaaactt tgagtttgtt aactgtttat atctccactt    14340
gtcatgtttc agattttaaa gttaaatga caaagtatct catagggttt aaacaagtga    14400
ctcttttcct gttaactgat actgtggcat gttgaagatg taaataagg ttgaaaagga    14460 aattgctttg cagcagtctt cataatgcca ggacaaagtg agaaacaggg tcagaatgat    14520
gatggctctc catctttgct acacatggct gcaagtattt acaaatacca gcagaacttc    14580
tacaaaccac ttacaggtaa aatgagtgca gattttttaac actagtccct atggaactat    14640
gacttgtagt tttggacaca cagggtgaat tacttgggt tgattgtatt tgaatttcta    14700
accttatgta attctagata ccagacattc ttgttgtgca atgcttctct ccctttttat    14760
tctcatgaga atgctgggtt gcagccggtt ggatcccata ccttgggacc atgactgata    14820
actggagtgg agaaaattca ctgatctgga aaggttgagc tttagggttc agagacttat    14880
ttaaggtaca catgtgattg tacccaataa ggaagtatat tggctttata taattgttat    14940
gatcacttgt tcaatgagta actatagaat tttactttt aagagtatga tcatagcatc    15000
tacttgtagg tttgttgagt atgtttgaca agcccaagat agatgctcat gttagaccca    15060
```

```
ttaagaagtt ggtgtagtga tggttatgga aagcagtaag atagaattta ggttctgttc   15120
tccttactgg agaaatgact agcttacttg tcttcactct ctcttgtttc tctcaaaact   15180
ttgtgaacca cctcagctga ctataaattt ttgtactagt atctccataa ttttaaaaaa   15240
gttgttcaca agtttgagtg tagtacttca tctttgcttt ttaatgcact tccaaaaaat   15300
gtaaatctgt tctcgcatat taggaacatt ttgatttgtt gtttatttt agctttgctt   15360 tttataagta atttatacag aaggtacacc atattcaaaa gaagaaaaat gggctgtgaa   15420
tttttgctga tgtactactc tcttcaaagg gaattgccta tgttcaggca tagaaatgca   15480
ggcagtctga catttaggta tgccatacag agtattgata ttttaattt gctacttta   15540 acattttgag atttgtcaca gtttgttctg tgggtgggta aaagtaatgg taattttaat   15600
tacagttgtc gtgcctcatt agccattgct aaaacctgcc ttaccaaatc acttatttc   15660 ttgatgcagt gttaaatcta gcttctatgt ccaggttata cattaatgag aacattcacc   15720
catctctcaa atgggttatt atagtatttt ctcctgaaat agatgatgca taaaaaaaag   15780
taaaaaagct tcaataggga taatgaaagc cagataacag agcatggtat atgagttatt   15840
cctcccgttt ttcttacctg tctgcactaa gaagggcacc cattaaatac cataattatt   15900
agttgtgctg cctctgaagt agagcaccag aatgtgagag taatacaatg agaccacacc   15960
cagattctat ccataacata ctgtcctggt cttattaatt ttttaacct gtttgttctt   16020 ttagcacttt tcctgctttt gtttgaagtc tcttgctttg aagttataga attttatat   16080 ttgccattgg ctgtaaagtt atctcagctc ttttataact tttcattata tttgcattaa   16140
aaggatcact ttgagcaccc tgtaattaat tcagatgatt attagctttt ttgtttgttc   16200
tactgtgcac tctcctatat acattataac agaagaaaaa accattcta caaatacagt   16260 gtctgatagt tcatcaaatc agaatgagca tcttaaaaag tgaattatta aaatattaat   16320
tcatttacat tcctatttta atgtaccaaa tgtaactgat gaaagaaga ataccataaa   16380 tgggtacctt tcaaaaatga aggaaaaaaa aatctcacaa ctaaagattc ttaccatata   16440
aattatttat tttagtaaat aattatttta gtacaaacag atacatttta gcaggaaaaa   16500
acacacttta aacctgtttt tatagatttt atctttcttc caatctagcc actgaaatgg   16560
ttttttctcc agtgaagtta tattatctac ataagttgaa tttaaaacaa ggttgtattt   16620
taattttgca gttgtctgcc acattacgct tgtggaaaaa cactggcaga aagcaaagct   16680
aatagacatt ttgctgttgg ctcaccttat taatggctaa gatttaatta tgtatttcta   16740
ctgaaaagca aacttgaaaa agacgtttgg ttactaactg tgggaactaa aaatttttat   16800
ttatttttat tttttatttt ttggtagagt ctcactctct tgcccaggct ggagtgcagt   16860
ggcatgatct tggctcactg cagcctcctc cttctgggtt caagcgattc tcctgtctca   16920
gcctcccgag tagctgggat tataggcacc agccaccatg cctggctaat ttttgcattt   16980
ttagtagaaa cagcgtttcg ccatgtaggc taggctggtc tcgaactcct gacctctagt   17040
gatccacccc cttctgcttc ctaaagtgct gggattacag gcatgagcca tcggcctggc   17100
caacttattt actgttacaa cttacttact ttgaaacaac ttatttactg ttaaaaaatg   17160
tggttcttat ttcaaataag attttatgga catcaactaa ttttttaaac atatattgta   17220
attttaaaac attttacca acattttca agagcatggg aaatctaggg tatggcattt   17280
taaagtgact ttaaagacac ttcttgggtt tgttgaagt cagaatatt ttaaaaatac   17340 aatgagttta atttactact gacagatttt ctttaatttt ttttgcattg ttataattag   17400
tcatgcctta atcctcgggg ttttgggaa actatattta ggggttaaaa acttagttat   17460
```

```
tgacattgta attttctca gtattggtaa gaattcaggt gtttaaggaa tggagtttac   17520
ttgttttctg ttcacaaacc cattgtaaaa gatataatga atgtagatga aggtgaaatc   17580
cgagatagga agagaggtaa aatgctactt ttttttcctt cacccaagga aagccattga   17640
atactgaatg ggtcatgttg taatttaatt gggtgtaaat tataactttg taaatcattt   17700
gcctacttag tgtatatctc tggtttttat gtaattcatc tcccataata tctcagttta   17760
cactgaagta aataagcaag caggaataag tcctgcaaat agaggaagta gaaagtgcat   17820
tcagaatgca ttgctgaaat tgtaaaactg atcctaaatt gaattaggta gagcagttaa   17880
tttagattac aagaaatgca acaggaaaaa aatattacag ttcttcctct tttttggaaa   17940 aaaaaaaga aagaaaagac aaataaatca cccttagtta gtgataattc cttgacatct   18000
gtatgctcat ttttagggcc aaaaaatagt aggcttctct ttggaaattg tagacgcttt   18060
ctctccttcc agttacacgc ggtcacatca acatttgaca cgtgggtacc gtgcacgtgg   18120
cagcagtatt tacaaacacc atcctaggat tccagagact cttatgtaac agtggagaga   18180
gtaagctttg agtgtctgtg ggcggaggaa tcaacacagt ttaattcatt gtccgggagc   18240
ccttgtctgg ctctgatagg gtcatgaacc aaagatcaag gtgtttaggt caggatattc   18300
cctaacgcat ggttttccta ccaaagcctc aaaagctgtg cctaaataca agattaatct   18360 tttctttct ttctttcttt ttttttttt ttttgagac ggagtttcgc tcttgctgcc   18420
aaggttggag tgcagtggcg ccgcgatctc ggctcactgc aacctccgcc tcaccggttc   18480
aagcgattct ccagcctcag acacccaagt agctgggatt ataggcatgc gccaccacgc   18540
ccggctaatt ttgtattttt agtacagacg gggtttctcc atgttggtca gctggtgtt   18600 gaactcccga cttaaggtga tccgcttgct tcggccccc aaagtgctgg gattacaggc   18660
ttgagccacc gcgcccagct aagattaatc ttttatgcc ctgcagcaaa caactagtca   18720
tgccaaacca ttttttgtgat ttggggaaac atgagcagat gatgcttggg atctgattat   18780
aattcacagt gctcttgtaa tttacgtgag atttgcatac ctgcctccca gcctcacaaa   18840
atgcctttaa aaaattacat cttggccagg atggctcacg cctgtaatcc cggcatttg   18900 ggaggccaag gcgggtggca agagatcgag atcatcctgg ccaacacggt gaaaacccgt   18960
ctctgctaaa aatacaaaaa ttagctgggc gtggtggcgg cgcctgtaa tcccagctac   19020 ttgggagact gtggcaggag aatcgcttga ccccgggagg cggaggttgc agtgagccga   19080
gatcgcgcca ctgcactcca gcctggcgac agaacgagac tccgtctcag aaaaaaaaaa   19140
aatcttgata tttgtatgca tcttaaaaag caagagaatt catgattgac ttcccaaact   19200
aaacggtctg accagaaaac actcaagaaa actcttggtt aatcatgctc cttagtatac   19260
cattatacct gcctctcccc tttccccatc ctctgtaaat tctctcaacc ttctctcatt   19320
tttaatttca taccaagacc tagagctaaa acaacaacaa caaagcttta agtctctata   19380
tttagggaat gtgcctccta tcccaaattg atttttagag cttttcattt attttatca   19440 atacaaagca agttgaaata aaaaaaaagg catcaaaaat ttaaatgtct aaccacgtat   19500
atttggtata tgtatactgg tgctatgtat tagctgtaag cagactggtt tgaatattta   19560
aaatatgaac agaatttgag ttctttttgt attgcatcta aggatcattt gagatggatg   19620
tcatcattta tcatccaaaa tagaagcctt cttgcctaac aaagaattgt aattagatca   19680
tcaaagatga aatttatagt aattgaaaag ttagctcatt tgactgcttc tttcatagac   19740 tgtgttttg taattacact accttctaa agataggaaa aatcagagtc tctgaaatgt   19800
```

```
aatactataa gtgaaatatg tatttttta  aataaaggat cttttcccaa gagctaaacc    19860
aagcaccaaa tctgtttttt ggggtttttt tggtttgttg gtttgtttgt ttgtttgttt    19920
ttgacagagt ctccctctgt cgcccaggct ggagtgaagc ggagcgatct gggctcaccg    19980
caacctccgc ctcctgggtt ccagcaattc tctgcctcag gcttcggagt agctgggatt    20040
acaggcactc gccaccacgc ccggctaatt tttgtatttt tagtagaggc ggggttttac    20100
catcttggtc aggctggttt tgaactcctg acctggtgat ccactcgcct cagcctccca    20160
aagtgctggg attacaggtg ttttctttta agtaatactt ggtataagag aactttatat    20220
ctggaataat ttaaatatta tctgaccgaa tctattattc acatatagaa actcaggttt    20280
tagccattta acatctaaag ctgttctcat ttagaggaaa ttaccaaaag agtgacttat    20340
ttaactaaca ataaaatcta aggatagata ttttttcatt ctgttgcaga gcaaaagcag    20400
ccttctggat atgaaaagat attacttctt tagtgtttat tacttataat ttattgtaca    20460
tttctgatac actgaattaa gatgcgatga gagtaggttg tagattttta aaagttctta    20520
tttgcgtgat ttatctactt gcttttttag tgtcggacta taaatgatgt atttctctca    20580
attatcctcg gcctaaatag taaaagcttg ggtgaaatta cttatgagta tacttttcct    20640
gcacagagca gagccattac tgaacactct cgagctttaa caaaaatcat cctatcttat    20700
attagaatat taatattttc cctctttctc ggacctttgt ttcacagtaa atcatatatg    20760
gatataagct gcaagtgctc agaatttgat taaggctata agttaatttc tactaaaaaa    20820
gggattcaaa tagaactttc atttggctgt actgtagttt cacttgaagg ggcaagcatg    20880
caataaacat tgacttattc aatgcatagg ctgtcttcat aaagatgaga ctgagtgaca    20940
gttgtctgtg tattataaaa tatcagaatg gtagattgaa tctgatgcat accaaggagc    21000
aatgtggaaa ttttaggctg ttcgtctttt ttcagttact actaagtgtg tgtatgtggt    21060
gtgtatgtgt tttgaacttt tcatatttaa gctgaatcct cttttggtaga aatggttaaa    21120 tagactatag taaaagtttc tgtctataaa tataaaatga aaaaatactg atatcttgca    21180
ttttccctaa tatgttgaaa gtgcacagaa tccttggggt cttttgtata aactgttttt    21240
atatggttcc tgtagaagac agctgaggca ccaaacacac acacaaaaca aacagcttgc    21300
ttggtgatga taacattcgt gcaagggagt tctctcttgc ataggagtcc caggttaccc    21360
taatgccttc ccacatggtc aaacacatgg agctttcata tttacacaca gctccagaat    21420
tctgaagcct gcagttgttt atcagtggga tacagggaga aagagtggtg tctatcttac    21480
taactgttta atgacctgga tcatgaatac tgatacagaa taagaaagca ctggcctgac    21540 tgcagggaa  acatggtaga tgcctaaagg aggcttttcc ctgccccaca ctgtttattt    21600
taaactatca ttatcacctg aaaggagctt ttcactttga acttaaaata gtagcttta    21660 accctgacaa gcaagtaggc actttagtat tcaagaactg aaggtgacaa gccctgagga    21720
gtgttactct ctttcataac caagctgact caaactcttt tagaagctag tgtagtaact    21780
taaccatctc taataatgtt gctgcatgcc ttcatagaaa cagttggagc aagagctgca    21840
ttttcttttt tttaagtgtt tattatttac atttattttt tgaaacatg ccattcctat     21900 tacatataga aatacttccc aaaatcactg tttgtataga actattttgc ttaacattag    21960
gattctattg aagagcctat atctgcaata atacggggag aaaatcccct tttgtgtgat    22020
agattaatga taaagagaaa gaaaggtgaa gaagtaattt tgggaaatat gcaatgataa    22080
actagtggta tttattgaac taaacaccag cagctgtgct tagcatggat aattgcctaa    22140
aaggatgaga aaaaaaagta aaaatcagga gactataaat ttttcagtga agaataaatt    22200
```

```
ttctgtcaca aattatgaac attttaaata tgtattttaa acttttcct acttgtaaca    22260 aattatcaga cttttaatc tacctttttt gagcttttca tcttttcc tgaattatag     22320 atttaattct gtgtatgtat gtgtgtgttt gaatatattt ttatatttta gatctagatt  22380
tgtaaactag agctgtttct aactgcttat aagacattgc cacctggatt gccaccactt  22440
tcactccagt atttcaataa acacttcatc aaaaacatag tttattttca aacatagaat  22500
catggattgc tacaagctga aaggacttta gagactcagt aaccccattc cttgcattta  22560
cagatgagaa aatggaggca tgggaaagta aagtcagttg cctcaaatag cgtaacaagc  22620
tatgtatatt tctaataata gctactattg attaagttct tatgttgggt taagtaccat  22680
gctaagcact ttccaaagat tatctaattc ttatgtcatc tatattttg ttggtgctat    22740 tactctcctc actttactaa ggaagaaacc aagacatggg gttaaataac ttccctataa   22800
attttgaatt atctttggca tcatctccct atttgcaaat ctccattgtc tctttgttcg   22860
taatcaatgt aaatcaactc ttaaacagtt ggatgccaac aagcagtctg gtgtttggag   22920
ctcgaaagtt tcgagagaga gagagagaga gagagagaga gagagagaga gagagagaga   22980
gtgtgtgtgt gtgtgtgtgt gtgtgtgtgt gtgttccagc tttgttgagg tataattgac   23040
aagtaaacag tccacaaaac tgtacacatt taagagatac agtgtgatgt tttaatatac   23100
attgtgaagt gattattact atcaggctaa ttcacatgtc catcacctct cagtcatttt   23160
ttgtgtttac ggtgagaaca cttaagagct actcaaatgt agtcaaggat accatacagt   23220
actaactgta gtcaccatgc tgtacattag atctccagaa tgtattaaat attcatctgg   23280
cataactgaa actgtgtatc ctttgacaaa cctatttccc ctactaccca gcccatggca   23340
accaccatgt tactctctgc gtttatgagt tcgacttctt tagattccac atataagtga   23400
gatcatgcaa taggaagatc taatttagca tcctgacttt ccttttatt agctgtgtat    23460 gtcatattca ggttgcctta gcatttgtga atctgcttct ctacctgtaa aatgagaaca   23520
actaataatt cttatctcat ggattactga gaggatcaga tgaagtaaca taaataaaac   23580
atccagcatg ttacttggca aaattgtagt gattgaataa atatttgttt attcttcaag   23640
catgtgttga gcatctatgt atcaggcaag aagagagcca tcatctttac ccttctggaa   23700
tatacaggct cataggaaat aatcaatgct ttgatctttt tttaaagcat aatgagatga   23760
aaattatagg actcatagac tggtcagttg aggaatttcc caggatgctt ccagcctctg   23820
ctcaaaaggt gtgaattccc agttgcctga ataggcgcca gagttggcat agctttctca   23880
gtattgggac ctgacaggga gattgcacaa gtgtaacagc acagcctctg aagattggct   23940
caagggggaa gagatgaagg attacttcca tccctttat tgtttcaatc aagatatata    24000
ttatgagctc atagtaccat cctttcatga tcatccttta ttgtctttat tagatacaat   24060
gaaaagatac aaatttgtcc atagaaatat taaatgatag caggcatgat ttaaaaagta   24120
ctaaggacta tagatattac tgttttttcct ctattttgta tcatattttc aggaagaaga  24180
gacaacattt tggcatacct tgcttaaaga tagatgatag ccgggtgtgg tggctcagac   24240
ctgtaattcc agcactttgg gaggccgagg cgggcagatc acctgaggtc aggagtttga   24300
aaccaacctg gccaacgtag agaaaccccg tctgtaccaa aaaatacaaa aattagccag   24360
gcgtggtggt gggcgcctgt aattccagcc actcaggaga ctgaggcacg agaatcactt   24420
gaacccagga ggcagaggtt gcagtgagct gagatcgtgc cattgcactc cagcctgggt   24480
gacagaggga gacttcgtct cccaaaaaat aaaaataaaa aataattgtc ttggtgtgct   24540
```

```
aatcaggagc ttcctgtgag agtggaaatt ccttacatgg cagtgtcatg aaattttagg    24600
cccatgtgaa agatgttttt gagtgtctca aaatagttaa cggtttaaaa atacattatt    24660
tatgtgtcag aaactgcttt cattgaaatt gaagtttctt tgagaactag gatcatatca    24720
tgtatatcta ttgaatttcc cacaacaatt atcacgcaag caaatgaata gcagaccctc    24780
aataacactt actgatgatt attgccatgt ataagttggg atactcttga gtacctttct    24840
aagtctgcat ttagggaaat acagaacaca aaatgaaatg tttgattggt tgcttagttt    24900
ccacagtgac ttttcaaaat gtataggagc atggtaacaa aactatttta aatactacaa    24960
tcttaagtat gcctttatta ttcttaccca caataatgca ttgctttaaa aaattgttta    25020
tcagtgtcag accataccti tctgagtctc tactatgtaa gatgtgaaag ttaatattct    25080
tcaattccag ctacttttct tttcctgcct tctgtcaact cctgtattcc atatcattac    25140
ttcttattgc taaatttata atatttatat tctggtttgc atctatagtt aattctcttg    25200
tgcttcattt ctcagtgcta attgaaaaag aaaacacatc acttacaatg ccatgattgt    25260
aataaataaa attcactgta acacctagca gtatggttga acatgtagaa aaggaaaaag    25320
tgatcctgtg acactaaaat ttagcttgtt ctaaggatgc tactttaagc attagggtaa    25380
aatggattcc cttttgctaa attctttcag ttcctcaaaa ttatgccaca ttttgtttc     25440 tttcacattt ggacttagat tttcctgtaa gcattcaatt tttcttgaaa attttaattg    25500
cattttttta ttcttgttga cagaagaaac attttcatca tatcacaatt ttttttcaga    25560
tttcttaatt ataccatttg atgaatgaaa tacactttct tcttgaagtc tgattttcct    25620
gttctaattt agagtttctt ctcattttcc tcctggctat gtctattatt gctttagtct    25680
catgtctttg tatttgatta ttatttttct ttttactact gttttcttc ttacagaaaa     25740 aaaaagaaaa aaaaacaggg gtttttacaa atattgtgct gagtctttac atgtccaaaa    25800
tgccttatat ttttccttat agtacattca taaattattg tgattagaac cataaattca    25860
aagtaatttt ctctcagagc ttgggaaaca ttggtacgtt gttaccctt atctaggatt     25920 gcttatgaga tagatatctg atgccagtct gattctgtct ttttagata cttttttcc      25980 ctattcatat gttattagg atctttatct tttcacttct gaaattcctc cagatatggc     26040
tctgttaaaa tgtattcttc tcagcacttg atgattctgt acaatctgga aacaactgcc    26100
tttatttagc ttaaggtact ttcttccat tgtacctttg attatttctt ccttctttt      26160 ttcaccctat ctttatgaaa ctcatgttaa tggtgcatta gaacttgtga actgattttt    26220
cttatttatt aaattccatc acatattttt catctgtta tctctgtata ttttatttc      26280 tcaacttttg atatttttgt taattgaaat ttaatttcca agaagtccat tttctattct    26340
ctgattgatt cttttaatg gtagcctatt tcgtggctca aatcatataa aatgtattaa     26400
attttgtggg aaaattaggc aaacaaagaa aattaaattt tacctaacta tatctaaaaa    26460
caatacaact aaacttaaga aaagtgcgta tatgtgtaca catatacata tgcgtgtata    26520
tgtgtacaca tatgctacat atacatgtat atgtagtata tgtacatgta gtatatgtgt    26580
gtatgtatgt atatacacat gtagtatatc tatatacatg tatatgtaca agaaaaaaat    26640
atgtatataa tagtttcact gtactttatt tgctcccctt ttaaaaataa cagtgctaga    26700
gttcatgact gactaatttt cagaacttgg tgtgtatggt tgtttattaa gccctcaata    26760
ataatgcttt agtattacag tgcccaggca tagtcagtga ctgtgctaat agtcctagca    26820
gtagcagttc atcctgtaca gatctaaggt gtaactattt tcattctgg gcccttggag     26880 attctttggt tgtcttcata tcttttacct atcttgctgt tcaataacag gtaatagaaa    26940
```

```
aggagataaa acttaaatgt catcatttcc cactgcttaa cagtctttaa aaataaatgt    27000
gaaacccgta aggacgtaat cttgcctagc tttaaggaat gaaggaaaca ctagaaacaa    27060
cagagagaaa aggaataact gatcctccaa catgttctgt tgactctacc tgtaaagtat    27120
attcaggatc tgactacttc acaccatttc accaatttcc atctccattc aaaccacctt    27180
catgtgttac tttgaaaagt gcagtttccc tgtcatgggt ttccctgttt ctagctttgc    27240 tccccttct tacctcaccg tgggtttta cccaaacaaa aattcaagtg atcatttaaa     27300
aattaagtca ggtcatgcct ctcctctgct taaaaccatt aatgggtctc tgtttcactc    27360
agaatataag ccaaagccct tttcatgacc caccagtcct caagtgaatt ggctgctatt    27420
tgtgtttctg attccatttc ttgccactat tctccctcat tctattctaa tttccttggt    27480
tttcttgctg tcctggcaac aagaagagca tcctttttcc tccaggcctt tgcacttgct    27540
gttccctctt cctggagcac ccttccttca gagagccaca ggtattgttt ctatctttcc    27600
ttctaatctc tccttgagtg ttacttttttc agagataaat tccctaacca ttctatctaa    27660
cagaactctg actattgacc ttgctttatt ttctctcttt ttttttaaaa ttttattttt    27720
ttattcccat aggttattgg ggaacaggtg gtatttggtt acatgggtaa gttctttagt    27780
ggtgatttgt gagatcttgg tgcacctatc acccgagcag tatacacttc accctattcg    27840
tagtctttta ttcctcaccc ccttcccacc cttttcccct gagtccctag agtccattgt    27900
gtcattctta tgcctttgca tcctcatagc gtagctccca cttatgagtg agaacatatg    27960
atgtttggtt ttccatccct gagttacttc acttagaata atagtctcca gtcttatcca    28020
ggtcactgca aatgccatta attcattcct ttttatggct gagtagtatt ccatcttata    28080
aatataccac agtttcttta actactcacc gattgacgag catttgggtt ggttccacat    28140
ttttgcaatt gcaaattgtg ctgctataaa tgtgtgtgca agtatctttt tcatataatg    28200
acttttttcc tctgggtaga tacccagtag tgggattgct ggatcaaatg gtagttgtac    28260
ttttagttat ttaaggaatc tccacactgt tttccatagt ggctgtacta gtttacattc    28320
ccaccagcag tgtagaagtg ttctctgttc accatatcca tgccaacgtc tactattttt    28380 tgattttta ttgccgttct tgcaggagta aagtattgca ttgtggtttt gatttgcatt     28440
tccctgatca ttagtgatat tgaacatttt ctcatatgtt tgttggtcat ttgtatatct    28500 tcttttaaa attgtctatt catgtcctta gcccactttt tgataggatt gtttgttttt     28560
ttccttgcta atttgttgga gttccttgta gattctagat attagtcctt gccggatgc     28620 atagattgtg aagattttct cccactctgt ggggttgtctg tttacgctgc tgactgttcc    28680
tattgctgtg cagaggctct tttgtttaat taagtctcac ctatttatct ttgttttgt     28740 tgcatttgct tttgggttct tggtcatgaa gtctttacct aagccaatgt ctagaagggt    28800
ttttctgatg ttatcttcta gaattttat agtttcagca cgtagattta gttttttgat     28860
ccatcttgag ttgattttta tataaggtga gagatgagga tctagtttca ttcttctata    28920
tgtggcttac cagctatccc agcaccattt gttgaatagg gtgtcctttta cctactaatt    28980 tatgttttg tttgctttgt caaaggtcag ttggctgtaa gtatgtgggt ttctttcttg     29040
gttctctatc cccccattgg tctctgtacc tattttata ccagtaccat gctgtttgg      29100 tgtctatggc cttctagtat aaagtcaggt aatgtgattc tgcccaattt gttctttgtg    29160
cttagttttg ctttggctct gtgggttctt ttttgtttc atatgaattt taaaattgtt     29220
tttcctaatt ctgtgaagaa tgatggtggt attttgatgg gaattgcata gtttatcaac    29280
```

```
ccttggcaaa gtgtttctgc ttttcttaaa caattttttat tgtctgcttt ctccagtaga   29340
tgtgagttct atgagatgag gaacattgtt tgggtcactg acatgtattg tcagcatacc   29400
aaacagtggc tagcacatgg tgagcactca ataaatattt ggtgaaagtt gcagtgaatg   29460
aaaatggttt ctaaaatggc aatgactata gtcccagcta ctctgaaggc tgaggcagga   29520
agattgcctg agtctcaaaa gtttggggtt gtagtgcact atgattgtgc ctgtgaatag   29580
ctgctgcatt gtagcctggt caacacagtg agaacccatc tctttaaaaa aatggcaatg   29640
aaataatctt attttttactg cttttctctt taaggctgcc agtgttgtct tttctctgct   29700
gatttatcct cattggaaat tgaagataga taaaatatcc attgattatt tataggtgaa   29760
attaggcttt tggatccatg aggaatagct gagacaatct tccaggagct tctggagccg   29820
aggaaacatt ggtcactaaa ataccattta tattggcaac tgtactcttt tccgatgcta   29880
gtgtttcaat tacattgtgc atttaaaagg ctgttgcggc tacctcaaaa tataaacatg   29940
atgtgcgaca ctacttgtta gttttgaaca actgatttat aaatagactt agggtgctca   30000
agcctcctgc aagatgagca ctgcctgtgt tcttccttct gcttccttta tttcagctgt   30060
gtgtctacca acttcctcct ccttctacac taggagaaat tgcactgttt ccaatatctt   30120
taacatctgc tatcatgatg agaaaatatc ttttctggat ttgaaatacc ttcttcattc   30180 tttttttta aatggcggaa ataaattcat agtgttttga gtgcagtttt cttcctgctg   30240
ttattgctgg ctcaaaatcc aggagcattt cagtgttatt tctgagctcc atgatggag   30300 ttccattttct gttttattca aagtgttatc tccagtgtct agcacagtgc ctggcacatt   30360
ataagcctat aatgtttatc tagtggatgt agaccaatac tattaaagaa ttatcattgc   30420
aaagatttag tggcatgaaa aaatgataat gattaatgct ctactccatg ctaaggaaat   30480
gaagtgcaaa tcgttctta tttttcttcc aagtatagag aactttctga aattaaagaa   30540
gcattgatta ataagttta atatatgtta ttgatcataa taatatgtaa tcatataacc   30600
aaataagata acacaggcca tcttttgttc tttaaaaaat gacaggaaga ttagaataag   30660
agaaaaaatt agaggtcaaa acagttttct tcaaaccagt agtgtaactt actgagatat   30720
cttctgtaat ccttaaattc tgtattgatg ctaccaagat gcaactcttg agctacaact   30780
gcctcttgat aaaggatgct ggtccctgct gccagtgtaa tgtttgctca tttacagtgg   30840
aatgtacaat atagtacctg ggatggtgaa gaaggtgaag caacaaattt aaaatagctg   30900
tgggtaaacc tacagaaaca gactattctc tttcttccag attgcattat tcatttttcat   30960 atgcctgcct ttatctgctt tggaagccta tttcctaatc ttccaagatt tatcatcacc   31020
ttcatatgtc catagcatgc atttctcaga caggtaagat agaattggta tatatttggt   31080
atagcaaaaa gtcaaggttg tctttagatt atatccttgg ttttttcatgt ggtactgggg   31140 agaaagccta ctgtttcttc atctataaaa tgaaggacct gggcaagata acattctgtg   31200
aaatttcact gaactttgag ctcagcaaag tagggatgcg tgtgtgtgtg tctatttgca   31260
atgcatcaca gaccttaaat aaatacagtt gacccttgaa taacatggag gttaagagca   31320
ccaaccccct gcactgtcaa aaatccacat gtaattttttg actccccaaa aacttaacta   31380
ctaatagcct gctgttgtct ggaggccctg ctgataacac acacagttga ctaacacata   31440
ttttctatga tatgtattgt gtactatatt cttacaataa actaagctag agaaaagaaa   31500
ctgttattaa gaaaatcgta aggtaaagaa aatatattta ctatttatta aatggaagta   31560
gatcatcata aagatcttca tcctttgttg tcttcacctt gagtatgctg aagaagagga   31620
ggaaaaggat gggttggtct tgctgttcca ggggtggcag aagtggaaga aaattcacat   31680
```

```
ataagcagtc catgcagttc aaacctgtat tttaaggtca acggtatttg ttacattgca   31740
ttttgtaagt gaccttgtta atttttttca atgaaaaaaa tagtgttcca ttcaaatgcc   31800
tgtatgttta tgagaaacat ttcagaacta tgaaagttga attcaaggtt tcttgcagat   31860
tgtttgtata ctttctgtaa tgtttgtcat ataatgagaa tactaatggt cttacaactt   31920
gaaactgatt aactgattaa ctctttaagc aacttaaaaa gaaatctttt cagtgaggaa   31980
agagtattca tcagaagtat tctagtagat gacatatttt tggtaatgaa attgatatgg   32040
gcaattaaca gcttttttcca gttggctat gctgctactc tcttattata caatgatact   32100 attttcaga gcagaaagca aattagtttt attttttataa accaaatttt aaatatccct   32160
ttagagaata gaaaatatga aaagtatttt gcttctcaga cctctcaaca atataaattt   32220
tcttcttaag aggaaattta ttcttgcatg ccaacacaaa ggataaaaag tttacctatc   32280
cttagtttct aagaggaaaa tgtgcataaa atttccatct gctgtgtgcc agttaccaaa   32340
acgataagtt ccaactcaat cttggttggg tgtggtggct cacgcctgtg atcccggcac   32400
tttgggaggc cgaggtgggc agatcacgag ctcaggagtt tgagaccagc ctggccaata   32460
tggtgaaaac ccgtctctac taaaaataca aaaaaaaaa aaaacaaaac tagcccggca   32520
tggtggtgtg ctcccgtagt cccagctact tgggaggctg aggcaggaga tcgattgaa    32580 cccaggaggt ggaggttgca gtgagccaag attgcaccac tgcactccag cctgggcaaa   32640
agagggagac tctctctcaa acaaacaaaa aagactcaat cttactaaaa aactgcagag   32700
aagaatgagt cattttagtc aataaaggaa ataaagaaat tctagttttg aaaatgacat   32760
aatttgctac aagaatgcaa aggtgatgac atgaggaaaa aaggggtttg ctgatttgtt   32820
ttctctacta ctcagcaaat gcaggccagg aacccattta ttcaaatatt tattacatgg   32880
taaattaaaa catttataaa attaggctca tattcttaga attcctgtta acaaagtgac   32940
atataaacaa gattataatc taatggagat taatattggt tgagaaaaat cttgagactt   33000
ctttaagact tcagtttaat aaaatattga cttaggtaga tatatgtgag gaaatatata   33060
ttttacccat gcatgcaaaa atgatgtatg tatttcttaa aagagtaggt agcaatgact   33120
tcaaaggacc atagctgtcc ctatcaacat atatattaac aaaacaatta gaaacatgag   33180
cttagtatgc taattatatt tctacccaaa gcctcaattt gttctatagc tatactgttc   33240
atatataagt aaaattttag gggtatcaga gagagttaga aaagagcaaa tacatgtatg   33300
aatttgataa gcctatccct taatttgata gatcttaaaa gatatttat cactgcattc     33360 ttctaaagaa atgtatttgt acattgcaaa acaacccttt ttgagaagta gactatgatc   33420
acagattttc ttgccactag tatttcctaa gatttatttg aatagaaga tcgatattt     33480 tctgggatga catatggtta aaagtaaaa aacaaaacaa aacaaaaaac tctttaaaaa    33540
cacaacaagt aaaaagctga atgaattgga aaattaacga atcttcttag atctgtcaga   33600
aaaatgagat tatagggcaa accactgcat caaatattag agaagcagac aggtagatag   33660
aaagaatcac aacttagtgg ggcaaaaacc tacaaggaaa attttgtgg gaaccggtgc    33720 caggtaggaa aacatgaact gtaattgaaa aattgttcag tgtgggcggt tgttcagtgt   33780
ggcaagtctg agggtaaaaa actccaggag gactcactta cggaagggcc tgtacttttg   33840
tgagtttaac ctccaggagt gttcacagtg actactggag aaaattccct aaggggagaa   33900
gaaaaggaac catcttgaaa tatgtcagag cattttgttg gactcaagcc tgctctcaag   33960
tgaaactatt ttaccagagc ctaaactttt gggatttat aagagtgtaa cctcccaaag    34020
```

```
ggaagggaaa tacctaagtt cagcccccctt ttagctttcc acatagggaa aggaaaatat   34080
ataactctgg acaactcaaa ccatcctgtc cacgttaggg ggcctagggg aactgagaaa   34140
actggtgaag ttcatagtcc atgggtacag tttcaccaaa gagggagacc aaattataag   34200
gctacagaat gcttcccttt cccacacctt ttactatcat attactaaaa gcctatttgc   34260
agcagtttct tttactgagt atatcatgtc tgtcattcaa ccaaaaaatt ataaggcatg   34320
ctaaaaggca ggaaatgcag tttgaagaca ctgaataagc atcagaagca gagtcaaata   34380
tggcagtgac attggaatta tcagaccaga aactttataa aaaactatgg ttaatatggt   34440
gagggattaa aaaaatgaca tacaagaaca gatggataat gtaaatatag agacggaaat   34500
tttaggaaag aaccaaagag aaatgccaag tatcaagcat agtgtacaga aatgattaaa   34560
atgtctttga taggctcata agtagattga acatagccga ggaaaaaatc tttgaagtta   34620
aggatatgat aataggaact tcaaaactaa aatgcaaaga gaaaaaagac tgtgaaaaaa   34680
acagaagaga ttattcaaga actgcaggag aactacaaaa ggtataatgt acgtgcaatg   34740
ggcatactag aaaaagaaag aaaggattag atgcaatatt tgaagaaata gtgtgtgaaa   34800
atctcccccca attaatgtca gacaccaaac tacttctcca gagagctcaa agaacaccaa   34860
gcaggataaa tgtcccaaaa ctactcatgg gcatattata ttcaaacttc agaaaatcaa   34920
agattaaaaa aatatcgaaa gaatccagaa ggaaaaaaca cctatagagg agcaaaaata   34980
ataaatttta tctgacatat cctcataaac catacaaata agagagtaga gtgagacatt   35040
taagatgttg aaagaaaaat ccggcagtgt acgattctgg accttgcaaa attgtccttc   35100
agaagttaag aaataaagtc tgtcttaaag aaacaaaaat ttcaggaatt tgttgccagt   35160
ggaccaccct tgcaaaaaat gtttaaagtt ctttagagag aggtaaaatg atacaggtta   35220
gaaactcaga tccacataag gaaaataaaa ttagggatat agtagtattc cccaacttga   35280
taaagaaaat acacaaaaaa cctacagttt acatcatact taattttag aaactcaaag   35340
cttttcctgct aagatcaaga acaagacaaa ggtgtctcct cttaccactt tgtttcctac   35400
tggaagtgct acctaatgca ataagacaaa ggaaagaaaa tgaaaagcat acagattccg   35460
gaggaagaaa tcaaactgtc tttgttcacg gatgacagtt gtttatatgg aatatccaaa   35520
ggatcagaaa aaagaaaact ggaactaata aatgattatt gtaaggttac agaatacaaa   35580
cttaatataa agaaagccaa tcactttcct gtataccagc aataaacaag tgtaatttga   35640
attaaaaaca cattaccatt tacattagca ccccaagaaa tgaaatactt ttgtataaat   35700
ctaacagaat atgtacatga tctatatgaa gaaaactaca aaagtgtaat gaaaaatacc   35760
agtgaactaa ataatgaaga gatgttacat gttcattgtc aagatgtcag ttcttcccaa   35820
cttgatctat agattcagtg caatgccatt aaaaaacaca gcacgatatt ttatggatat   35880
caacaaaagg attctaaagt ttatatggag aggcaaaaga gcagaatagc caactcagta   35940
tttgaggaga acaacaaagt cagaggactg acactacctg gctttaaagc ttactataaa   36000
gctcagataa tcaatgtagt gggtactggt gaaagaatat tcaaatagac caatggaata   36060
gaataaagag cccaaacaaa cccatgtaaa tataatcaaa tgatctttga caagggagca   36120
aaggcaatac aatggagcaa agatggtctt ttcaacaaat aatgctggaa aaactacaca   36180
ttaacataca acaacaaaaa ttttttaaat ccaaattgag tgtaaacaca gatcttatac   36240
cctttgcaaa aattaacttg aatcatagac ctaaatgtaa aatgcagaac tataaaactc   36300
ccagaagata acacaggaaa aatcctagat gactttggta tggcagtggc atttttaga   36360
tacagctcca aaggcacgat acatgaagga aatgattgac aagctggact aactaaaat   36420
```

```
ttaaaacttc tgctctgtga aagacaatat taagagaatg agaagacaag ccacagatgg    36480
aaaaattatt tgcaaaagat acttctcata aaggactatt gttcacaatg tgcaaacaac    36540
tcttacaact caacagtttg aaaatgaaca actcaactta aaaatgagc aaaaaacctg     36600 aacagacaac tcaccaaaga agatacacaa gtgtcaagaa agcataggaa aagatgttaa    36660
acatcatagt cattagggta ttgaaaatta aacaacaat gagataccgc tacatacctg     36720
ttagaatggc tgaagtcaga acactgatga accaagtgc tggtgagaat gtggagcaac     36780
aggaaccttc attcattgct ggtaagaatt caaaatggca tagtcacttt ggaagacagt    36840
ttggcagttt cttacaaaat aaacatactc ttcccatatg attcagcaat agcgctcctt    36900
ggtatggact tgaaaactta tgtcctggcc gggcacagta gctcacgcct gtaattgcag    36960
cactttggga ggcccaggca ggtggatcat ttgaggtcag gagttcaaga ccagcctggt    37020
gaaatcccat ggtgaaaccc cagctctact aaagatacaa aaaagtagct gggtgtggca    37080
gtgtgcgcct gtaatctcag ctactaggga ggctgaggca ggagaatcac ttgagcccag    37140
gaggcggagg ttgcagtgag ctgagatcat gccattgcac tccagcctga gtgacagagc    37200
aaaactccat ctcaaaaaaa aaagcaaaaa caaaacaaa caaacaaaac ttatctccac     37260
ataaaaacct gcacacattg tttaacagct ttacataatt gccaaaactt gggtgcaatc    37320
aagatatcct ttaatatttg agtggataaa ctgtggtaca tccagatgta agaatattat    37380
tcagcactaa gaaatgagct atcacatcat aaaacgacat ggatgaaact taaatgcata    37440
ttataaagtg aaagaagcta atccgaaaag gctaaatact gtatgattcc aactatatga    37500
cattccggaa aagccaaaat tatggagaca gtaaaaagag cagtgttttc cagagggagg    37560
aatgtatagg caaattttta gtgcagtgaa atgaatctat gtaatactat agtggtggat    37620
ccatgtcatt atacatttgt ccaaacacgt aggatgtaac caccaatagt gaaccctaat    37680
gtaaactatg gggtttgggt atcaaaatgc atcaatgtag gtttatcagt tgtaacaaat    37740
ataccactct ggtatgggat gttgataatg gggaaggttg tgggtctgtg gggacagggg    37800
tatatgggaa ctttctactg tttactgtg aatcaatttt actgtaaagt ttattaatgt      37860 taaaaattt aatgcacatg taccctaaaa cttaaagtat aataataata aaataaattt      37920
aggcaatctg aaaaaatgtt aataaaaaag aaaataaact agttgaatgt atcagttcat    37980
tttcatactg ctataaagta ctgcctgaga ctgagtaatt tataaaggaa agagatttaa    38040
ttgactcaca gtttagcatg gctggggagg tctcaggaaa cttaacagtc atggcaggtg    38100
acttcacaaa gtggcaggaa ggagaaatga acgcagaagc aactaccaaa cacttataaa    38160
accatcagat ctcatgagaa ctcactccct atgatgagaa cagcatgggg gcaactgccc    38220
ccatgatcca attcttcca cctggtctct gccttgacac atgggtatta tggagattat      38280
ggggattata attcaagatg agatttgggt ggggacacaa agcctaacca tatcagtgat    38340
aaaactatgt ctttctttt atggggtgct atagtgtttc atttcaagtt gtcttttga      38400 cctccatttt ccaattctg gttaggaaaa ataactttgt ctcctcctta attgacccac      38460
aaccttgttt gcaatgaaga atcaacacaa atctttcatt aaaagaaata ggggaggtga    38520
tgggggatat ccatgagtgt ccatgggcat aattcagttg ccttcattca atgccaatga    38580
tactgcaaag cctacaaggc aaattcatgt acctacagac agactccatc ctttttctca    38640
aactattcaa gataaaaaat cttgtttcat tttatgtgag gattttttc accatctatc     38700 ctcaaaaaat gaaaaatatc ctcttcattt gggaaatgag tgcttataat agaaagtaat    38760
```

```
ttgtagtcag ctgttacact tagatgattt gtgtcacctc tgacctgctt tctgataatg    38820
catgacttca ttcatggctc tctaggtgac ctgtgtaccc tgacctggca taaaccacta    38880
gagtattaag tcatttcagt ggcacatgtt tgagggaaga ttgacatccc actggaagac    38940
tatctacagt gagatcctct aaagcagctg cattcctagt gaggcatgat taagtttatc    39000
ccactattag gttctggagt attacttgtc atgcccaaga ggaaagtttt tctagcatgc    39060
agagtatctg gtttttaatg gctactgagc tgaaataaaa tgtgcctact aagggttgtt    39120
catttgtctg tctcccttct ttcactgttt ttttcttgg aggttacagt agttatgcct    39180
ttctggtcag ctggctgttg acctatcata gaaatgacac tttcacatct tcaagtgtaa    39240
ggaattagat gttccagcct tcactttgtt tctcatccaa aatcaatgac aaaactttca    39300
gtattgattt ctcatggcct atgaacctga gtcaacttgg cataaaggac ttttcagaca    39360
agcttctcta aatgcagagt cagtggcttc ttttgccaa actccacttt gctcagtgat    39420
aacattaaaa tggtgatttg attcattcct agtctaaaaa tacttcctca tattccaaaa    39480
tctcagtcat taatacatgg aggaaaatac aaattattac atgcctgtgc ttctcggctg    39540
ttgtagatag ataaaatata tacaattgtg ttctataatt attgagttct tttaagtttt    39600
atcttttttt gttttaccag gaagcaaaat tatgtttatt tcagagctta tttactgcat    39660
ttagaatctc atgacactta aaaaacctt ctaaaacgta aatattctcc atgatctcca    39720
tggtcacaaa cagtatttca cgttctaatt gatattgcca ttttatcatt tttttttttt    39780
tcttggagac agtctcactc tgttgcccag gctgggatgc agaagcacga tcttgcctca    39840
ctgcaacctc cacctcctga gttcaagcga ttctcctgcc tcagcctgcc gggtagctag    39900
aattacaggc atgtgccacc acacctggct aattctgtat ttttagtaga cagggttt     39960 cacgatgttg gccagactgg tcttgaactc ctgacctcag gtgatccacc caccgcagcc    40020
tcccaaagtg ctggaattac aggcgtgagg cactgcatct ggccttttta tctttctttt    40080
aactcaaatc ctcaaatata tccctccatg tgaagttgcc ttccctaatt atgtactgtc    40140
ctagtttaat cttcattcct tgtttgcctc tataaaacca agtttaaaaa tagtctctga    40200
ttctgtaaat catcactctt atgctcattt atatttctat ctagaatatt ttaaatcctt    40260
tgtaacaaag tttctactat gcagtctacc tttctcagct acgatctata tactccttgg    40320
ccatgtcttt tgttattgtg tgtgtttgtc tttgtgtgtg tctgtatagt agtggtttgt    40380
aaattctcca tttagtcaca atatgctttt tgaggatttt cctttcctg ggaatttctt    40440 gatgattttt attttgtcat gtgatgaaga atgtatgtca aagcaccact gcagaaaatag   40500 tgctttttcta tttacttgca ctcttccatc ttagaagagc tggtgataga caaccgactc    40560
ttcttttatc ttggtttcta caacacagag gttgctaagc gactttaatc ccttttaaca    40620
caggacaatc aacaacaaat tccttctttc tttagattca gatatttcac ttagaaaatc    40680
tagcaaataa aaaatggttt aaaacttctt taaaatgtgt aattctgtac aatctcctac    40740
atctgtaacc cctgccccaa atattttta cttatgctat tcttgagca ttatgatatg     40800 cttattcata ggcaatcaac ttgtaagtag caatagtgta gccccttcta ggaaatcgaa    40860
gatgtgaaaa tccagtttaa tgtgataatg agttactttg atgaaaaata ctatgtcaca    40920
atttgttata aaaatactca tttggatttc tgattcactt atattcccct ccaaccttaa    40980
gtatgattga atttatagct ttttatacta cttctttat ttagggagga gtgtatttaa     41040
attctgttat ctcggttatt acttgaaagt tcaacctcat actttcattt ttatataatt    41100
ttaatattat gaaaatattt tatgtaattt tatgtataat tcgaaaacat ttttaaatat    41160
```

```
tgcatcttta aatttttatt tcttttatca aattttccct atcatttgtt ctctggctac    41220
aaccaaagtt aatagttaca ttttttttcca gtgacaaatg gtaatttgca aagacttgta   41280
acagttgctt aatactttt tatcccttat ttaagaatca tgcaaacaac cagagctgat    41340
aggcagcagg tgcacatgag tgtggctgtg ctgatggtta ctgaaagatt tccaaggtag   41400
ctagtaattc tgctacccta agccactata gctccttccc cattactccc tgggtctacc   41460
caccatcctg cagctagaat aataaatggc atgtaggttc ctctaggatc ctcctccagc   41520
actatgtctc atgcctggac atatgagctg ttaaatattt tgattatcac tcctgtgtgg   41580
taagggagac gtctacttgt cgtaacttga tgtttactaa actactttta agattacctt   41640
atgataaaag tagacacttg caattttgca gaatgcatag tttgttttta acaaaccagg   41700
taaacataac tgcagagttt tcctatacgt tttgaaatct ttaaaaaagt atttttatt    41760 tgcctttcta ttagaaatag attagataaa aatttccttg tttcaatttt tagaatgaac   41820
attagagaat attgttactg aaggaatttt tttaaaaata gtgactgatc aaatgtcagc   41880
agctttatac tatagtgtaa aatttttattt tgtagtttgc catcccatta agcattagaa   41940
tttttataat tgatcctttg atgtttatat tcatgatatt aatgtaatgt ctttaaacct   42000
tagctcatat aggtcatatg acttaaagca tccttagatg aagatatttg ggctataaat   42060
aatttatgac ataagtgatt taaaaattca ttctttccat ccattttgaa gaaattgtaa   42120
ggtagggttc atgtatacct aatacttatc cccccaaaat acgaaaaata aaatcatttt   42180
taaaatatct gggttaatgc tatagattgg aagcagtttt taaaaagcac ttaaagtcta   42240
ccagtttatt gatcctcaat ctgtggctgt tttaaatgga tgcaattagc agttcagtct   42300
aagagaacca tggtagtaga ctcattactc cccagaaacc attacatcat tttgtaatat   42360
taaattacta aatataagga atagaatata tattgtaaaa attgctttgg aatcaataat   42420
aagtattgtg gctatcaatt atagtttatat attacaatgt aagggatatc cttttataaa   42480
cttaatatca cacaagtaga cttagaataa ttccattaat ataattttgc ttgtgttttt   42540
atacctattc atttcaataa ctcttttttcc tatatatatt ttttatctca aattcgatag   42600
tatctaaatc atggaatcat aaaaccttaa agctgggttg gaacagaaat aatacaattt   42660
aacatcttat aggctctcta gtcctcagtt tccctaagtg atcggctcaa gatcatgaat   42720
ttatggagga ttagagtcag aattagaacc caagattaat ttatactttg ttatctcttc   42780
tacagcctac cccctttagtt tgcctgtggg tttatggaag ttacaggaga gacattctga   42840
gattcagcta aaaacctagc tcccaataga attattgccc tgtagtcagc cgcgcaaata   42900
caatcacaaa tacctgaagt tccttgtgtg aagaaaaaga aaatgactat taaagcatca   42960
aaatcaatgc aagttacctt tctttgcccc tttcttcccc tttcactcct ttcttctcct   43020 atacttacttg aaatttctag cggggatctc taaaatgcct ggatgttagg aatggtaagt  43080
ctattgtaga gaattatatt ttctatttta gtggatgaaa aataaaccat accottaaga   43140 ggcttttcaa agttaagatt ttgagcacat ccttcattgg cccagtctct gaccagtgag   43200
gtcaagtatt agccagtgtc agaatgtcgt gaaaagtttg tgtttcagat gcagaatttt   43260
tttttgcatt ttctgtgtga tgtttatagg gtattttctt ctgaaatgtt ttccatcttg   43320 gttttttaaaa atatctatta ttttaaaaaa tattccctca taacttcttt ttattttcgg   43380
aaactatata aattgatctg ataatctata cacaatgcct tgtgaattta tacctgtacc   43440
tctcatgttc cagtgtttgg ttcttaaata atcactttgt ataatggaaa tactatgtta   43500
```

```
aattgtttat aactggtggt tgatatttca gccttgtttg gctatcgtag ttatataaag   43560
actgttaatt agaaacaacc tcatatggtg tatgcttgtt tttatcttca tggaatttgt   43620
tctgcaaaca ctgagttctt tactgggagt caccactttg tctatgttag gaggagcagg   43680
aagtgaatac atttaaggtc tttaattttc ttcttaaaac tttgactact gtagtggttt   43740
tttaaagcat taacaggaga atagccatca ctgccaagta gctgacattc tgaaatagca   43800
cttcccttta ggcactgtac agttggaatc atttacttgc agagaggtgt gtgtgtgtgt   43860
gtgtgtattt atgtgtgtac tcatgtgtat aagaatagga gaaacacttt gtgggcatat   43920
cctgctgagg tgagtaacgt gctgattagt gaactccagt ctcatcccat ttaaacctgg   43980
aggagaacca catcaagcac agaagcagcc aaagcagcat ttcaacagga aggaaacatc   44040
tattactggg gctttgaaga aacatgccat gaaggtgtac taatatcaca agggaaggg    44100 aaggactaaa ttcagcatga taaacaaagt ccctttttg taacgaaagt gtttgatgat    44160
gtttgatcaa tggtggatct atctcttgaa aggaaaatgc atttaaaccc caaatggagg   44220
attcttatat aaggtgccta gcttgtaatg atatattcat gtttataggt agagtgactg   44280 gttttagag aagaggtttt ttttttcct tcattttga acgaaaactt gtctgtctct      44340
aggctttgaa atgtagaatt atttaccttt ccccaaaatg aaatgtttca ctgaatctcc   44400
tacaagcttg tggaggccat gaagcatgtt gaataagagc acaggctctg gaggccctgc   44460
cacccacaaa gggtgtgcta aggtaaacaa ctgatagtat tttgaaaatt agatgactta   44520
gaatccattc aataaatttt agctattttt attgtcttt ttttctaaat ctatttggaa    44580
aatattgcag ataaagtaga taatacccttt ctaaaacaca gtgagaccag cgcagtggc   44640 tcatgcctgt aatcccagca ctttcggagg ccgaggtatg cggatcacga ggtcaggaga   44700
tcgagaccat cctggctaac acggtgaaat cccgtctcta ctaaaaatac aaaaattagc   44760
caggcgtggg ggcatgcgcc tgtaatccca gctactcagg aggctgaggc aggagaatgg   44820
cgtgaaccgg ggaggcggag cttgcagtga gccaagatcg caccactgca ctccagcctg   44880
ggctacagag caagactctg tctctaaaaa ataaaaaata aaatagaac agtgaatagt    44940 ttataaagat aaaatagaat aggcttcaat ttagggaaca aaggaaaata tgtttaggaa   45000
tgatattatg ctcaaaatga ttgcaacttt gatggtgaag tgtattttat tcaattaaaa   45060
atgtagatat ggctgggcgt ggtggctcac acctgtaatc ccagcacttt ggaaggttga   45120
cgcaggtgga tcacttgagg ttaggagttt gagacctgcc tgggcaacat agtgagacct   45180
catctctaca aaaataaac aaaaaatgtg ctgggtgtgg tggtacatgc ctgtagtcct    45240
agccacttgg gagactgaga tggaaggata gcttgagtct gggaggtcag tgctgcagtg   45300
agccgagatc gtgccactgc acttgagcct gggtgacaga gcaagaccct gtctcaagaa   45360
aacaaacaaa aaaacaaaaa caacagtaga tatgtgtgtg ggaatgagaa catttaaatg   45420
tgctcatcgg cttagatttt tcttttaaccc ccttcatggc ccttatctta acctctgtct   45480
tcagcactac ccttcatatg tttgttccgt tttatcttct aagtgatttt tttataactc   45540
tcaatgtatc atggcagaag gaaaactcag tgtataagct gactgtattt tgcatttct   45600 tttttttttt tttttttttg agatggagtc tcactctgtc acccaggctg gagtgcagtg   45660
gtgcgatctc agcttattgc aacctccgcc tcctggaggc gattctcccg cctcagcctc   45720
cccagtagct gggactacag gcttgcacca ccatgcctgg ataattttta tattttagt    45780 agagacgggg tttcatcatg ttgtctaggc aggtctcaaa ctcctgacct caagtgatcc   45840
acccaccttg gcctcccaaa gtgctgggat tgcaggcatg agccaccgcg gcctggcttc   45900
```

```
atgatccaaa atagcatcat taagcttctc tttcaaaaca tgtatataag cctgtgagtc   45960
atcactgtat ttatcagaat attatcatat tggagacttt gcaaagctga acaaagccag   46020
aattattggc tactgaggaa ctatattcta gcaagagact attctatttg ttggggatca   46080 cctctttta ctaaggggga ctgttttggg catataaaac tagaattcat ggtttctcct    46140
tgatagtttg ccagcttgat tcccagtcaa ccagataact gctggtagtg acactcatgt   46200
cctccaggac tcccaatctt gtgccagctc agagagggaa atcccctag aactgctcac    46260 accattccaa gaaccacaag caccaccttg gtatagttaa aaatgtgata ccaactcaaa   46320
ttctgataaa aacaagttct ataaagctta ataaagttat atttttact ttttaagttt    46380 tgttttacta ttttaaacag aaaacagaag gtaaaaactc ctctgccttc ctcagtatt    46440 ggtttgtcag ttgctgaact cagatttaag agtctaatca tatacaggca ataaccctct   46500
tctaatctta ataatgtttc tttgatcatt tctttaaaaa gaaaaatgaa atagcctatt   46560
gactccaacc ctgacctcct gtacttcacc tgcctgatga atatttattt ggaatacata   46620
agttttttca aatgcatcat gtcaagaatt tgtcatttca gattcctttc tagaattatc   46680
tatttatctc attagtagca tcattctttc agacaaccaa actcaaaagc tttatcacta   46740
taattgaatt tcttttttct tcttacattt aaaatgttac taaatgccat tcatttcttt   46800
atcagtaata tttctgtttg atcattttat ttcatttatt ctgccaccct ctcattccaa   46860
ctattgctta tacttgagta ctgcaataag ccaatatctt gcatatgatt atttataaca   46920
cctaaatctt ctaccacttc acactcactg ggatggatat aattttttaaa acatacaata   46980 acaggtgtta gtgcggatat ggaaaaattg gaaccctgac acattgctag tggaatgtaa   47040
aaaggtgcag ccactttgca aaacagtttg gcagttcatc aaaagattaa gcatggaact   47100
accataagac ccagtagttt cgctcttagg gattccactc tcaagagaat tgaaaacata   47160
tgcccataca aaaacttata aacattgtat atccatgttt gttgcagcat tattcacaat   47220
agcctaaagg tagaagcaac ccaaatgcct acagatggat gaatggataa acagaatgtg   47280
gtatagacat acaatggact attattcaac cttaaagagg aagaaaattc tgacacatgc   47340
tagaaaataa atggatcttg tatacattct actaagtgga ataagccaat cacacaaaga   47400
aaaatattat gattccactt acatgaggta cttagaatag tcaaattaat agaggcatac   47460
agtagaataa tgattgccag gggctgggag gaggagcaaa tgggaagtta ttgtttaatg   47520
agtatagaat ttctgtttag gaagatgaaa aagttctgga gatgggtggc agtgatggtt   47580
gcacagcaat gtgaatgtac ttaatgccac agaatagtat acttaaatat ggtttgaatg   47640
gcaaactttg ttacatacat tttatcacaa ttaaaaagtt tgaaatgaat atccaaagaa   47700
gcattattta tgaggctaaa agtggaagta acccaaaagt tcatcattga tagctaaagg   47760
aaacatggca tatcaaaaca gtagaatatt agtcatacaa aggaataaag tacagacaca   47820
tgctgcaata cagatgcacc ttaaaaacat tacactaagt gaaagaaacc agacgtaaaa   47880
ggccaaattt tgtatggttt tatatatata aagtcgttca aaataggaaa acccataaag   47940
actgaaagtt gattagtggt caccaaggcc cggggagga atgaatgaaa actggctcct    48000
aatgggtact gggttttttg gggcgagggg gacagagtga tgaaaatatt gtagaatttg   48060
atagtaatga taggtgagag tggcataatt ttttttaata tactaaaacc cactgactca   48120
tatactttac aaggatgtat tttatggtat gtgaattata tctcaaaaca cccctttaaat   48180 tttaacgtat ggcttttatg atgccatgtt tctaaagaag caacgtgtcc cagtctcagc   48240
```

-continued

| | |
|---|---|
| ttactatttc taggcatgtg actttgagaa aaaattaaga gacctcccctt cttactctgt | 48300 |
| aaaatgggaa taataataat gatgataatg ataataataa tgatcttacc agattttttt | 48360 |
| gagtgttaaa tgaggtaaca tatgtagtgc atctagcata gtgtctggca tttaccaaga | 48420 |
| accccgggaa cctgagcttc aactgcttct gatactattc cagatactat ttcaggatat | 48480 |
| tccaatactg tttccatata ttcaggacaa tggaccaact cctttagcca ttttatcaaa | 48540 |
| actctttaga ttctgtttca aatcggtctt tccaaagtct tcttgtgctc ctttgtagac | 48600 |
| actcttcagt cagagagagc ttttttaatct cctccaattt gctgcagctg tatctgtgcc | 48660 |
| tcaaaacaac gctttctccc cattcctctt ttctctctgc ccttggaact ctgtggactt | 48720 |
| ctctcatgtt tttaacctac tcccttttat cagtgcatgt catctccact tatttgtagc | 48780 |
| acccaatatt tttactacat ctttgaccaa ttaagtctta cttgggttat gttttttaaag | 48840 |
| taggtatctt attaggtggt ccttttaaag tatatgtcca gtctctccag ctaaattaaa | 48900 |
| acccttgagc acagagacca catgttataa tgttttacct tttccatagc acttagcatg | 48960 |
| ttaccttgac atggcatata ctgaatgaat gcttgctatt tatgagttta gttagtgcca | 49020 |
| catctcatga agtacaggga cttaatgatt ctcaatcctg acttcatctt acagtcacct | 49080 |
| ggagaataaa gtttcctctt agctcaacaa gtcagaatct ctgagcaaaa tcctcaactt | 49140 |
| cttacctagg tgatactctt gtaagccaca ctgtgaacca ctggattcaa cagatgaagt | 49200 |
| aatataagcc actggctctt aagcctcatt gattattgcg gtgaagatgt gaagactaaa | 49260 |
| gatgctttgg gcatggcaaa gtgttctaca gatattagaa ttgttattat ggtacatttg | 49320 |
| agagtgtcat tgctttgaga aagattctct aagttttta acagccacac tgtaatggaa | 49380 |
| atatccaatt ataggtatcc aaaacctttt aaactcttta tatcaggtgt ataccctg | 49440 |
| ttccttttg ctaacttaaa aatgttcaaa ctctgtcttc tctaggctgg caaacattca | 49500 |
| gcagcacacc ctctcaagat tgtttacttg cctttgctcc tgttgagtta caacgcttgg | 49560 |
| aagcaggaga tgggctcagc agcagccaat aggacatgat ccaggaagag cagtaaggga | 49620 |
| ctgagctgct ggtaagacag tggagacagt tgacacttgt ttgtcaagta tgaatttatt | 49680 |
| cctaatgtaa tggtaatctc tctcccaaac ttcaacttca agttaccctg caccctctca | 49740 |
| aatactttc tttattgtct atgcttagga cacatggatt agattgttaa gatttgtgaa | 49800 |
| tttactaaag ttgtgtactg acttatgtat agctgtattt ttctggagaa agatagattt | 49860 |
| ttatcaattc tcaatgtcta tggagttttt aaaagaggt aaggattatt caaatgtaac | 49920 |
| tataaacata agaaaatgtg atatctataa ccagttgtta gagtatttat cgcctccatt | 49980 |
| ttgcttcact tgtagccact tcgtctcaat cttgttaagg accaaataaa tggtatttgt | 50040 |
| ggttacttgc tgatctgaaa agtgagtacc tcctgcacct ggctagtcag tcttgtgaca | 50100 |
| atttggtgcc atagaactag cagagaacta aattatggaa tggcagatct caggagcagc | 50160 |
| tatgtgattt tacatacggt ttgttttttaa tggatagaga cagagtctgg ctatgttgcc | 50220 |
| caggctgctc tgaaactcct gggttcaagc catcatcctg ccttagcctc ttaaggagct | 50280 |
| gggattacag gtgcatgccc ccaggcccag ttcatatgat tttctgaaaa tacaaaagaa | 50340 |
| agagggagat acaaaatact ttttttaatca tgttcttata attatcttaa taaaaatcaa | 50400 |
| tttgctctga atgccatgac ctgctgagtg tcccaaccta agggttgtca gaccattttc | 50460 |
| tcatatatgc atgtatagaa gtagggaact aatatatttt tgtctaaaat gtttaagatg | 50520 |
| aagatgagaa tgaattctac aatatataat tttgcctgaa ctataagaa cagttaaaat | 50580 |
| tatagagaca ttgcaggaga gactctggat tagatagaaa aaaggaagaa ttaggctttt | 50640 |

```
tttttgtcta taatcctttt agtaggtaat tcagcttcag tttcactaaa tcttgtttat   50700
gcattcagca taacaaatct tctaataagc ctgtatagct ctaatctctg ccttactgca   50760
gacacctgag gatataagta tccactctgc cacttgatac ttctcagaga ctgttctggt   50820
gctgagaaat cctttccagt gtgtcctcag ttgaactccc atgattcctg gatgttgcca   50880
ttttcaagac acagggcaag cgcatctgtc tagattacct ctctaccttg ggaattttaa   50940
gtcactctgt gagggaaaga gaactcagta tagtagtaac tctcagaatg aaaattttcc   51000
ccttgcatgt taatattttt agagtaatca ttgtcactga aaatagactt cctctttccc   51060
ctctcatgct ggaaaatctt aggtaattat gaataaagca ttctttactt ttcccctcct   51120
cccttgatga ttgctttacc tcactctgtg agaactgtga ctactcattc tgctcttgtc   51180
ttttacatga gaactgagag cgcatttttta agatggaatt ttcctcctta atgaagtcat   51240
aacattagtc agaagatttt ctcttcttga acgttaagcc tgggtaagga ataaagtgca   51300
gaagtttatg gaaaattata agataactta aaaaaaaac gaagacaaca aattaaaata   51360
ttagccattg agggaaaagg ttttacaggt agctctctga ggagttcttc cctcatatct   51420
cctcaaaaat cttgttttgc atttaatttt ttacagttgg ataagctcag cccttgacat   51480
attttcaata gcaaataagc ctagagttta tttttagtac atttattagg aatgtgttct   51540
tgggaaaatt atttaacctc tgtaagccct gctttaaatg gcaaagaaga aagtaggtaa   51600
taatagataa taacaggatt attttatgca ttacctgtac attgcccaac atatagtaag   51660
ttctcaattt tatattggta tttgttttat tattaaccac ttttattaat gttgctttta   51720
gttttttgaaa tatgaattca ttcaaaaata tttcttgagc acctgccaaa taccaggcac   51780
tcttctagga actagagtgg cattaatgag taagaggcaa aaatctcttc ccttgttgag   51840
cttagaatcc attagagtaa gagacagaca catacaaaat aaaatgtata atatagtaaa   51900
taccaagaag tgctaagttt taaaaatgta aagcagaaaa aggaaattga gtggcagggt   51960
taggtagtaa ttgaagatat agtagtcaag taaggcagct tcaagagaag attatgtctt   52020
aaataaaaat ctgataaaga tataaaaaca agccatgaag ttatctgaag gaattgcagg   52080
tagtggagaa cagccaaaag acctggagta gtaaaaggtt ttatgcagag tgatttaaaa   52140
agaatcacag tatcttatac atcagtaaat atttacacat acacttaagt aagtgatatg   52200
gacaagaact ttggaagttg aatagcaagg tccatctgga ctataacaga ggaggcttca   52260
caaaggaagg tgacagggca tggcctggat cctgaaggac aggaagaatt gggatcgata   52320
acaaagaatg acatcccagt ggagagaagt ggaggggaaa cagcatgaaa tggagtgaaa   52380
taagaatgtt ggcctttagg gcaggaatgg gccaggcaga gggcaagtgg gaagcaggaa   52440
aaaggcgacc ttgtataaag ttcatgttgg caaatagaga gaagatggga aagcagggta   52500
aggccaaatt tagtaaaatc ctaaagtcaa gctaaagatt attgcatgct atcctgaaaa   52560
tattggggaa taattagagc agatgagtag aaaggtgaat tcttgtattt agctatatca   52620
ttatttttac aaatttaaac aaataaggaa atggaggcag tagttggagt aatttaggag   52680
ataaattgaa aatggatttt gttaagagag aagggaagat agattttata tattttaagg   52740
aaaaatcatg aggatttatt tgctgactgc acgtaagaga taaagagag gagtcaaaga   52800
tttctctaaa attttcaaaa tgattaatta cgtgttggta ttaaaagaaa tagggaagtt   52860
gggacatatg agtttgaatt cagcatgagt cagttaagac aatcagatgc agatattctt   52920
aaggcaacta aagttcattt gatatttgtc atataggctg aattaagttt ctaagagctg   52980
```

```
tttttactat gcattaaatc cgtgtaatac taacatagta caaaagttgt ttgctatcca    53040
aattttgtat ttttataata agttggagag acagagaatc aaaaaattat tgatttggaa    53100
ccattagaca tcagctagtc caattagttc attttgtgga aggaaaaagg atacccagag    53160
atgttacatg actttatagc catgcctcta gctagtatct aacttggtct agcccaggtc    53220
tccatactga gactctcctc ctgctaataa aaaataata aaaagtatt agtggtttgt    53280 attttgctgg cttgcttgtg gagaatagga ttagaaggtt tgacttgcct gttagcactc    53340
tcttgtagcc attttctaa ttaacataca cattttaccc tttctcatga aacagatcta    53400
acttgtttag aagcttcagt cttcttgatt taattaatca cttctcccca cctttagtca    53460
ttgttgaagt ttcctgattt acaatgttat cttttatct tttcagtagt ataaggagga    53520
atgatatttc tactgttgta ctattttct gtttatcttt cagaagaaaa atagcttttc    53580
ttattggccc aaaaaccat caccctacag gaaataaatc acactctttg cttgattttc    53640
ctgatctggc tactgatttc tcttcaaatt taagccaata cttagacttt aagacttcat    53700
tgttacttcc ttacaggtca ttcttatgaa ctaaaatcca tagtcattgt tctagcaagc    53760
ctgagcagtt tattctttga gtcacaggat tataaaagaa aaaatagacc ttagagatca    53820
taatacagtg ctcttcaaac tgtactcttc aattttcta ctacttatca gttgtttttt    53880
attctaataa aatataatta cctagcaagt gagcagacat gtatttacag tagctttaca    53940
attctttata cacttcttta ctctctccat tacacatgcc acatggtatg atacaagtca    54000
taactcaact atgtgaaagc aaaaccactc ttatacatgg tgtcttgcat atatattaag    54060
gcccagagtg gtatcagtag tctctgtgtc ccaagagact gaattaaaca agactgttga    54120
ccttcttgtg gcatttatct gacaaccttg gcaatccta aattcacaaa tagctgtata    54180
gcattttttg catttaatgc atatccacat atgatgtgtc ctttgattt agaacaagta    54240 aagcatgcta aaatagactg caccttatga aagtcatttt cactattctt gtgtttcagt    54300
ttcctcatca aaaggtgaaa tatcagctgc ctctgttgat ctcaggatct tttaagtaga    54360
aatggaagag tcttagtgaa aacagtttgt attctgaaag aaaattgcaa tgtaaataca    54420
ggcactaaaa acgtttattc atcttttacag atgttaatct gaccagacat ttttctcaaa    54480
atgtgaaaat agtatggatt ttcttagctc atttaatatt gaaagactag aaaaacaagt    54540
aatgatgttc tagaagaatc tatgatcata taattacagt tgtccttcag tatctgtggg    54600
agattggttc caggaccccc catggatatc aaaatctgtg gatcctcaag tctcttatat    54660
aaaatagtgc agtatttgca catgatttac atatacccctc ccatatactt cgaatcatct    54720
ctcgattatt tataatacta caatgtccat gctatgtaag tagttattac actgtattgt    54780
ttagggaata gtgacaagaa aattaatctg tacatgttca ttacaaacac agcaatccat    54840
tttttttctg agtattttga tctgtgattg attgaatcca cagatgctgg aatccatgaa    54900
tacccatggg gggctgacta taatgttgtc tatgtgcgta gcaatttttgt aattctcaac    54960 caaggacacg tatagtcctt gaatcttggt aggagtcttg gggacttttc ttaaaatatt    55020
ttgaccatct tctcaagatc ttgactccta cccccacttg tacacgtgca catacttgtg    55080
cacactcaca cacaataccc ttccttaagt cctgctcacc agcttgcttc ctattgcatt    55140
gagagcattc aacctgtaga ccaagaactt ctaccatatt tttccacctc taccccaaaa    55200
cacagtttag acatatccat tcttttcatt cttcagagtc atctcaccac ttccataaat    55260
tatttcctaa ttgttccctc tgcctctgtt cttttttttt tttctgatga tcagttcaaa    55320
gtacctctgt atgcccattc ttaagtgcaa atctgaccat ctataccct tcttaatatc    55380
```

```
ctttctttta tggatacccca tttcagactt tattaaagga gtggaagctt ccccctcccc   55440
acctcaccac ttgaagtttt tgcaattaga atggagttta tttggttaat gcaaaaatag   55500
atgtgatgta gaattcttgg ggacacctac ttatcccctt ttcagagtgg ccctgaatag   55560
ctctgtgaac ccaggaatct gaagaactca gtacagaaaa ccatcagcct acagaaagta   55620
gatcaaactc tatgcttgat attcctgatc tggctcctgg ttactcttca aattcctcct   55680
tactatattg tcccttcaga tttgtaaatc tttaccgtga catcgtattt tacacactga   55740
acctttgtac cgctgttcct ctcctgatga acttcccttt tctcttaact acacagctca   55800
gatttctcat aagggaagct tcatatttgt tgtggcactg ttgttcctca aacatcctac   55860
ttactgtagt catttgttta tgcttgtctc ctttgcagat tctgaaattc ctagggcaaa   55920
ggctgcatct tgtcttctta ttactaatat tttacacagt atctggttac atagtaggca   55980
ttcaatcata caatttaaaa gaagaggttg actttgtgat cttttcata tgttttattt   56040 ccctctcccc ctactggcaa cttcttccta cttcttaaaa tagatacagc acttgcccac   56100
taagtggagg gaagaggtgt gggagtcgag tagttggaac ttcaagtgtc aaaacatgat   56160
aatctcattt gcaaagttac attatatcgg agcttgaacc tcagagatac ttaattataa   56220
gcaacacttg tggaacattt gatacctaca ttttttttcac taaagtatcc tatcaaaatt   56280
aaatgtgttg cagttgagat ttgtgaggtt ttagctattt agagacttta gggatatgtt   56340
tagtgttcta attctaatag tattgatgaa tataaatgtt tcactgtaga aagagaagtt   56400
tgagagctgt tgtgaatgat atttgatgtc tattaggtga taatttctga tgactaaaca   56460
tgctcaagac cttagtgaga aatacatgaa tacagaaaat attttgaaaa ttatgagaag   56520
tttatcattg attatagatt ttcttatcca gcagttttg gttgtgttct gtttttcact   56580
gtcagagaag cagaaagtgg tcagtggact ttagaatgta ggctcttgta ggaggccata   56640
tgtttgagag tgctgtccag gtgctttgtg atgtggctga aatggatgc aggcttgcag   56700 ggaaaaacta atactgtaga tctctagaga gcattttagg aaagacttct aagctttagg   56760
ttccctgacc aaagagtaaa aagtgattct taatatccat agctatagag gaaagtaaat   56820
acacttccca catcaaatgt agaattaaat atttaggcat ttcaagtgta tttcatttag   56880
aacaaaataa aatcatatat tcactaatga aatataaaac cagatggtct ctgaaaggtt   56940 tttccccttta ctcactttca gagtaaggca aggaagagta gttttgtttt ttaatttata   57000
ttttaattgt ccctttctgt tttttccaaaa gttttatttt ttgaaagtga gtcaccttttt   57060 agacatttga aaaattagaa ttactatgat gtttatttta ttagtaagtc ttcctagagt   57120
agcaacgtag aaaagcatct ctgaatgcct acatagtaag tatttaataa atgtttttttg   57180 ggccaggtga ggtagctcac tcctgtaatc ccagcaattt gggaggccga ggcgggtgga   57240
tcacctgagg tcaagagttt gagaccagcc tgaccagtat ggtgaaaccc catctctact   57300
aaaaatgcaa aattagctgg gggtggtggt gcatgcctat aataccagct actcgggagg   57360
ctgaggcagg ggaatcgctt gaactcagga ggtggaggtt gcagtgagcc gagatcgtgc   57420
cgttgcactc cagcctgagc aacaagagtg aaactctgtc tcaataaata aataaataaa   57480
taaaatacat aaataaatgc ttttttgattt aacgaaggtg tcattgtcct atgaaaagga   57540
aaactatcaa aatatatttt ttaaaactta gcttttgata atgatatgga agatatttct   57600
cttaattaac ctaagtcaga aactaaaata tgttataaaa tgctaacatc aaatatttga   57660
gaccagttaa aggagacaga aggaagttat ggagaaagaa gcagtagcca gaaaataagg   57720
```

```
gcaagaaaat gttttctaaa tttatgagaa tcagaatgtt tacaaaattg ctattattat    57780
catctggaaa aaatatgcct tgtaggctga aaaaatgaac attcccttc cataccatgc     57840 aggaaccttc tttactgcat tcctaagagg actagtctag cacctaattg gatacttgtg    57900
gtaatatttg ggaactcact gatctggtac atcagtgtgg gagtcgagta gtcagaactt    57960
caagtgtcaa acatgatag tctcatttgc gaagttacac tatattagag cttgaacctc     58020
agagatactt aattataatt aacacttgca gaacatttga tacttacatt tttttttcac    58080
taaagtgtcc taccaaaatt aaatgtgttg cagttgagag ttgtgaggtt ttagctattt    58140
ggaaacttta gggatatgtt tagtgttcta attccaatag tattgatgaa cataaatgtt    58200
ttactgtaga aagagaagtt tgagagcaag ttgagcaaga atctgtcact ctaggtcttc    58260
tactctttat taaagaatgt tggattcatt tataacttac tggtccctta aatattaaag    58320
tttggtgttt ggtatcttaa acatgattac atccttatag ggctctcttc taattgcctg    58380
gatactgcac atctattaat acagtctcaa agcacacttg cttttttgat agtaagagcg    58440
tacgatttaa tcacattgaa gttagtccgc aaaggttttt gtcttttttt caggcaagca    58500
gctgatgaat gaatctctac tatccttcac tttgtgactg tgattttcta aataaatgtt    58560
ggagatttta acttacaatt tattaatttc catcttgttt cttcaagtcc ctcctttaag    58620
gaaatttatg gaaatctttt tccataccat caagtggctt atttcttttt aactttttc     58680 cttaagttca ggagtacacg tgcaggtttg ttgcataggc aaccttgggt catgggagtt    58740
tgttgtacag gttatttcat cacccaggta ttaagcctag tacccattag ttatttttcc    58800
tgatcctctc cctcctccca ccctccaccc tctgataggc cccggtgtgt gttgttcccc    58860
tctgtgtcca tatgtcctca tcatttagct cccacttata agtgagaaca tgcagtattt    58920
ggttttctgt tccatgtta gtttgctatg gataatggcc tccagctcca tccatgtcca     58980
tgcaaaaaac atgatcttat tctcttatat ggctgcatgt tattccatgg tgtatatata    59040
acacagtttt tttttatcca gtctattatt ggtgggcatt taggttgatt ccatgtcttt    59100
gctattgtga ataggactgc agtgaaaata tgtgtgcatg tgtctttata atagaataat    59160
ttttttttcc tttggtatat acccagtagt ggggttgctg ggttgaatag tatttctgtc    59220
ttgaggtctt tgaggaatcg ctacactgtc ttccacaatg gttgaactaa tttacattcc    59280
caccaatagc atataagtgt tcctttttct ccgcaacctc actaacgtgt tattttttga    59340 cttttttaata atagccgtcc tgactggtgt gagatggtat ctcattgtgg ttttgatttg    59400
catttctcta atgatcagtg atgttgagct ttatttcata tgtttgttgg ccgcatgtat    59460
gtcttctttt gtaaagtgtc tgttcatgtc ctttgcccac ttttttcaatg gggatgtttg    59520 tttgtttgtt tgttttttcct gtaaatttaa gatccttata gatgctggat actattgtca    59580
gatacataaa ttgcaaaatt tttctcccat tctgtaggtt gtctgttttc tctgttgata    59640 gtttatttg ctatgaagaa tgtctttagt ttaattagat cccatttgtg aattttttgct    59700 atgaactgga tctgatataa gcatatgttt aattttaact cccaggtcac actgtttttt    59760
tttgtttgtt ttgttttttgt ttttgttttt gttttttgttt tttggagat ggagtctcac    59820 gctgtcacca gtctggagtg tggtgataca atcttggctc attgcaacct ccacattccg    59880
ggttcaagca attcttctgc ctcagcctcc tgagtagctg ggactacagg cacacaccac    59940
catgcccagc taattttttgt attttttagta aagatggggt ttcaccatgt tggccaggat    60000
ggtctctatc tcttgacttc atgatctgcc cgcctcagcc tcccaaagtg ctgggattac    60060
aggcttgagc caccacacct ggccccaggt catactttta atcaaaatga gaaaaaagat    60120
```

```
tgacttcact ggagtgctta tgtcttgttt tatattcaag ttttaaattt atgttcttga    60180
gattattaca tcttgagtta cttgataata ccacggttga atccatgtt gttgaatcct    60240 tcaacccctt gaggactgag aattccctt aattatctgt ctgaatcatt aaatacttgt    60300
aaatcaagag ttcaatttag aaatgttata cttgatacat tttttaaagc tggataaatt    60360
aacctattaa acaaaattat ctcttcttca aaaaaaggc atcacttccc ccacaaatgt    60420
gtaatttagg aattgttttc tattggagtg gttcacgctt atatatttta gttgctctaa    60480
tgcaaggtgt ttcctaaaaa gtttaaggaa agtataactt tattttcatg tatgatagta    60540
aataatacaa taggggtgc atttgtgcta tgcttgtttt tgttcccatt tcagtgctca    60600
attactgtag cttctaataa ataaaattat cagttgctaa catttaaatc aaacagttcc    60660
acaagtggaa gtattgctta tttgtgagag ttgtgttttt ttaaacttaa ccttactgag    60720
gggttttaag gactgctaat tatagattgt actaagcaaa gtataaagta atagaaggtt    60780
accaagttga ggctagaatt caattagtgc caatacagtt aaaatggtat cattaacaga    60840
acatcttcat ccaggacctt tttttttttt ttttttttt ttttcagaca gggtttcact    60900
cctgttgccc agactgcggt gcagtggcct gattgaggct cactgcagcc tcaacttccc    60960
aggctcaggt gatcctccca cctcagcttc cagagtagct gagaccacag gggcatgcca    61020
ccacccctgg ctaattttt gtattttttg tagagacagg gttttgccat gttgcccagg    61080
ctgttcgcaa actcctggcc tcaagcaatc cacctgcctc ggcttcccaa agtgctggaa    61140
ttatgggaat gagctgccac acccagcccc tccggaatct ttagattacc aacttctgtc    61200
ttccaggttt ttatgtcctt ggaaatttat gcatatttt agaggtaaga cccatcctca    61260
tcttcttcct aatccttgac atattgtgaa cacagatata tatacaatta agtagttccc    61320
tgagttacaa atatacttaa atatacttta acttattata gaaggcttac aaaaactgtg    61380
gataaataac atatatttat cttagttaat gaataactga tgctgaaaat aatgtgaatg    61440
tcaaattagt tctctttttt tctagccctc acctttgaaa agcctgagcc tctgagatgt    61500
gagatgactg ctgtaaagtg aagcagcgaa tttctagagg ctgggttcac gcttcaggtc    61560
ctctaaatcc taggtcgctt cccactacta catactaccc taaaaaatct gtaattcgca    61620
aatttatttt ttgatctttt tcataactta ttaaatttt attgaacaaa tacaggaaac    61680
agttttaaat tactcattgc tcttgaatac attggtgatt attttcttc tctgaaattc    61740 tgttttcctt aaaggcagtc atttttggt ctcttctaaa tgacacttag tatttttagt    61800
aacatcataa cttcagtggc cacagtgagc cctcattttg caacatatgc ctacttttca    61860
tatctggctt gcctttatt atttataatt taatgaaaag aaagtaccac tctttccata    61920
gttttgtaat agaattgctg tcaacaaagt agtggatgca ctatgttata aagatttcat    61980
tgtgaaaaca tgaaatggct gttaactata catcaggcaa aataaaaaca ggaaatataa    62040
acatttcctg gaacagggca gagtatgagt aataaggtat caaatataat tggatacctg    62100
accaaatatt tttaaatgtc ttaagaaatg tcactggaaa gactggagta cttggatttg    62160
tctcttattc ttattttgat tcctaacact gtgcttggca catggtaggt aattaataaa    62220
tgtgtgatgg atgaataatg attgtcattc aattagtgac taagagagtt ggaaagggct    62280
atcaatttca aattggttcc tttaagacat ttttacgtaa gatttgggag aaaagtaaaa    62340
gagcaccata tgattatgct ttactaagag ctgcttccat tcctcacttg accatgtgga    62400
ctcatatttg gcctatataa ttacattaga ataaacaaag caccaaaagt tggaaaagga    62460
```

```
agtagtagta ggagagggtt ttaagctatg tatttactgg gaaaaaaagt catgttttct    62520 ttttttaaaaa tgttctaaac agtactgtaa tcacttggga attgaatgtg ctttgtgtca   62580
gacaaaggtc tttgtataca atacattaca ttttgtatac caatacatta cattacacag    62640
aagggagtgc ctggctttgt atacaataca ttacattttg tataccaata cattacatta   62700
cacagaaggg agtgcctggc tttgtataca atacattacg ttttgtatac caatacatta   62760
cattacacag aagggagtgc ctggcttttgg gaaacacatc tacctaaact cttaacatag   62820
cacaatgctg ccatacggta ggtaatacca agacaaatca gggccgttat taacaacctt   62880
gaggaaatgt cttgggaaat atttaaataa ttttttgttta attataataa ggaatctaca   62940
gcctctgtga agtcatccca aactcttcga ggcaaattta gtctcctccc accctgttt    63000 tttaatgttt ctaaaggatg ttatgtataa tctattagaa aactggccaa gtgcagtggc   63060
tcatgcctgt aatcgcagca ctttgggagg ccaaggcggg tagattaccct gaggtcagga   63120 gtttgagacc agcctagcca atatggcgaa accctctcta ctaaaaatac aaaaattagc   63180
caggcgtagt ggcaagtgcc tgtaatccca gctactcagg aggctgaggc aggagaatct   63240
cttgaacccg ggaggcgagg ttgcagtgag ttgagttcgc gtcactgcat tccagcctgg   63300
gcgacggagt gagactccgt ctcaaaaaac aaaaacaaac caaaaaaaaa aaaatatat   63360 acacacacac acacacacac acacacacac acacatacat acatacatta gaaaactaat   63420
tacattgttt tcttaaaatg ttttaagcat ctctcttcct caaggacaag aatcttgaat   63480
ccttagtgca tatgaggtac ttaatagata tttaaatgaa tagtgagcta ctattgccta   63540
aaaatattag acatcatgta atatcaggcc tacagttgat agaaaaagta ttctcaacta   63600
agaataattt accaatggag aaaactgtta gtttttccctt cttttctctt gctttataaa   63660
atttaaatga cattaagagt tacgtttctt ggaaaattga aaagaatatc tgtggcacaa   63720
tgggctctgg gtataattgc aggataattt gaaaagttta aagaatattt tcaataggta   63780 taagttttatt taggctctgt gtctcctctt gagatgactt tagcagtata tatttccctg   63840
gaacaccatg cactctaggt tttctaattt attggtttaa aatacatggc atttttactac   63900 gtaaatattc tctgtatctg taggtacagc acctctgtgt acactaagtt agtgtatgta   63960
ttttttttaa attgccttag ttttgctatt cactagatta ttttccaagg aacctactct    64020
tagatttatt aagcctacta tatatattt gttattaact aattctctta ttttttaaaaa   64080 ttacttttcc tttctttgct taaattgct ttgtttttcct aaattagtga tttggaatac   64140
ttaattgttt ttattttgtt ttgttttgtc aataaaagag ttttaagact ctagttatac   64200
tatagctata gccaatgcat tttgagaggt gcttacatat tacaattatt ttcagaaatt   64260
ccttatttca aagctttgct ttcttttgaac aaagagttat ttaggaaaag aaaggaataa   64320
aaatctcaac ttattctcca cttgactagc tttattattt gcagtattct gttttttact   64380
tgttctaata cttctttata ttttgttgtg gaattatgtc acctaacaat atttttcctta   64440 acttcttaat tttagcctgt tttccaagtt aatcatttat ctgttgtttc aatgaatacc   64500
taagaaaatt ttcttttgtca ggataaggca catgaggtct aagatttatt tctagaacag   64560
taagcaaatc atttctgaaa gtgtgttctt ctactattaa gtaacatgtt tattttttgtc   64620 ttttagttga agtccccccc aacccaatag gtactattct gatttgttct cctattcaca   64680
cattcttgaa ggagagctga tttatctgta cccacaaaat tataatataa ttttctcaga   64740
gtattcaaaa cattgtcttt tttattttttc ttttttttga gttttcact cttgttgcct    64800 aggctggagt gcaatggcag gatctcagct cactgcaacc tccgcctccc ggtttcaaga   64860
```

```
gattctcctg cctcagcctc ccgagtagct gggattatag gcatgcacca ccactcctgg    64920
ctaatttttt tctattttta gtagagacgg agtttctcca tgttggtcag gccggtctca    64980
aactcccaac ctcaggtgat ccacctgctt cagcctccta aagtgctagg attacaggcg    65040
tgagccacca cacccagccg aaaacattat cttaatggag catttagaac gttatcactg    65100
acaaactttt ttctattgaa aatactgctt aaaagatcag gtcatgccca ccccacaacc    65160
cacacccttt gtatttctct tttacttgtc ttggcctcta gttcagattt atagtttggt    65220
aatgtctgat tttctttgtt agtgcttcag cccatctggt tggggaacag ctctatccca    65280
ctgggacctc tccctttcct catgagtgac gccagggtcc tgctgcccat aagcattctg    65340
tttgctgagt ttgtatatat ttcctttccc cagcttcgct gcctttggct gctttgtgat    65400
taagtaagac atacccatgt ttcctaaagc ctccttcgcc tttagtcctt gatgctgggg    65460 acctttggt tgggaagaca gcttccttat gtcagggtga gcctgctaca caggtatgta     65520
actcagacag tgacctactg ttgagttct gtttagtgtt tctttgtctc cctcaaatgg      65580
tacaaacgtg gagggcttca actgcagtct acctttgtcc tgttagtttt gtctatcaca    65640
gcccatgccc tccaaataag agatgatgga gcagtctgct tattttctgt agcactccac    65700
aactgacttt aaaagaggga ctgggattgg gctcttagtg atgacttta atgtggattc      65760 atctgcattt tctctagaaa ttcttaaac tctctgcctc tcagctggca ctattccatg      65820 gtatttagt gctaatgggg gatcttttct aattttgtt tttctttgac tgtttaaatc      65880
atttactgga aagagggctt agatatctgc tcatatgctc ctgctagtct acaagtcctc    65940
cagcctgatt ttgttcatga acatgatgga ataagcttc ttaaatgcct ttaatattgg      66000
atactgcttt caaggaaatt taaaatagca agcaggcttt caagaagaga gaataaatta    66060
tcagccagtc tcgcaagaac aaaataagc caagtcatat aaaacaagtt tggagtaaac     66120 ttgttttttac atttcaaatt cgagttgaac tcttcaagtg aagcttcaga gatataaaaa    66180
actttaactg ataaagattc caaacattaa tatatggaaa tgtatgagct cactgaaaat    66240
tttacataaa ttttactaga agaggtgact gaccagttgc ttttataaga ttctcaaaaa    66300
gatctcaaat cttagggact aatattgtaa gtatacgggg aaattaagac aaagatttac    66360
tatcttgtga gttttagtt tggataatga acttaattc acaagaaatt gctttagcac      66420
aaacatgaaa accttaagca tgagaactct ccttttgaag tacaaaggga gactaaagtg    66480
aataactcaa actggaaatg tagaaaattg aatttgctat gatttgaagt cctttcagaa    66540
tagccaacag attttaaaca agagttttat tgcatagttt ctttgggata tacattgaag    66600
gagaaaggag gagggagttt taaaagacaa gtggaaagcc ctttctgctt gttttggcta    66660
tggcttccat ttcagtgtct gtatttaagg gatcataaaa ggaactggaa agactggtca    66720
caatggcagc tctgtacctg tatgatttcg gatgtgaaaa gagtttagcg atttccttgt    66780
taacctatac tgctgtggaa gtcattcatt atgcagttag gcattagcag aacaaataaa    66840
gttcacagct ctaggaacca aatttaactt tatcactctt ctgatttaga atattttcat    66900
atgctttcat atgtcctaca gacgataaga agatagaatc aatacttggt gattgatagg    66960
ttatttttta aagggaaga aagaattaaa catccatggt ttcttcttaa gtaactgggg     67020
ggatgatagt atccctcaca ccaatgggga gtatagatga caggtttgga gtgaaagaca    67080
gtgaattcca ttttggataa gttgaatttg aagtgcctat gggacataca ggtacagatg    67140
actaggagac aattgaaaat ccaaattgtg aactctgctg aagattagaa gtacagatct    67200
```

```
gagattaaat tgctacttga gttcatggga ataaaatagg tcattctgca aatggttatc   67260
tcaatatctt cctggccatc tcttgggtca ccttgccaac ttttcattct ctttacaatc   67320
tctaaattct catgttttta aggctctcat cttaggccaa cttatcttgg gtcaccttgc   67380
taacttttca ttctctttac agtctctaaa tttgtgcttt taaggcccca ttctcaagct   67440
ggcttctctg ttttggtggg aactggtagc aaacattcat ttgtaaacaa cccaaatggc   67500
tagcattgag caggactccc caacatactc ctctgaatta cattttgagt tatctgaagg   67560
atcaatatct caaactagga aactgtagct ttctcattta ttttcatcat ctaattattt   67620
ttcttgcctt taagtataag ggatagagac ttgattgatt tttatgtaca acaagttaaa   67680
aaatttaatt aggcgtcttt gccatttaat cagtttatac ttcttgaatc ttttccagtc   67740 atcaaaagt tgctgagcat gcgcagcttt acttactagc ttatagcatg aagaagagta   67800
aaataggagt ggataaaggc acagtggtga gtagtcagtg tttccaatta atctcaaagt   67860
ttaggattaa tttagcgtga attctgttct tttgtgtctt cctgcttttt gacgtggtaa   67920
cctgccataa caaaaggaaa cagcaggaaa cttggtacca attaaaacag tcttcttccc   67980
ccaaagaacg aactgtcagc aaacaatctc aaattcaaag tgataagtgt tttagagtga   68040
aacaaggata aagagacaag gctattaaat tttaacatct gctggaacac aaagcgcatg   68100
ccagtagaat taagtttggc atttaataag atacaatttg cacatcagaa atgaaataga   68160
tgcctcaagg catggtatat atatatatat atatatatat atatatatat atatatatat   68220
atatgtttga gcgaggggca cttctagcaa aactgaatac actggtataa atgtctgcgt   68280
gaaaattttt ttatccattc acttttggtg tgtattccag ctgtgagtta ttcaaccagg   68340
ctcactaagt ttgagtctga ttaataacgt ttaaggtcac atctgattaa cagtatttga   68400
agtttgaatt tgttctaaga tgactcaagc gcaataacat tttctatatc aaaatgaatt   68460
tccatccaaa tagggaggaa atctgaaatt tcagttccag tgttgactga gatgctctgg   68520
atgagcctgg actcagagct caccaacttt ggatctttat gttaagtagt cagtggggtt   68580
gacttctaga ctagagatca aaatgttcta cacctcttga tataggtcag tggctgatgt   68640
aatgtgcttc caacaacttt cttttaacta aaacagtaca tataccaagt tggtttgtca   68700
caatgggaac aaaacagaaa tctgacaaca gatttctcta attttttgtg tgtatgtttc   68760
tgaatgggct aaaatacata attttactct tccttggtga agatgctttt ataagaggac   68820
gtgtttaaga aaattaagaa atgttgtagg tagccatgaa agaattattt taaacagaat   68880
tagtatagag gtgtgaagat ctactgaagg gtgataagta agtgtggaag agatggtgtt   68940
cagcattggg cttcagtatg aataggtaga agatgagcaa ggcttagaga caagaagttc   69000
attcaatagg ctgttgcggt tatccagcaa tgagatggtg acagcatgag ccatggtagt   69060
aaaagtaagg acatggataa tttgtgggtt ctacagacaa taagaacata gaaccgatag   69120
gttatttttt aaacgggaag aaagaattaa acatccatgg tttcttctta agtaactgcg   69180
tggatgatag tacccctcac actgatgggg aatgtagatg acaggtttgg agtgaaagaa   69240
tgaattccat tttggataag tagagtttga agtgcctatg ggacatacag gtacagatga   69300
ctaggagacg attgaaaatc caaattgtga actctgctga aggttagaag tatagatctg   69360
agattgaatt gctacttgag ttcatgggaa taaaataggt cattcagtaa attgttatct   69420
caatatcttc ctggccatct cttgggtcac cttgttgact tttcattctc tttacaatgt   69480
caaaattctg gtgtttttaa ggccccaatc tcaggctggc ttctccaact gtactcttac   69540
ttgggatgat cttatctagt catggggcat taaataccat tggtaggtta acacagttca   69600
```

```
caatttctc cagcttagac cccttgctga tttcctgact tgtacactca actgcctgcc    69660 taatatacc  actttaatga taatgtacat ctcaaactga gcttattcga aatagaagcc    69720 ttaattttc  tgtcagtcat attgttccca tttacccatc ctaacaaata gcaccatcat    69780 caaccttta  gctcaagaca aaactctagg cattatcttg ctttcattcc tttcatgtac    69840
tttctcacat ctaatccatt accaagttgt tctgtttctg ccttcaaaat gtgtcctaaa    69900
tttatccatt tctctgccac tgctattctc tagttcagga cattctatcc tttctcttgt    69960
attactgcgg tctctaaact tcatgtatct atgttttata cttttaattc attgtctata    70020
cagctaccag agtgatcttt taaaggtcta aatcagttca tgtcactgct ttatatataa    70080
tgcacctatg gcttcccact ggatttaaat aataatctta acactttact cctccatggc    70140
ctttacatac ttctagccgc acctcaaaac actcctcttg ttcactgaga actaactaga    70200
ccagtttctc ttctcctcag ctatatcatg ctaatttatg cttcagtgcc ttttgtactt    70260
ttgttccctc tagctgaatc attcttccag gtcattctat cattggcttt ttcattcagt    70320
tcagatagat atcagcaaat caagagagtc tttccttacc tgctctatct aaatagtcct    70380
gttttagtcc tctttatctc atcactcaga tttatttccc tcatagcact catcagtctg    70440
aaattgtttg tttatttggc tacttgtttg tctagataaa cttcactggt gaaggaatcc    70500
agactatctt gttcatccct acatccctag aacctagaac aatatgttaa agataaataa    70560
ataaatagat gaaagaatgt tgaagagaag agggtccagt ccagccccct gaggtgacca    70620
gcatttaggg aataagccga ggcagaggag ggccattaag aaggagcaat gagagataga    70680
ggaaaactaa gaacaaggtg tccctaaagt gagagtgtcc taacacaggt ctaaatgaaa    70740
ggatagttca gaagagggca ctgcagctgg ctgaaagaga acaagaaagg ctgtaaggtg    70800
gaggtgaatt tttaattgag ccgtgaaaga tagggaaatt ctgtatgaag gagtaaatgg    70860
aggcatagag gcatagaggc agaagatgca tgcctgtttg gggaatagtc atcccatttg    70920
tctttcacat atctcattta atacttctca tttaatcctt ttagtgttaa tgttgtcact    70980
agattaaaaa acaaaggctc catcaggatc acacagtaaa cagaagaata tggatttaaa    71040
tggagatcta tctgactgca aagactactt actgtaactt aagtcattga gattcattat    71100
ggccacctca tattcaccct gcatataaca gtatgccaat gtaggaatga ggcgtgaata    71160
agcagggtaa caatagaaac atattctcac cttgattatt cctttggtag cttcaaggga    71220
aattgagttt gaggataaag taactcttcc catgtcagca ctttatctgt cctgaaacat    71280
gagaaattcc aaatgttcaa gccatgcagt ttttatctag tcagatggtt gagaagtcca    71340
ggttacccat agttgtaatg aatacctcct ctttatcttc ttaatgttct gctttgccaa    71400
atgatctata aagattactc agtgtacctt tcagattgag gtccagcaga ctttcagaac    71460
actacattta attacagaaa cccaactaat aaaataataa gctcatgtta gtttcaggtg    71520
ttgatttgtt tttaatgtag tcaataatat ttacatataa tgactggcaa cttaacagag    71580
ttataataga ttattcacct gtatttgcct ttatttgtgg gtatacacac atatatacat    71640
gccttaaact agagtaaaat catttatgca tactaaatca aatttgagag tcccaaaatt    71700
ttcaaattgt gtatggctgg tctatatttt ctaggactgt cctttctggt ttaaatgaaa    71760
ttaaaaattg aattaatgat attagtctct tttaattttc tatttttttc atgattaaaa    71820
aatattaatt tccagccagg tgcggtagct cacgcctgta atcccagcac tttgggaggc    71880
tgaggcgggt ggatcacctg aagtcaggag ttcaaaacca gcctggccaa catggtgaaa    71940
```

```
ccctgtctct actaaaaata caaaaactag ccaggcatgg tggcacgtgc ctgtagtccc   72000
agatacttgg atggctgagg caggagaatc acttgaaccc aggaggcgga ggttgcagtg   72060
agctgagatt gtgccactgc actctagcct ggtcgacaga gtgagaatct gtctcagagg   72120
aaaaaaaaaa attaattttc cccattcccc cacccaccca ccaaaagact ccattggagt   72180
tttattttac aaatgcatct gctcatctac ttctttttaa gtgcataaac tagttttaca   72240
agcttgagtt taaatcttaa ctcctcaatt cttttttctga catagaaata tacaggtgca   72300
ttatgaaata gctaatagtg actattttct agggctgtaa ctcaatattt ataagcataa   72360
tgatataacc tgctgaagtt tgacacgtca gtatagttct tttgttattc taagtcataa   72420
aggcagaatt tggaaaaatt cacagctttt caaatatgca gaagaggaaa aattgagagg   72480
aagcatacta aaatttcttt agccaatttt aatcaaattg agtttgaaac ttacaggatt   72540
atgcttcaaa gcttgtaatg atcgtcaaaa gtagccttat tcaaaatgac acactaattt   72600
ctaccacatc tgtattcttc tcattgtaag atgttacata tacctatgct tgaccaaatg   72660
gacttcctgc tattttaaga tatttttctg tgttttaagt ctttctacaa attttctcaa   72720
gcatttccct ttacctagga tgttcttctt tcactgcaag tgaagacatt ctaaaaattc   72780
ctaaagcaca ctaccaaaag cccttcattt ggatgaccca ccttcctatg agtctccata   72840
gttgcatgtc tgatggcatt tattttaact ctatgatctg cttctaaatt agataaaagc   72900
tctcagagag aactatgacc aattgtcatt ctgtttccca tggcacctag tacagtactc   72960
tgctcacagg ctcaataagt aatgagttga gctacgtttt tttaaggcag agtctccctc   73020
tgtcgcccag ggtggagtac agtggtgcaa tctctgctca ctgcaacctc tgctgctggg   73080
ttcaagtgat tctcctgtct cagactcccg agtagctggg actataccac catgccacca   73140
tgcctggcta acttttagta gaaacaaggt ttcaccatgt tggccaggct ggtctccaac   73200
tcctggcctc aagtgatcca cctgccttgg cctcataaag tgctaggaca aagtttgcc   73260 attgtcatgt tacgatatat attggttttt gtccatggtt tctggttcat agctccaata   73320 tccctttta cagtcttttg ttagaatgtg gggtgtgttg gacctcgggg caggccttag   73380
aaaacagaat ctctcctgcc ttcctttcac ttgtcccccg agggagattt ttttttttt   73440 tttttttttt gagacaagac ttccctgtgt cacccaggct ggagtgcagt ggtgtgatca   73500
tagctcaccg cagcctcagc ctcctaggtt caagcaatcc tcccatctca gcctcccaag   73560
tacctgggac tacaggcaca tgccaccaca cctggcattt ttttttttt tttttttttt   73620 gtagagaggt ttcgccatgt tgcccagtct ggcctccagc tcctgggctc aagtgatcca   73680
cccaccttgg ctcaaaccac cacacccaac cctgagggag attctaatct tccccaccct   73740
tctgattttg agtcttaaaa ccccagagaa ggtcccaccc tttgcactgg ggaaaggaat   73800
gctgatgatc atgaagcctc cataaaaact caggaggatt gagtctgggg agcttctgga   73860
tagctgaacc agtggaggtt cctggaaggt ggctcatcca gggaggactt agaagctccg   73920
tgcactttcc ttatacttca ccctaagcat ctcttcatct gtatcctttg ataaaccagc   73980
aaatataagt aagtgtttct tgagttatgt gagctgcttg accaaacgta ttgaacccaa   74040
agagggtgtt gtgggaaccc caactcgaag ctggttggtc agaagttctg gaggcctgga   74100
tttgtgactt gtgtctgtgg caggagcatc ttgggaactg agcgtttaat ctacggggtc   74160
tgacactgtc tccgggaatt aaattggagg acacccagct agtgtctgct gcttgttatt   74220
ggggagaaac cctcacacat ttggtcacaa gagagaagtt ttctgttttg aatattgttg   74280
tgatgtgaga gcagaggaaa aatgcatttt ggagaggttt tttcctacac agccataggc   74340
```

```
agtgataaga atatgatgct tttttccaga aaatgctaca tgagaccttt ttataaaatc    74400
taattttctt caactgagta gcatttaaac taaaaagaat aggttatttc agtgtctctc    74460
tgtaataaca tcttacaatc acttgtcaga ccatgaaata atgttctaga aaatcagtga    74520
aagagctttt taaactttgt gacatttgac ttatatttat taccaaaaag cctgaattat    74580
tattcagcac attataattt tatttaaaat ttaaattaga gatgaaatac ttgtaaatgt    74640
ttataagatt ggtagctgtg tgggcttcca gagttagaaa tgcctctgag aaaagattta    74700
gagttttgaa agtattttga aaaagaaac agaaggaat acaacatttt tcccagcact    74760
gcttcaataa tgcagtcttc agcatcatct caaagcaata actgcagtac agatgagatc    74820
agccagtttt ttttccccc ttatctgcag tgattttacc atctcttcat gctacatctt    74880
accacaaaga gaacattgaa acatgggaaa gagtttgctt tgatttcaac cagaatgcca    74940
actcatttct ggggttctaa accataacct tttttagcag agcagtgtag aattttttata    75000 cgataccata aatggtcggc ctgagtaaca ttttaactgt aagtcaatac ctttgaagag    75060
acatgtctga caactcagag ttctatttc tccatgtgtg actaaagtac cttttctatt    75120
aagagatcaa ccaccatttc cttctactct ttgttctccc cttaaataaa gttaattcag    75180
cttcaaaata ttttatgatc ttgattacta actgtgggtc tttagaagac aatgtaaaac    75240
atttccatgc tgtgaatatt agagctagta tacttggagt ttggctagta tttctggggg    75300
aggtagaaga ggagacatag agtacaaatg agtattttta aagccacgct gactaaaaca    75360
aaaggaatgt tttatacatg tttatttcat agtacttctt tgaaacaggt cgggggagg    75420 agagttaaaa tattgctttg aattttaatc aaagttcttt catggaattg ttggtgcttc    75480
tggtaataac agttctataa tctttgtgag ttaatctgaa atgctctttt tcttcatcgt    75540
aattcagtgc ttgtcttaac tggtggactt attttatggt attatgttta taagatggca    75600
actaaaatca gatttttat actcctaaaa gatggatacg atagaggga aagggggtaa    75660 gctacaactt ttaggttgtt ggtgatattt gaagtgttta ttgcttctga tttacattta    75720
tatattatat tcaaatataa actttaaaag taatgatttg ccacaggtta aagcagaaca    75780
tttatatgat atttcctaga tgttttcctc tacaatcctg ttttgttct atgaaaaatg    75840 ccataaactt ggatcattca ctaattaatt tgaagctgtt ttcaaacaaa aagctaattc    75900 atctttagc ggatttagtt ataatcgtga taacagatgt atagctaagt ctgttggaca    75960
aactgttggt cacatcaatc ttaaatgcat catacagcgt gatgtgaatt tatgatattt    76020
cctaggtaat gttaaggtta tatggaaatt tctttgcagg tagttaagtc ttattttgaa    76080
ttcaaatgtt attttcaata catacgtgga agtgtatttt ttgtttgtcc taaatgttta    76140 gatttttga gttacaatt tttttgtgtg ttctttcttt gttcttgccc ctccctgcat    76200
tctctatgaa gatacatgtc agcactatgc aacactaaaa taacaatcaa ccaaattata    76260
tcctatgaac agacctttct cttcatttca aaggcataac ttggatggtc tgtttagctc    76320
atggtgaaaa aaaaaagtta tgattttgta tttgggcaaa gtacaggtga agagcgtgaa    76380
tcattagaac agcaatataa ctggaagaag atagttagt ttttacaagt taaatttgaa    76440
gctaaagcaa aacttgcata ggtatgtgtc ctttgctctt gaaaatgaac tcagaactct    76500
acatctgagt ggttttatga atttatactc tcctagtcca caggttctca tcagtgcctc    76560
aagatctatg cacagattaa aattacataa gatatcatat actacatctg aattagggtt    76620
ttccaaagta tgctattcca tggaaatact gtttattcag ggtgctccat aaacaatgat    76680
```

```
cctgtgtttc attatgtcca ggaaatgcca cacagcacct ttccagacat cctatcatca    76740
tattaaagac tttgaggcca tgcattaaag aaagttttaa attagaaaaa aaataagttt    76800
tcttgcttga gcacagaact ttatttttc tcaggctggt tctccttttt taaaattaca    76860
cgttaatatc ccaaagaacc agtcccatag atagatatca catatgataa gaatctgttt    76920
caatggtgtt ggtgtacatg tgtgttcagg tacctacaca ttaggacaca tctctagttt    76980
attaatactg cacttataaa gagacatggt agagacatca agaagacatc attttagggt    77040
ggacaccatt gcctaggacc tgcttcttaa tgtcaaaaat tcagaaaccc aattttatct    77100
ctcccgcaga gttgactcga gtgaaggaaa ttgagttgtt ttaattaaac tcacatgaga    77160
ttgatgttta aacaaaattg taagtttatc aattaataat caagaattct gatttttaat    77220
tttcaaaata ttatttatgt ccactgtcca gggtacttgc tttaagggca cccagtgatt    77280
cttgaagatg aagagtctta ggaatattta ttttctagac ctcaatgaag aaagcttttt    77340
aatcatcctg ccccatagaa gaatttatgt tcctagtgat gtgatcatat tggccaatcc    77400
agtgtttctt ttccaaggac agtactgata aggagccacca aatctacctc tttgtcctga    77460
acagatcatc tccatctatt catagttggg ctcagaagtt ggacaaggct gcattttata    77520
tctacttctt cctcatgtcg gctatgccat gccgtttcgt tcttttagct tgtttactta    77580
tgtgtaaaat gaggtaaaaa ttacaccctt caaaccgaaa gtggtcttcg tgatgagtta    77640
tttaattgaa gccccagtag atatttatca ttgccagttt tagagaatca tagcatttta    77700
gaacacaaga tgaccttaga tgtaatcatg ttcattcccc tcgtattata aattttaaa    77760
aattgagatg tggggtggtt gtgacttgct cacaaaccca catttagaac caaaactcag    77820
cattcttgtt ctgactgtgt ctatgtcctg taggtatatg tcttgtcttc tcagttaaat    77880
aattaaagat tcttaaagat agagaccata ttttatgcaa cttctggatc ccataaatta    77940
tgtttccaga agaacctttt gtaatgaaaa aatatatata atgtctatat tatatatata    78000
gtctattact attttgataa tctaaaacat gctatataat tttaggcgat cttaacctat    78060
ttatcagagc ttttcagatc aaagaaaatt agagtaatct tcatcatgta tgggaacatt    78120
gatgtatttt tctgatgaac acatggttat atgatactct tttaaagcat ctgtattact    78180
ctttcttctg atagactggt tattttgttt atgttatgaa ataatgttgg cagcttttca    78240
ttagaactga tacatattga aatttcttaa attgatagct catggatgtg cagttggttt    78300
aatggcatct ccattattaa tctttaagaa gatcttcatc ttactctcaa aaataaccgt    78360
aatatcctac aaattaacta aaacatgatc attgctagtt gttccaaaat aggaagaata    78420
aaaatgacca gattgttatg gtaaccagtt gattaagact agatcaatag gaaaacgaat    78480
ttattcaagt ctgtacaaaa cttctccaaa acatagatgg catgccttt gaggcaatgg    78540
tagggaacaa atatttttg agaaggagca gattttaggg atacagtaca gtacataatt    78600
gccaaaatgc ttgtgttaca aggattcctg gtacagagtt tttaaataaa atgctaggta    78660
tgtcatgttt gtttcacatt aatattgtag agtcccctgg ggatgtgaca atttagttga    78720
ccaactctaa tatagttaat ttctaccttt tgatagcttt gtggggtttt gtttgtttgt    78780
ttttgttttt gccattcttg atttttaggg ctgaagatatg agacaatgta tcaaacagta    78840
aagaattatg cattgattaa gatcatcttg gtgaattaga tgtttattat ataactcgac    78900
tttaagactt tgttcagatc tcactatctt aatgagattt accctcatta tatagtattt    78960
aatagggcaa ccactccccg atactcttga ttcctcgtta gctgccctat tatttctttg    79020
tttttccctt agcactcaac attttcttac cacaccacat aatttacttt cttattgtgt    79080
```

```
ttattgtttt tctcctcatt agaatatcag gtccaagaag acaggagtat ttatctcttt   79140
tgttcagtgg tgtgttactg gtgactacta gagtgcctga cacatagaat atgttcaata   79200
aatattcgtt gcatgaaaga atgaatacct tgacagatta tttttataac tctaccagtg   79260
tcattatata actacactga atgattatga gccctcctag aaattacata aagttcttat   79320
atattattag aacccatttg ttggccttat gtaatggttc tattggaaaa atcatacctc   79380
cgtatataaa aatgaaagta ttttttttct acaattgccc ctcatatata ctattatagt   79440
ctccttcacc ccattcagcc attaatgtct tcttgaccag gtaacataat ttttacagca   79500 cctttggtt attagaacaa ttttatttgt ctttcaaact cagtcctatt cattttaaaa    79560
ctcccaactc aagcctgagt cagtgttctt ctcccagcac aaacttaaac actggctcca   79620
acccttggag ttgaaagtag gggagcctca ctcctgatac ctcccctccc cctctaccgt   79680
gagcaccagt gcctaggaga ttgggcagga ctgaggaagg atgaaaagga gctcagggct   79740
ccttaagcac ctgaacaaga ctggaggact ttggatgttg ctattttct gcctggcatt     79800 gactggctat tggacgccct ctgtgaggca ggcatccgaa tactggcttt cttgacatat   79860
atggagcgtt ctttagagag gcctacaagg gctctcactg cacagtaccc tgataggaga   79920
gatctgtcct tatttcttct atcaccatag ctacttcagc tttgcctgct gagtccaccc   79980
cacagtctct ttctgctggg gcatccttgc cctggacaga ttcttagagc atgaccaagc   80040
ctaaacaact tctgcaattt ttctaagtac acttttattt aattgaaagt ttcaagcatt   80100
ggataatata aatgtatcct agacagtgtt ccagtaagga caaccagctc acaattatcc   80160
attctaataa tgggagtcaa ctgaaataga aaaatataga tttttaaaat aatttatgag   80220
aaacaaatat ttgtgacaca gtacatttct aattatgttt atctttatta ttattattat   80280
cgtttccttc agtacacact agtttggtga gacttggaga aaggccagga ataagcccaa   80340
attcaaaaaa caattccagg attaacagat aagtggataa tagagaattg acaaaagatc   80400
atgctcattt taccaataag aaactggttg gttaacttgg gttgcaaact gaaagcagat   80460
ttatactaaa ctggcaggtg tctccagatc ttaaatgcag atctctatct ctgagttaat   80520
ctgcctctca tcttcaatgg cattcctctg aattttctc cctcaaataa tctatatatt     80580
attaaatttt gtttatactg ccattttaag aaacagattt taaaacttta aacatgggaa   80640
ttaaataggc cctactgagg attatgaaaa acctgacaaa acctcctatg cacatgattt   80700
agattaggag cagtgcacac gctgtatgtg tatgtgcagc tacttgtcca attaacacct   80760
tttcagaaat ggaggaactt tctctgagga ctttgacata tttgtgtgtt cagcagtcct   80820
tttttctttt ttttattttt tattttttta ttattatact ttaagtttta gggtacatgg   80880
gcacaatgtg caggttagtt acatatgtat acatgtgcca tgctggtgcg ctgcacccac   80940
taactcgtca tctagcatta ggtgtatctc ccaatgctat ccctccccg tccccccacc    81000 ccacaacagt cccagagtg tgatgttccc cttcctgtgt ccatgtgttc tcattgttca    81060
attcccacct atgagtgaga atatgcggtg tttggttttt tgttcttgtg atagtttact   81120
gagaatgatg atttccaatt tcatccatgt ccctacaaag gacatgaact catcatttt    81180 tatggctgca tagtattcca tggtgtatat gtgccacatt ttcttaatcc agtctatcat   81240
tgttggacat tagggttggt tccaagtctt tgctattgtg aatagtgccg caataaacat   81300
acgtgtgcat gtgtctttat agcagcatga tttatagtcc tttgggtata aaccagtaa    81360 tgggatggct cagtcaaatg gtatttctag ttctagatcc ctgaggaatc gccacactga   81420
```

```
cttccacaat ggttgaacta gtttacagtc ccaccaacag cgtaaaagtg ttcctatttc   81480
tccacatcct ctccagcact tgttgtgtcc tcactttta atgatcgcca ttctaactgg    81540
tgtgagatga tatctcattg tggttttgat tttcatttct ctgatggcca gtgatggtga   81600 gcatttttc atgtgtcttt tggctgcata aatgtcttct tttgagaagt gtctgttcat    81660
gtgcttcgcc cactttttga tgggattgtt tgttttttc ttgtaaattt gtttgagttc    81720
tttgtagatt ctggatatta gcccttttgtc agatgagtag gttgcgaaaa ttttctgcca   81780
ttttgtgggt tgcctgttca ctctgatggt agttccttttt gctgtgcaga agctctttag  81840
tttaattaga tcccatttgt caattttggc ttttgttgcc attgcttttg gtgttttaga   81900
catgaagtcc ttgcccgtgc ctatgtcgtg aatggtgttg cctaggtttt cttctagggt   81960
ttttatggtt ttaggtctaa cgtttaagtc tttaatccat cttgaattga tttttgtata   82020
aggtgtaagg aagggatcca gtttcagctt tccacatatg gctagccagt tttcccagca   82080
ccatttatta aatagggaat cctttcccca tttcttgttt ttctcaggtt tgtcaaagat   82140
cagatagttg tagatatgtg gccttattc tgagggctct gttctgttcc attgatctat    82200
atctctgttt tggtaccagc accaggacca tgctcagcag tccttttca agagatgtga    82260 agtacatctt cacagatttt taaatattta gatagaaagt tcttacagaa tgagaaataa   82320
aaagttagct ttgccttaaa aatattaatt caccttatat tctccatact taatccatat   82380
aggaaacatt atattccagg tctaacatgt ggcttgctta cattaatttt gctgttgaaa   82440
aatatatgtt ttggattatg ttttttaaaat tttagctttta atatttaaat attaaataat  82500
gttaacttta aattaacgaa gaatagtttt taatttata agaaatgccc tataaaaaac    82560
actttcttta cctcaagagt gagacttggc aaccatacca atattacata gtaattttaa   82620
agtcaaacga aatggagaga acttaataga tacagaagat aagaatttaa actaacattt   82680
tgctcgggat tttagaacac tatacagagg gaaatttagt agacaataat gaagtccata   82740
gcattgcaca catcttgaaa taagtgtata attgacacaa gctatgtccc atgttgatag   82800
gaagaatcca aaatagtttt ggagaataat gccatctatg caggaggtgt ggccatatac   82860
atcatcttta ctcagtgttt ttcatgtcaa taaatattta attcctaaca ctctgaatta   82920
ctaatagagg tgaagcctgt cagtggaagt gacagagaga tacacagtga ttcccgtaag   82980
tttgatcctg aaacacagtg cctttagcag atatagttcc cataagcaag cagtctgaag   83040
tatttaccct cagtaatctg aatgtataaa taaacaggat tcatgatggt agagtaattt   83100
atatatactt gtagtattag gacatgcaaa acttattttta tggaaaaaaa taatttacta   83160
ccttatagta tggcaactat acaaatctat aaattgactc ttttgtcccc ttgaaaaaaa   83220
gctgacataa aatttaaatg atgtgtattt tttcttagag caataaaaga tatacccccca  83280 cctagaaaag caataaacca aaaataaaa caaaaacaaa atcaagccct cttcacaaat    83340
ttgagcatat ctacagcttt atgtggtgag agatacagct accattcttg agtaatccga   83400
agagtcaaat ggtatggagc aaaattacag tcctaaatgc atattggtga aatgagatgc   83460
tgatccattt gcacactaat gtgctatttt taagtcatgc atcatagcat cttcaaagag   83520
gcctgtcata attatgatgg attagactgc agagtcagtc ctagatgcag taattgtttc   83580
acagatgctg ccaatgcgac tagaatttat aataaattat tttcagagag gcgggagaag   83640
gaacaaaatc aaaggaaaac tgctgtggct aaaacctgtt ttggtcttag gaaaccaaaa   83700
tgttagctag tagtcaaaag gccagtattt tcaactgaga taaacatgct tcattaatac   83760
atgcctctga catagaagat aaaggttaac ataattgaca tatcagccag tctctctctc   83820
```

```
tctctctctc tctctctctc tctctctctc tctgtctcgt agcttatgaa aatttattct    83880
ggggcattag ctgaaattat tgagtggcca tataattgtt gcatgtttct atttatgtta    83940
aattgcctgg ttataatttg acctttagaa tttctgaaaa aaatggtggt atttatagta    84000
aatagaaata ttcttttgg ttccttggaa gcccatgcat tacaaagaac attagattat    84060
tggaataaaa ggatagacat acataatatg actagtggga tctaaattat aaccttttaa    84120
aattgtaatt taattagtct gtcatttagg caaatgataa tttctaaaac tgccttttta    84180
gacttaaaaa aataccaaag ttcttataac tttagcatta tgttttgttc attcttaaag    84240
tttaattcac tttgttgcct ttttggtaaa cctatgaaga atctcatgc tgcaccatat     84300 agtaaaaaat cgtgtgtgtg tgtgtgtgtg tgtgtgattt gaataatgag ctatgtgtta    84360
tattttgata agcaaagata agtttatagt gaagcagata aacatgccat gtattttcct    84420
aggttaaggg ttcaataatc agaagagctt ctacaactca tttgccttct cactagtttt    84480
tttgaaattg cgctctatga gttttttatg tggtgttctc tgtacttgct gactactgat    84540
gcacatttct ccttaggtca ctggttctcc tccctcagca atgttgtagg tagctttgat    84600
gaacattcgt tgtcagcctt ttaccttga cttagtgttt ttctctcata ctacggcaag     84660
aagaaatgaa gttaaatttt acaagagtga cttgggtggc tgatatgccc acattgacag    84720
ggacaagagc tctagtcttc ccctctcctg tattcccatg gcacttcagt agtctcattg    84780
cctcaacata accacagttc agggcagtag aggatgtttg catctttgtg ttagctccat    84840
gccatggcaa ctgcactgag tgaggattca actcagtgca gcaggactga aaaataaat    84900 gaactaatgt gtcttgagct ccaattctct gagtgacatt atcaggggag attcataaat    84960
catcctcaaa tattctagag aaaaatcatc agcagtccag cattgcaaag ataatctggg    85020
aaggtggcaa agaagggatc agaataactc tgtggcagct tcaaattcca tgtcctaaaa    85080
gtttacgttt tctttttat tctatcccaa accacataaa gaaatgattt gttggcaaaa     85140
gacatgcaaa atgcccttaa tcatcttaat aattacagac ctacagatac gtagccaaaa    85200
tacttgtttt ttaatcctaa accttaaaaa aaaagcttaa attgttggct aaatgtgaat    85260
ttaataacaa aacttactcc tttaattatg cacttgtctt agtattgtgt ggtgggaaga    85320
gctttagaga gctgccagag tgcttaggcc tagtccctgt gggagcctct gttttggtgc    85380
ttcaccatgg gcagattcct cagttttcac atctttaaaa tgagaaaatg gtactagatc    85440
cttgctgcta ctctgaaatg tttatacatt gttaggacca ttgttacata ttattactta    85500
tatttgagtg tcaccttaga atttcttagc cgtgtgtatat ggtttggttg ttggctcctc    85560
taaatctcct gttgaaatat aatccccagt gttggaggtg ggggcctggt gggaagtgtt    85620
tggattattg gggcagatcc ctcatggcat ggtgctgtcc tcctgatagt gagttctcaa    85680
gagatctggt taagggtgtg tggcacgtcc ccctccctgt ctccttccct ccctctctcc    85740
ttccctccct ctgtccttcc ctccctcttc ctccctcttc ctctctcttt ttctcccact    85800
ccagccatgt tagatgcctg ctcccctttt gctttctgcc atgattataa gttttgtaag    85860
gcctcaccca aagcagatgc cagtgctttg cctcctatac agcctgcaga accatgagcc    85920
aattaaacct atttctttat aaattaccca gacagctatt tctttatagc aactcaaaaa    85980
cagcctaaca tacctttcaa aaggttaaaa tgctatttag tcattccaga agcaagatct    86040
ctttgtccag aattctggaa ataaagatgc caaaataata tggcatgtat ttgatctcag    86100
ggaattttca tttttttcaaa aggaggaaaa aagagtaata taattttttta atattttggt    86160
```

```
agctctaaca gtgcttagaa ccagttctca agagcacatt gtgaaacttt caggaattgc    86220
atgagctgta ggttgataac atgatgccag ctataaccca taagagcatc tcctgaggaa    86280
tatgttaaaa actgtattca ttcttaaatt ttaactaaat gcaatgagtg aagtattgac    86340
atcatgaaaa tcatccctgg gtaaacaatt agtcactcca ggttttccca aaggttcttc    86400
tgtctctgtt cttgtatata aacttcgtaa ccagtttaac aaccccaaaa aaggccttaa    86460
ttttgattgg ccagcatcct cttaggaaag acattgccat cctcttgtaa agttgcttct    86520
cattctaaaa taagaattgt ttccatctag ggaatgattt ttataggtag aatcttattt    86580
ggcatggact cttttgcata cagtgaatta caatgtgtag accttcaata gcaaggtgtt    86640
tgaatattta gttgcacaat agagcagtat cttaatattg tataccatat taattttgtg    86700
ttctctggtg taagaaaaaa tagaaggatg tttaatttca actaaaaaat caatcatgat    86760
aattcaaaat atttctgatg agtcatttat aagagcagat atgaattaaa attatatttt    86820
tgttcttagt ctctgagaag caaaaatcac acaaataatc tccatagcaa aaatttatat    86880
ttatctgaaa aacagtttaa cttttgaaaaa cttttctttg caatcattta aattcataaa    86940
aaaaattcat taactctact ttcactgaat agcaggtgaa tagcaggtca atatctacaa    87000
aaattcatct ttgaagattt ttttatctta cgcaaaaatt attgacttca tgtagacttt    87060
ttatgcaagc ttgaaaacac tgtgtaaatg accccataaa aactacagca tgaaagcttt    87120
ttcagtattt ctacaatgag caaaatgcat aggtctcatt tccttctctt ttattaagca    87180
aaataatact ttatcaacat cagtatgcaa gcactaagag cttgaaagag tactgtgcaa    87240
gtgggttact ggatcataat attccagggt atgtatataa aaagtgtgat ttagcacata    87300
ttaaagtaaa agaaaatatt gcatttttct ccttctaaaa tggcagttta ttagtttaaa    87360
tttcctgaaa taagatttaa agaccaataa caaattttcc tcattctaac atataacttt    87420
cctgcccttc ttgtgaaaaa gttaaccatt aaacttttca cacaaatggt tgtataaagg    87480
acttgctgtc acagacaaaa tagttctgta taatgtttaa aaatggccat tgtgtttaaa    87540
actccatatt gaaatacatt tcttttttag tcaccttcat ttcttagtag ctattattat    87600
actcaaagga tttgcccttg acactttaaa gaatgtccaa aattatgtgg aatggattat    87660
aataaaagat aatatattaa atgcttaaaa tattttatac cttagaaagt agaaaaacat    87720
gtattatgta cagatcctac aaattttata taatttatca taaatgtaca catgtatata    87780
catgtaaata cctttttgatt gctctgtata tgaattggtg ttttacagtt accaaaagaa    87840
aagtgccttt ttttggtagt atctggacag gtaattgact ttctttctgc aggatttatt    87900
tagatttatg tctatgctcc ttaattttg aaaagtgata gtgtcctgat tttggagaag    87960
cctctcatat caaagactac aaatcaattt tcatgatttt aaaacctaaa gtttctttat    88020
taggtgttat tgatgattaa aagccattgt ctcacccaaa ttttctactt gttcaataga    88080
aacataatgt aagccacatg gaattttaca ttttctagta ctcacattaa aacaagtgaa    88140
aaagaaacaa attgatgata cgtttgattt aacccaatac atttaaaata gttcaacatg    88200
tattaaatat tttttgagta ttttttgtgtt ttttaacac taaatctttg aaatccaaac    88260
taaatgtttt catagatacc acatctcaat ttggactaga cacattttaa gggctcaata    88320
gctatatgtg actagtcact gttggatgat gtatatctag accatctctt aatgtatgga    88380
aggaagtaaa tctagcagaa ataaaaacat cactttgttt tctttgtcca atatgagtta    88440
taactttatt tttttgagac agagtctcgc tctgttgccca ggctggagtg cagtggcgcg    88500
atctcggctc actgcaacct ccgcctcctg ggttcaaatg attctcctgc ctcagcctcc    88560
```

```
caagtaactg ggactacagg catgcgccac catgcccagc tactttttgt attttttagta    88620 gtggcggtgt ttgaccacgt tggccaagat ggtctcgatc tcttgacctc gtgatctgcc    88680
tgcctcagcc tcccaaagtg ctgggactac aggcgtgagc caccgtgcct ggccttttat    88740
tttatttatt aagtaataca catgcttgga agttatttaa aaaaaaaaaa aaggaatagt    88800
taaaagtaat cccctccca gtgcttttct ccagctgccc cattccttt cctggaggca     88860 aattattatg gccagttcat tatatattct ccagagatga tttttttta ttttacaaag    88920 gtataggttg tagcattctt atataaactg ttgtgtagct tcctttattc catttaatta    88980
ctgggagata cttccatctg aaatataga gatactaatt ttaatagcta catggtatta    89040
tattgtgtgg ctgtaccata aattatttaa cataacccctt attgatgtag gttgtttcta   89100 acctttatt actgcaaaag attgtgccta catcatttaa tgtatatatg agcatatttg    89160
tcagatatat atatatatat tttttgagac agtgtctcac tctgtcaccc aggctggagt    89220
gcagcatcac aatctcacct cactgcagtg tccacctcct gggttcaggt gattcttctt    89280
cctcagcctc ccaagtaact gggattacag gtgcctacca ccatgccctg ctaatttttg    89340 tatctttta ggagagacgg gatttcacca tgttggccag gttggtctag aactcctggc    89400
ctcaggtgat ccactggcct tagcttccca aagtgctggg attataggcg tgagctacca    89460
cacccagcct gtcagataaa ttcttaaaag ggtcaaggaa agtgtttctg aaattttata    89520
catattgcca aattgtcatc ctacatgata tttgtggcag ttttgactct caaaagccac    89580
atgagagagt atctgttttc ccacatgctt gccaaacata gtatagtatc aagcttactg    89640
atcttcacta attggagaag agaaaaaaac tgtaccttgt tgcagttta atttgcattt    89700 cttttatga gcaatagtag atatcttctt aaatacttaa gagccattca catttcattt    89760
tctatgaact gtccatgtcc cttgtccatt ttttagtatg tggttattca tttatttgta    89820
ggcgtcctat atgttaagaa agtttttata caacttttaa ctcttttac atgtttattt     89880 tggcacatat aaattttagc aaacttccc atcttttatg acttctagat tttgtttcac     89940 aaaaaaaagag cttagccagt cattagattt tttttaagttt tctcagattg ttttttaactt 90000 ttgggggggt tttatttcct gtattcaaat attaaattca tctagaattt atcttaaagt    90060
gtaagggaat gatcccactt tatcatttt tcaggagatt acccagttgt tctaatatca    90120
agtatgtctt tgaaatccca tccttatctt gtagcatatt tctgtggttt gggtctattt    90180
ttgaacattc tgttttattc cattgatcat attaatatta tatgtgcaaa cacaaactat    90240
tttaagtata gtagctttgt tgcttttaaa tatcttttaa tttggctact aggccccata    90300
caattctttt tcagaatatt cctggctacc caatttgttt attttttccaa atgaactttg   90360 gagtcaactt ccttaattcc tcaaaatatt ctgcaagtac ttttagtaag agtatattaa    90420
gtgaataatt tgacaactat ctaagaacat attatagctt ttcccttgtt ttgttttttgt  90480 acttatatat tagtatagtt ttaaagttat attaaaatag gtcttccaca ttttaaaaac    90540
ttattcctag tgtattaatt tcttctatta taactacagt attttattcc agtaaaactt    90600
ctgactggtt tgatgctctta taaatcaagg ctataaattt ttcttcagct actttgctga    90660
attctcacaa actgtaacca tttttactt gattctctag gttgaccagt atataatctt     90720
tttatctgta aacaataact ttagcgttgc tttcaacatc tatattctta ttctatttca    90780 ttttttcttgt ttatcaagaa atagctgttt taatagagtt gttttttcgcc caaaagaaa   90840 atagtctttc ttttttctact tatatctttta aaataaatgt aatgagaaag actgtgggaa  90900
```

```
aataaagcag acaccttata caatggatta attttttag tgccatttct tctggctttc     90960
tctattattg ggactctgaa atcttcgtta gtactactct caaaaatgtt cgaatgaatg     91020
caatcagatt caagggtaca agtgcaggtt ataggtga  attgcatgcc ttggggtttt     91080
ggtgtacaga ctattttgtc acccaggtaa taagcgtagt acttaatagg tagttttttg     91140
atcctctccc ttctcccatc ctcaaagtat ccctgctgtc tgttgttccc cctctttgtg     91200
tccatgtgtt cttgctgttt agctgccact taagagaaca tgtggtattt ttctgttcct     91260
ttgttagttt gtttaggata atggcctcca gctccatcca tgttgctgca cagaacacga     91320
ttttgtgttt ctttatggct gtgtagtatt ccatggtgta tatgtaacac tttctttatc     91380
cagtctacta cttacggaca tttaggttga ttccatgtct tcgctatcat taatagtgct     91440
gtgatgaaca tacgtgtgca aatgcctttt atggtagaat gatttatatc cctttgggta     91500
atatgccgaa taatgggatt gctcggtcag atggcaattc taagtcctct gaaattaccg     91560
cactgctttc cacaacagct gaactagttt acattcccac aagcaataag gggataagtg     91620
ttccctttc tctgcaggaa tgattaattc ttttagagag tcaaagatgg aatcctaggg     91680
aagatgatat ctgaggcagg tttagagtca ttgggcaaat aaggggatta agaaggcatt     91740
ctaggcagac agaaaaccaa aggcatgaag ctctgaaaca gcttactatg tttggatatt     91800
tataagctgt tgttattgtt ggagtataaa ctgtaagaga gagtaggagg acagaaaaaa     91860
cagcctgtat gcggggggaa gaaaacattt aaacagaaat tctcaaaaga tttgggcagc     91920
cagcccctct agagaaaaac atagaatcac ctagaaaggg ttttttcataa agtacactt  t   91980
tcatcacccc tattctgtca cctggaatat tgataacact gaagggagtg tgccttatct     92040
ctcaggtgta tttggatgaa atagtttgag aaccatgcag gcaagtttaa gccagtgtgt     92100
taaagagaat atgacatcag atttgcattt tacaatcttc cttttgataa caagggaac      92160
cttaaagggc tggaggggaa gggcagacgg ggctagggga ggagaaccct tttaaaagc      92220
tactgcaggt ggggtgcggt ggctcacacc tgtaatccca gcactttggg aggccaaggc     92280
aggcagatca cctgaggtca ggagttcaag accagcctgg ccaacatagt aaaacccat      92340
ctctactaaa aatacaaaaa ttagctaggc atggtagcag gcacctgtaa tctcagctac     92400
ttgggaggct gaggcaggag aattgcttga acctgggagg cagaggttgc agtgagccaa     92460
gattgtgccg ctgcactcca gcctgggcaa gagagtgaga ctccatctca aaaaaaaaa      92520
aaaaaagct  actgcagtag atcaggagga ggcacagtga taaagagaag atctgagcta     92580
tgaagtggca gtcaagatga ttaaaggaat atataggaag tacagttgat agaacttagc     92640
aagtgattag gtaaatgaag tgctagagaa aataaggggg atattttca attgttttta      92700
gcatttggc  aaaaaattat ttaggaatga aattgatgct agtaactaag agtatgaact     92760
tcccacatta gctggtaatt ttgatcaccc ttgttctcca tgaccataaa tatttagag      92820
ttgctatgaa gacaagaatg tttatttcct gagtagctgt cagttgtcac tatgaaacat     92880
gaaaataaat atcagtttgc tatgtctagg tattccgata tttatccaca attattcctt     92940
aagatatatt agtattttta tagatagata gatagataga tagaaataaa cacattttaa     93000
tttttgtttc catgctcttt agaattcaac tagagggcag ccttgtggat ggccccgaag     93060
caagcctgat ggaacaggat agaaccaacc atgttgaggg caacagacta agtccattcc     93120
tgataccatc acctcccatt tgccagacag aacctctggc tacaaagctc cagaatggaa     93180
gcccactgcc tgagagagct catccagaag taaatggaga caccaagtgg cactctttca     93240
aaagttatta tggaatacc  tgtatgaagg gaagccagaa tagtcgtgtg agtcctgact     93300
```

```
ttacacaaga aagtagaggg tattccaagt gtttgcaaaa tggaggaata aaacgcacag   93360
ttagtgaacc ttctctctct gggctccttc agatcaagaa attgaaacaa gaccaaaagg   93420
ctaatggaga aagacgtaac ttcggggtaa gccaagaaag aaatccaggt gaaagcagtc   93480
aaccaaatgt ctccgatttg agtgataaga aagaatctgt gagttctgta gcccaagaaa   93540
atgcagttaa agatttcacc agttttcaa cacataactg cagtgggcct gaaaatccag    93600
agcttcagat tctgaatgag caggagggga aaagtgctaa ttaccatgac aagaacattg   93660
tattacttaa aaacaaggca gtgctaatgc ctaatggtgc tacagtttct gcctcttccg   93720
tggaacacac acatggtgaa ctcctggaaa aaacactgtc tcaatattat ccagattgtg   93780
tttccattgc ggtgcagaaa accacatctc acataaatgc cattaacagt caggctacta   93840
atgagttgtc ctgtgagatc actcacccat cgcatacctc agggcagatc aattccgcac   93900
agacctctaa ctctgagctg cctccaaagc cagctgcagt ggtgagtgag gcctgtgatg   93960
ctgatgatgc tgataatgcc agtaaactag ctgcaatgct aaatacctgt tcctttcaga   94020
aaccagaaca actacaacaa caaaaatcag ttttgagat atgcccatct cctgcagaaa    94080
ataacatcca gggaaccaca aagctagcgt ctggtgaaga attctgttca ggttccagca   94140
gcaatttgca agctcctggt ggcagctctg aacggtattt aaaacaaaat gaaatgaatg   94200
gtgcttactt caagcaaagc tcagtgttca ctaaggattc cttttctgcc actaccacac   94260
caccaccacc atcacaattg cttctttctc cccctcctcc tcttccacag gttcctcagc   94320
ttccttcaga aggaaaaagc actctgaatg gtggagtttt agaagaacac caccactacc   94380
ccaaccaaag taacacaaca cttttaaggg aagtgaaaat agagggtaaa cctgaggcac   94440
caccttccca gagtcctaat ccatctacac atgtatgcag cccttctccg atgctttctg   94500
aaaggcctca gaataattgt gtgaacagga atgacataca gactgcaggg acaatgactg   94560
ttccattgtg ttctgagaaa acaagaccaa tgtcagaaca cctcaagcat aacccaccaa   94620
tttttggtag cagtggagag ctacaggaca actgccagca gttgatgaga aacaaagagc   94680
aagagattct gaagggtcga gacaaggagc aaacacgaga tcttgtgccc ccaacacagc   94740
actatctgaa accaggatgg attgaattga aggcccctcg ttttcaccaa gcggaatccc   94800
atctaaaacg taatgaggca tcactgccat caattcttca gtatcaaccc aatctctcca   94860
atcaaatgac ctccaaacaa tacactggaa attccaacat gctgggggg ctcccaaggc    94920 aagcttacac ccagaaaaca acacagctgg agcacaagtc acaaatgtac caagttgaaa   94980
tgaatcaagg gcagtcccaa ggtacagtgg accaacatct ccagttccaa aaaccctcac   95040
accaggtgca cttctccaaa acagaccatt taccaaaagc tcatgtgcag tcactgtgtg   95100
gcactagatt tcattttcaa caaagagcag attcccaaac tgaaaaactt atgtcccag    95160 tgttgaaaca gcacttgaat caacaggctt cagagactga gccatttca aactcacacc    95220 ttttgcaaca taagcctcat aaacaggcag cacaaacaca accatcccag agttcacatc   95280
tccctcaaaa ccagcaacag cagcaaaaat tacaaataaa gaataaagag gaaatactcc   95340 agactttcc tcaccccaa agcaacaatg atcagcaaag agaaggatca ttcttggcc     95400 agactaaagt ggaagaatgt tttcatggtg aaaatcagta ttcaaaatca agcgagttcg   95460
agactcataa tgtccaaatg ggactggagg aagtacagaa tataaatcgt agaaatttcc   95520
cttatagtca gaccatgaaa tcaagtgcat gcaaaatacaa ggtttcttgt tcaaacaata  95580
cacacctagt ttcagagaat aaagaacaga ctacacatcc tgaactttt gcaggaaaca   95640
```

```
agacccaaaa cttgcatcac atgcaatatt ttccaaataa tgtgatccca aagcaagatc   95700
ttcttcacag gtgctttcaa gaacaggagc agaagtcaca acaagcttca gttctacagg   95760
gatataaaaa tagaaaccaa gatatgtctg gtcaacaagc tgcgcaactt gctcagcaaa   95820
ggtacttgat acataaccat gcaaatgttt ttcctgtgcc tgaccaggga ggaagtcaca   95880
ctcagacccc tccccagaag gacactcaaa agcatgctgc tctaaggtgg catctcttac   95940
agaagcaaga acagcagcaa acacagcaac cccaaactga gtcttgccat agtcagatgc   96000
acaggccaat taaggtggaa cctggatgca agccacatgc ctgtatgcac acagcaccac   96060
cagaaaacaa acatggaaaa aggtaacta agcaagagaa tccacctgca agctgtgata    96120
atgtgcagca aaagagcatc attgagacca tggagcagca tctgaagcag tttcacgcca   96180
agtcgttatt tgaccataag gctcttactc tcaaatcaca gaagcaagta aaagttgaaa   96240
tgtcagggcc agtcacagtt ttgactagac aaaccactgc tgcagaactt gatagccaca   96300
ccccagcttt agagcagcaa acaacttctt cagaaaagac accaaccaaa agaacagctg   96360
cttctgttct caataatttt atagagtcac cttccaaatt actagatact cctataaaaa   96420
atttattgga tacacctgtc aagactcaat atgatttccc atcttgcaga tgtgtaggta   96480
agtgccagaa atgtactgag acacatggcg tttatccaga attagcaaat ttatcttcag   96540
atatgggatt ttccttcttt tttttaaatct tgagtctggc agcaatttgt aaaggctcat   96600
aaaaatctga agcttacatt ttttgtcaag ttaccgatgc ttgtgtcttg tgaaagagaa   96660
cttcacttac atgcagtttt tccaaaagaa ttaaataatc gtgcatgttt atttttccct   96720
ctcttcagat cctgtaaaat ttgaatgtat ctgttttaga tcaattcgcc tatttagctc   96780
tttgtatatt atctcctgga gagacagcta ggcagcaaaa aaacaatcta ttaaaatgag   96840
aaaataacga ccataggcag tctaatgtac gaactttaaa tatttttttaa ttcaaggtaa   96900 aatatattag tttcacaaga tttctggcta atagggaaat tattatcttc agtcttcatg   96960
agttggggga aatgataatg ctgacactct tagtgctcct aaagtttcct tttctccatt   97020
tatacatttg gaatgttgtg atttatattc attttgattc ccttttctct aaaatttcat   97080 cttttttgatt aaaaaatatg atacaggcat acctcagaga tattgtgggt ttggctccat   97140
accacaataa aatgaatatt acaataaagc aagttgtaag gactttttgg tttctcactg   97200
tatgtaaaag ttatttatat actatactgt aacatactaa gtgtgcaata gcattgtgtc   97260
taaaaaatat atactttaaa aataatttat tgttaaaaaa atgccaacaa ttatctgggc   97320
ctttagtgag tgctaatctt tttgctggtg gagggtcgtg cttcagtatt gatcgctgtg   97380
gactgatcat ggtggtagtt gctgaaggtt gctgggatgg ctgtgtgtgt ggcaatttct   97440
taaaataaga caacagtgaa gtgctgtatc aattgatttt tccattcaca aaagatttct   97500
ctgtagcatg caatgctgtt tgatagcatt taacccacag cagaatttct ttgaaaattg   97560
gactcagtcc tctcaaactg tgctgctgct ttatcaacta gttttttgta attttctgaa   97620
tcctttgttg tcatttcagc agtttacagc atcttcattg gaagtatatt ccatctcaaa   97680
cattctttgt tcatccataa gaagcaactt cttatcaagt ttttttcatga cattgcagta   97740 actcagcccc atcttcaggc tctacttcta attctggttc tcttgctaca tctccctcat   97800
ctgcagtgac ctctccacgg aagtcttgaa ctcctcaaag taatccatga gggttggaat   97860
caacttctaa actcctgtta atgttgatat attgaccccc tcccatgaat tatgaatgtt   97920
cttaataact tctaaatggt gataccttttc cagaaggctt tcaatgtact ttgcccggat   97980
ccatcagaag actatcttgg cagctgtaga ctaacaatat atttcttaaa tgataagact   98040
```

```
tgaaagtcaa aagtactcct taatccatag gctgcagaat caatgttgta ttaacaggca   98100
cgaaaacagc attaatcttg tgcatctcca tcggagctct tgggtgacta ggtgccttga   98160
gcagtaatat tttgaaagga ggttttggtt ttgttttttg tttttttttt ttgtttttta   98220
gcagtaagtc tcaacactgg gcttaaaata ttcagtaaac tatgttgtaa aaagatgtgt   98280
tatcatccag actttgttgt tccattactc tacacaagca gggtacactt agcataattc   98340
ttaagggcct tggaattttc agaatggtaa atgagtatgg gcttcaactt aaaatcatca   98400
actgcattag cctgtaacaa gagagtcagc ctgtcctttg aagcaaggca ttgacttcta   98460
tctatgaaag tcttagatgg caccttgttt caatagtagg ctgtttagta cagccacctt   98520
catcagtgat cttagctaga tcttctgcat aacttgctgc agcttctaca tcagcacttg   98580
ctgcctcacc ttgtcctttt atgttataga cacagctgcg cttcttaaac tttataaacc   98640
aacttctgct agcttccaac ttctcttctg cagcttcctc attctcttca tagaactgaa   98700
gggagtcaag gccttgctct ggattaagct ttggcttaag gaatgttgtg gctgacgtga   98760
tcttctatcc agaccactaa agcgctctcc atatcagcaa taaggccgtt ttgctttctt   98820
acctttcatg tgttcactgg agtaatttcc ttcaagaatt tttcctttac attcacaact   98880
tggctaactg gcatgcaagg cctagctttc agcctgtctt ggcttttgac atgccttcct   98940
cacttagctc gtcatatcta gcttttgatt taaagtggca ggcatacaac tcttcctttc   99000
acttgaacac ttagaggcca ctgtagggtt attaattggc ctaatttcaa tattgttgtg   99060
ttttagggaa tagagaggcc cagggagagg gagagagccc aaacggctgg ttgatagagc   99120
aggcagaatg cacacaacat ttatcagatt atgtttgcac catttaccag attatgggta   99180
cggtttgtgg cacccccccaa aaattagaat agtaacatca aagatcactg atcacagatc   99240
gccataacat aaataataat aaactttaaa atactgtgag aattaccaaa atgtgataca   99300
gagacatgaa gtgagcacat gctgttgaaa aaaatgacac tgatagacat acttaacacg   99360
tgggattgcc acaaaccttc agtttgtaaa agtcacagta actgtgactc acaaaagaac   99420
aaagcacaat aaaacgaggt atgcctgtat ttttaaaaaa agcttttgt taaaattcag   99480 gatatgtaat aggtctgtag gaatagtgaa atattttgc tgatggatgt agatatatac   99540
gtggatagag atgaagatct taattatagc tatgcagcat agatttagtc aaagacattt   99600
gaaaagacaa atgttaaatt agtgtggcta atgacctacc cgtgccatgt tttccctctt   99660
gcaatgagat accccacact gtgtagaagg atggagggag gactcctact gtccctcttt   99720
gcgtgtggtt attaagttgc ctcactgggc taaaacacca cacatctcat agataatatt   99780
tggtaagttg taatcgtctt cactcttctc ttatcaccca cccctatctt cccactttc   99840 catctttgtt ggtttgcaac agcccctcct ttttgcctga ctctccagga ttttctctca   99900
tcataaattg ttctaaagta catactaata tgggtctgga ttgactattc ttatttgcaa   99960
aacagcaatt aaatgttata gggaagtagg aagaaaaagg ggtatccttg acaataaacc  100020
aagcaatatt ctgggggtgg gatagagcag gaaatttat ttttaatctt ttaaaatcca  100080
agtaataggt aggcttccag ttagctttaa atgttttttt tttccagctc aaaaaattgg  100140
attgtagttg atactacata taatacattc taattccctc actgtattct tgtttagtt  100200 tcatttattt ggtttaaaat aattttttat cccatatctg aaatgtaata tattttatc  100260 caacaaccag catgtacata tacttaatta tgtggcacat tttctaatag atcagtccat  100320
caatctactc attttaaaga aaaaaaaatt ttaaagtcac ttttagagcc cttaatgtgt  100380
```

```
agttgggggt taagctttgt ggatgtagcc tttatattta gtataattga ggtctaaaat   100440
aataatcttc tattatctca acagagcaaa ttattgaaaa agatgaaggt ccttttata    100500 cccatctagg agcaggtcct aatgtggcag ctattagaga aatcatggaa gaaaggtaat   100560
taacgcaaag gcacagggca gattaacgtt tatccttttg tatatgtcag aattttccca   100620
gccttcacac acaaagcagt aaacaattgt aaattgagta attattagta ggcttagcta   100680
ttctagggtt gccaacacta cacactgtgc tattcaccag agagtcacaa tatttgacag   100740
gactaatagt ctgctagctg gcacaggctg cccactttgc gatggatgcc agaaaaccca   100800
ggcatgaaca ggaatcggcc agccaggctg ccagccacaa ggtactggca caggctccaa   100860
cgagaggtcc cactctggct ttcccacctg ataataaagt gtcaaagcag aaagactggt   100920
aaagtgtggt ataagaaaag aaccactgaa ttaaattcac ctagtgttgc aaatgagtac   100980
ttatctctaa gttttctttt accataaaaa gagagcaagt gtgatatgtt aatagaaag    101040 agaaacatac tatttacagc tgcctttttt tttttttttc gctatcaatc acaggtatac   101100
aagtacttgc ctttactcct gcatgtagaa gactcttatg agcgagataa tgcagagaag   101160
gcctttcata taaatttata cagctctgag ctgttcttct tctagggtgc cttttcatta   101220
agaggtaggc agtattatta ttaaagtact taggatacat tggggcagct aggacatatt   101280
cagtatcatt cttgctccat ttccaaatta ttcatttcta aattagcatg tagaagttca   101340
ctaaataatc atctagtggc ctggcagaaa tagtgaattt ccctaagtgc ctttttttg    101400 ttgtttttt gttttgtttt ttaaacaagc agtaggtggt gctttggtca taagggaaga   101460
tatagtctat ttctaggact attccatatt ttccatgtgg ctggatacta actatttgcc   101520
agcctccttt tctaaattgt gagacattct tggaggaaca gttctaacta aaatctatta   101580
tgactcccca agttttaaaa tagctaaatt tagtaaggga aaaaatagtt tatgttttag   101640
aagactgaac ttagcaaact aacctgaatt ttgtgctttg tgaaatttta tatcgaaatg   101700
agctttccca ttttcaccca catgtaattt acaaaatagt tcattacaat tatctgtaca   101760
ttttgatatt gaggaaaaac aaggcttaaa aaccattatc cagtttgctt ggcgtagacc   101820
tgtttaaaaa ataataaacc gttcatttct caggatgtgg tcatagaata aagttatgct   101880
caaatgttca aatattttga ttgcctcttg aattcatttg ctaattgtat gtgtgtgtgt   101940
ttctgtgggt ttcttttaagg tttggacaga agggtaaagc tattaggatt gaaagagtca   102000
tctatactgg taaagaaggc aaaagttctc agggatgtcc tattgctaag tgggtaagtg   102060
tgacttgata aagcctttgg tcttaaatct tgggcatttt gatttgtaaa tctgaccctg   102120
agaattgggt tacccagatc aaagactcat gccagttaaa aagaacatta cctgtatttt   102180
ttatcatgtg ttatctctta agaagaggca gattagttct aaaatcaaca aattgtattt   102240
aattgaaata atttagtgat gaggaagagg tccattctag tgcctgctaa atgtataatc   102300
cttcttagaa tgtgaagttg tccttaaact tttaaatacc ttcagttaat ctttatattg   102360
tcatttatga aaaccttgaa ctaagactta tgtatctttc atctagctct ggttttaatg   102420
caggtagcat ttaattgtcc ccactgtact gggtatagtc tgctaaacat taaggagtag   102480
ttttgcatct ctccttgttc tgatactagg gtcaaagccc acttttata gatgggcagc    102540 aaaaggcaca ttggacatgc tgataaatgt tgccctaatt gtgatctaaa catgataaaa   102600
tatacataca taagtgccct tatctgctgc aagtgaccct tgttttgttt tggttggggt   102660 gggggtgtt tgggatggaa tggtgatcca cgcaggtggt tcgcagaagc agcagtgaag   102720
agaagctact gtgtttggtg cgggagcgag ctggccacac ctgtgaggct gcagtgattg   102780
```

```
tgattctcat cctggtgtgg gaaggaatcc cgctgtctct ggctgacaaa ctctactcgg    102840
agcttaccga gacgctgagg aaatacggca cgctcaccaa tcgccggtgt gccttgaatg    102900
aagagtaagt gaagcccagg gcctctcccc tctttgcggc cactgatagg aaagcccaat    102960
ctttggttga aaggaagaga gttcagcgtg cacttttaca tttataaaat gggcatcaaa    103020
atgcctgttt ggcagtcatg cgataagaag ttgtatttgc taatgtgaat aacttgagat    103080
gatttcatta tctgaattgt acagtttagc cattaattag gagcagtcag agtgtctgta    103140
accacatggc ctcagttata ccataaactt gaaattgttt atgtgctcac atgctacaag    103200
tgacggctcc tgtgtgcctg ccactatat tagtatgtat tgactccact tccatgttgc    103260
agtatctgaa acagaaagta agtctaatga gaaactttgg gattcccagg tcaaatacct    103320
tccatatgta tgtagcaaaa acaaaataca aagcctagaa gttctgtaga aatagaactg    103380 attttactt tcattcaaac tattcattat ttccacaata gtaatcaaaa ctgcttctac    103440
ttttactgct gctaaatgat cagcaaatta ctggatatgg atatatatta ttttccagga    103500
atataagaat ttagaataga actgcaagag tatgcactta aatatattta gtgcatccag    103560
ttgctaatgt tttgttttaa acaccatcca ctttgcatga agtctaaacc ttcagttgga    103620
aaaagcctca ttttttaatat tcctctactg tgctgataat cctgtataac actaaaagaa    103680
tagatgaatg ttcacggtgc tacacagaaa tgtttttttt tttttttttt tttttttga    103740 gatggagttt cgctcttgtt gcccaggctg gagtgcaatg gcgcgatctt ggttcaccgc    103800
gacctccacc tcccaggttc aagagattct cctgcctcag cctccctagt agctgggatt    103860
acaggcatgt gccaccacac ccggctaatt ttgtattttt agtagagaca gggtttctcc    103920
atgttggtca ggctggtctc gaactcccga cctcaggtga ttcccacct cggcctccca    103980 aagtgcctta caggcatgag ccgccgcgcc tggccagaaa tcttacaagt tatttgccc    104040 acgattggtt ttaaaataat tttaattttg cactatttcc tttagtgtct ttttctctgc    104100
atccaccaaa ctatagaatc atttgctgag cttataagaa atgctcatac tgctcattgc    104160
aacagctagc caaatttgtc ctttgctgtt taaaactcta actagcatgg ttttactaaa    104220
tttatgttaa cacagtttct ctctctgggt tgtggggaga caaatcaatt ataaataatc    104280
tctttagaaa agttactctt tctatatgaa agtgtgactt gactttctat gataattatg    104340
atccaaaaat tttatggtgt gtacctgacc acttttacaa atgattaatt ggaaggtaga    104400
aattgctgat tcataacatg taacttataa acttatgatg gactacttta agcataaatt    104460
tttttttttt tttaagaca gagtttcact ctgtcaccca ggctggagtg caatggtgcg    104520
atctcggctc actgcaacct ccatctcctg ggttcaagca attctcctgc ctcagcctcc    104580
cgaatagctg ggattacagg catgcactac cacacccagc taattttgta tttttagtag    104640
agacagggtt tctccatgtt gatcaggctg gtctggaact cctgacctcg ggtgatccgc    104700
ccgcctcggc ctcccagagt gctgggatta caggcatgag ccactgtgcc cagcctgaaa    104760 tatttttta atctaccctg actcctcttg ctctttctga agaaaatttt ttaaaaatgt    104820
atgtaggtgc ctttaattag aaaaaaaatt aaaaattaag gcaacttgtg ctcatattgg    104880
taatagcatt tcttcaaga actcagtaat actgcattgt ctttaaagca taatatctct    104940
tagacttgac ggtttgagat tctaaatcac tgaagaacct cttgtgaaaa tgatagtttt    105000
aaaatttctt ttcaaaaata gtcctattgc aaaatgtttg attttcttga agtttcctgg    105060
aaactatatt tcattcattg taatgaattt aattttcatt aacatagatc tctaatatt    105120
```

```
ttctcagctc accacaacct ccacctcccg ggttcaagtg attctcatgc cacagcctcc    105180
cgagtagcta gaattacagg cacccacccg gctcattttt gtattttag tagagacagg     105240 gtttcaccat gttggccaga ttgatctcga actcctggct tcaggtaacc cacccaccct    105300
ggcctcccaa agtgctggga ttacaggtgt aggccaccat gcccagccag cttttccata    105360
attcttataa atgccaatgc ctgaaatgga atctgacata taaaaaatta catgaagaac    105420
ttttattatt ttgcatttga aaaccatgaa aaatagttgg accagagtct cagaaagctt    105480
gtagtttgtt agtttaactg ctctaaatgt caggcagata caaaactatt aaaagacatg    105540
cttcaaatat gaagacaatt taaaagcaca gctgtacact tttgcttttt gtctagtttc    105600
aaggtaaaga tgaataatca tttagataat gcttaagcta tgcttatgca tacttagagc    105660
aattctccaa aataaaaaat tttaatactt aaatacatga ttaaaataga cacgtatcca    105720
atgtcaatac agactttact cagaaatagc ttttgaagtt tcttctaccc cataaataga    105780
ttttatttta tggctggcag aaatgaaaat tacaacttt tgccaagaac agagaataga    105840
ataatctcaa attgggctg cggactcagt tttatgttca aagctgtgtg aacctcatca     105900
ctgagttctt acaaatccct gtgtccacat gctccaaacc acccactgtg agttcagaaa    105960
agaactctga gtgcatcttt cagtaggaaa gtaaaaactg attttttacat ttcctttgag   106020 ccaaaccagc tgtttcttct ttaaagattt ccctttgaga tttccatttt atgactaagt    106080
ctaaccagta ttttttttggc aagtaagagt tgtgggagtg tatctgtcat cataaggaaa   106140
tcaaagccag aaatgccttc tgccatggtg ggtgatgtta acatttcaa ggaactttat     106200 attataaaaa ttgtcaaaca taaaggaaa agtgcaatat aatgaattcc atggacccat     106260
cacacagcat caatatttat caacatttta tcaatatttt ttcatatatt tttcccacat    106320
ccactcccac tagtgtttga aagcagaaga cagataactt accatcttac ctgttaacat    106380
ttcaggatgt atttctaaca ggtaaagact ttatcattta atatttagac tgtgtttgtt    106440
caaattatct gattagattc tatttcagaa aacacacaca taaacaaaaa tgataatgag    106500
aaaaagaaag cccttccaca tgattgacac ttctgagtag tgtgatccca gttcatgtcc    106560
attgtctggg atagctatta aataaaactt cctctcataa aattctctcc atttagaaga    106620
taaattctgt gattcacaag cctctttta tttataatag ccttcccct ttctttatga      106680 atttgaattt gtttttttaaa gaaactgtga ttttctctgt aaaattcccc acattctgga   106740
tttggccgat tcatcttgg ttcttttgtt tactttaacc tattcctcta tccccagtat     106800
cttctgtgga ctggtagttt gactggttct ttttcttttc tttttttttt tttttttttt   106860
tttttgagac aggctctcgc tctgtcgctt aggctggagt gcagtggccc aatctcagct    106920
cactgcaacc tccacctccc aggttcaagc tattctcatg cctcagcctc ctgagtaact    106980
gggactgcaa gcatgtgcca cctcatcctg ctgattttg tactttagt agagacgggg      107040 tttcgccatg ttggccaggc tggtctggaa ctcctggcct caagtgatcc gcccaccttg    107100
gcctcccaaa gtgctgggat tacaggcatg agctatcacg cccagctgat ttttaagtaa    107160
tataagtatg tgtgcatgta tagtatacat tggcaaaaac acttcataag tagtgctaaa    107220
atcatcttat ttatatacat caggagacac ataatgtctg tttgtttccc attttagtga    107280
tattaagagt gtttagcatg tttagttgtc agcctgatcc atcattatgt tcttcatcaa    107340
actttcacca gatagtttca catcaattga tgatcattgc ctgtttctat tattttgttt    107400
tcaagttgac agttttctct cacttgatgt tgtgtaaatt tagttatata aagttaaatt    107460
attttgctat ttttctatg ctgtatacat ttgaataact gacctaattt ttactttaaa    107520
```

```
aatattttac aattagaagt ccaaatagta aatcaaaggt taagaatttt tgcagaaatc   107580
tgttatatag atgacatttt aatatttgcc ctttatatca tttaccatga gccaaatttc   107640
aagtcatatt aaaatgactg tcatgtgcta attctaacaa tatttgaaag acccctatca   107700
aaataaatat acctttagt agccactta ttagaaaatc aactttaagt tattccccca    107760 tgttttttc taattgagat ataattcaca taccataaaa tttaccctt taaagtatac    107820 aattcagttg tttcagtaca ttcacaaagc tatgcaaatg tcacctctac ctagtttcag   107880
aacgttttca tcattcccag aaggaaaccc tgtatttatt aggcagtcac ttccccttct   107940
ccccttcttc cttcctctaa gtggcaacca caaataaaca ttcagtttct ctggatttac   108000
ctattctggg cattttgtat tagtgaaatc atgtatttgg cctttctctc tggcttcttt   108060 catgtaccctc aatgttttca agtctcattc attttattaa aaaaaaaaag tacctttttt   108120
ctttttcttt ttttttttt tgtccacgta tatattcaca ccacattttt tgagacagag   108180
tctcgctctg ttgcccaggc tagggtgcaa tggtgcaacc tcagctcact gcaacctctg   108240
tctcccgggt tcaagtgatt ctcatgcctc agcccccaag tagttgggat tacagttgtg   108300
caccaccaca cccagctaat ttttgtattt ttagtagaga cagggtttca ccatgttggc   108360
taggctggtc tcaaactcag cctcaagtga tccttctacc ttagcctcct aaagtgctgg   108420
gattacaagc atgagccact gtgcccagcc acatttctt tttccatta ttagttaatt    108480 gacatttgga tcgtttctac tttttggcga ttataaatta tgctgcaatg aacatcggtg   108540 tacaagttt tgtgtgaaca tgttttcagt taccttggga tatacaccta ggagtgacat    108600
tgttagtaat atggtaactt tatgtttaac tttttgaaga actgccaaac tgttttccaa   108660
agtagcttta tgcttttaca tttctgccaa caatgtatga aggttccagt gtatctccac   108720
atcctcaaga aaatgttatt gtctttttaa ttgtaaccat ccaagtgggt atgaagttta   108780
tctcgtgatt ttgatttgca ttttcctaat ggctgatatt gggcatcttt tcacgtgtgt   108840
attgaccatg tattttttg agaaaagtct acttatatgt tttaattgt attattttta     108900 gagttgtaag aatatgttat gttgatactt gaactttgtc aaatgcctgg tttgcagata   108960
ttttctccta tcccacaggt tgtcgcttca ctttgataat gtccttaaag tacaaaagtt   109020
ttaaattgat tttgatgaaa ctcaatttct ttttaattgg cagcttgtgc atttggggtc   109080
atatttaaga aatcattgcc tcattcaaga tctgaaagat ttacacctat gctttcttct   109140
cagagtatta aactttagt tcttacattt agattttaa ttaatgttga gttaattga     109200 tggtgagaga taagagtcca acttcattcc tttgcaagta gctgtccagt tttctcagca   109260
ccatttgtta aaagactgtt tttttcaat taactgacca agatgtatgg gtttatttct    109320
ggactcttaa ttctgttaat ctgcatgact tttcttatgc cagtaccaca ctgtgctgat   109380
tcctgtagtt ttgtagtaaa tttgaaatc aagacaggta agtcttccaa ctttgtactt    109440
ttgcctacca tgtttcttgg gtttccatat gcattttaag atcagcttct ccgtttcctt   109500
tctggatttt tttttttttt tttttttttt tttttttggt ggagctggag tcttactata   109560
ttacccaagc tggttttgaa ctcctggcta aagagatcct ccctcctagg cttcccagag   109620
agctggggtt acaggcatga gccaccacat ccaaccccct tctgggactt tgactggggt   109680
tctgttgaat ctgttggtca atttggagag tattgatatc ttaacattaa agcttccaat   109740
ttatgaacac aggctatttt tccatttatt cttaaatttc tttcagtaat gttttggatg   109800
aaacatgtac aaagtcctgc acttttatt ttttttaaga cagagtcttg ctctgctgcc    109860
```

```
cagtccagag tgcagtgctg ccatctcagc tcactgcaac ctccacctcc gggttcaagt    109920
gattctcctg cctcagctgg aactacaggt gcgcgccacc atgcctggct aattgttttg    109980 tgttttggt ggagacaggg tttcaccatg ttggccaggc tggtctcaaa cacctggcct    110040
caagtgacct gactgccttg gcctcccaaa gtactgggat tacaggcatg agccaccacg    110100
cctggcctgt acttctgtta aaatttttc tatgtatttt ttttatccta ttgcaaaatc    110160
aaattttttg ttgataatat atggtcataa atttcattt tatatattgg tctcatatcc    110220
taccaacttg ctgaactagc ttattagcac taactttttt tggtagattc cttaggattt    110280
gctgcataca agattatgtc atctacaagt agagatagtt ttgtttcttc acttccaatc    110340
tgggtggctt tatgttttt tcttgcctga ttacccagtt agaacttcca gaaaatgtca    110400
ggtacaatta acaactgcaa acatccttgt cttattcatt ttagaaagaa attttagtt    110460 tttcaccatt aagtatgata ctagttgtag gttttgttta aaaaagact gtgtcaagtt    110520 cagaagttcc cttctgttgc tagtttgttg aataatttta tcacgaaagg gtgttgaact    110580
tttctcaaat gctgtggcta catctaatga aatgatcatg cgttcttctc ctttattcta    110640
ttaatatggt atattatatt gattcattt tatacattag attaacatta tatttctgga    110700
ataaatccca cttggcctca gtgtgtatta cttttatat attgctggag tctgtttgca    110760
ggtatttcat tgaggacttt cgcatctctg ttgataaggt atactgatct ttagttctct    110820
tgtgatatct ttggttttgg tgtcagagta attctgagtt cacaaaatgc attgggaaat    110880
gttcccttct ctatctttg gaagagttta caaaggattg gtttaactct tttttaaatg    110940
tttgaggaaa ttctctaccc ctgggctttc ctttgtggga attttaaac attttaaaa    111000 tagattattt ttaaagcaat tttagggtaa aagcacattg aatgaaaggc acagagcttc    111060
cttaagtaca tgctgcccct gtatgtgcat agcctccctc attatcaaca tccttacca    111120 gaatggtaca tttgttgcag tcaatgaacc tgcattgaca attgtcgatg aaagttcata    111180
gtttagagtt cacctttggt gttatgtatt ctgtgagtct ggatccatgt ttaatgatac    111240
tcattcacca ttacagtatc attcagagta atttcactgc cttaaaagtc ctctgtaccc    111300
tacctatttt tctctcctac cccactaacc cttagcaacc aatgatcttt ttatctcaat    111360
aattttgcct attccagaat gtcatatagt tggaatgata cagtatatgg agccttttca    111420
gactggtttt tgtcacttag taataagctt ttaaattttc caccatgtca tgatcgttca    111480
tttcttttca gcattgaata atattccatt gtctggttta tcacagttga tttatccatt    111540
cacatagtga aagacatctt agttgcttcc aagttttgac aattatgaat aaagctgtta    111600
taaaagtatg taggtttttg tgtggacaaa agttttcagc tcctttgagt aaataacaca    111660
gagcacagta gcttgattga cagtaagagt aagaaatatt ttttctcagt ctgtgtctta    111720
ttttttcatt cacttgacag tgccatttgc agaacaaaca gaaagtttta atttaatga    111780 agtctaggtt atcagttaat tcatgaataa tgttttggt attgtatcta aaaagtcaac    111840
accaaggtca tctatatgtt ctgtgttatc ttccagaaat tttatagttc tgcattttac    111900
atttagggct gtgacccatt ttgcattaat tttgcaaaag ctataaagac tatgtataga    111960
ttcacttgtt tgcatgtgga gttgtccagt tgttcccgta ccatttctta aagactatct    112020
ttgctttatt gtattacctt tgctactttg tcaaagatca gttgattata attaagtggt    112080
ctgtttctgg actctttatt ctgttccatt gatatatttg tctagacttt caccaatacc    112140
acactatctt gttaacttag ctttagagt aagtcttgca atcatgtagt gtcagtcctc    112200
tgacattgtt tttctccttc agtattgagt tggctattct tttgcctatt actaagtaaa    112260
```

```
aaaagcagtc tgaaaaggct atatatacag tcatttattg gtcttttgcc tcttgatata    112320
aactttaaaa ttactttgtc agtatcctca aaatcttgca ggaattttga tagattgcac    112380
tgcatttcta gattgagtta gaaatactgc catcttgaca atacacatct tcctatccat    112440
gaacatggaa catctctttc ttggatatcc ttcattagaa ttttgcattt tccccatata    112500
gaccatgtac atattagatt tatacataaa tatttcattt ggggggggtgc taatggtaat    112560 gtattttat ctcagattct gcttgtacat tgctggtatg cagaaaagtg atcaacttttt    112620 gtatattaaa cttgtttcct gcaaccatgt tatataatca ctttagatcc agttttttt    112680 tttttggtca ttctttcata ttttctaggt gatcatgtca tctagcaaag acaacttctt    112740
tctaatctgt ataccttta ttttcttgtc ttaatgtatt agctagcatt ccagtatga    112800 tgttgaaagg cattggtgag aggcaacata cttgccttgt tcctgatctc agcaggaaat    112860
cttcaatttt atgttagctc tatggttttg tagatattct ttatttacat taaatatgtt    112920
agctgtatgg ttttgtatat attctttatc aggttcaggt agttccctc ttttcctagt    112980 ttactgagag gcttttgaaa atcattaatc agtgttggat tttgtaaata ctttttttcc    113040
acctattgat attaccatat gattttttctt tagcttatta acgaaatgga ttacattaat    113100
tgattttcaa attttgaact agactggcat acctggagca aatcccacat ggttgtgata    113160
cattatttat gaatgcattc atggtcatgg ttgctattag tctgtagtta tcttttattg    113220
taaagacttt ggtgttggta ttaaggtaat gctgccctca tagaataagt tatgaagtat    113280
tttctctgct tctgtcttaa ttgagattgt agagaattca tataatttct tccttaaaac    113340
tttggtagaa atcagaatga accatctgtg tctggtactt tgttttgaaa agttattgct    113400
gattcaattt ctttcataga tataggccta tttagattat tattttgcat aaatattggt    113460
agttgtgtcc ttcaaggaat tggtccattt caccttgatt attaaatgtg tgggcacatt    113520
tgttcataat atttctttat tatcctttgt ttttgagaca gggtctcact ctggttgccc    113580
aggctggagt gcagtagtat gatctcagct cactgcagcc ttgacttcct gggctcaagt    113640
gatttaccca cctcagcctc ccaagtagct cggactacag gcacatgcca ccatgcctgg    113700 ctaattttt tattattatt agagatggag ttttcctatg ttgcccagtg tggtcttgaa    113760
ctcctggact caagcaatct gcctgcctca gcctccaaag agtgatggga ttgcaggcat    113820
gagccatcac acctagcctg atggcagaac ttttaggaa caatagaatg gtatatggca    113880
ttttcaaaaa ttgttttccc ctcctcctat ggaagcatga agggattttt ctctagtatt    113940
cattgtgaga acctcatctg gctcctgaat gtagaaaact cacaaaactg tgaggaacct    114000
attatgactg gatgcctttg gagttgttca cactgaacct ccagcaattc atcaattata    114060
tttcagattt tcctatccca acactggttc ctacagaggt ttctgctcca gtaagctgta    114120
attcttttta tccatctgct tccttggttg tgagggcagt gattttccct gtgacctcat    114180
ttctctgaca gatctaagta gtcttgatta catcttttaa cctgttgtag gtatattcag    114240
attttctatt tcttcttcag tcaatttag tagtttgtgt ttttctagaa gtttgttctc    114300
tagctctgct ttagctccat ccaataaaat atgagtatgt cgagttttca tttacaacaa    114360
ggtattttct aatttctatc atgtttttttt gattcctgac tgtataggag tatatttta    114420 cctattaccc aaatttgctt gttattcatg tataatttta tcagaaaaca cactttgcac    114480 aattttgca gtgttacatt tatttagact tgttttataa cttgacatac agtccatcct    114540
ggagaatgtt tcacgtgtgc ttgagaagaa tgtgtatatt cagctgttgg tgggtggcat    114600
```

```
gttttataga tgtctgttag acctagttgg tttatagtgt ttttttacaac ttctgttttc 114660
tttttaatct tctatctact tttagccatt attgaaagtg gattagtaaa ttatctatttt 114720
attcctttaa ttctgccatt ttttgcttca tgtattttgg tgctctgttg cttattacat 114780
gtatgtttac atttgttaca tcattttaat ggcttgaact ttttattata aaatgtgtat 114840
atcttgtaga tatcgtatag ttaaatcttt ttaaaaattg atattgctag tctttgcctt 114900
ttaattttc aatttatata catttaacat aattattgat aaggtaggat ttgtctgcca 114960
ttttgtctgt atcttgtctt ttttttgtgtt caatagatat tttctagtgt actgttttaa 115020
ttcccttgtc ttttactaaa ttttttgatg ttcttaatgg tttccctggg gattacaact 115080
aacttataac agctagtctg aagtaatacc aatttcatta caatataagg aaactttgtt 115140
cccatatagc tacattccct cttttttactc tgtgctatta tacaaattac attttatttt 115200
atgcccatta acacagatta tgtttttttct tttaaatcag attgatattg tcatttaaat 115260
caaatatgag aaaaatagtt acaaaaaaat acatatatga tttcatattt acctatgtaa 115320
ttatctttac tggtgctctt taagttctta ggtgtatttg aggtactgtc tagtgtcctt 115380
tcctttcagc ctgaagtata catttagtat tttttgtagg acatgcctga aaacaataaa 115440
ctcttattta tcagagaatg tcctaattta ttatataata catttctgaa agatagtttt 115500
gcaaaataca gaattcttgg ttggcagtct ttttcttgtg gttctatgtc attctactgc 115560
cttctggtct tcattgtttc tgatcagaga tcagctatta atcttattgg gaatcctgca 115620
tacatgataa tcatacagtt ttcatgattt tcttgtgttg gctttcagca gtttggttat 115680
gatgtttata tgtatgcata tctttgggtt tatgttacat ggagttagtt gagcttcttg 115740
gacatgtaga ttgatgttgt tcatcaaatt tgagaagttt tcggccatta tttttcaaat 115800
attcttccta ttctttattc ttcatcctct actttgggga cctgcattat gtctatgttg 115860
gtatgcttta tggtcttcca cagatctctg aggttctgtt tatgttttca tttttcagac 115920
tgaataatct caattgactt atcttcaagt cccttttttcc cctccttttc aactctgcta 115980
ttgaacccct ctaatttta ctgcagttat tacactttca gctttagaat tctatttaat 116040
aatatctttt tcttgagttt atctcatgta tttaataaaa tgctgtagtc ttacttttagt 116100
tatttaaata cagttttctt tcattatttg ggcatacatg aaatagctga cttaaagtct 116160
ttgtccagtg gcctaacatc tggactttt caggaatagc ctctattgac tactttatag 116220
gggccatact ttgtttctgt ttctcttaat tgtttagaca ttttaaacta atgtaatggc 116280
tgagagcagt ggctcgtgcc tgtaatccca gcacgttgag aggccaaagc aggagcatca 116340
cttaagccca ggagttcaag actagcctgg gcagcatagt gagaccctgt ctctacaaaa 116400
ataaaaataa ataaaataat ataatctggt aaatctgaaa atcagattct accccctgcc 116460
cagaatatgt tactgtttct ggtggttgtt gtttatttct ttttaactac tcctataaag 116520
tttgtattgt ttctcataga tagccatcga agtctttgct tggttaactt agaggtcagc 116580
taaggattag acagaattcc ttaggtgcct gagatcaata agtcagtctt tgacaaaggg 116640
gtctgtatgt gtgttggggc atgcattcaa cactcagcca ggctatttgc agctctggat 116700
tagcctttat tccctgcttg tgcagagtct caaggttaga ctgtggtgag agtttagggc 116760
tttctgaggt cttttgtggg ccctacagtt gcatgtggct ttctaaattc ccaggaatat 116820
attttcaaag cctcctgtgg atcatctcat ttcccaggta atttacttttt aagctttttt 116880
agttatctta tgttttgctc cagttattag ctacacctga gtcagtgaca atattcaaca 116940
gctgcctatg attatttgac aaatgcctct gtggaaaagg tggttcacac taggtgaact 117000
```

```
ccaagttaga taaagtaaag ataaccttac tagtgggatc ttccaggaaa ctaccaaaca  117060
ggtcaaataa tgtaaggtct ctgtgaatgg gactttagag tatatccaac cagtctagag  117120
tatatccaac caatctggcc tcctctagtg gcagcctggc tgctgctttt cataataaat  117180
gtgggctgtt ttgatttgaa ggctaccata gagctgtggg gaaagttaaa ataccacaga  117240
gctcactctt ctcactgaaa tcctgtcttt ttttcccttg aacaaattct ccctatattg  117300
ctgcaagctt tttgctaatt tccagatctg aaaaagctga ttctgacaat atttatcagt  117360
acttttattg cttttatgga ggataaaatt ttcagagatc cttattctgc cattttttgct 117420 gacatgtgta aagtgatcat ttctaattgt aaaattcctt ttgcatttat tagctggaat  117480
actttacagg acttttcctc atcaaccgtt agttaccatt taatatagtt tgtaagaatg  117540
atagaataaa tgcatggcaa gaatctttac ttctcaaatt tcagagattt tgatgggaaa  117600
ttatatttag agatcacaat cagtgtctag atgtgctccc tgctatggag gtgtcattac  117660
ttttaggctt ttttaatggg caaatacatg aagtaattat tttttagaaa gaaaatctga  117720
gattaactca aatcattaat tcatactgat ttttcctatt catagttgac agagtattat  117780
tatcttttgt tctgcttctc ttgtacactg aaattcttgg tttttgatat taacaattat  117840
ttacttatat cacaatatac atacattaat ttaaaaataa tttacagtgc tacctgaata  117900 tttttttcttg taagttgttt tatctctctt tgcttacttg tatgtttgtt tattgtcatt  117960
agaatgtatc aaactagggc tataaagctg taatactata ttttagccag aaactaggac  118020
ctagcactca aatgcccatc aatggtagaa taattcatca catttttata agatggaata  118080
tggtactcaa tgaaaatgaa taaagtacaa ctacatgcag tgatttggat ggatatccca  118140
aacataatgg aaaaagcaca cacaaataag cttatattat ataattccat atacctatgt  118200
atatatcaag tataaaagta ggcaaaacaa gctactgatg gtggcacaca cctatagttc  118260
cagctatttg ggaggctgag gcgggaagat cacttgagcc cagaagttca ggttcaacct  118320
gagcaacata gcaagacccc atctgtaaaa aagaaagcat tattaacata aaaataggca  118380
gaactactat attcttagag aagttactgt tagggagaca gacagtgagt gactgaaagg  118440
caaaatgagg ggaaattcca ggggatagta aatattttgt ttcttagtgt gggttctact  118500
taactgggta ttttccattt gtaaactgta aaattatgtg cacttttctg tatgtgtatt  118560
acattgcaat aaaattgttt aaaagtcaat tgaaatagtt ctgtgtgtgg ttatgccaca  118620
gcttaataca gagttagatt agacttcttt tcaaactcat tttgcatata gacacctata  118680
atatcagctg cacagcctat ataatgctat ccatagcaat gaatttggtc ttttgatttt  118740
tcaggagaac ttgcgcctgt caggggctgg atccagaaac ctgtggtgcc tccttctctt  118800
ttggttgttc atggagcatg tactacaatg gatgtaagtt tgccagaagc aagatcccaa  118860
ggaagtttaa gctgcttggg gatgacccaa aagaggtttg tttacttcct gatgtataat  118920
cgctttattt ttcatagaga attcattagc ttagatgaag tgaacaatat gacatatctt  118980
ggtaagctct tattaatcaa agttttctcc aaactgtaga tacacactat tttttaagtt  119040
ggcataataa tcatattatg ccaaaataat agataaaatt tgagcaacaa aaacttcctc  119100
tttggtcttt tatgttaatt ccaaagtttt aaggggtgt cacttcattg ttaaaactaa   119160
atgagaattg gtgatgtttt tcatattttg actctgaatt atggaagtta cataagtact  119220
acattcagaa aagaccattt ttagtcacat ttatgtgcaa tgagattcaa ataatttaaa  119280
gtcactgtaa tgaatgcatt taataaagtc actgtaatga atgcatttaa gtaactaaaa  119340
```

```
catttagatt ttaatataac tctgtaatgg aaataaatgg acactaattt ctcactgaag   119400
tcattggttt ttgtcttgtc tgtagaatac gtatttctta taatttgcaa attgataaat   119460
ttaacaactt ttgggtggca tgtagtctag agtatagata cttcttgact tatgaggaga   119520
ctacattcct ataaatccgt tgtaaaatga aaatccattt ataccccca ataaacccat    119580 cctaaagtaa aaaaaaaacg aagccattat aggtcaggga ctgtctccgt actaattgaa   119640
tgatgagaaa acctcagtat atttagcatt tagctatgac cacattttca gtcattctat   119700
acacttacaa ttatcttttg aatttcgaat acaattaaaa tatttccata ctatagatat   119760
tataacattg atgagtccct ttaaatgaag aatttgttaa ccttattaag ctttcactta   119820
ctattatagt cacagttaat aaagcaagtg caaaaactcc tgaaatcaca gtataagttt   119880
tttaaaggat gttttcaata attaaagttt acttaaatgt gcgagacatc atttcataag   119940
acaagaatat gaatattaat aacttaatga aaagtactga ttttgcttgc tgtcatttta   120000 atttctaca gataactttt ttttaacca ctgttttatc aagtgataaa tgtttatcac     120060
tttcacgagg tttcatgtaa accaaatcca gaggatacca agtaacttat tgcctctgtt   120120
gggtaggaga gctctgttca gaaacctcct caccttctaa aatttacatc tctgccaggt   120180
ggttatgtct cacaacttt tttttttaga gaaatatcaa tctgaaatga agacttcaa    120240 gtataaatgg agcagctaaa tatgatcacc taccattttt taacagtata ttacttggaa   120300
aatctgttct tcatgagcag ggcaggtggg ggtgtaactg agcatttccc ctttcaagta   120360
aattctgcaa aggttttcat gtatcctgca ttctagttct gaagcatttt atccatattt   120420
gaagtgtcca gtaaattta gttgctctat ggagagatca ttccaaatta tttaaatact   120480
atctttataa acataaaatg taaagattag aaatagacaa attaagctaa agaagttctt   120540
ttaatagttc atcttccttg gtagctaaaa aatgtgacct cttaagacc atacggctta    120600 attcccctaa ccctactcct ggcacaggct tgtgtgtata aaatgcaaaa tatctgcatg   120660
cagttagaaa atcaatctta tgaaaaaaac aaatagctag atatttacta gcacatatga   120720
aattaaatga tagtcatgtt ttaaagatgc tttatttagt aataaaggca ccatatattg   120780
tgtttgggat tcaaaatgta aggggaataa tctaactgat agtctctttt acatagagaa   120840
aatggactta gaatttaata tgtagaatta ttcactttat acaggaagag aaactggagt   120900
ctcatttgca aaacctgtcc actcttatgg caccaacata taagaaactt gcacctgatg   120960
catataataa tcaggtaagt ttaaataatc attggcagca attgtaacaa cttacttgtt   121020
actaatgacc tatgtccaaa atatttttg aaacaatgat ttttaaatat tattctaact    121080
tttcctctta attgttgaaa ccactgcagt gttcagtttc gagtatataa aaattatacc   121140
atacaaaagt acattttttt tgtcttttag ctgtaaagac atgcgcttct aaaagtcaca   121200
ggctgttcta tctactaatc ttgttctcat atgaataatt ttgtttctgt aaacagacta   121260
tggagattac atcaaaatta tgtggcccaa gctataggtt ctaactacct attttactg    121320 caagtctata agtataaatg agtattcata agaatttata gacttacaaa tattcacata   121380
aagctatgca tatactaaca ttgtaagtat atatatttcg gtccagatgt gtcagatttt   121440
gctgatcttc cttttttgtt tgaccttgac ttcatacacc aagcaaaaac attttttttt   121500
tctattttac atgtgtattc taaactatag ctagttaaga caggtagatg atttggtcag   121560
aaatctctca tcatgaaggc aaaaaactaa aatcttcact gtttcagtaa catcaacaac   121620
aaaagcatta agtgaaagtc tattacaaac taaacactgt gtttagtcac tgggaacata   121680
aaggtgagca gtgccatctc tgtctgtctt taagaattcc gtctttgctg ggtacggtgg   121740
```

```
ctcacacctt taatcccaac actttgggag gccaaggcag gtggatcacc tgaggtcagg 121800
agttctagac cagcctgatc aacatggaga aaccctgtct ctactaaaaa tacaaaatta 121860
gctgggtgtg gtggcaggca cctgtaatcc cagctactcg gaaggctaag gcaggagaat 121920
agcttgaacc tgggaggtgg aggttgcagt gagccgaagt caaaccattg cactccagcc 121980
taggcaacaa gagcgaaact ccatctcaaa aaaaaaaaa aattcatctt taactgggtg 122040
cggtagttta tgcctgtaat cccagctacc caggagacca ggagtctgag gctgcggtga 122100
gccatgattg catcactgtg ctccatcctg ggtgacaaag atgacccaga ttctaaaaaa 122160
aaagcaaaaa acaaaagaat tccttcttta gtggagacag agacatataa aataaatagc 122220
aattttagaa ttacacagtt ccagctggaa tagaagaatg tgcacatttc taaaaaaatt 122280
taaaaacaaa acccaaaagt agactagatg tcacaagcag ccttagacgc taaataaaga 122340
tctttgaact ttattctgta ggtaaccatt gggctgtttc aagtgtgtgt tggggatgga 122400
agggtaaagt gatgtaattc gtattttgaa aaatttactt aaaagccaag taagggaaat 122460
ataacttaaa tctatgtaag attagagaga gaagaaagct attgcaatca ttgggcaaga 122520
gattttaagg acctaaagaa atggcaggaa ttaagtatgt acactaacta aggtggagct 122580
tagagaactt ggtgactaga tgtatggatg agaaaagaat ttggagatac aacaaatttc 122640
cagtttggac aggtagttct attaactagt atcagaaatt ggtaagaaat agtaagtttt 122700
gggatgggga gaagatatca aaattttgga catgctaggc ttctaggtta attagatgga 122760
gaatcaggag aaaaattcag gctagcactg tagatttgag agtcagaatg ctggcaggac 122820
ttaaagttga atacatagga atgaaaggag gttttcaaag tagagattat aaagaggaca 122880
aagggctgat gatgggattc tggagccatc aatcatttta ggcatgagtg gaggaagaga 122940
agccaatgaa gtaagaactg ggggagggag tagaagaaat gtagtaggaa aagtgaaaga 123000
gggagatgga tggatggagg aaagctggaa tgatgagaag acacccagag cagagtatac 123060
aggagcaata ggtatggggc tctgggatgg gtgctctgtc atttacttga taatattaaa 123120
gactctcgtg ggattagatt agtttacaca gcagacatgg acaagggact aatcctaaaa 123180
tgatttagct actcttcttt tccactgtgg actttaacgt cccaaacatt ttttttttt 123240 tttggttcga acaatagagg caaattaaac gatggtctat ttgtaagtta ttttatgtca 123300
aattatgttt ttagaaatgt gtatgaatat ctatgaaaag ttttaaaca ctattaatag 123360 ttggattaat actgttattt tgtttagcta gtatcacaaa gtataaggag tgctttgata 123420
ctgtcgtaaa agtttaattc tcagcaagaa cttctgaaat aaatcaagct ataaaataa 123480 ataaatgaat gagtctatgt tgctagattt aaagttgggt catttttctat taaatgaatt 123540 tttaataggt gctgttaatc aaatggcttt acttgaggca gaataacaaa gcattgatgt 123600 tcttttttgct cccttgattc ttattatgga ccgtctcata cttgaaacta ttttatacat 123660
ttcctaaaac ttaagtaccc aaaatatgaa gccatcaaat atgttcaagt tttaatattt 123720
atatatgaaa atgtgttgat gtaatgtcta gataaattaa gtcaattaat agttgtaaat 123780
ggatgagatg cttctgaatg gataaaatat ttttatattg catggtaggt actattggta 123840
atattcatcc atgtatgtta atatgcttta gagatcaaaa taatagccat gtgatgtttc 123900
cacacagtac acgggaagac catttgatgt tatagatgct gtcataaaac ctactatttg 123960
atctttacct ccttttcccca actgagtgtc gtatctctat ttctcacatc tgaatattct 124020
tccttgcttt attccttgat ttcatgaagt cttattgcta aagtttagtt ggctctccac 124080
```

```
agcatctctt ctgtcagtcc catggaatta gagcttcagt tttctcaact taaatgtcct    124140
ttcttcgtgt ctatccagta gacatatatt tggctctgtc ttttctatgc ctgccttaca    124200
atttaacagt agacctgaaa tagcaggtgt caatctcaaa atcgtgtgct atttatcata    124260
catgaagatg acattttaga caaatgcttc taagagagct ttctatgaag atggaaatat    124320
tctctattta tgctgttcag tgtaataggc actagccaca tgtggttatt atttaacagt    124380
tgatacgtgg ctagtgtaat tgagtttaaa ttaatgtaaa aattaacaca aacagccaca    124440
tgtggataat ggttaccata gtgaacagca caaccttaga ccatgagaaa gttatgcatt    124500
tagaattgtc ttccagacat ttagatggat ttccagtaat tcattcacaa aatcctgcat    124560 ggtattttt aggagatggc ataagtgtaa tttctagctg attgtatatc tgttttgtt     124620 caagaaacag aataaagcta actagaccac agcatgaact gaacggccac aaagcacaca    124680
tctatgttaa agagtagttg gtaccttcat tttcctttgg ccaaagtttt atgaggttag    124740
atagacaaat acatatatga atccaacagt aaataaatg aagccaccac aaactttat     124800 cctaatgcaa gttcatcttc tagccatgat ggagtaaaca gagactacat atgccgttac    124860
acatttaaga aaaactgac aaaatatatg aaacaatggt ttttagacat agaataagaa     124920
attcaagaga cagtggcacc agagagaaag gaagtaaaaa ggtgaaccta taaataccc     124980 agtttacttc ctgaagagag tattaggctc cagtgtagcc agtaggaacc caaacacacc    125040
cagccttatc tctgtattaa ggagacaaag ttcaaaattt ggagaggcca aggtgacgag    125100
agttcactat tcagaatatc agagaggaga gagtgttatt gagaaaagct ccagagacct    125160
gcagagggtt ctgatccagt cttcagctga gtattaaaca gcacatgcat gtgaaaaaac    125220
tgccaaggct aggtagggaa agaaccatca gaagaagcag gcagaataat ccctgtgatct    125280 cacacaggac ctggaaatagt tcttgatcat accagccaga cggagaagac ttcataatac    125340
tattcataat tgtattgcct tggtagtaga agtaaatttg gcagttctga cctcatctaa    125400
aaatgcttaa aatgaaaaca tagaagggcc aaactgattc taagtaattt aactgcatca    125460
cagtacaaaa attaaaaaaa aaatctacca acaaggtaaa atttatagtc tagcattcca    125520
tcagaaaata caaggcatac aaagaaaaaa gaaaatataa cctttactgg ggaacaggca    125580
gaaatcaatc aataaaaata gtcccagaac tgacatatgt gatacaatat gtaaataagt    125640
tcattaaaat ggctatcata tttcatatgt taaaatgcca gaggaaagca tgagagtgat    125700
aaggaaagat cagaagatat taaaatacc tacaatgacc ttctagaagt gaaaaatata    125760
tatctagatt aaaaatacac taggcggaat taacagatta aggaacttga agacatagta    125820
atagaaattt ttcagtataa agaaaaaact gaaaaaaatg aatatataaa agacctatta    125880
gccaatattg ttacactaat atatgtgtaa ttggagtacc agaaggaggt gggagacaga    125940
aaaatattta agaaacaat ggccaaattt ttttcagatt tgttcaaaac tgtgaaccca    126000
cagatctcag cagctcagca aaccccagat taaaaaacaa agacataaaa aaagactatc    126060
aaaaatttat aatcaacttg cttacaatct gtgataaaga gaaactcaga aaggcaaatg    126120
gagaaaaaag gacatattac actaggtggg aaaaataag acaggagact tcattcagaa    126180
aaaggcaaga gagaagatgt aagagaaaca tcttttaacat actaaaagaa aaagactct     126240 ccacccagaa atatataacc aatgaaaaca actctcaaaa aagacagcaa aataaagaat    126300 atttttcag acatacatac aaagctgaa agaattcacc accaacaaac tagcactta      126360 aaaatgttaa acgaaatcct tcaggaagaa agaacatgat accagacaga aatccagatc    126420
aacataatga aatgaacagt atcaaaaata gtaaacatgg ttaaaagact tttaaaaaaa    126480
```

```
tgataacttg ctatcttaaa aatatattaa caatgtatta tgaggtttat aacacgtaga 126540
agtagcacag aggctgagga attgaaagta tattattgta aagtacttat acgatatgtg 126600
gactgggtat attacttggc tgtaaactgt gagacgttag agtacactgt gtaccttaaa 126660
ccactaaaaa aaaaaaaaaa agtatatagc taatcagcca gtaaagacag aaaaatgaaa 126720
tcaatccaaa aatgttttta aaatatata ggaccaaaaa aagataaata taaaaataaa 126780
acaaatagca agatggttta tttaaaccca actgtatcaa caaccacatt aaatgtaaat 126840
ggttttaaca cccctaatta taaggcagag cttgtgatat tgaaaaaaaa gcaaaaacca 126900
agaaaaccac tttaaatata aagatacaaa taaattaaaa agatattttt aacataaaaa 126960
atgatgttga aaagacataa caggaaaaaa tatgattatt gcagtaggta cagaaaaacc 127020
atttgataat attcaacatt cataaaagga aactttctca acctattaaa tacataaatg 127080
gaaagccaaa agctaatgct atacttagtg gtgaaagact aatacttgac ccctaagata 127140
aggaacaaga caacaatgtc cattttaac caactgcttc tattcaacat caaactgtaa 127200
attttagaaa gtgcagtaag gcaataaata aagcagtcaa gattgggtag gaaaaaataa 127260
aactgtactt atttgcagat gacatgtttg tctacataag aagtctcaaa aaatctacca 127320
gaaaatgaaa ttaatatatg aatttagcaa agttgtgaaa tacaaaattc aagtgtattt 127380
ttatatacta gcaataaata aatcaaaata aaccattaaa atagcatcaa aatataaaat 127440
tcttagacat acatttgaca aaaatgtata agattatata ctggaaacta aaacattgct 127500
gagataaatt atagaaaact tcagtaactg gagagataca ctatgttaat ggatcaaaag 127560
actaaatatt attaagatgt cagttctccc caaactaatc aatatgttca atacatgatg 127620
tttcaaaacc ccagcaggtt ttttgaaaga attggacaag atggctgtaa aatatatata 127680
cttggaaatg caaaggactt ggaatagtca aataatattt taaaataagg gcagaatttg 127740
agactatata ttgcatggtt ttcagattta ctgaaatcta taattgctac tgtctgtcaa 127800
gacagtttga tattgcccag gcgcagtggc tcacgcctgt aattccagca ctttcggagg 127860
ccgaggtggg tggatcactt gaggccagga gttttgagac cagcctggcc aacatggcaa 127920
aactctatct ctaataaaaa tacaaaaaat tactggggca tggtggcgcg tgcttatagt 127980
cccagctgct tgggaggttg aggcctgaga atcgcttgaa tccaggaggc agaggttgca 128040
gtgagcccag atcgtgccac tgcactccag cctgggtgac agagtgggac tctgtctcaa 128100
taaataaata aaatttttaa aaagtttgat attgacatac ctacatacac accattatac 128160
acaagtggat cagaatagag aatccttaag tagacccaac atatataata tggtcaattg 128220
atttttaaca aagatgattc aattgggaag ggataaccat tttatccagt agtatctgaa 128280
cagttggaaa gccataaggg aaaaaaggta atcttgaccc ttaatttcac accatttata 128340
aaaattaact ccaaataaat ccatttatat gaaattctag aaaatgaaaa tctgtagtga 128400
tagattagta gttgtctgag aacaaagcag gaagcatgaa ttatacaggg gcatgaggaa 128460 attttttaaga gtaatgaata tgtactttat tttggttgtg acaaatatat atcaaaactc 128520
aaatagcata ctttatggcc tcaataacac tataaaataa aaattttacc atgtcaagat 128580
atttgctcta ttttgtgtca ttccatttg tttctggata tatatttaag ttcaaaacat 128640 tttttttaaag ttctaaatgg tctaaatact agtgagtttt cggtgtaaga gtaaaactaa 128700
ctactttcgc attcacacac acttttattt ttcagattga atatgaacac agagcaccag 128760
agtgccgtct gggtctgaag gaaggccgtc cattctcagg ggtcactgca tgtttggact 128820
```

```
tctgtgctca tgcccacaga gacttgcaca acatgcagaa tggcagcaca ttggtaagtt    128880
gggctgagga cagcttagca gctgttgagt ctgttctcac actgctaata aagacatatg    128940
caagactggg taatttataa aggaaagaga tttaattgac tcacagttcc acatggctgt    129000
ggaggcctca caatcatagc tgaaggcaaa tgaggagcaa agtcacatct tacatggcgg    129060
caggcaagag aacatgtgca ggggaactcc cctttataaa atcatcagat ctcatgagac    129120
ttactctcct gagaacagca tgggaaagat ctgcccccat gattcaatta cctcccactg    129180
ggtccttccc aaaacacatg ggaattttgg gagctacaat tcaagatgag atttaggtag    129240
ggacacagcc agaccatatc agcagcatct catgttgagg agcagaacac tggaatttag    129300
tagcattcgg ttagagtaat atgttgtctg caggtttcac tggacagcaa tattttcatg    129360
aatgaattcc tgttgcaaag tgacctgctt tggcataact agcactctca tgataggttg    129420
gcacattagt ttcctgtcaa ttgtgttgac aagcacatga gaatcatgga aatccttggt    129480
gttaatctaa accagtgact atgcattgcc agttacagtt aacttccagg aaaatctcaa    129540
aattcagtgc cagttacctg gtagattgta atcagttaag caaaaagcca aatacaagcc    129600
attcacctta cagagagaga agcatattca ccttacagag agagaagcat aaatgagaaa    129660
cacatcatca ttgtcacagt aactgtggta acctattgta aaagattcac agtgcaaaag    129720
agcctgacta catattacag tgggtaaaat ggatcggtct tgtaattgga ggcagtggtg    129780
agggaaaaat agatacatgt tatatatata tatatatata tatatgttct ataccaacaa    129840
agggttcagg gtataatttt gcatgtaaag gggtgaccca gagtagagat aaagaacaaa    129900
atattctgtt gaaaaaacta tgaatcaatc aacctaatga attatcaaca tggatgtagg    129960
tgtagttgaa gaagatggtc agtgagaata tggaaacaga tatcaggaat taaagtcata    130020
ttctagggca gaaaagcatt catggaggta ttagatgata gctgaagtaa tttgaagaag    130080
ctggtgtgaa gttttttgttg agaagcagag aagatattaa tttaatgttc tagatcagag    130140
attggaaaac tcttctctat aaagggcaag atggtaaata ttttagggac tgcaggccac    130200
ataggatttc tgtcacattg tttggtgggg ttttttttgtt tattttgttt tttaaaaact    130260
ccttgaaaat gtaaaaacca ttcttagttt actggccata caaacacaag ctgtgaggca    130320
cattagccgt aggttctggt ttcctaactt ctgatccaga agaacaaaca caaggcctac    130380
caaccacccc aacatctaaa atcatcacta atcatgtact cagcacctgc tcattattag    130440
gaggctatgc tagtttctga aaagcagaag tagtaaatga taactggggc tatagtgcat    130500
cctaatataa ccatgtttca ttccaggaag gtgacagaga gtaagatgat gagaaggatg    130560
tttagaatca agaagaattt gcctctgata gagcatgggt tctgtgaagt aaaatggaaa    130620
ggagcactag ataagaactg aatagggtta aatatgtatg ggaaaagtaa caaggtgctc    130680
agagacatga atttgaagac ttctgtgcag aaagtgacag gctcattaat accatctcat    130740
gttgaagtta tttctaaagt cagtccattg tgatcacatt tctctcaaga atatcttcta    130800 attttattt agatcacatt agatcacatt gtctccattg atcaaaaaca ctaaatacta    130860
aaaagttagt atttaaaaac cacaaataat cttttaccaa agctagtgta attgtagtaa    130920
ctaaagcaaa aagtaccatt taattatcaa agcaacagag gtagctttcc tccctccacc    130980
ccttacccct ttcagagtac ccacttatat ggtcatattt cagaaaagaa atgaagaaaa    131040
gagaaagtta ggtttgacag agtacaaagg aggagagaca agagagtgaa aatagtatta    131100
agttgcatat tacctgtatc agccaaatct ttacctttc attttttata tttttacttc    131160
agttatctta tggaaatttc ttaaacagag agagttaggt gtcaggtatg tgaaaagaca    131220
```

```
tgaaatttgt gttcagaagt atgagatgag gcaaatgtga tactaccaaa aacagaggaa    131280
gtcatttcgt agaaaaaact tttagcctgt ttttgaagag gcttcacatc tagcacatct    131340
atttttgaag tgtgaaaagc aagagagtgc ttcattttgg gggagtgttg cttcttccca    131400
tagacagaaa catatgtgaa gaacaagggt caccacagct aactgttcct gatagactca    131460
gagaaagggt gggtgggcaa tgtcaatttg tcttatctcc ctgtaccatt ttgttgctat    131520
tttcattaat aacaggtagg atggttttat ggtaatatat atgtcactga tctggatcaa    131580
ctaggccacc aacacaaatc tgaatactga gaggagaaag atacacacac acacacacgt    131640
tttctttggg acctgtagtt gaggctgtaa tgtcttactt ccctaccagg tatgcactct    131700
cactagagaa gacaatcgag aatttggagg aaaacctgag gatgagcagc ttcacgttct    131760
gcctttatac aaagtctctg acgtggatga gtttgggagt gtggaagctc aggaggagaa    131820
aaaacggagt ggtgccattc aggtactgag ttcttttcgg cgaaaagtca ggatgttagc    131880
agagccagtc aagacttgcc gacaaaggaa actagaagcc aagaaagctg cagctgaaaa    131940
gctttcctcc ctggagaaca gctcaaataa aaatgaaaag gaaaagtcag ccccatcacg    132000
tacaaaacaa actgaaaacg caagccaggc taaacagttg gcaggtaaat ttaatgtaaa    132060
gcatttgtag ataaatgtgt tgtgtggtat attaaaaatg aaaattattt tggttttgcc    132120
cccatcaact tgtaagttct ggggtacaca tgcaggatgt gcaggtttgt tatacaggta    132180
aacatgtgcc atggtgattt gctgcacaga tcaacccatt acctaggtat taagcccagc    132240
atcttcctga tgcaccccta ccaataggcg ccagtgtgtg ttgtcccac tccccacca    132300 tgtgtccatg tgctcttatt gtaaaatgaa cattgttaat tttggaaagt tatatcaatc    132360
atggtcttag ttctgtgcca gagtcttctc taaagtagca agggccaggc tttgttctca    132420
gagatggtaa tgagatattg caccatcaac atggaaaaca tggaaaagtc tggattttat    132480
tctataataa acagcaactt tttttaacag gtaagtgata cgatgaaatt cattgtaatt    132540
tggcagtagg ccaaattagt agaggagcta atagtttgga gataaacaca gtaaaccaga    132600
actgaggtaa caagaccttg aattttgttg gttagtagca aagatatagc aaaatgatgc    132660
aaatgagctc ttccaaaatg ggaaaaagaa atacattgg tgacaaaaca ctggaatgaa    132720
agagaagaaa agtttaaaga tgaccccaaa gttttaaacc taaacttaac ctactgtttt    132780
aggtttctaa aacagtacta tttattgaaa taagtaagtt tgaaaatatg attgagagag    132840
agagagggga gaatgaaaca ttttttcctta gacatgttga gtctgtggtt taggaggggt    132900
tctacatgta gattatgcta caaaactttt acccatcaaa atagattaca gctgtagtaa    132960
taacaataga acattattca tgaatactaa gttattgtct ttccatagcc tcctgcttta    133020
tgtctgcagt ttgtaaaaag aaaaaaaatc caaaatttgg gatggtattg gcctggccat    133080
taacaaaagc aaaccagttt gcttaaaact agccatcttt gctgcttcat gaagtcaaat    133140
ttctctactg attcatttcc aagctcagag gaactaagtt aaataattta gaatatgcta    133200
aagatgcttg ataagtgttt attgactggt tgacttaaca ctaagtaaat actgttcact    133260
taggttagct gtgaaatata attagataga accttgtctc tgctcccttt taactggctt    133320
ctgcaggtaa taatcccttc tgttctcaga actgccattg cagtttcatc tatttgttct    133380
taactcatat gacttttaa agtgaggtca aaacagaagt atgactttta aagtttcat    133440 ttacaaagct gaaagtttct ttaaagtgtt atctacaact gtgttaactt cctttctgga    133500
aagcctgctt ataaagtagc acttgttgat tatataagat gcttttgtg tttaaatacg    133560
```

```
tgtcattctt ttttttcaca acattcccga atcttacata ataaatctta ttttaattat  133620
ttagcaaatt ccattgcatg ccaggcaatg aagaagtaag taaaataaaa cattttcctt  133680
cccatttagg aatttactta ccagtggggg tgaagagagg gctaaaaaca taactataat  133740
acattgtgag tattgcttta tcagatctat ctttgcagtt gagtattaca aaagcactag  133800
aagatgaggt caaagcggtc ccttgaggaa gggatgacta caccaaggaa ggatagggag  133860
agagggagga aaagggaggc acttcaagca gaggcatgtt cagaagttcc aaagaacatt  133920
ttgctctcaa tggaatggct ttggatgttt attacatttt ttttttcact aagttttgta  133980
tttctaatgc cttagacaaa aaattgtgct ggacaatgat cagaaccctg actttgctct  134040
tatctttgct taatgggtgt cgtatatcac tagtggagtt tcttacctac atttaagtat  134100
cctcactagc cttcataaaa taatcatcaa catcaaagat acctgtttct gttctctctt  134160
accctgtcca cagaactttt gcgactttca ggaccagtca tgcagcagtc ccagcagccc  134220
cagcctctac agaagcagcc accacagccc cagcagcagc agagacccca gcagcagcag  134280
ccacatcacc ctcagacaga gtctgtcaac tcttattctg cttctggatc caccaatcca  134340
tacatgagac ggcccaatcc agttagtcct tatccaaact cttcacacac ttcagatatc  134400
tatggaagca ccagccctat gaacttctat tccacctcat ctcaagctgc aggttcatat  134460
ttgaattctt ctaatcccat gaacccttac cctgggcttt tgaatcagaa tacccaatat  134520
ccatcatatc aatgcaatgg aaacctatca gtggacaact gctccccata tctgggttcc  134580
tattctcccc agtctcagcc gatggatctg tataggtatc caagccaaga ccctctgtct  134640
aagctcagtc taccacccat ccatacactt taccagccaa ggtttggaaa tagccagagt  134700
tttacatcta aatacttagg ttatggaaac caaaatatgc agggagatgg tttcagcagt  134760
tgtaccatta gaccaaatgt acatcatgta gggaaattgc tccttatcc cactcatgag  134820 atggatggcc acttcatggg agccacctct agattaccac ccaatctgag caatccaaac  134880
atggactata aaaatggtga acatcattca ccttctcaca taatccataa ctacagtgca  134940
gctccgggca tgttcaacag ctctcttcat gccctgcatc tccaaaacaa ggagaatgac  135000
atgctttccc acacagctaa tgggttatca aagatgcttc cagctcttaa ccatgataga  135060
actgcttgtg tccaaggagg cttacacaaa ttaagtgatg ctaatggtca ggaaaagcag  135120
ccattggcac tagtccaggg tgtggcttct ggtgcagagg acaacgatga ggtctggtca  135180
gacagcgagc agagctttct ggatcctgac attgggggag tggccgtggc tccaactcat  135240
gggtcaattc tcattgagtg tgcaaagcgt gagctgcatg ccacaacccc tttaaagaat  135300
cccaatagga atcaccccac caggatctcc ctcgtctttt accagcataa gagcatgaat  135360
gagccaaaac atggcttggc tctttgggaa gccaaaatgg ctgaaaaagc ccgtgagaaa  135420
gaggaagagt gtgaaaagta tggcccagac tatgtgcctc agaaatccca tggcaaaaaa  135480
gtgaaacggg agcctgctga gccacatgaa acttcagagc ccacttacct gcgtttcatc  135540
aagtctcttg ccgaaaggac catgtccgtg accacagact ccacagtaac tacatctcca  135600
tatgccttca ctcgggtcac agggccttac aacagatata tatgatatca cccccttttg  135660
ttggttacct cacttgaaaa gaccacaacc aacctgtcag tagtatagtt ctcatgacgt  135720
gggcagtggg gaaaggtcac agtattcatg acaaatgtgg tgggaaaaac ctcagctcac  135780
cagcaacaaa agaggttatc ttaccatagc acttaatttt cactggctcc caagtggtca  135840
cagatggcat ctaggaaaag accaaagcat tctatgcaaa aagaaggtgg ggaagaaagt  135900
gttccgcaat ttacattttt aaacactggt tctattattg gacgagatga tatgtaaatg  135960
```

```
tgatccccccc ccccgctta caactctaca catctgtgac cactttaat aatatcaagt  136020
ttgcatagtc atggaacaca aatcaaacaa gtactgtagt attacagtga caggaatctt  136080
aaaataccat ctggtgctga atatatgatg tactgaaata ctggaattat ggcttttga   136140
aatgcagttt ttactgtaat cttaactttt atttatcaaa atagctacag gaaacatgaa  136200
tagcaggaaa acactgaatt tgtttggatg ttctaagaaa tggtgctaag aaaatggtgt  136260
ctttaatagc taaaaattta atgcctttat atcatcaaga tgctatcagt gtactccagt  136320
gcccttgaat aataggggta ccttttcatt caagttttta tcataattac ctattcttac  136380
acaagcttag ttttaaaat gtggacattt taaaggcctc tggattttgc tcatccagtg   136440
aagtccttgt aggacaataa acgtatatat gtacatatat acacaaacat gtatatgtgc  136500
acacacatgt atatgtataa atattttaaa tggtgtttta gaagcacttt gtctacctaa  136560
gctttgacaa cttgaacaat gctaaggtac tgagatgttt aaaaaacaag tttactttca  136620
ttttagaatg caaagttgat ttttttaagg aaacaaagaa agcttttaaa atattttgc   136680
ttttagccat gcatctgctg atgagcaatt gtgtccattt taacacagc cagttaaatc   136740
caccatgggg cttactggat tcaagggaat acgttagtcc acaaaacatg ttttctggtg  136800
ctcatctcac atgctatact gtaaaacagt tttatacaaa attgtatgac aagttcattg  136860
ctcaaaatg tacagtttta agaattttct attaactgca ggtaataatt agctgcatgc   136920
tgcagactca acaaagctag ttcactgaag cctatgctat tttatggatc ataggctctt  136980
cagagaactg aatggcagtc tgcctttgtg ttgataatta tgtacattgt gacgttgtca  137040
tttcttagct taagtgtcct cttaacaag aggattgagc agactgatgc ctgcataaga   137100
tgaataaaca gggttagttc catgtgaatc tgtcagttaa aaagaaacaa aaacaggcag  137160
ctggtttgct gtggtggttt taaatcatta atttgtataa agaagtgaaa gagttgtata  137220
gtaaattaaa ttgtaaacaa aacttttta atgcaatgct ttagtatttt agtactgtaa   137280
aaaaattaaa tatatacata tatatatata tatatatata tatatatatg agtttgaagc  137340
agaattcaca tcatgatggt gctactcagc ctgctacaaa tatatcataa tgtgagctaa  137400
gaattcatta aatgtttgag tgatgttcct acttgtcata tacctcaaca ctagtttggc  137460
aataggatat tgaactgaga gtgaaagcat tgtgtaccat cattttttc caagtccttt   137520
ttttattgt taaaaaaaaa agcataacct ttttcaatac ttgatttctt agcaagtata   137580
acttgaactt caaccttttt gttctaaaaa ttcagggata tttcagctca tgctctccct  137640
atgccaacat gtcacctgtg tttatgtaaa attgttgtag gttaataaat atattctttg  137700
tcagggattt aacccttta ttttgaatcc cttctatttt acttgtacat gtgctgatgt   137760
aactaaaact aattttgtaa atctgttggc tctttttatt gtaaagaaaa gcattttaaa  137820
agtttgagga atcttttgac tgtttcaagc aggaaaaaaa aattacatga aaatagaatg  137880
cactgagttg ataaagggaa aaattgtaag gcaggagttt ggcaagtggc tgttggccag  137940
agacttactt gtaactctct aaatgaagtt ttttgatcc tgtaatcact gaaggtacat    138000
actccatgtg gacttccctt aaacaggcaa acacctacag gtatggtgtg caacagattg  138060
tacaattaca ttttggccta aatacatttt tgcttactag tatttaaaat aaattcttaa  138120
tcagaggagg cctttgggtt ttattggtca aatctttgta agctggcttt tgtctttta   138180
aaaaatttct tgaatttgtg gttgtgtcca atttgcaaac atttccaaaa atgtttgctt  138240
tgcttacaaa ccacatgatt ttaatgtttt ttgtatacca taatatctag ccccaaacat  138300
```

```
ttgattacta catgtgcatt ggtgattttg atcatccatt cttaatattt gatttctgtg    138360
tcacctactg tcatttgtta aactgctggc caacaagaac aggaagtata gtttgggggg    138420
ttggggagag tttacataag gaagagaaga aattgagtgg catattgtaa atatcagatc    138480
tataattgta aatataaaac ctgcctcagt tagaatgaat ggaaagcaga tctacaattt    138540
gctaatatag gaatatcagg ttgactatat agccatactt gaaaatgctt ctgagtggtg    138600
tcaactttac ttgaatgaat ttttcatctt gattgacgca cagtgatgta cagttcactt    138660
ctgaagctag tggttaactt gtgtaggaaa cttttgcagt ttgacactaa gataacttct    138720
gtgtgcattt ttctatgctt ttttaaaaac tagtttcatt tcattttcat gagatgtttg    138780
gtttataaga tctgaggatg gttataaata ctgtaagtat tgtaatgtta tgaatgcagg    138840
ttatttgaaa gctgtttatt attatatcat tcctgataat gctatgtgag tgttttaat     138900 aaaatttata tttatttaat gcactctaag tgttgtcttc ctgaagtttt tttagtgctt    138960
gaatgactgc cacctcaatg aagaaaaggg aataaaaaat aattttaaa gacactttta     139020 agatagatag ttagtcttat gttaaactat atctaagata atacccaaat aattaaggcc    139080
gaagtatttc tctggttaaa tggtgtagat attcactcac ttttccttcc aactaacttg    139140
ttagtgtatt cactttgcat gtgtagacag tgtaaatcag atagagagta aagcacctct    139200
aatcttagat tgccccctcc agtgttttgt gaagggtttc agtgatatag caggtgcact    139260
aaggttgaat tcatattgct tagaactaag gccaactctg ttttcagact ctcaccttcc    139320
acttcttgcc tactcttctt aagggaagat acttcttcct gtacatcaga aaggcagggt    139380
ggtaggctgg aggaatgggg agaggaggcc tggaaggtat cagacaaata tacttgtcct    139440
catctagtcc cacatggctt caaggagctt gaggctaaat catcctcatc tctacccatt    139500
ctctgccatg tgaatcatcc catatataat atcagtgcac tccagctgaa acacttccta    139560
gaaccacaag atgctaaaca atagttgtgg gaatcttcca gccctccatt ccttcccaaa    139620
ttggcagaga aatcattttc atcatgcatg aagtaaagga attcccttc tcacatttct      139680 ctctgttcag cctgggccaa atctgattca aatagtgcaa cccaggaaat gactaccatt    139740
tagtaacctc tgagcttatt gactgggaga ttcctccagg actctgcaag ccaggatatt    139800
aagagaagcc acaacatcac tgttaaaaca caatgatcta atgacttggc ttttgtttta    139860
atttcaaccc tctgagcaca ttgtcaaccc tcatttcacc atccatcatc tggctgaacc    139920
ttgggaacct cccactccac atttgcaagt ctccactgcc cagggcaggg agaattttag    139980
actccacaag ctcaaaagcc tttcctgcta gagccccatt ctgctaggat ctctactagt    140040
ggaggctggt gatgctagca caccataaat gaacgtgtgg gaaggcctgc tgcttctgag    140100
cctgcaggtg gacttgaaca ggggaaacag ctggaaatga cagatgagcc agcattcaca    140160
aagctttatt ggccccttgc ctctcctgga aagacataac aaggccaaac ctttttcttgt    140220 aggcacacac agctgccctg tcacacagta ccacccgttt cttcctcact tttttcagt     140280 tggtttatca taaaaatcct tccactatgg gtaattctag cttatctttg agtcctgcct    140340
gattccactg cccagcactc atcggctgtg taagagccag acttagcgag aaaagtcatt    140400
tttcaacaag gcacctaatc cgtagagtgt ggggaatttt agattgattt tgttggttta    140460
aaggccatct ggaggcgagt atcaaaaaaa gaaaaaaggg tgtggggaag catctttct      140520 tcccttaatt gatttgaggg aagtgcttgt ttcatgaaga cacttgttta ttaacttcaa    140580
tcacccaact tatccgtaag gcgtcaggga ctttatcttc cccaccccca ttgccccct      140640 cccccaatac actcacagtt gttgaaagaa tgaaaaagtg ttcacaaaag atgcttagaa    140700
```
ttaactcatt tatgttattt tggttttact aggagaattg tttcaaagaa cgaagatgct   140760
tttgttccca tatattagag gctacctgcc taaattctct ctaaccaggt agtttctcac   140820
aaacttcctt ggttttctca tccaacattc actctttaaa agagccacac tttccctcac   140880
atatatactc aacaaatata gttttttgga gggatttctt tttatgctg                140929

<210> SEQ ID NO 2
<211> LENGTH: 9796
<212> TYPE: DNA
<213> ORGANISM: Homo sapiens
<400> SEQUENCE: 2
ggcagtggca gcggcgagag cttgggcggc cgccgccgcc tcctcgcgag cgccgcgcgc    60
ccgggtcccg ctcgcatgca agtcacgtcc gccccctcgg cgcggccgcc ccgagacgcc   120
ggccccgctg agtgatgaga acagacgtca aactgcctta tgaatattga tgcggaggct   180
aggctgcttt cgtagagaag cagaaggaag caagatggct gcccttttagg atttgttaga   240 aaggagaccc gactgcaact gctggattgc tgcaaggctg agggacgaga acgaggctgg   300
caaacattca gcagcacacc ctctcaagat tgtttacttg cctttgctcc tgttgagtta   360
caacgcttgg aagcaggaga tgggctcagc agcagccaat aggacatgat ccaggaagag   420
cagtaaggga ctgagctgct gaattcaact agagggcagc cttgtggatg ccccgaagc    480 aagcctgatg gaacaggata gaaccaacca tgttgagggc aacagactaa gtccattcct   540
gataccatca cctcccattt gccagacaga acctctggct acaaagctcc agaatggaag   600
cccactgcct gagagagctc atccagaagt aaatggagac accaagtggc actctttcaa   660
aagttattat ggaataccct gtatgaaggg aagccagaat agtcgtgtga gtcctgactt   720
tacacaagaa agtagagggt attccaagtg tttgcaaaat ggaggaataa aacgcacagt   780
tagtgaacct tctctctctg ggctccttca gatcaagaaa ttgaaacaag accaaaaggc   840
taatggagaa agacgtaact tcggggtaag ccaagaaaga aatccaggtg aaagcagtca   900
accaaatgtc tccgatttga gtgataagaa agaatctgtg agttctgtag cccaagaaaa   960
tgcagttaaa gatttcacca gttttttcaac acataactgc agtgggcctg aaaatccaga  1020
gcttcagatt ctgaatgagc aggagggggaa aagtgctaat taccatgaca agaacattgt  1080
attacttaaa aacaaggcag tgctaatgcc taatggtgct acagtttctg cctcttccgt  1140
ggaacacaca catggtgaac tcctggaaaa aacactgtct caatattatc cagattgtgt  1200
ttccattgcg gtgcagaaaa ccacatctca cataaatgcc attaacagtc aggctactaa  1260
tgagttgtcc tgtgagatca ctcacccatc gcatacctca gggcagatca attccgcaca  1320
gacctctaac tctgagctgc ctccaaagcc agctgcagtg gtgagtgagg cctgtgatgc  1380
tgatgatgct gataatgcca gtaaactagc tgcaatgcta aatacctgtt cctttcagaa  1440
accagaacaa ctacaacaac aaaaatcagt ttttgagata tgcccatctc ctgcagaaaa  1500
taacatccag ggaaccacaa agctagcgtc tggtgaagaa ttctgttcag gttccagcag  1560
caatttgcaa gctcctggtg gcagctctga acggtattta aaacaaaatg aaatgaatgg  1620
tgcttacttc aagcaaagct cagtgttcac taaggattcc ttttctgcca ctaccacacc  1680
accaccacca tcacaattgc ttcttctctc ccctcctcct cttccacagg ttcctcagct  1740
tccttcagaa ggaaaaagca ctctgaatgg tggagtttta aagaacacc accactaccc  1800 caaccaaagt aacacaacac ttttaaggga agtgaaaata gagggtaaac ctgaggcacc  1860

```
accttcccag agtcctaatc catctacaca tgtatgcagc ccttctccga tgctttctga    1920
aaggcctcag aataattgtg tgaacaggaa tgacatacag actgcaggga caatgactgt    1980
tccattgtgt tctgagaaaa caagaccaat gtcagaacac ctcaagcata acccaccaat    2040
ttttggtagc agtggagagc tacaggacaa ctgccagcag ttgatgagaa acaaagagca    2100
agagattctg aagggtcgag acaaggagca aacacgagat cttgtgcccc aacacagca    2160
ctatctgaaa ccaggatgga ttgaattgaa ggcccctcgt tttcaccaag cggaatccca    2220
tctaaaacgt aatgaggcat cactgccatc aattcttcag tatcaaccca atctctccaa    2280
tcaaatgacc tccaaacaat acactggaaa ttccaacatg cctgggggc tcccaaggca    2340
agcttacacc cagaaaacaa cacagctgga gcacaagtca caaatgtacc aagttgaaat    2400
gaatcaaggg cagtcccaag gtacagtgga ccaacatctc cagttccaaa acccctcaca    2460
ccaggtgcac ttctccaaaa cagaccattt accaaaagct catgtgcagt cactgtgtgg    2520
cactagattt cattttcaac aaagagcaga ttcccaaact gaaaaactta tgtccccagt    2580
gttgaaacag cacttgaatc aacaggcttc agagactgag ccattttcaa actcacacct    2640
tttgcaacat aagcctcata acaggcagc acaaacacaa ccatcccaga gttcacatct    2700
ccctcaaaac cagcaacagc agcaaaaatt acaaataaag aataaagagg aaatactcca    2760
gacttttcct cacccccaaa gcaacaatga tcagcaaaga gaaggatcat tctttggcca    2820
gactaaagtg gaagaatgtt ttcatggtga aaatcagtat tcaaaatcaa gcagttcga    2880
gactcataat gtccaaatgg gactggagga agtacagaat ataaatcgta gaaattcccc    2940
ttatagtcag accatgaaat caagtgcatg caaaatacag gtttcttgtt caacaaatac    3000
acacctagtt tcagagaata agaacagac tacacatcct gaacttttg caggaaacaa    3060
gacccaaaac ttgcatcaca tgcaatattt tccaaataat gtgatcccaa agcaagatct    3120
tcttcacagg tgcttcaag aacaggagca gaagtcacaa caagcttcag ttctacaggg    3180
atataaaaat agaaaccaag atatgtctgg tcaacaagct cgcgcaacttg ctcagcaaag    3240
gtacttgata cataaccatg caaatgtttt tcctgtgcct gaccagggag gaagtcacac    3300
tcagacccct ccccagaagg acactcaaaa gcatgctgct ctaaggtggc atctcttaca    3360
gaagcaagaa cagcagcaaa cacagcaacc ccaaactgag tcttgccata gtcagatgca    3420
caggccaatt aaggtggaac ctggatgcaa gccacatgcc tgtatgcaca cagcaccacc    3480
agaaaacaaa acatggaaaa aggtaactaa gcaagagaat ccacctgcaa gctgtgataa    3540
tgtgcagcaa aagagcatca ttgagaccat ggagcagcat ctgaagcagt ttcacgccaa    3600
gtcgttattt gaccataagg ctcttactct caaatcacag aagcaagtaa aagttgaaat    3660
gtcagggcca gtcacagttt tgactagaca aaccactgct gcagaacttg atagccacac    3720
cccagcttta gagcagcaaa caacttcttc agaaaagaca ccaaccaaaa gaacagctgc    3780
ttctgttctc aataattta tagagtcacc ttccaaatta ctagatactc ctataaaaaa    3840
tttattggat acacctgtca agactcaata tgatttccca tcttgcagat gtgtagagca    3900
aattattgaa aaagatgaag gtccttttta tacccatcta ggagcaggtc ctaatgtggc    3960
agctattaga gaaatcatgg aagaaaggtt tggacagaag ggtaaagcta ttaggattga    4020
aagagtcatc tatactggta agaaggcaa aagttctcag ggatgtccta ttgctaagtg    4080
ggtggttcgc agaagcagca gtgaagagaa gctactgtgt ttggtgcggg agcgagctgg    4140
ccacacctgt gaggctgcag tgattgtgat tctcatcctg gtgtgggaag gaatcccgct    4200
gtctctggct gacaaactct actcggagct taccgagacg ctgaggaaat acggcacgct    4260
```

```
caccaatcgc cggtgtgcct tgaatgaaga gagaacttgc gcctgtcagg ggctggatcc    4320
agaaacctgt ggtgcctcct tctcttttgg ttgttcatgg agcatgtact acaatggatg    4380
taagtttgcc agaagcaaga tcccaaggaa gtttaagctg cttggggatg acccaaaaga    4440
ggaagagaaa ctggagtctc atttgcaaaa cctgtccact cttatggcac caacatataa    4500
gaaacttgca cctgatgcat ataataatca gattgaatat gaacacagag caccagagtg    4560
ccgtctgggt ctgaaggaag gccgtccatt ctcaggggtc actgcatgtt tggacttctg    4620
tgctcatgcc cacagagact tgcacaacat gcagaatggc agcacattgg tatgcactct    4680
cactagagaa gacaatcgag aatttggagg aaaacctgag gatgagcagc ttcacgttct    4740
gcctttatac aaagtctctg acgtggatga gtttgggagt gtggaagctc aggaggagaa    4800
aaaacggagt ggtgccattc aggtactgag ttcttttcgg cgaaaagtca ggatgttagc    4860
agagccagtc aagacttgcc gacaaaggaa actagaagcc aagaaagctg cagctgaaaa    4920
gctttcctcc ctggagaaca gctcaaataa aaatgaaaag gaaagtcag ccccatcacg    4980 tacaaaacaa actgaaaacg caagccaggc taaacagttg gcagaacttt gcgactttc    5040 aggaccagtc atgcagcagt cccagcagcc ccagcctcta cagaagcagc caccacagcc    5100
ccagcagcag cagagacccc agcagcagca gccacatcac cctcagacag agtctgtcaa    5160
ctcttattct gcttctggat ccaccaatcc atacatgaga cggccaatc cagttagtcc    5220 ttatccaaac tcttcacaca cttcagatat ctatggaagc accagcccta tgaacttcta    5280
ttccacctca tctcaagctg caggttcata tttgaattct tctaatccca tgaacccta    5340 ccctgggctt ttgaatcaga atacccaata tccatcatat caatgcaatg gaaacctatc    5400
agtggacaac tgctccccat atctgggttc ctattctccc cagtctcagc cgatggatct    5460
gtataggtat ccaagccaag accctctgtc taagctcagt ctaccaccca tccatacact    5520
ttaccagcca aggtttggaa atagccagag ttttacatct aaatacttag gttatggaaa    5580
ccaaaatatg cagggagatg gtttcagcag ttgtaccatt agaccaaatg tacatcatgt    5640
agggaaattg cctccttatc ccactcatga gatggatggc cacttcatgg gagccacctc    5700
tagattacca cccaatctga gcaatccaaa catggactat aaaaatggtg aacatcattc    5760
accttctcac ataatccata actacagtgc agctccgggc atgttcaaca gctctcttca    5820
tgccctgcat ctccaaaaca aggagaatga catgctttcc cacacagcta tgggttatc    5880 aaagatgctt ccagctctta accatgatag aactgcttgt gtccaaggag cttacacaa    5940 attaagtgat gctaatggtc aggaaaagca gccattggca ctagtccagg gtgtggcttc    6000
tggtgcagag gacaacgatg aggtctggtc agacagcgag cagagctttc tggatcctga    6060
cattggggga gtggccgtgg ctccaactca tgggtcaatt tcattgagt gtgcaaagcg    6120 tgagctgcat gccacaaccc ctttaaagaa tcccaatagg aatcacccca ccaggatctc    6180
cctcgtcttt taccagcata agagcatgaa tgagccaaaa catggcttgg ctctttggga    6240
agccaaaatg gctgaaaaag cccgtgagaa agaggaagag tgtgaaaagt atggcccaga    6300
ctatgtgcct cagaaatccc atggcaaaaa agtgaaacgg gagcctgctg agccacatga    6360
aacttcagag cccacttacc tgcgtttcat caagtctctt gccgaaagga ccatgtccgt    6420
gaccacagac tccacagtaa ctacatctcc atatgccttc actcgggtca gggccttta    6480 caacagatat atatgatatc cccccttttt gttggttacc tcacttgaaa agaccacaac    6540
caacctgtca gtagtatagt tctcatgacg tgggcagtgg ggaaaggtca cagtattcat    6600
```

```
gacaaatgtg gtgggaaaaa cctcagctca ccagcaacaa aagaggttat cttaccatag    6660
cacttaattt tcactggctc ccaagtggtc acagatggca tctaggaaaa gaccaaagca    6720
ttctatgcaa aaagaaggtg gggaagaaag tgttccgcaa tttacatttt taaacactgg    6780
ttctattatt ggacgagatg atatgtaaat gtgatccccc cccccgctt acaactctac      6840 acatctgtga ccacttttaa taatatcaag tttgcatagt catggaacac aaatcaaaca    6900
agtactgtag tattacagtg acaggaatct taaaatacca tctggtgctg aatatatgat    6960
gtactgaaat actggaatta tggcttttg aaatgcagtt tttactgtaa tcttaacttt      7020
tatttatcaa aatagctaca ggaaacatga atagcaggaa acactgaat ttgtttggat      7080 gttctaagaa atggtgctaa gaaaatggtg tctttaatag ctaaaaattt aatgccttta    7140
tatcatcaag atgctatcag tgtactccag tgcccttgaa aatagggggt acctttcat      7200 tcaagttttt atcataatta cctattctta cacaagctta gtttttaaaa tgtggacatt    7260
ttaaaggcct ctggattttg ctcatccagt gaagtcctg taggacaata aacgtatata     7320
tgtacatata tacacaaaca tgtatatgtg cacacacatg tatatgtata aatatttaa     7380 atggtgtttt agaagcactt tgtctaccta agctttgaca acttgaacaa tgctaaggta    7440
ctgagatgtt taaaaacaa gtttactttc attttagaat gcaaagttga ttttttaag     7500 gaaacaaaga aagcttttaa aatattttg cttttagcca tgcatctgct gatgagcaat    7560
tgtgtccatt tttaacacag ccagttaaat ccaccatggg gcttactgga ttcaggggaa    7620
tacgttagtc cacaaaacat gttttctggt gctcatctca catgctatac tgtaaaacag    7680
ttttatacaa aattgtatga caagttcatt gctcaaaaat gtacagtttt aagaattttc    7740
tattaactgc aggtaataat tagctgcatg ctgcagactc aacaaagcta gttcactgaa    7800
gcctatgcta ttttatggat cataggctct tcagagaact gaatggcagt ctgcctttgt    7860
gttgataatt atgtacattg tgacgttgtc atttcttagc ttaagtgtcc tcttttaacaa   7920 gaggattgag cagactgatg cctgcataag atgaataaac agggttagtt ccatgtgaat    7980
ctgtcagtta aaagaaaca aaaacaggca gctggtttgc tgtggtggtt ttaaatcatt     8040
aatttgtata aagaagtgaa agagttgtat agtaaattaa attgtaaaca aactttttt     8100 aatgcaatgc tttagtattt tagtactgta aaaaaattaa atatatacat atatatatat    8160
atatatatat atatatatat gagtttgaag cagaattcac atcatgatgg tgctactcag   8220
cctgctacaa atatatcata atgtgagcta agaattcatt aaatgtttga gtgatgttcc    8280
tacttgtcat atacctcaac actagttggg caataggata ttgaactgag agtgaaagca    8340
ttgtgtacca tcatttttt ccaagtcctt ttttttattg ttaaaaaaa aagcatacct      8400 tttttcaata cttgatttct tagcaagtat aacttgaact tcaacctttt tgttctaaaa    8460
attcagggat atttcagctc atgctctccc tatgccaaca tgtcacctgt gtttatgtaa    8520
aattgttgta ggttaataaa tatattcttt gtcagggatt taacccttt atttgaatc      8580 ccttctattt tacttgtaca tgtgctgatg taactaaaac taattttgta aatctgttgg    8640 ctcttttat tgtaaagaaa agcatttaa aagtttgagg aatctttga ctgtttcaag      8700 caggaaaaaa aaattacatg aaaatagaat gcactgagtg gataaaggga aaaattgtaa    8760
ggcaggagtt tggcaagtgg ctgttggcca gagacttact tgtaactctc taaatgaagt    8820
ttttttgatc ctgtaatcac tgaaggtaca tactccatgt ggacttccct taaacaggca    8880
aacacctaca ggtatggtgt gcaacagatt gtacaattac attttggcct aaatacatt     8940 ttgcttacta gtatttaaaa taaattctta atcagaggag gcctttgggt tttattggtc    9000
```

```
aaatctttgt aagctggctt ttgtcttttt aaaaaatttc ttgaatttgt ggttgtgtcc    9060
aatttgcaaa catttccaaa aatgtttgct ttgcttacaa accacatgat tttaatgttt    9120
tttgtatacc ataatatcta gccccaaaca tttgattact acatgtgcat tggtgatttt    9180
gatcatccat tcttaatatt tgatttctgt gtcacctact gtcatttgtt aaactgctgg    9240
ccaacaagaa caggaagtat agtttggggg gttggggaga gtttacataa ggaagagaag    9300
aaattgagtg gcatattgta aatatcagat ctataattgt aaatataaaa cctgcctcag    9360
ttagaatgaa tggaaagcag atctacaatt tgctaatata ggaatatcag gttgactata    9420
tagccatact tgaaaatgct tctgagtggt gtcaacttta cttgaatgaa tttttcatct    9480
tgattgacgc acagtgatgt acagttcact tctgaagcta gtggttaact tgtgtaggaa    9540
acttttgcag tttgacacta agataacttc tgtgtgcatt tttctatgct tttttaaaaa    9600
ctagtttcat ttcattttca tgagatgttt ggtttataag atctgaggat ggttataaat    9660
actgtaagta ttgtaatgtt atgaatgcag gttatttgaa agctgtttat tattatatca    9720
ttcctgataa tgctatgtga gtgttttaa taaaatttat atttatttaa tgcactctaa    9780
aaaaaaaaaa aaaaa                                                     9796
```

<210> SEQ ID NO 3
<211> LENGTH: 2002
<212> TYPE: PRT
<213> ORGANISM: Homo sapiens

<400> SEQUENCE: 3

```
Met Glu Gln Asp Arg Thr Asn His Val Glu Gly Asn Arg Leu Ser Pro
1               5                   10                  15

Phe Leu Ile Pro Ser Pro Pro Ile Cys Gln Thr Glu Pro Leu Ala Thr
            20                  25                  30

Lys Leu Gln Asn Gly Ser Pro Leu Pro Glu Arg Ala His Pro Glu Val
        35                  40                  45

Asn Gly Asp Thr Lys Trp His Ser Phe Lys Ser Tyr Tyr Gly Ile Pro
    50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95

Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220
```

-continued

```
Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
            245                 250                 255

Thr Asn Glu Leu Ser Cys Glu Ile Thr His Pro Ser His Thr Ser Gly
        260                 265                 270

Gln Ile Asn Ser Ala Gln Thr Ser Asn Ser Glu Leu Pro Pro Lys Pro
    275                 280                 285

Ala Ala Val Val Ser Glu Ala Cys Asp Ala Asp Ala Asp Asn Ala
290                 295                 300

Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
            325                 330                 335

Glu Asn Asn Ile Gln Gly Thr Thr Lys Leu Ala Ser Gly Glu Glu Phe
        340                 345                 350

Cys Ser Gly Ser Ser Asn Leu Gln Ala Pro Gly Gly Ser Ser Glu
    355                 360                 365

Arg Tyr Leu Lys Gln Asn Glu Met Asn Gly Ala Tyr Phe Lys Gln Ser
370                 375                 380

Ser Val Phe Thr Lys Asp Ser Phe Ser Ala Thr Thr Pro Pro Pro
385                 390                 395                 400

Pro Ser Gln Leu Leu Leu Ser Pro Pro Pro Leu Pro Gln Val Pro
            405                 410                 415

Gln Leu Pro Ser Glu Gly Lys Ser Thr Leu Asn Gly Gly Val Leu Glu
        420                 425                 430

Glu His His His Tyr Pro Asn Gln Ser Asn Thr Thr Leu Leu Arg Glu
    435                 440                 445

Val Lys Ile Glu Gly Lys Pro Glu Ala Pro Pro Ser Gln Ser Pro Asn
450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
            485                 490                 495

Thr Val Pro Leu Cys Ser Glu Lys Thr Arg Pro Met Ser Glu His Leu
        500                 505                 510

Lys His Asn Pro Pro Ile Phe Gly Ser Ser Gly Glu Leu Gln Asp Asn
    515                 520                 525

Cys Gln Gln Leu Met Arg Asn Lys Glu Gln Glu Ile Leu Lys Gly Arg
530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
            565                 570                 575

Ser His Leu Lys Arg Asn Glu Ala Ser Leu Pro Ser Ile Leu Gln Tyr
        580                 585                 590

Gln Pro Asn Leu Ser Asn Gln Met Thr Ser Lys Gln Tyr Thr Gly Asn
    595                 600                 605

Ser Asn Met Pro Gly Gly Leu Pro Arg Gln Ala Tyr Thr Gln Lys Thr
610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
```

-continued

```
                645                 650                 655
Ser His Gln Val His Phe Ser Lys Thr Asp His Leu Pro Lys Ala His
                660                 665                 670

Val Gln Ser Leu Cys Gly Thr Arg Phe His Phe Gln Gln Arg Ala Asp
                675                 680                 685

Ser Gln Thr Glu Lys Leu Met Ser Pro Val Leu Lys Gln His Leu Asn
690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                725                 730                 735

His Leu Pro Gln Asn Gln Gln Gln Gln Lys Leu Gln Ile Lys Asn
                740                 745                 750

Lys Glu Glu Ile Leu Gln Thr Phe Pro His Pro Gln Ser Asn Asn Asp
                755                 760                 765

Gln Gln Arg Glu Gly Ser Phe Phe Gly Gln Thr Lys Val Glu Glu Cys
                770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
                820                 825                 830

Ser Cys Ser Asn Asn Thr His Leu Val Ser Glu Asn Lys Glu Gln Thr
                835                 840                 845

Thr His Pro Glu Leu Phe Ala Gly Asn Lys Thr Gln Asn Leu His His
                850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
                900                 905                 910

Gln Leu Ala Gln Gln Arg Tyr Leu Ile His Asn His Ala Asn Val Phe
                915                 920                 925

Pro Val Pro Asp Gln Gly Gly Ser His Thr Gln Thr Pro Pro Gln Lys
                930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
                980                 985                 990

Met His Thr Ala Pro Pro Glu Asn Lys Thr Trp Lys Lys Val Thr Lys
                995                 1000                1005

Gln Glu Asn Pro Pro Ala Ser Cys Asp Asn Val Gln Gln Lys Ser
                1010                1015                1020

Ile Ile Glu Thr Met Glu Gln His Leu Lys Gln Phe His Ala Lys
                1025                1030                1035

Ser Leu Phe Asp His Lys Ala Leu Thr Leu Lys Ser Gln Lys Gln
                1040                1045                1050

Val Lys Val Glu Met Ser Gly Pro Val Thr Val Leu Thr Arg Gln
                1055                1060                1065
```

```
Thr Thr Ala Ala Glu Leu Asp Ser His Thr Pro Ala Leu Glu Gln
    1070            1075            1080

Gln Thr Thr Ser Ser Glu Lys Thr Pro Thr Lys Arg Thr Ala Ala
    1085            1090            1095

Ser Val Leu Asn Asn Phe Ile Glu Ser Pro Ser Lys Leu Leu Asp
    1100            1105            1110

Thr Pro Ile Lys Asn Leu Leu Asp Thr Pro Val Lys Thr Gln Tyr
    1115            1120            1125

Asp Phe Pro Ser Cys Arg Cys Val Glu Gln Ile Ile Glu Lys Asp
    1130            1135            1140

Glu Gly Pro Phe Tyr Thr His Leu Gly Ala Gly Pro Asn Val Ala
    1145            1150            1155

Ala Ile Arg Glu Ile Met Glu Glu Arg Phe Gly Gln Lys Gly Lys
    1160            1165            1170

Ala Ile Arg Ile Glu Arg Val Ile Tyr Thr Gly Lys Glu Gly Lys
    1175            1180            1185

Ser Ser Gln Gly Cys Pro Ile Ala Lys Trp Val Val Arg Arg Ser
    1190            1195            1200

Ser Ser Glu Glu Lys Leu Leu Cys Leu Val Arg Glu Arg Ala Gly
    1205            1210            1215

His Thr Cys Glu Ala Ala Val Ile Val Ile Leu Ile Leu Val Trp
    1220            1225            1230

Glu Gly Ile Pro Leu Ser Leu Ala Asp Lys Leu Tyr Ser Glu Leu
    1235            1240            1245

Thr Glu Thr Leu Arg Lys Tyr Gly Thr Leu Thr Asn Arg Arg Cys
    1250            1255            1260

Ala Leu Asn Glu Glu Arg Thr Cys Ala Cys Gln Gly Leu Asp Pro
    1265            1270            1275

Glu Thr Cys Gly Ala Ser Phe Ser Phe Gly Cys Ser Trp Ser Met
    1280            1285            1290

Tyr Tyr Asn Gly Cys Lys Phe Ala Arg Ser Lys Ile Pro Arg Lys
    1295            1300            1305

Phe Lys Leu Leu Gly Asp Asp Pro Lys Glu Glu Lys Leu Glu
    1310            1315            1320

Ser His Leu Gln Asn Leu Ser Thr Leu Met Ala Pro Thr Tyr Lys
    1325            1330            1335

Lys Leu Ala Pro Asp Ala Tyr Asn Asn Gln Ile Glu Tyr Glu His
    1340            1345            1350

Arg Ala Pro Glu Cys Arg Leu Gly Leu Lys Glu Gly Arg Pro Phe
    1355            1360            1365

Ser Gly Val Thr Ala Cys Leu Asp Phe Cys Ala His Ala His Arg
    1370            1375            1380

Asp Leu His Asn Met Gln Asn Gly Ser Thr Leu Val Cys Thr Leu
    1385            1390            1395

Thr Arg Glu Asp Asn Arg Glu Phe Gly Gly Lys Pro Glu Asp Glu
    1400            1405            1410

Gln Leu His Val Leu Pro Leu Tyr Lys Val Ser Asp Val Asp Glu
    1415            1420            1425

Phe Gly Ser Val Glu Ala Gln Glu Glu Lys Lys Arg Ser Gly Ala
    1430            1435            1440

Ile Gln Val Leu Ser Ser Phe Arg Arg Lys Val Arg Met Leu Ala
    1445            1450            1455
```

```
Glu Pro Val Lys Thr Cys Arg Gln Arg Lys Leu Glu Ala Lys Lys
1460                1465                1470

Ala Ala Ala Glu Lys Leu Ser Ser Leu Glu Asn Ser Ser Asn Lys
1475                1480                1485

Asn Glu Lys Glu Lys Ser Ala Pro Ser Arg Thr Lys Gln Thr Glu
1490                1495                1500

Asn Ala Ser Gln Ala Lys Gln Leu Ala Glu Leu Leu Arg Leu Ser
1505                1510                1515

Gly Pro Val Met Gln Gln Ser Gln Gln Pro Gln Pro Leu Gln Lys
1520                1525                1530

Gln Pro Pro Gln Pro Gln Gln Gln Arg Pro Gln Gln Gln
1535                1540                1545

Pro His His Pro Gln Thr Glu Ser Val Asn Ser Tyr Ser Ala Ser
1550                1555                1560

Gly Ser Thr Asn Pro Tyr Met Arg Arg Pro Asn Pro Val Ser Pro
1565                1570                1575

Tyr Pro Asn Ser Ser His Thr Ser Asp Ile Tyr Gly Ser Thr Ser
1580                1585                1590

Pro Met Asn Phe Tyr Ser Thr Ser Ser Gln Ala Ala Gly Ser Tyr
1595                1600                1605

Leu Asn Ser Ser Asn Pro Met Asn Pro Tyr Pro Gly Leu Leu Asn
1610                1615                1620

Gln Asn Thr Gln Tyr Pro Ser Tyr Gln Cys Asn Gly Asn Leu Ser
1625                1630                1635

Val Asp Asn Cys Ser Pro Tyr Leu Gly Ser Tyr Ser Pro Gln Ser
1640                1645                1650

Gln Pro Met Asp Leu Tyr Arg Tyr Pro Ser Gln Asp Pro Leu Ser
1655                1660                1665

Lys Leu Ser Leu Pro Pro Ile His Thr Leu Tyr Gln Pro Arg Phe
1670                1675                1680

Gly Asn Ser Gln Ser Phe Thr Ser Lys Tyr Leu Gly Tyr Gly Asn
1685                1690                1695

Gln Asn Met Gln Gly Asp Gly Phe Ser Ser Cys Thr Ile Arg Pro
1700                1705                1710

Asn Val His His Val Gly Lys Leu Pro Pro Tyr Pro Thr His Glu
1715                1720                1725

Met Asp Gly His Phe Met Gly Ala Thr Ser Arg Leu Pro Pro Asn
1730                1735                1740

Leu Ser Asn Pro Asn Met Asp Tyr Lys Asn Gly Glu His His Ser
1745                1750                1755

Pro Ser His Ile Ile His Asn Tyr Ser Ala Ala Pro Gly Met Phe
1760                1765                1770

Asn Ser Ser Leu His Ala Leu His Leu Gln Asn Lys Glu Asn Asp
1775                1780                1785

Met Leu Ser His Thr Ala Asn Gly Leu Ser Lys Met Leu Pro Ala
1790                1795                1800

Leu Asn His Asp Arg Thr Ala Cys Val Gln Gly Gly Leu His Lys
1805                1810                1815

Leu Ser Asp Ala Asn Gly Gln Glu Lys Gln Pro Leu Ala Leu Val
1820                1825                1830

Gln Gly Val Ala Ser Gly Ala Glu Asp Asn Asp Glu Val Trp Ser
1835                1840                1845

Asp Ser Glu Gln Ser Phe Leu Asp Pro Asp Ile Gly Gly Val Ala
```

```
                 1850                1855                1860
Val Ala Pro Thr His Gly Ser Ile Leu Ile Glu Cys Ala Lys Arg
    1865                1870                1875
Glu Leu His Ala Thr Thr Pro Leu Lys Asn Pro Asn Arg Asn His
    1880                1885                1890
Pro Thr Arg Ile Ser Leu Val Phe Tyr Gln His Lys Ser Met Asn
    1895                1900                1905
Glu Pro Lys His Gly Leu Ala Leu Trp Glu Ala Lys Met Ala Glu
    1910                1915                1920
Lys Ala Arg Glu Lys Glu Glu Cys Glu Lys Tyr Gly Pro Asp
    1925                1930                1935
Tyr Val Pro Gln Lys Ser His Gly Lys Lys Val Lys Arg Glu Pro
    1940                1945                1950
Ala Glu Pro His Glu Thr Ser Glu Pro Thr Tyr Leu Arg Phe Ile
    1955                1960                1965
Lys Ser Leu Ala Glu Arg Thr Met Ser Val Thr Thr Asp Ser Thr
    1970                1975                1980
Val Thr Thr Ser Pro Tyr Ala Phe Thr Arg Val Thr Gly Pro Tyr
    1985                1990                1995
Asn Arg Tyr Ile
    2000

<210> SEQ ID NO 4
<211> LENGTH: 9236
<212> TYPE: DNA
<213> ORGANISM: Homo sapiens

<400> SEQUENCE: 4
aaacagaagg tgggccgggg cggggagaaa cagaactcgg tcaatttccc agtttgtcgg      60
gtctttaaaa atacaggccc ctaaagcact aagggcatgc cctcggtgaa acaggggagc    120
gcttctgctg aatgagatta aagcgacaga aaagggaaag gagagcgcgg gcaacgggat    180
ctaaagggag atagagacgc gggcctctga gggctggcaa acattcagca gcacaccctc    240
tcaagattgt ttacttgcct ttgctcctgt tgagttacaa cgcttggaag caggagatgg    300
gctcagcagc agccaatagg acatgatcca ggaagagcag taagggactg agctgctgaa    360
ttcaactaga gggcagcctt gtggatggcc ccgaagcaag cctgatggaa caggatagaa    420
ccaaccatgt tgagggcaac agactaagtc cattcctgat accatcacct cccatttgcc    480
agacagaacc tctggctaca aagctccaga atggaagccc actgcctgag agagctcatc    540
cagaagtaaa tggagacacc aagtggcact ctttcaaaag ttattatgga ataccctgta    600
tgaagggaag ccagaatagt cgtgtgagtc ctgactttac acaagaaagt agagggtatt    660
ccaagtgttt gcaaaatgga ggaataaaac gcacagttag tgaaccttct ctctctgggc    720
tccttcagat caagaaattg aaacaagacc aaaaggctaa tggagaaaga cgtaacttcg    780
gggtaagcca agaaagaaat ccaggtgaaa gcagtcaacc aaatgtctcc gatttgagtg    840
ataagaaaga atctgtgagt tctgtagccc aagaaaatgc agttaaagat ttcaccagtt    900
tttcaacaca taactgcagt gggcctgaaa tccagagct tcagattctg aatgagcagg    960
agggaaaag tgctaattac catgacaaga acattgtatt acttaaaaac aaggcagtgc   1020
taatgcctaa tggtgctaca gtttctgcct cttccgtgga acacacacat ggtgaactcc   1080
tggaaaaaac actgtctcaa tattatccag attgtgtttc cattgcggtg cagaaaacca   1140
catctcacat aaatgccatt aacagtcagg ctactaatga gttgtcctgt gagatcactc   1200
```

```
acccatcgca tacctcagqg cagatcaatt ccgcacagac ctctaactct gagctgcctc    1260
caaagccagc tgcagtggtg agtgaggcct gtgatgctga tgatgctgat aatgccagta    1320
aactagctgc aatgctaaat acctgttcct ttcagaaacc agaacaacta caacaacaaa    1380
aatcagtttt tgagatatgc ccatctcctg cagaaaataa catccaggga accacaaagc    1440
tagcgtctgg tgaagaattc tgttcaggtt ccagcagcaa tttgcaagct cctggtggca    1500
gctctgaacg gtatttaaaa caaaatgaaa tgatggtgc ttacttcaag caaagctcag    1560
tgttcactaa ggattccttt tctgccacta ccacaccacc accaccatca caattgcttc    1620
tttctccccc tcctcctctt ccacaggttc ctcagcttcc ttcagaagga aaaagcactc    1680
tgaatggtgg agttttagaa gaacaccacc actaccccaa ccaaagtaac acaacacttt    1740
taagggaagt gaaaatagag ggtaaacctg aggcaccacc ttcccagagt cctaatccat    1800
ctacacatgt atgcagccct ctccgatgc tttctgaaag gcctcagaat aattgtgtga    1860
acaggaatga catacagact gcagggacaa tgactgttcc attgtgttct gagaaaacaa    1920
gaccaatgtc agaacacctc aagcataacc caccaatttt tggtagcagt ggagagctac    1980
aggacaactg ccagcagttg atgagaaaca aagagcaaga gattctgaag ggtcgagaca    2040
aggagcaaac acgagatctt gtgcccccaa cacagcacta tctgaaacca ggatggattg    2100
aattgaaggc ccctcgtttt caccaagcgg aatcccatct aaaacgtaat gaggcatcac    2160
tgccatcaat tcttcagtat caacccaatc tctccaatca aatgacctcc aaacaataca    2220
ctggaaattc caacatgcct gggggctcc caaggcaagc ttacacccag aaaacaacac    2280
agctggagca caagtcacaa atgtaccaag ttgaaatgaa tcaagggcag tcccaaggta    2340
cagtggacca acatctccag ttccaaaaac cctcacacca ggtgcacttc tccaaaacag    2400
accatttacc aaaagctcat gtgcagtcac tgtgtggcac tagatttcat tttcaacaaa    2460
gagcagattc ccaaactgaa aaacttatgt ccccagtgtt gaaacagcac ttgaatcaac    2520
aggcttcaga gactgagcca ttttcaaact cacaccttttt gcaacataag cctcataaac    2580
aggcagcaca aacacaacca tcccagagtt cacatctccc tcaaaaccag caacagcagc    2640
aaaaattaca aataaagaat aaagaggaaa tactccagac ttttcctcac ccccaaagca    2700
acaatgatca gcaaagagaa ggatcattct ttggccagac taaagtggaa gaatgttttc    2760
atggtgaaaa tcagtattca aaatcaagcg agttcgagac tcataatgtc caaatgggac    2820
tggaggaagt acagaatata atcgtagaa attcccctta tagtcagacc atgaaatcaa    2880
gtgcatgcaa aatacaggtt tcttgttcaa acaatacaca cctagtttca gagaataaag    2940
aacagactac acatcctgaa cttttgcag gaaacaagac ccaaaacttg catcacatgc    3000 aatatttttcc aaataatgtg atcccaaagc aagatcttct tcacaggtgc tttcaagaac    3060
aggagcagaa gtcacaacaa gcttcagttc tacagggata taaaaataga aaccaagata    3120
tgtctggtca caagctgcg caacttgctc agcaaaggta cttgatacat aaccatgcaa    3180 atgttttttcc tgtgcctgac cagggaggaa gtcacactca gaccctccc cagaaggaca    3240 ctcaaaagca tgctgctcta aggtggcatc tcttacagaa gcaagaacag cagcaaacac    3300
agcaacccca aactgagtct tgccatagtc agatgcacag gccaattaag gtggaacctg    3360
gatgcaagcc acatgcctgt atgcacacag caccaccaga aaacaaaaca tggaaaaagg    3420
taactaagca agagaatcca cctgcaagct gtgataatgt gcagcaaaag agcatcattg    3480
agaccatgga gcagcatctg aagcagtttc acgccaagtc gttatttgac cataaggctc    3540
```

```
ttactctcaa atcacagaag caagtaaaag ttgaaatgtc agggccagtc acagttttga      3600
ctagacaaac cactgctgca gaacttgata gccacacccc agctttagag cagcaaacaa      3660
cttcttcaga aaagacacca accaaaagaa cagctgcttc tgttctcaat aattttatag      3720
agtcaccttc caaattacta gatactccta taaaaatttt attggataca cctgtcaaga      3780
ctcaatatga tttcccatct tgcagatgtg taggtaagtg ccagaaatgt actgagacac      3840
atggcgttta ccagaattga gcaaatttat cttcagatat gggattttcc ttcttttttt      3900
aaatcttgag tctggcagca atttgtaaag gctcataaaa atctgaagct tacattttt       3960 gtcaagttac cgatgcttgt gtcttgtgaa agagaacttc acttacatgc agttttcca      4020 aaagaattaa ataatcgtgc atgtttattt ttccctctct tcagatcctg taaaatttga      4080
atgtatctgt tttagatcaa ttcgcctatt tagctctttg tatattatct cctggagaga      4140
cagctaggca gcaaaaaaac aatctattaa aatgagaaaa taacgaccat aggcagtcta      4200
atgtacgaac tttaaatatt ttttaattca aggtaaaata tattagtttc acaagatttc      4260
tggctaatag ggaattatt atcttcagtc ttcatgagtt gggggaaatg ataatgctga      4320
cactcttagt gctcctaaag tttccttttc tccatttata catttggaat gttgtgattt      4380
atattcattt tgattcccttt ttctctaaaa tttcatctttt ttgattaaaa aatatgatac     4440
aggcatacct cagagatatt gtgggtttgg ctccatacca caataaaatg aatattacaa      4500
taaagcaagt tgtaaggact ttttggtttc tcactgtatg taaaagttat ttatatacta      4560
tactgtaaca tactaagtgt gcaatagcat tgtgtctaaa aaatatatac tttaaaaata      4620
atttattgtt aaaaaaatgc caacaattat ctgggccttt agtgagtgct aatctttttg      4680
ctggtggagg gtcgtgcttc agtattgatc gctgtggact gatcatggtg gtagttgctg      4740
aaggttgctg ggatggctgt gtgtgtggca atttcttaaa ataagacaac agtgaagtgc      4800
tgtatcaatt gattttttcca ttcacaaaag atttctctgt agcatgcaat gctgtttgat     4860
agcatttaac ccacagcaga atttctttga aaattggact cagtcctctc aaactgtgct      4920
gctgctttat caactaagtt tttgtaattt tctgaatcct ttgttgtcat ttcagcagtt      4980
tacagcatct tcattggaag tatattccat ctcaaacatt cttttgttcat ccataagaag      5040 caacttctta tcaagttttt tcatgacatt gcagtaactc agccccatct tcaggctcta      5100
cttctaattc tggttctctt gctacatctc cctcatctgc agtgacctct ccacggaagt      5160
cttgaactcc tcaaagtaat ccatgagggt tggaatcaac ttctaaactc ctgttaatgt      5220
tgatatattg accccctccc atgaattatg aatgttctta ataacttcta aatggtgata      5280
cctttccaga aggctttcaa tgtactttgc ccggatccat cagaagacta tcttggcagc      5340
tgtagactaa caatatattt cttaaatgat aagacttgaa agtcaaaagt actccttaat      5400
ccataggctg cagaatcaat gttgtattaa caggcacgaa aacagcatta atcttgtgca      5460
tctccatcgg agctcttggg tgactaggtg ccttgagcag taatattttg aaaggaggtt      5520
ttggttttgt tttttgtttt tttttttgt ttttagcag taagtctcaa cactgggctt       5580
aaaatattca gtaaactatg ttgtaaaaag atgtgttatc atccagactt gttgttcca       5640 ttactctaca caagcagggt acactagca taattcttaa gggccttgga attttcagaa       5700
tggtaaatga gtatgggctt caacttaaaa tcatcaactg cattagcctg taacaagaga      5760
gtcagcctgt cctttgaagc aaggcattga cttctatcta tgaaagtctt agatggcacc      5820
ttgtttcaat agtaggctgt ttagtacagc caccttcatc agtgatctta gctagatctt      5880
ctgcataact tgctgcagct tctacatcag cacttgctgc ctcaccttgt cctttttatgt     5940
```

```
tatagagaca gctgcgcttc ttaaacttta taaaccaact tctgctagct tccaacttct    6000
cttctgcagc ttcctcattc tcttcataga actgaaggga gtcaaggcct tgctctggat    6060
taagctttgg cttaaggaat gttgtggctg acgtgatctt ctatccagac cactaaagcg    6120
ctctccatat cagcaataag gccgttttgc tttcttacct ttcatgtgtt cactggagta    6180
atttccttca agaattttc ctttacattc acaacttggc taactggcat gcaaggccta    6240
gctttcagcc tgtcttggct tttgacatgc cttcctcact tagctcgtca tatctagctt    6300
ttgatttaaa gtggcaggca tacaactctt cctttcactt gaacacttag aggccactgt    6360
agggttatta attggcctaa tttcaatatt gttgtgtttt agggaataga gaggcccagg    6420
gagagggaga gagcccaaac ggctggttga tagagcaggc agaatgcaca caacatttat    6480
cagattatgt ttgcaccatt taccagatta tgggtacggt tgtggcacc ccccaaaaat    6540 tagaatagta acatcaaaga tcactgatca cagatcgcca taacataaat aataataaac    6600
tttaaaatac tgtgagaatt accaaaatgt gatacagaga catgaagtga gcacatgctg    6660
ttgaaaaaaa tgacactgat agacatactt aacacgtggg attgccacaa accttcagtt    6720
tgtaaaagtc acagtaactg tgactcacaa aagaacaaag cacaataaaa cgaggtatgc    6780 ctgtatttt aaaaaagct ttttgttaaa attcaggata tgtaataggt ctgtaggaat    6840
agtgaaatat ttttgctgat ggatgtagat atatacgtgg atagagatga agatcttaat    6900
tatagctatg cagcatagat ttagtcaaag acatttgaaa agacaaatgt taaattagtg    6960
tggctaatga cctacccgtg ccatgttttc cctcttgcaa tgagataccc cacactgtgt    7020
agaaggatgg agggaggact cctactgtcc ctctttgcgt gtggttatta agttgcctca    7080
ctgggctaaa acaccacaca tctcatagat aatatttggt aagttgtaat cgtcttcact    7140
cttctcttat cacccacccc tatcttccca ctttccatc tttgttggtt tgcaacagcc    7200
ccttcttttt gcctgactct ccaggatttt ctctcatcat aaattgttct aaagtacata    7260
ctaatatggg tctggattga ctattcttat ttgcaaaaca gcaattaaat gttataggga    7320
agtaggaaga aaaaggggta tccttgacaa taaaccaagc aatattctgg gggtgggata    7380
gagcaggaaa ttttatttt aatcttttaa aatccaagta ataggtaggc ttccagttag    7440
ctttaaatgt ttttttttc cagctcaaaa aattggattg tagttgatac tacatataat    7500
acattctaat tccctcactg tattcttgt ttagtttcat ttatttggtt taaaataatt    7560
ttttatccca tatctgaaat gtaatatatt tttatccaac aaccagcatg tacatatact    7620
taattatgtg gcacattttc taatagatca gtccatcaat ctactcattt taaagaaaaa    7680
aaaattttaa agtcacttt agagcccta atgtgtagtt gggggttaag ctttgtggat    7740
gtagccttta tatttagtat aattgaggtc taaaataata atcttctatt atctcaacag    7800
agcaaattat tgaaaagat gaaggtcctt tttatacca tctaggagca ggtcctaatg    7860
tggcagctat tagagaaatc atggaagaaa ggtaattaac gcaaaggcac agggcagatt    7920
aacgtttatc ctttgtata tgtcagaatt tttccagcct tcacacacaa agcagtaaac    7980
aattgtaaat tgagtaatta ttagtaggct tagctattct agggttgcca acactacaca    8040
ctgtgctatt caccagagag tcacaatatt tgacaggact aatagtctgc tagctggcac    8100
aggctgccca ctttgcgatg gatgccagaa acccaggca tgaacaggaa tcggccagcc    8160
aggctgccag ccacaaggta ctggcacagg ctccaacgag aggtcccact ctggctttcc    8220
cacctgataa taaagtgtca aagcagaaag actggtaaag tgtggtataa gaaaagaacc    8280
```

```
actgaattaa attcacctag tgttgcaaat gagtacttat ctctaagttt tcttttacca    8340
taaaaagaga gcaagtgtga tatgttgaat agaaagagaa acatactatt tacagctgcc    8400 ttttttttt ttttttcgcta tcaatcacag gtatacaagt acttgccttt actcctgcat    8460
gtagaagact cttatgagcg agataatgca gagaaggcct ttcatataaa tttatacagc    8520
tctgagctgt tcttcttcta gggtgccttt tcattaagag gtaggcagta ttattattaa    8580
agtacttagg atacattggg gcagctagga catattcagt atcattcttg ctccatttcc    8640
aaattattca tttctaaatt agcatgtaga agttcactaa ataatcatct agtggcctgg    8700
cagaaatagt gaatttccct aagtgccttt tttttgttgt ttttttgttt tgtttttaa    8760 acaagcagta ggtggtgctt tggtcataag ggaagatata gtctatttct aggactattc    8820 catatttttcc atgtggctgg atactaacta tttgccagcc tcctttttcta aattgtgaga    8880 cattcttgga ggaacagttc taactaaaat ctattatgac tcccccaagtt ttaaaatagc    8940 taaatttagt aagggaaaaa atagtttatg ttttagaaga ctgaacttag caaactaacc    9000
tgaattttgt gctttgtgaa attttatatc gaaatgagct ttcccatttt cacccacatg    9060
taatttacaa aatagttcat tacaattatc tgtacatttt gatattgagg aaaaacaagg    9120
cttaaaaacc attatccagt ttgcttggcg tagacctgtt taaaaaataa taaccgttc    9180 atttctcagg atgtggtcat agaataaagt tatgctcaaa tgttcaaata tttaaa      9236
```

<210> SEQ ID NO 5
<211> LENGTH: 1165
<212> TYPE: PRT
<213> ORGANISM: Homo sapiens

<400> SEQUENCE: 5

```
Met Glu Gln Asp Arg Thr Asn His Val Glu Gly Asn Arg Leu Ser Pro
1               5                   10                  15

Phe Leu Ile Pro Ser Pro Pro Ile Cys Gln Thr Glu Pro Leu Ala Thr
            20                  25                  30

Lys Leu Gln Asn Gly Ser Pro Leu Pro Glu Arg Ala His Pro Glu Val
        35                  40                  45

Asn Gly Asp Thr Lys Trp His Ser Phe Lys Ser Tyr Tyr Gly Ile Pro
    50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95

Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205
```

```
Asn Gly Ala Thr Val Ser Ala Ser Ser Val Glu His Thr His Gly Glu
    210                 215                 220
Leu Leu Glu Lys Thr Leu Ser Gln Tyr Tyr Pro Asp Cys Val Ser Ile
225                 230                 235                 240
Ala Val Gln Lys Thr Thr Ser His Ile Asn Ala Ile Asn Ser Gln Ala
                245                 250                 255
Thr Asn Glu Leu Ser Cys Glu Ile Thr His Pro Ser His Thr Ser Gly
            260                 265                 270
Gln Ile Asn Ser Ala Gln Thr Ser Asn Ser Glu Leu Pro Pro Lys Pro
                275                 280                 285
Ala Ala Val Val Ser Glu Ala Cys Asp Ala Asp Asp Ala Asp Asn Ala
    290                 295                 300
Ser Lys Leu Ala Ala Met Leu Asn Thr Cys Ser Phe Gln Lys Pro Glu
305                 310                 315                 320
Gln Leu Gln Gln Gln Lys Ser Val Phe Glu Ile Cys Pro Ser Pro Ala
                325                 330                 335
Glu Asn Asn Ile Gln Gly Thr Thr Lys Leu Ala Ser Gly Glu Glu Phe
            340                 345                 350
Cys Ser Gly Ser Ser Ser Asn Leu Gln Ala Pro Gly Gly Ser Ser Glu
        355                 360                 365
Arg Tyr Leu Lys Gln Asn Glu Met Asn Gly Ala Tyr Phe Lys Gln Ser
    370                 375                 380
Ser Val Phe Thr Lys Asp Ser Phe Ser Ala Thr Thr Thr Pro Pro Pro
385                 390                 395                 400
Pro Ser Gln Leu Leu Leu Ser Pro Pro Pro Leu Pro Gln Val Pro
                405                 410                 415
Gln Leu Pro Ser Glu Gly Lys Ser Thr Leu Asn Gly Gly Val Leu Glu
                420                 425                 430
Glu His His His Tyr Pro Asn Gln Ser Asn Thr Thr Leu Leu Arg Glu
        435                 440                 445
Val Lys Ile Glu Gly Lys Pro Glu Ala Pro Pro Ser Gln Ser Pro Asn
    450                 455                 460
Pro Ser Thr His Val Cys Ser Pro Ser Pro Met Leu Ser Glu Arg Pro
465                 470                 475                 480
Gln Asn Asn Cys Val Asn Arg Asn Asp Ile Gln Thr Ala Gly Thr Met
                485                 490                 495
Thr Val Pro Leu Cys Ser Glu Lys Thr Arg Pro Met Ser Glu His Leu
            500                 505                 510
Lys His Asn Pro Pro Ile Phe Gly Ser Ser Gly Glu Leu Gln Asp Asn
        515                 520                 525
Cys Gln Gln Leu Met Arg Asn Lys Glu Gln Glu Ile Leu Lys Gly Arg
    530                 535                 540
Asp Lys Glu Gln Thr Arg Asp Leu Val Pro Pro Thr Gln His Tyr Leu
545                 550                 555                 560
Lys Pro Gly Trp Ile Glu Leu Lys Ala Pro Arg Phe His Gln Ala Glu
                565                 570                 575
Ser His Leu Lys Arg Asn Glu Ala Ser Leu Pro Ser Ile Leu Gln Tyr
        580                 585                 590
Gln Pro Asn Leu Ser Asn Gln Met Thr Ser Lys Gln Tyr Thr Gly Asn
    595                 600                 605
Ser Asn Met Pro Gly Gly Leu Pro Arg Gln Ala Tyr Thr Gln Lys Thr
610                 615                 620
Thr Gln Leu Glu His Lys Ser Gln Met Tyr Gln Val Glu Met Asn Gln
```

```
                625                 630                 635                 640
Gly Gln Ser Gln Gly Thr Val Asp Gln His Leu Gln Phe Gln Lys Pro
                    645                 650                 655

Ser His Gln Val His Phe Ser Lys Thr Asp His Leu Pro Lys Ala His
            660                 665                 670

Val Gln Ser Leu Cys Gly Thr Arg Phe His Phe Gln Gln Arg Ala Asp
            675                 680                 685

Ser Gln Thr Glu Lys Leu Met Ser Pro Val Leu Lys Gln His Leu Asn
        690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                725                 730                 735

His Leu Pro Gln Asn Gln Gln Gln Lys Leu Gln Ile Lys Asn
            740                 745                 750

Lys Glu Glu Ile Leu Gln Thr Phe Pro His Pro Gln Ser Asn Asn Asp
        755                 760                 765

Gln Gln Arg Glu Gly Ser Phe Phe Gly Gln Thr Lys Val Glu Glu Cys
770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
        835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
            900                 905                 910

Gln Leu Ala Gln Gln Arg Tyr Leu Ile His Asn His Ala Asn Val Phe
        915                 920                 925

Pro Val Pro Asp Gln Gly Gly Ser His Thr Gln Thr Pro Pro Gln Lys
    930                 935                 940

Asp Thr Gln Lys His Ala Ala Leu Arg Trp His Leu Leu Gln Lys Gln
945                 950                 955                 960

Glu Gln Gln Gln Thr Gln Pro Gln Thr Glu Ser Cys His Ser Gln
                965                 970                 975

Met His Arg Pro Ile Lys Val Glu Pro Gly Cys Lys Pro His Ala Cys
            980                 985                 990

Met His Thr Ala Pro Pro Glu Asn Lys Thr Trp Lys Lys Val Thr Lys
        995                 1000                1005

Gln Glu Asn Pro Pro Ala Ser Cys Asp Asn Val Gln Gln Lys Ser
    1010                1015                1020

Ile Ile Glu Thr Met Glu Gln His Leu Lys Gln Phe His Ala Lys
    1025                1030                1035

Ser Leu Phe Asp His Lys Ala Leu Thr Leu Lys Ser Gln Lys Gln
    1040                1045                1050
```

```
Val Lys Val Glu Met Ser Gly Pro Val Thr Val Leu Thr Arg Gln
    1055            1060                1065

Thr Thr Ala Ala Glu Leu Asp Ser His Thr Pro Ala Leu Glu Gln
    1070            1075                1080

Gln Thr Thr Ser Ser Glu Lys Thr Pro Thr Lys Arg Thr Ala Ala
    1085            1090                1095

Ser Val Leu Asn Asn Phe Ile Glu Ser Pro Ser Lys Leu Leu Asp
    1100            1105                1110

Thr Pro Ile Lys Asn Leu Leu Asp Thr Pro Val Lys Thr Gln Tyr
    1115            1120                1125

Asp Phe Pro Ser Cys Arg Cys Val Gly Lys Cys Gln Lys Cys Thr
    1130            1135                1140

Glu Thr His Gly Val Tyr Pro Glu Leu Ala Asn Leu Ser Ser Asp
    1145            1150                1155

Met Gly Phe Ser Phe Phe Phe
    1160            1165
```

<210> SEQ ID NO 6

<400> SEQUENCE: 6

000

<210> SEQ ID NO 7

<400> SEQUENCE: 7

000

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctccaagca gatgcagca                                              19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggctgtattc ccctccatcg                                             20

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgacagtgat gagaatgacc tgttc                                       25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gctaccaaac tggatataat cagga                                      25

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcaccttaca cctaccagag t                                          21

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cggagtccgg gcagg                                                 15

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cagccagatg cagttaacgc                                            20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ccgaagtcat agccacactc aa                                         22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tgacttcaag aacatccaga gctt                                       24

<210> SEQ ID NO 17

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttgagacca tccagagctt ga                                              22

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgccatatg gagctgaca                                                  19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagcagcaag tgctccaatc                                                 20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggtgcctgg tctgatga                                                   18

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcagactgaa ggactgggaa ca                                              22

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcccatgcc gagagtct                                                   18

<210> SEQ ID NO 23
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
catctggttc agtgctttga tct                                             23

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atgcctcgcg ctttctctc                                                  19

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtgatgctca ggtatccatc ca                                              22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tagagtgcaa ggagttcggg                                                 20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtgctactgg ggctcatttg t                                               21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtttctgctt tcaccactcc a                                               21

<210> SEQ ID NO 29
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 29
tcccagattc tgaaggcttg                                                 20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
attacccgcc cgagaaagg                                                  19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gacagtgcaa ctgcgagaag                                                 20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acaaggcacg ggacctatg                                                  19

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccggatgtga ggcagcag                                                   18

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccagttggta acaatgccat gt                                              22

<210> SEQ ID NO 35
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 35
ttggaagcag cccttcatct                                            20

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccaggtagct atggtactcc agaa                                       24

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aaacttctgc ctgacgagct t                                          21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctgggtaga gaatggatga a                                          21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcctactcat tgggatcatc ttg                                        23

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caagggagct tcagggtcaa                                            20

<210> SEQ ID NO 41
<211> LENGTH: 26
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 41
cttgagagtg gctatgactt ctgtct                                          26

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccttgagagt ggctatgact tctgt                                           25

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgtggaatct tccggctgta                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cacacacttg gcggttcctt                                                 20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtggtaaccg ctcaggtgtt g                                               21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaggccctt gaatgaaggt                                                 20

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 47
cagaggcgca ccaaacct                                               18

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acccgtgagt tattccatga gt                                          22

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtagtcccgc tgacagtatg c                                           21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cacagttctc aaagcacagc g                                           21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccggcatata cgagtgtgaa                                             20

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggagtaagag gacacttgcg aat                                         23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 53
gagtccaatt tactccaggt cag                                          23

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtgagacgtt ggaaggcagt                                              20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcgcagcaaa gatccacaca g                                            21

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgactccaga tagtagctga caa                                          23

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tcccagtcag tcctggaaat g                                            21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aagtgtgtca tcgtggtgga a                                            21

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 59
cctgcgttta aataacatca gctttagctt                                         30

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtgcatctac gtgcctacct t                                                  21

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcacaatgtg acgtcgttta gcatcgaa                                           28
```

AGE-ASSOCIATED CLONAL HEMATOPOIESIS ACCELERATES CARDIO-METABOLIC DISEASE DEVELOPMENT

CROSS REFERENCE TO RELATED APPLICATIONS

This application claims benefit under 35 U.S.C. § 119(e) of U.S. Provisional No. 62/368,338, filed Jul. 29, 2016, the contents of which are incorporated herein by reference in their entirety.

GOVERNMENT SUPPORT

This invention was made with Government Support under Contract Nos. HL081587, HL116591, HL131006, and HL132564 awarded by the National Institutes of Health (NIH). The Government has certain rights in the invention.

SEQUENCE LISTING

The instant application contains a Sequence Listing which has been submitted electronically in ASCII format and is hereby incorporated by reference in its entirety. Said ASCII copy, created on Aug. 29, 2017, is named 701586-087532-US_SL.txt and is 248,386 bytes in size.

TECHNICAL FIELD

The technical field relates to compositions, methods, and assays for the treatment, prevention and diagnosis of cardio-metabolic diseases, chronic kidney disease, and other age-dependent chronic diseases that involve pathological inflammatory responses.

BACKGROUND

Macrovascular diseases (CVD and stroke) steeply increase with age and account for >85% of chronic disease deaths in those >70 years of age (from Belsky et al. Proc. Natl. Acad. Sci. USA 2015). While cardiovascular disease (CVD) is the leading cause of death in the elderly, almost 60% of elderly patients with atherosclerotic CVD have either no or just one conventional CV risk factors (e.g. hypertension, hypercholesterolemia, etc.). As can be seen in Khot et al. (JAMA 2003), more than 60% of patients with CVD display either zero or one conventional risk factors. Similarly, retrospective analysis of CVD patients revealed that up to 50% of these patients were classified as low-risk when applying predictive scales based on traditional risk factors (Akosah et al. JACC 2003). Consistent with these findings, the recent PESA and AWHS studies have reported that subclinical atherosclerosis can be detected in more than 57% of asymptomatic adults categorized as "low CV risk" on the basis of conventional 10-year risk prediction algorithms (Fernández-Friera et al. Circulation 2015; Laclaustra et al. JACC 2016). Among others, these clinical studies suggest that there are as-yet-unidentified causal risk factors that drive cardiovascular disease in the human population.

SUMMARY

The present invention is directed, in part, to a new paradigm of causal risk for cardiovascular and related diseases and provides novel compositions, methods, and assays for treating, preventing, and/or diagnosing the same. Epidemiological studies show that hematopoietic stem cells (HSCs) develop mutations that promote their clonal expansion at a relatively high frequency in the aging population. While very few of the HSCs acquire subsequent mutations in oncogenes that lead to blood cancers, the mechanistic findings of the studies described herein, using Tet2 as an example, show that a single mutation that occurs frequently can predispose an individual to CVD and stroke that are common in the elderly (>50% of individuals). Accordingly, the findings described herein demonstrate that there is a common mechanistic basis between age-associated CVD and hematological cancers. These data provide the first experimental evidence supporting a mechanism whereby somatic mutations in HSCs represent a new causal risk factor for CVD, potentially adding to the predictive capabilities of the conventional risk factors (hyperlipidemia, hypertension, diabetes and smoking) that were deduced approximately 50 years ago. These data also provide the first mechanistic evidence for how somatic mutations in HSCs can lead to chronic, non-cancerous diseases, providing novel personalized therapies or preventive strategies for individuals carrying somatic mutations in blood cells. For example, where neutralizing antibodies against IL-1β are being tested in large, ongoing clinical trials for the treatment of CVD, the data described herein indicate that IL-1beta blockade or NLRP3 inflammasome inhibition can be particularly effective for the prevention/treatment of CVD in individuals carrying somatic mutations in TET2. In some embodiments, other clonal hematopoiesis driver gene mutations mediate IL-1β pro-inflammatory diseases as well.

As described herein, competitive bone marrow transplantation strategies into Ldlr$^{-/-}$ mice were used to examine the contribution of the clonal expansion of Tet2-deficient hematopoietic cells to atherosclerosis development. Bone marrow reconstitution with as few as 10% Tet2−/− cells was sufficient for its expansion into all blood cell lineages and led to a marked increase in atherosclerotic plaque size. Mechanistically, the exacerbated atherosclerosis was related to the effects of Tet2 on pro-inflammatory activation of macrophages, but independent of changes in blood cell counts and macrophage proliferation or apoptosis. Tet2−/− macrophages exhibited a pronounced increase in pro-inflammatory cytokine/chemokine expression, particularly of IL-1β. Tet2 deficiency also enhanced NLRP3 inflammasome priming and IL-1 receptor 1 expression, supporting a predominant role for increased IL-1β signaling in the exacerbated atherosclerosis associated with Tet2-deficient cell expansion. These results provide mouse genetic evidence supporting a causal connection between somatic mutations in TET2 in blood cells and cardiometabolic diseases, such as CVD, in humans, and document a new mechanism of pro-inflammatory IL-1β signaling regulation.

Accordingly, provided herein, in some aspects, are methods for treating a subject having, or at risk for, a TET2 mutation-mediated IL-1β proinflammatory disease comprising administering a therapeutically effective amount of a pharmaceutical composition comprising an inhibitor of TET2 mutation-mediated IL-1β (interleukin-1β) proinflammatory activity and a pharmaceutically acceptable carrier to a subject having one or more TET2 somatic mutations in a sub-population of peripheral blood hematopoietic cells.

In some embodiments of these methods and all such methods described herein, the one or more TET2 somatic mutations in the sub-population of peripheral blood hematopoietic cells cause clonal hematopoiesis in the subject.

In some embodiments of these methods and all such methods described herein, at least 2% of the peripheral blood hematopoietic cells have the one or more TET2 mutations.

In some embodiments of these methods and all such methods described herein, the one or more TET2 somatic mutations are selected from an S282F mutation in SEQ ID NO: 3, an N312S mutation in SEQ ID NO: 3, an L346P mutation in SEQ ID NO: 3, an S460F mutation in SEQ ID NO: 3, a D666G mutation in SEQ ID NO: 3, a P941S mutation in SEQ ID NO: 3, and a C1135Y mutation in SEQ ID NO: 3.

In some embodiments of these methods and all such methods described herein, the inhibitor of TET2 mutation-mediated IL-1β proinflammatory activity is an IL-1β inhibitor.

In some embodiments of these methods and all such methods described herein, the IL-1β inhibitor is an IL-1β inhibitor antibody or antigen-binding fragment thereof that binds to IL-1β and reduces IL-1β binding to its receptor(s).

In some embodiments of these methods and all such methods described herein, the IL-1β inhibitor antibody or antigen-binding fragment thereof is selected from ABT981, an anti-interleukin-1β inhibitor antibody by ABZYME, APX002, Canakinumab/Ilaris, CDP48, immunereszumab, LY2189102, MEDI8968, and XOMA052.

In some embodiments of these methods and all such methods described herein, the IL-1β inhibitor is an IL-1 receptor antagonist.

In some embodiments of these methods and all such methods described herein, the IL-1 receptor antagonist is selected from CDP484, CP412245, CYT013 IL1bQb, XL 130, AMG108, HL 2351, IL1Hy1, AXXO, orthokine, PRT 1000, anakinra, and rilonacept.

In some embodiments of these methods and all such methods described herein, the IL-1β inhibitor is a small molecule or microRNA inhibitor that inhibits IL-1β-mediated pro-inflammatory activity.

In some embodiments of these methods and all such methods described herein, the small molecule inhibitor is selected from AC201, CP412245, MCC950 or CRID3, inflabion, inflammasome modulator OPSONA, PGE3935199, PGE527667, TRK530, β-hydroxybutyrate (BHB), and microRNA-223. In some such embodiments, the small molecule inhibitor is MCC950.

In some embodiments of these methods and all such methods described herein, the method further comprises monitoring hematopoietic cell clonality, IL-1β proinflammatory activity, or a combination thereof following the administration of the inhibitor of TET2 mutation-mediated IL-1β proinflammatory activity.

In some embodiments of these methods and all such methods described herein, the method further comprises decreasing the number or percentage of hematopoietic cells comprising the one or more TET2 mutations in the subject by performing therapeutic cytapheresis on the subject.

In some embodiments of these methods and all such methods described herein, the method further comprises administering one or more additional therapeutic agents to the subject, in addition to the inhibitor of TET2 mutation-mediated IL-1β (interleukin-1β) proinflammatory activity.

In some embodiments of these methods and all such methods described herein, the TET2 mutation-mediated IL-1β proinflammatory disease is a cardiometabolic disease or disorder.

In some embodiments of these methods and all such methods described herein, the TET2 mutation-mediated IL-1β proinflammatory disease is a chronic kidney disease or disorder.

Also provided herein, in some aspects, are methods for treating a subject having, or at risk for, a TET2 mutation-mediated IL-1β proinflammatory disease comprising: (a) sequencing a hematopoietic cell sample from a subject to identify one or more somatic mutations in TET2 in the hematopoietic cell sample; and (b) administering a therapeutically effective amount of a pharmaceutical composition comprising an inhibitor of TET2 mutation-mediated IL-1β (interleukin-1β) proinflammatory activity and a pharmaceutically acceptable carrier if one or more somatic mutations in TET2 are identified in the hematopoietic cell sample.

In some embodiments of these methods and all such methods described herein, the hematopoietic cell sample is a peripheral blood hematopoietic cell sample.

In some embodiments of these methods and all such methods described herein, the hematopoietic cell sample is enriched for myeloid-derived cells.

In some embodiments of these methods and all such methods described herein, the one or more TET2 somatic mutations identified in the hematopoietic cell sample cause clonal hematopoiesis in the subject.

In some embodiments of these methods and all such methods described herein, at least 2% of the hematopoietic cells are identified as having one or more TET2 mutations.

In some embodiments of these methods and all such methods described herein, the one or more TET2 somatic mutations are selected from an S282F mutation in SEQ ID NO: 3, an N312S mutation in SEQ ID NO: 3, an L346P mutation in SEQ ID NO: 3, an S460F mutation in SEQ ID NO: 3, a D666G mutation in SEQ ID NO: 3, a P941S mutation in SEQ ID NO: 3, and a C1135Y mutation in SEQ ID NO: 3.

In some embodiments of these methods and all such methods described herein, the inhibitor of TET2 mutation-mediated IL-1β proinflammatory activity is an IL-1β inhibitor.

In some embodiments of these methods and all such methods described herein, the IL-1β inhibitor is an IL-1β inhibitor antibody or antigen-binding fragment thereof that binds to IL-1β and reduces IL-1β binding to its receptor(s).

In some embodiments of these methods and all such methods described herein, the IL-1β inhibitor antibody or antigen-binding fragment thereof is selected from ABT981, an anti-interleukin-1β inhibitor antibody by ABZYME, APX002, Canakinumab/Ilaris, CDP48, immunereszumab, LY2189102, MEDI8968, and XOMA052.

In some embodiments of these methods and all such methods described herein, the IL-1β inhibitor is an IL-1 receptor antagonist.

In some embodiments of these methods and all such methods described herein, the IL-1 receptor antagonist is selected from CDP484, CP412245, CYT013 IL1bQb, XL 130, AMG108, HL 2351, IL1Hy1, AXXO, orthokine, PRT 1000, anakinra, and rilonacept.

In some embodiments of these methods and all such methods described herein, the IL-1β inhibitor is a small molecule or microRNA inhibitor that inhibits IL-1β-mediated pro-inflammatory activity.

In some embodiments of these methods and all such methods described herein, the small molecule or microRNA inhibitor is selected from AC201, CP412245, MCC950 or CRID3, inflabion, inflammasome modulator OPSONA, PGE3935199, PGE527667, TRK530, β-hydroxybutyrate (BHB), and microRNA-223. In some such embodiments, the small molecule inhibitor is MCC950.

In some embodiments of these methods and all such methods described herein, the method further comprises monitoring hematopoietic cell clonality, IL-1β proinflammatory activity, or a combination thereof following the administration of the inhibitor of TET2 mutation-mediated IL-1β proinflammatory activity.

In some embodiments of these methods and all such methods described herein, the method further comprises decreasing the number or percentage of hematopoietic cells comprising the one or more TET2 mutations in the subject by performing therapeutic cytapheresis on the subject.

In some embodiments of these methods and all such methods described herein, the method further comprises administering one or more additional therapeutic agents to the subject, in addition to the inhibitor of TET2 mutation-mediated IL-1β proinflammatory activity.

In some embodiments of these methods and all such methods described herein, the TET2 mutation-mediated IL-1β proinflammatory disease is a cardiometabolic disease or disorder.

In some embodiments of these methods and all such methods described herein, the TET2 mutation-mediated IL-1β proinflammatory disease is a chronic kidney disease or disorder.

Also provided herein, in some aspects, are pharmaceutical compositions comprising an inhibitor of TET2 mutation-mediated IL-1β (interleukin-1β) proinflammatory activity and a pharmaceutically acceptable carrier for use in a subject having one or more TET2 somatic mutations in a sub-population of hematopoietic cells.

In some embodiments of these compositions and all such compositions described herein, the one or more TET2 somatic mutations in the sub-population of hematopoietic cells cause clonal hematopoiesis in the subject.

In some embodiments of these compositions and all such compositions described herein, at least 2% of the hematopoietic cells in the subject have the one or more TET2 mutations.

In some embodiments of these compositions and all such compositions described herein, the one or more TET2 somatic mutations are selected from an S282F mutation in SEQ ID NO: 3, an N312S mutation in SEQ ID NO: 3, an L346P mutation in SEQ ID NO: 3, an S460F mutation in SEQ ID NO: 3, a D666G mutation in SEQ ID NO: 3, a P941S mutation in SEQ ID NO: 3, and a C1135Y mutation in SEQ ID NO: 3.

In some embodiments of these compositions and all such compositions described herein, the inhibitor of TET2 mutation-mediated IL-1β proinflammatory activity is an IL-1β inhibitor.

The pharmaceutical composition, wherein the IL-1β inhibitor is an IL-1β inhibitor antibody or antigen-binding fragment thereof that binds to IL-1β and reduces IL-1β binding to its receptor(s).

In some embodiments of these compositions and all such compositions described herein, the IL-1β inhibitor antibody or antigen-binding fragment thereof is selected from ABT981, an anti-interleukin-1β inhibitor antibody by ABZYME, APX002, Canakinumab/Ilaris, CDP48, immunereszumab, LY2189102, MEDI8968, and XOMA052.

In some embodiments of these compositions and all such compositions described herein, the IL-1β inhibitor is an IL-1 receptor antagonist.

The pharmaceutical composition, wherein the IL-1 receptor antagonist is selected from CDP484, CP412245, CYT013 IL1bQb, XL 130, AMG108, HL 2351, IL1Hy1, AXXO, orthokine, PRT 1000, anakinra, and rilonacept.

In some embodiments of these compositions and all such compositions described herein, the IL-1β inhibitor is a small molecule inhibitor that inhibits IL-1β-mediated pro-inflammatory activity.

In some embodiments of these compositions and all such compositions described herein, the small molecule inhibitor is selected from AC201, CP412245, MCC950 or CRID3, inflabion, inflammasome modulator OPSONA, PGE3935199, PGE527667, TRK530, β-hydroxybutyrate (BHB), and microRNA-223. In some such embodiments, the small molecule inhibitor is MCC950.

In some embodiments of these compositions and all such compositions described herein, the TET2 mutation-mediated IL-1β proinflammatory disease is a cardiometabolic disease or disorder.

In some embodiments of these compositions and all such compositions described herein, the TET2 mutation-mediated IL-1β proinflammatory disease is chronic kidney disease or disorder.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, an "inhibitor of TET2 mutation-mediated IL-1β (interleukin-1β) proinflammatory activity" refers to any agent or molecule that significantly blocks, inhibits, reduces, or interferes with the downstream effects of somatic mutations in TET2 that lead to increased IL-1β proinflammatory activity or signaling in vitro, in situ, and/or in vivo, including increased IL-1β transcription, increased NLRP3 inflammasome-mediated IL-1β secretion, and/or increased IL-1-receptor I (IL-1R1)-mediated IL-1β signaling.

As used herein, the terms reduce(s)/reduced/reducing/reduction, inhibit(s)/inhibiting/inhibited or decrease(s)/decreasing/decreased generally means either a reduction or inhibition of at least 5%, at least 10%, at least 25%, at least 50%, at least 60%, at least 70%, at least 80%, at least 90%, at least 95%, at least 98%, or more, compared to the level of IL-1β transcription, IL-1β translation, NLRP3 inflammasome-mediated IL-1β secretion, and/or IL-1β binding to IL-1 receptor and consequent IL-1-receptor I (IL-1R1)-mediated IL-1β signaling under the same conditions but without the presence of inhibitors of TET2 mutation-mediated IL-1β proinflammatory activity described herein.

A disease or medical condition is considered to be mediated by "IL-1β (interleukin-1β) proinflammatory activity" if the spontaneous or experimental disease or medical condition is associated with, or mediated by, for example, elevated levels of IL-1β in bodily fluids or tissue, or if cells or tissues taken from the body produce elevated levels of IL-1β in culture.

As used herein, the phrase "cardiovascular condition, disease or disorder" is intended to include all disorders characterized by insufficient, undesired or abnormal blood vessel or cardiac function, e.g. hypertension, ischemic heart disease, hypertensive heart disease and pulmonary hypertensive heart disease, valvular disease, cardiac arrhythmia, vascular disease, myocardial infarction, congestive heart failure, peripheral vascular disease, myocarditis, atherosclerosis, restenosis, and any condition which leads to congestive heart failure in a subject, particularly a human subject.

As used herein, an "IL-1β inhibitory compound" or "IL-1β inhibitor" or "inhibitor of IL-1β" refers to a compound or agent capable of specifically inhibiting or specifically preventing activation of cellular receptors to IL-1β and consequent downstream effects of IL-1β signaling.

As used herein, "antibodies" or "antigen-binding fragments" thereof include monoclonal, human, humanized or chimeric antibodies, single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

The terms "antibody fragment" or "antigen-binding fragment" include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10): 1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

As used herein, an "interleukin-1 receptor antagonist" ("IL-1ra") is any agent or molecule, including small molecules and antibody or antigen-binding fragments thereof, that binds to an interleukin-1 receptor thereby preventing binding of IL-1β to the receptor and thereby inhibiting IL-1β-mediated pro-inflammatory activity.

As used herein, "small molecule inhibitors" include, but are not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da.

As used herein, the terms "TET2 activating compound" or "TET2 potentiatior" or "TET2 activator" or "TET2 agonist" refer to a molecule or agent that mimics or up-regulates (e.g., increases, potentiates or supplements) the biological activity of TET2, thereby decreasing or inhibiting IL-1β (interleukin-1β) proinflammatory activity caused by deficient TET2 activity.

The terms "biological sample" or "sample" as used herein refers to a cell or population of cells or a quantity of tissue or fluid from a subject comprising one or more hematopoietic cells. Most often, the biological sample has been removed from a subject, but the term "biological sample" can also refer to cells or tissue analyzed in vivo, i.e., without removal from the subject.

As used herein, the term "population of hematopoietic cells" encompasses a heterogeneous or homogeneous population of hematopoietic cells and/or hematopoietic progenitor cells.

The terms "isolate" and "methods of isolation," as used herein, refer to any process whereby a cell or population of cells, such as a population of hematopoietic cells, is removed from a subject or sample in which it was originally found, or a descendant of such a cell or cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1G demonstrate expansion of Tet2-deficient cells after competitive bone marrow transplantation in LDLR-KO mice. LDLR-KO mice were transplanted with bone marrow cell suspensions containing 10% CD45.2+ Tet2−/− cells (10% KO BMT) or 10% CD45.2+ Tet2+/+ cells (10% WT BMT) and 90% CD45.1+ Tet2+/+ cells. 1A.

Figures 1A, 1B:
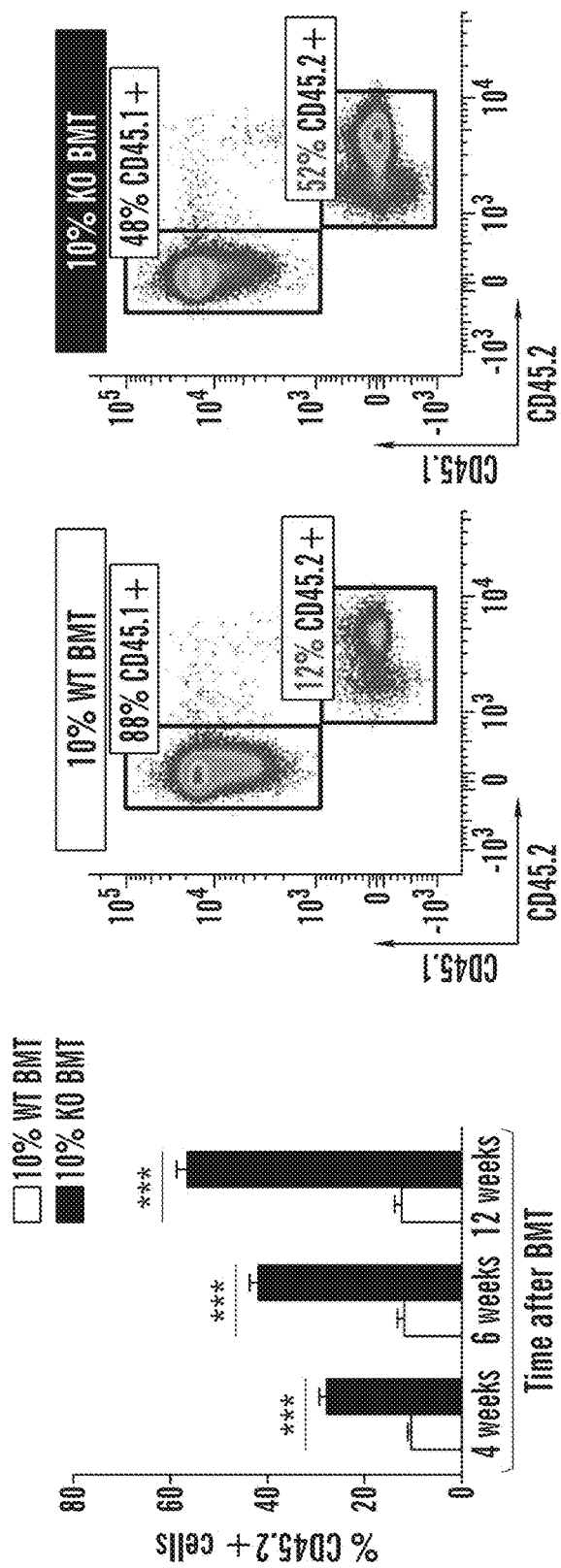

Percentage of CD45.2+ white blood cells (WBC) in peripheral blood, evaluated by flow cytometry (n=9 mice/genotype). 1B. Representative images of CD45.1/CD45.2 flow cytometry analysis of WBC populations. 1C. qRT-PCR analysis of Tet1, Tet2 and Tet3 transcript levels in magnetically-sorted CD45.2+ WBCs from 10% KO-BMT (n=9) and 10% KO-BMT mice (n=7). 1D-1F. Percentage of CD45.2+ cells within the main hematopoietic lineages in bone marrow (1D), spleen (1E) and peripheral blood (1F) 13 weeks after bone marrow transplantation, measured by flow cytometry (n=15, 10% WT-BMT mice; n=18, 10% KO-BMT mice). 1G. Representative images of CD45.1/CD45.2 flow cytometry analysis of peripheral blood monocytes and T cells in 10% KO-BMT mice. Statistical significance was evaluated by 2-way ANOVA with Sidak multiple comparison tests (*p<0.05,  p<0.01, * p<0.001).

FIGS. 2A-2H demonstrate exacerbated atherosclerosis after Tet2-deficient hematopoietic cell expansion. 10% KO-BMT (n=8) and 10% WT-BMT mice (n=10) were fed a high fat atherogenic diet for 9 weeks. 2A. Body weight. 2B. Blood glucose levels. 2C. Insulin tolerance Test. 2D. Plasma cholesterol levels. 2E. Aortic root plaque size, average of five independent sections. Representative images of hematoxylin-eosin-stained sections are shown and atherosclerotic plaques are delineated by discontinuous lines. 2F. Plaque macrophage content, evaluated by immunohistochemical staining of the macrophage marker Mac3. 2G. Percentage of CD45.2+ cells within the total immune cell (CD45+) population, F4/80+ macrophages and CD3+ T cells in the atherosclerotic aortic arch (n=4 pools of 2 aortic arches per genotype). 2H. Representative images of CD45.1/CD45.2 flow cytometry analysis of aortic macrophages and T cells. Statistical significance was evaluated by two-tailed unpaired Student t test (2A, 2D, 2E, 2F), regular 2-way ANOVA with Sidak multiple comparison tests (2B, 2G, ***p<0.001) or repeated measures 2-way ANOVA (2C).

FIGS. 3A-3G demonstrate increased pro-inflammatory activation of Tet2-deficient macrophages. Thioglycollate-elicited peritoneal macrophages were isolated from Tet2−/− mice or WT controls (n=3 mice/genotype in 3A-3C; n=4 mice/genotype in 3D-3F) and treated with a combination of 10 ng/ml LPS and 2 ng/ml IFNγ to induce pro-inflammatory activation. 3A. Heat map of genes with expression change greater than 1.5-fold (q-value<0.05) from the genome-wide expression profiling by microarray. 3B. PANTHER analysis of genome-wide expression profiling by microarray. Three over-represented protein classes were identified in Tet2−/− macrophages compared to all genes in Mus musculus (with a Bonferroni correction P-value<0.05). 3C. Heat map of selected genes upregulated in Tet2−/− macrophages with expression change greater than 1.5-fold (q-value<0.05) from the genome-wide expression profiling by microarray. 3D-3F. qRT-PCR analysis of transcript levels of pro-inflammatory cytokines (3D), chemokines (3E) and COX2 (3F). 3G. ELISA analysis of IL-6 protein levels in the supernatant of cultured macrophages treated as indicated for 16 hours. Statistical significance in 3C-3F was evaluated by 2-way ANOVA (p value for genotype effect shown in graph) with Sidak multiple comparison tests (*p<0.05,  p<0.01, * p<0.001).

FIGS. 4A-4K demonstrate enhanced NLRP3 inflammasome-mediated IL-1β production and signaling in Tet2-deficient macrophages. 4A, 4B. qRT-PCR analysis of IL-1β transcript levels in Tet2−/− and +/+ peritoneal macrophages treated with a combination of 25 μg/ml oxLDL, 5 ng/ml TNF and 2 ng/ml IFNγ (4A, n=6 mice/genotype) or in aortic arch samples (4B) obtained from HFD-fed 10% WT-BMT mice (n=9) and 10% KO-BMT mice (n=8). 4C, 4D. Western Blot analysis of intracellular IL-1β and β-actin in peritoneal macrophages isolated from Tet2−/− mice and WT controls (n=3/genotype) after 6 hours of LPS/IFNγ treatment (4C) or after the same treatment combined with a final 15 minute incubation with 5 mM ATP (4D). 4E. Western Blot analysis of IL-1β protein levels in the supernatant of Tet2−/− and +/+ macrophages (n=3/genotype) after 6 hours of LPS/IFNγ treatment combined with a final 30 minute incubation with 5 mM ATP. 4F. ELISA analysis of IL-1β protein levels in the supernatant of Tet2−/− and +/+ macrophages (n=3/genotype) after 6 hours of LPS/IFNγ treatment combined with a final 30 minute incubation with 5 mM ATP in the presence or absence of 10 M MCC950. 4G. qRT-PCR analysis of NLRP3 transcript levels in LPS/IFNγ-treated peritoneal macrophages isolated from Tet2−/− mice or WT controls (n=4/genotype). 4H. Western Blot analysis of NLRP3 protein levels in peritoneal macrophages isolated from Tet2−/− mice and WT controls (n=3/genotype) and treated for 6 hours with LPS/IFNγ. 4I. ELISA analysis of IL-1β protein levels in the supernatant of Tet2−/− and WT macrophages (n=3/genotype) after 8 hours of oxLDL/TNF/IFNγ stimulation in the presence of 1 mg/ml cholesterol crystals. 4J. qRT-PCR analysis of IL-1R1, IL-1R2 and IL-1β RA transcript levels in LPS/IFNγ-treated peritoneal macrophages isolated from Tet2−/− mice and WT controls (n=4/genotype). 4K. qRT-PCR analysis of IL-6 and IL-1β transcript levels in Tet2−/− or WT macrophages after 12 hours of treatment with 10 ng/ml IL-1β. Statistical significance was evaluated in 4A, 4F and 4G by 2-way ANOVA (p value for effect of genotype shown in graph) with Sidak multiple comparison test (*p<0.05,  p<0.01, * p<0.001); in 4C, 4D, 4E, 4H, 4I, 4J and 4K, by two-tailed unpaired Student t test; and in B, by two-tailed unpaired Student t test with Welsh's correction for unequal variances.

Figure 5A:
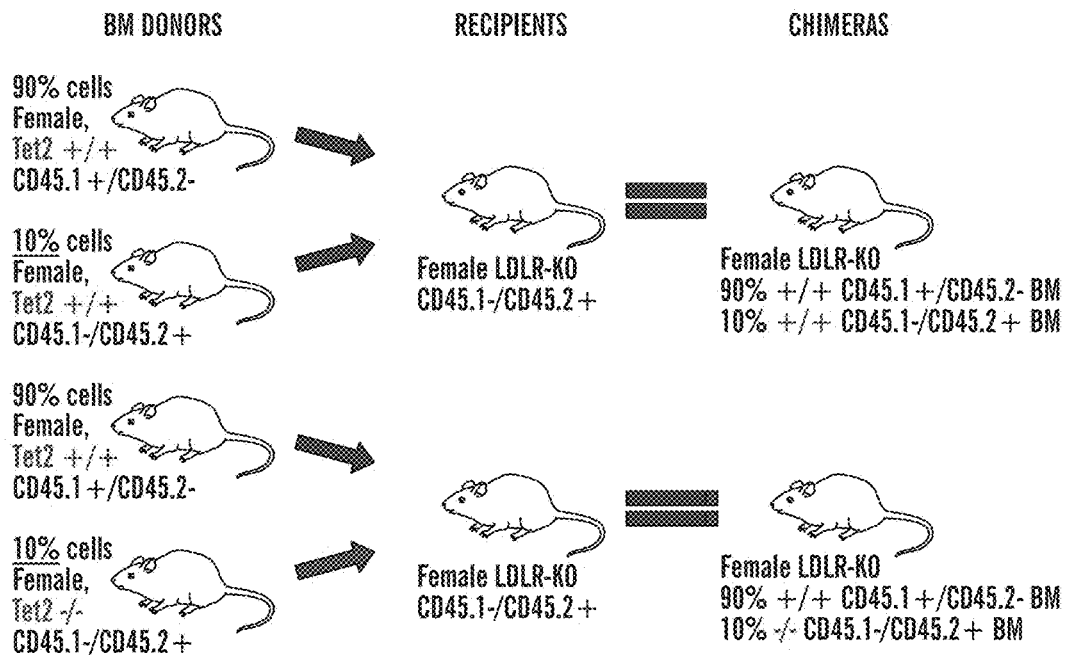
Figure 5B:
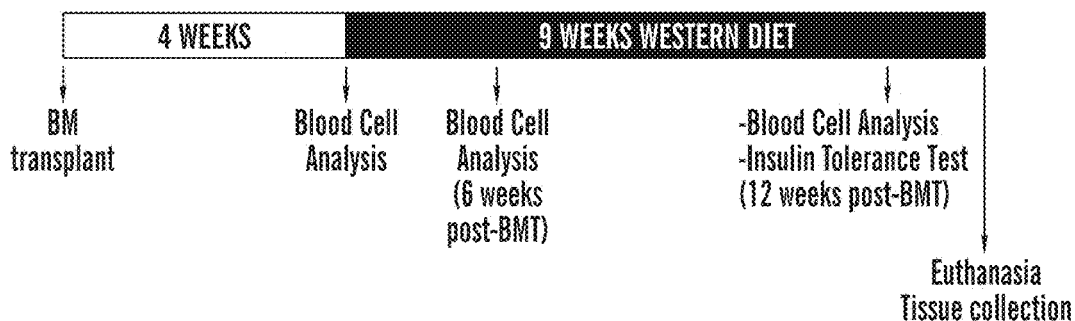

FIGS. 5A-5B depict an exemplary research strategy to study the role of clonal hematopoiesis associated with Tet2 deficiency in atherosclerosis development in hyperlipidemic mice. 5A. Competitive bone marrow transplantation strategy. 5B. Timeline of bone marrow transplantation and hematological, metabolic and atherosclerosis studies.

FIGS. 6A-6E demonstrate effects of expansion of Tet2-deficient hematopoietic cells on bone-marrow derived cell populations. LDLR-KO mice were transplanted with bone marrow cell suspensions containing 10% CD45.2+ Tet2−/− cells (10% KO-BMT) or 10% CD45.2+ Tet2+/+ cells (10% WT-BMT) and 90% CD45.1+ Tet2+/+ cells. 6A. Representative images of the flow cytometry analysis of the purity of the CD45.2+ WBC fractions analyzed in FIG. 1C. 6B. Absolute cell number of Lin−, Sca1+, Kit+ (LSK) cells in the bone marrow and spleen of 10% KO-BMT mice and WT controls 13 weeks post-BMT (9 weeks on HFD), quantified by flow cytometry. 6C, 6D. Percentage of CD45.2+ LSK cells in bone marrow (6C) and spleen (6D), evaluated by flow cytometry. 6E. Absolute cell numbers of main WBC populations in peripheral blood.

Figure 7:
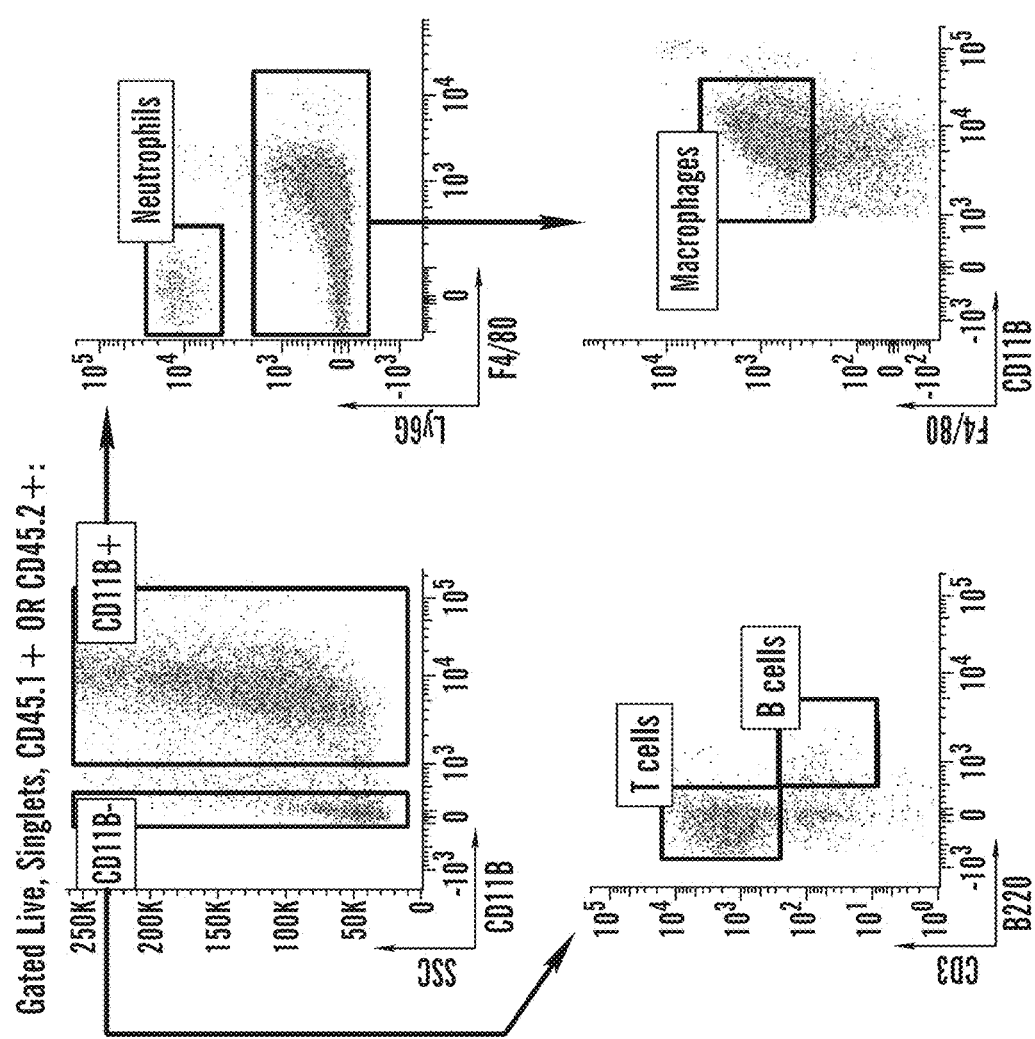

FIG. 7 depicts an exemplary gating strategy for the flow cytometry analysis of immune cell populations in aortic arch samples (related to FIGS. 2G, 2H).

Figure 8:
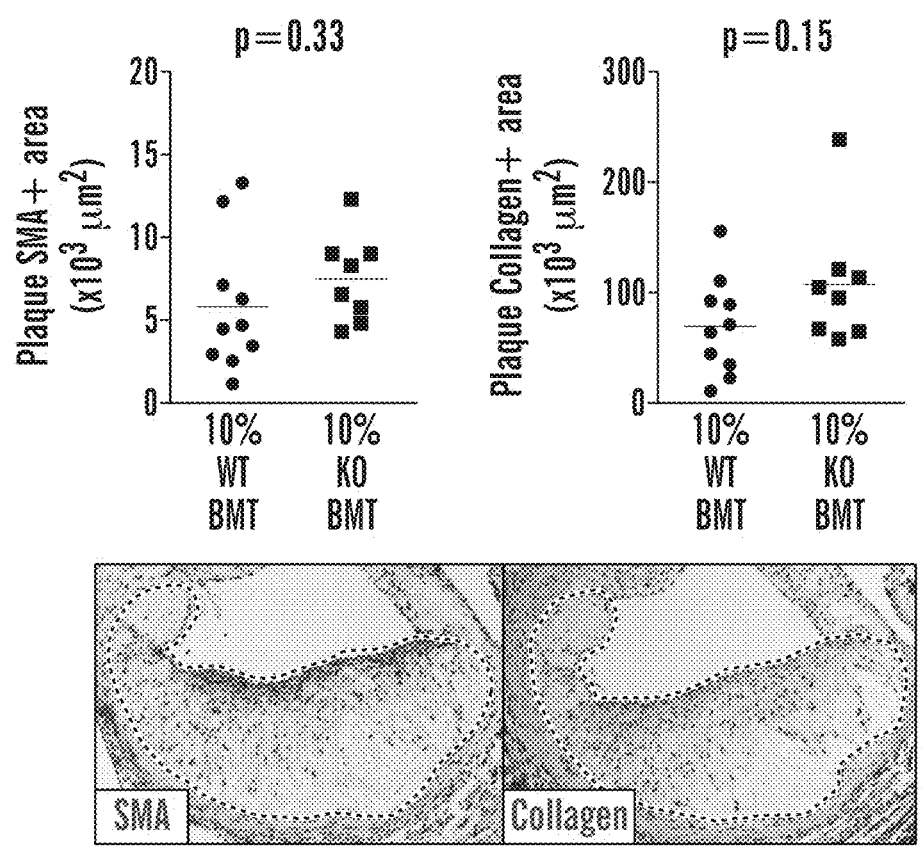

FIG. 8 depicts atherosclerotic plaque composition in the aortic root of HFD-fed 10% KO-BMT mice (n=10) and WT controls (n=8). Immunohistochemical staining was used to evaluate plaque content of vascular smooth muscle cells (SM-actin+ area). A modified Masson Trichrome staining was used to quantify collagen content in the plaque. Representative images of plaques in 10%-KO-BMT mice are shown for each staining and atherosclerotic plaques are delineated by discontinuous lines.

Figure 9A:
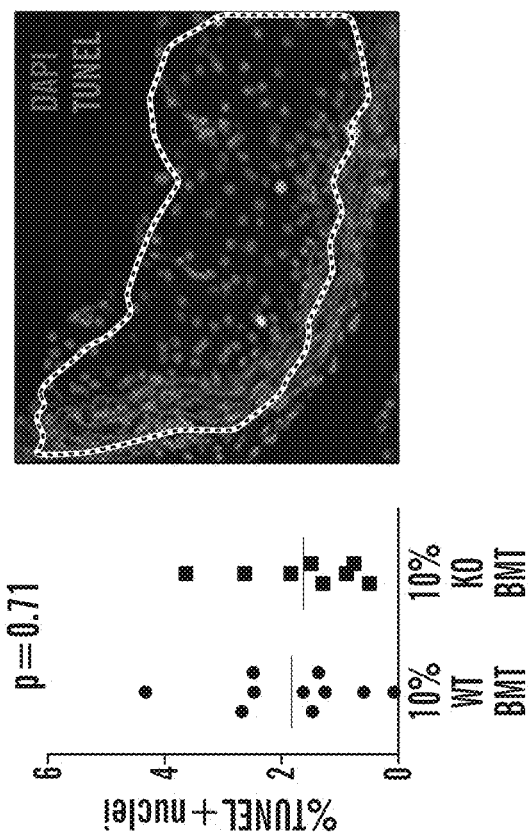
Figure 9B:
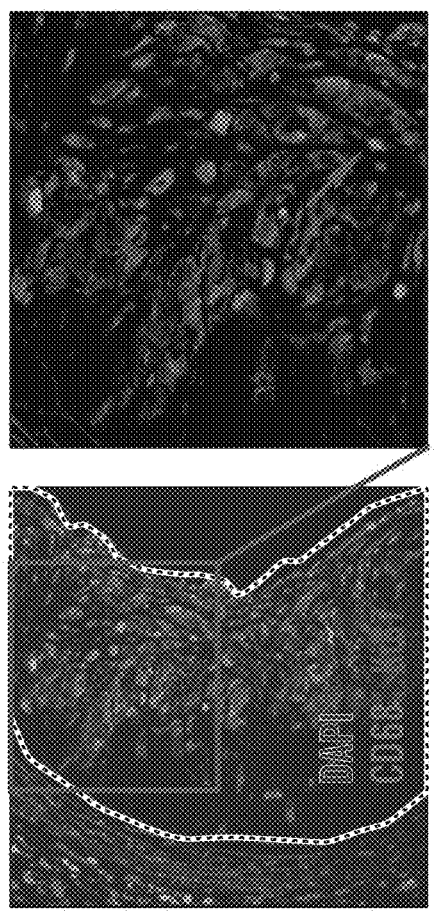
Figure 9B:
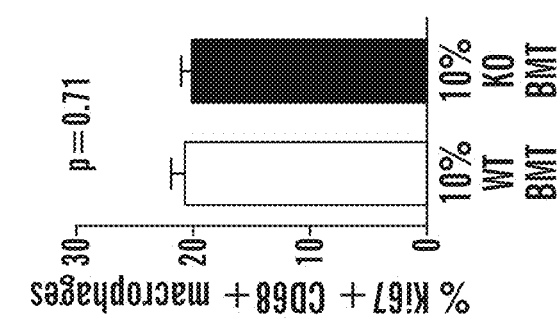
Figure 9B:
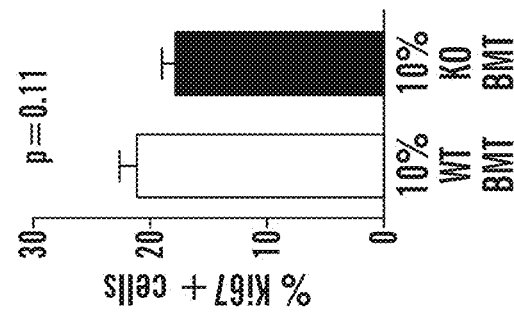

FIGS. 9A-9B demonstrate atherosclerotic plaque cell apoptosis and proliferation in the aortic root of HFD-fed 10% KO-BMT mice and WT controls. 9A. TUNEL staining to detect apoptotic cells. An image representative of plaque cell apoptosis in 10% KO-BMT mice is shown and atherosclerotic plaque is delineated by discontinuous lines. 9B. Plaque cell proliferation, examined by immunofluorescent analysis of the proliferating cell-specific antigen Ki67 and the macrophage marker (CD68). Atherosclerotic plaques are delineated by discontinuous lines. An image representative of plaque cell proliferation in 10% KO-BMT mice is shown. Examples of proliferating (Ki67+) macrophages (Mac3+) are indicated by arrows.

FIGS. 10A-10D demonstrate effects of Tet2 deficiency on culture macrophage proliferation, apoptosis and oxLDL uptake. Bone-marrow-derived (10A) or peritoneal (10B, 10C) macrophages were obtained from Tet2−/− mice or WT controls (n=3 mice/genotype). 10A. Cell-cycle progression analysis by propidium iodide staining and flow cytometry after synchronization of macrophages in G0-phase by 36 h of MCSF deprivation and subsequent re-stimulation with 15% L929-cell conditioned medium (LCM) as a source of MCSF. 10B. Quantification of apoptotic macrophages after 16 hours of treatment with 20 µg/ml 7-ketocholesterol, identified by flow cytometry as the sub-G0/G1 population after propidium iodide staining. 10C. Quantification of fluorescent dil-oxLDL uptake by macrophages, detected by flow cytometry. 10D. qRT-PCR analysis of expression of the scavenger receptors SR-A and CD36.

Figure 11A:
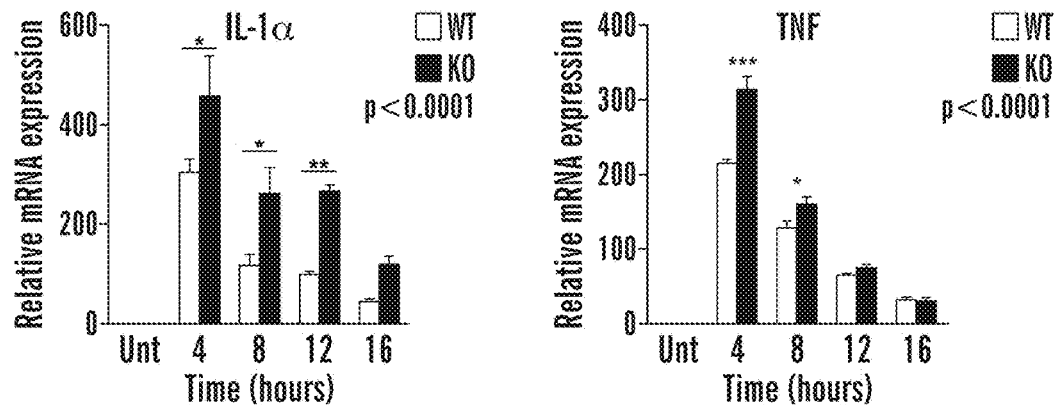
Figure 11B:
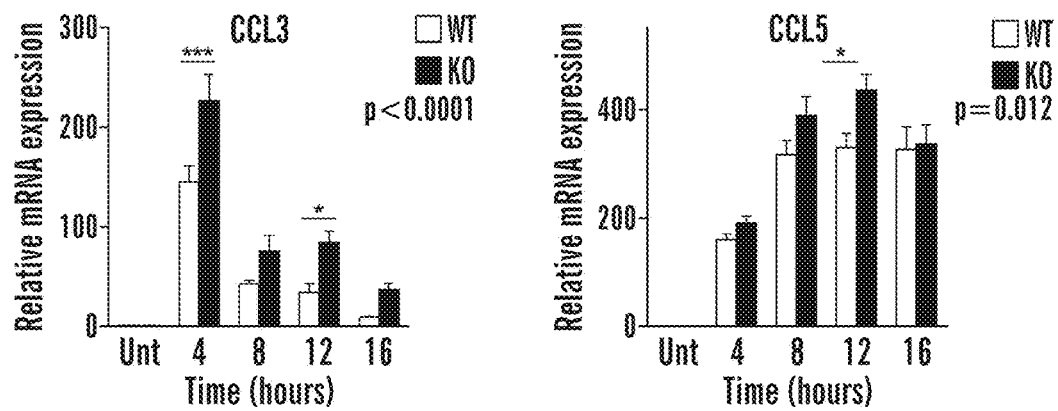
Figure 11C:
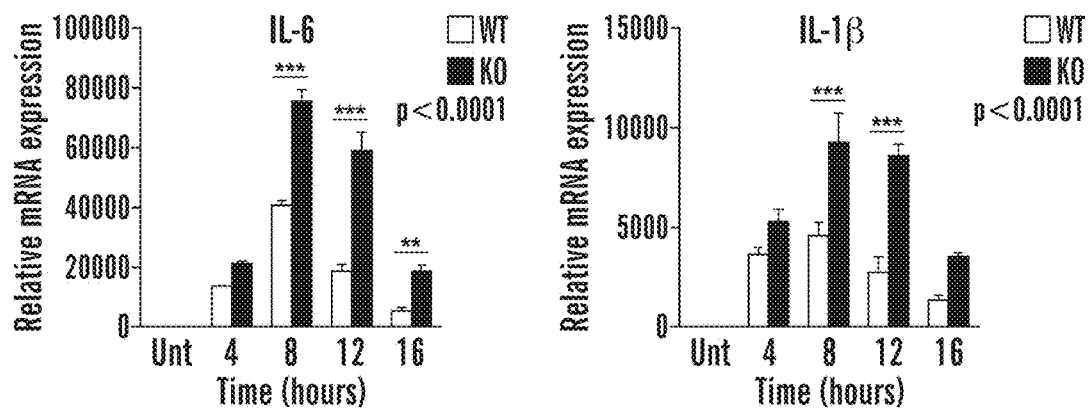

FIGS. 11A-11C demonstrate effects of Tet2 deficiency on the expression of pro-inflammatory cytokines/chemokines by cultured macrophages. Peritoneal macrophages were obtained from Tet2-KO mice or WT controls (n=4 mice/genotype in 11A, 11B; n=3 in 11C) and treated with 10 ng/ml LPS and 2 ng/ml IFN-γ (11A, 11B) or 100 ng/ml LPS and 20 ng/ml IFN-γ (11C). qRT-PCR was used to analyze the expression of pro-inflammatory cytokine/chemokine expression.

Figure 12A:
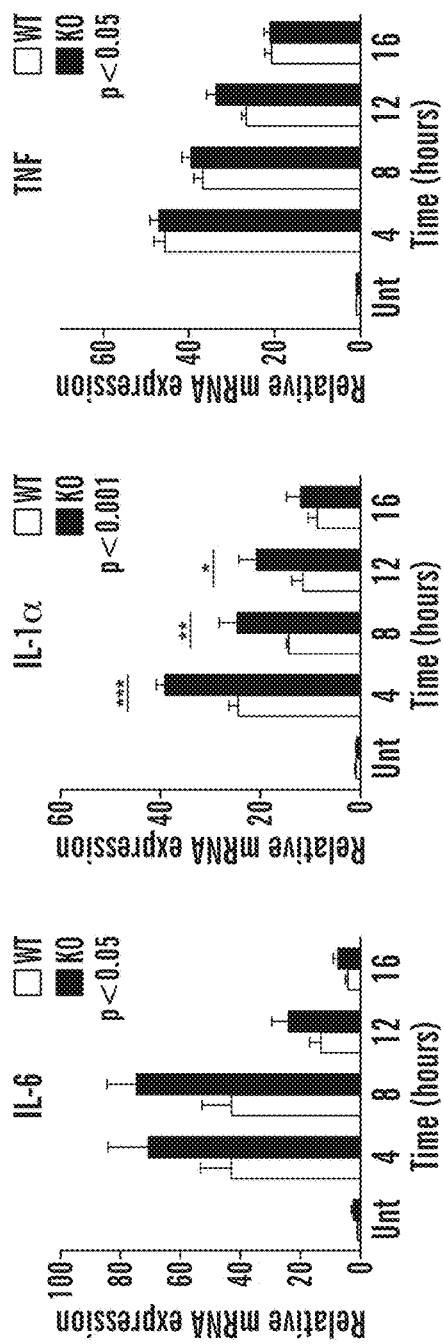
Figure 12B:
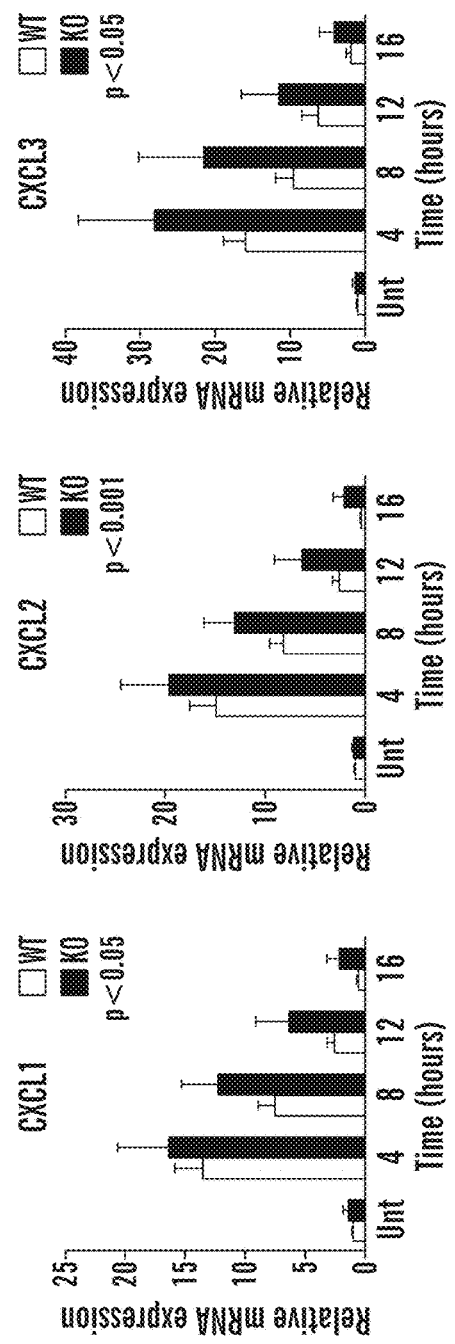

FIGS. 12A-12B demonstrate effects of Tet2 deficiency on the expression of pro-inflammatory cytokines/chemokines by cultured macrophages in the presence of low doses of oxLDL, TNF and IFN-γ. Peritoneal macrophages were obtained from Tet2-KO mice or WT controls (n=6 mice/genotype) and treated with 25 µg/ml oxLDL, 5 ng/ml TNF and 2 ng/ml IFNγ. Gene expression of selected pro-inflammatory cytokines (12A) or chemokines (12B) was analyzed by qRT-PCR.

Figure 13A:
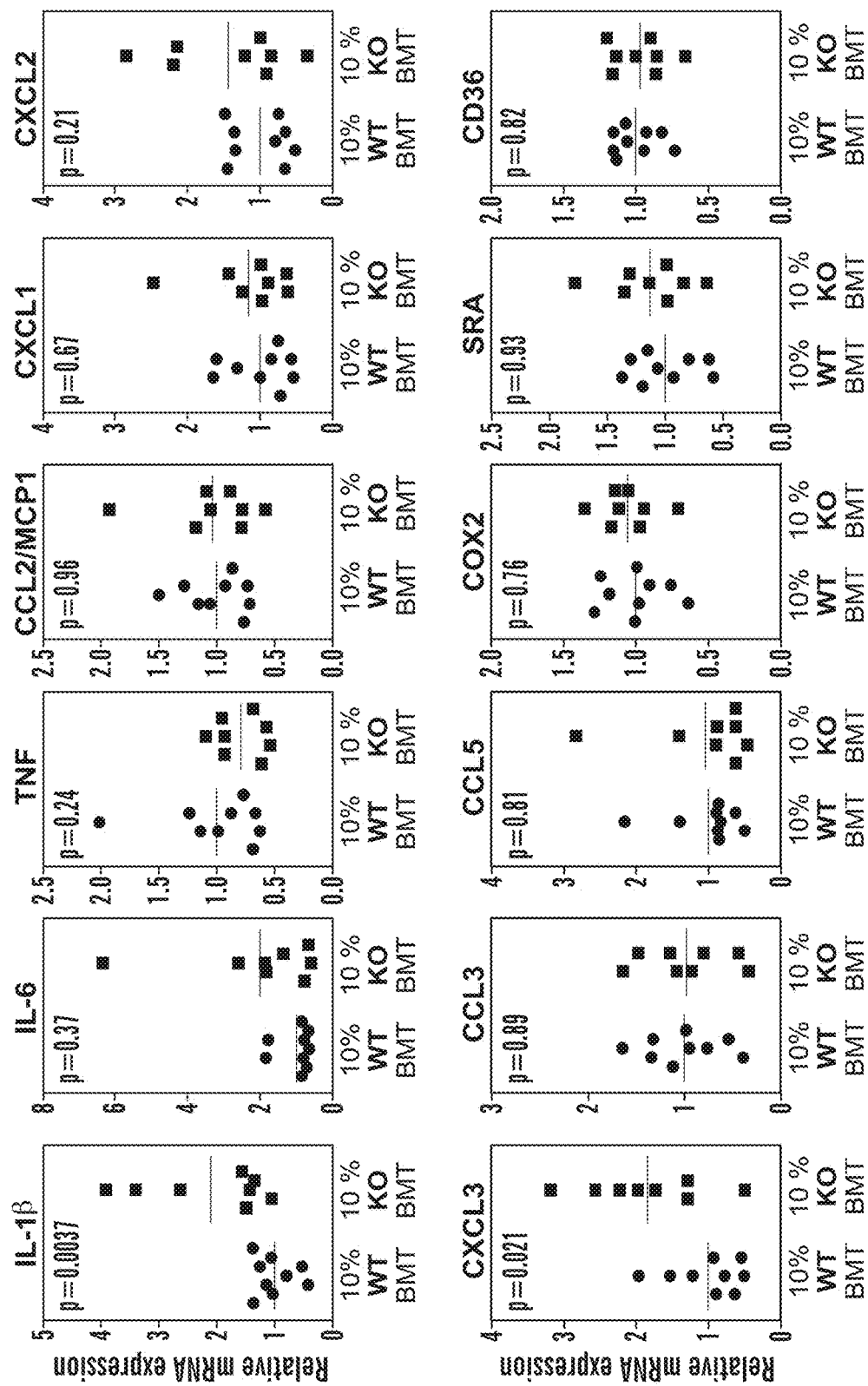
Figures 13A, 13B:
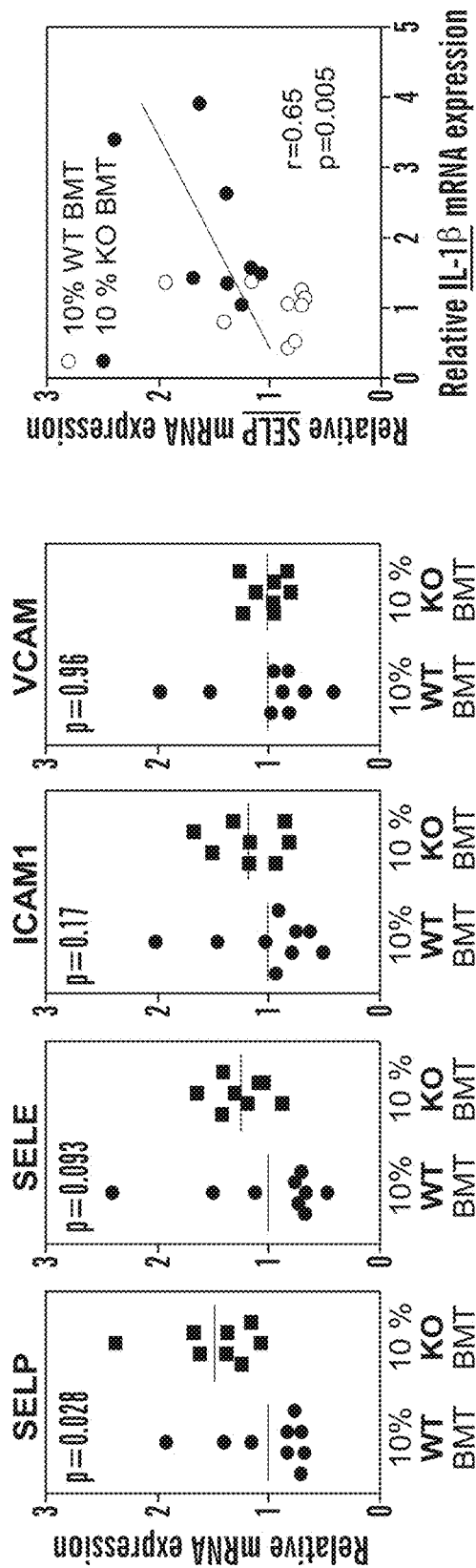

FIGS. 13A-13B demonstrate effects of Tet2-deficient hematopoietic cell expansion on the expression of pro-inflammatory cytokines, chemokines and adhesion molecules in the atherosclerotic vascular wall. 13A. Aortic arch samples were obtained from 10% WT-BMT mice (n=9) or 10% KO-BMT mice (n=8) and gene expression was analyzed by q-RT-PCR analysis. 13B. The Pearson correlation coefficient (r) was used to evaluate the association between SELP and IL-1β expression in the aortic wall.

FIGS. 14A-14D demonstrate role of changes in histone acetylation in the increased expression of pro-inflammatory cytokines in Tet2-deficient macrophages. 14A. qRT-PCR analysis of IL-1β expression in peritoneal macrophages isolated from Tet2−/− or +/+ mice (n=3 mice/genotype) and treated for 8 hours with 10 ng/mL LPS and 2 ng/ml IFNγ in the absence or presence of 0.5 µM Trichostatin A (TSA). 14B. ChIP analysis of H3 acetylation in the IL-1β promoter of macrophages isolated from Tet2−/− or +/+ mice (n=6/genotype) after 10 hours of LPS/IFNγ treatment. 14C. qRT-PCR analysis of IL-6 expression in peritoneal macrophages isolated from Tet2−/−/ mice or +/+ controls (n=3 mice/genotype) and treated for 8 hours with 10 ng/mL LPS and 2 ng/ml IFNγ in the absence or presence of 0.5 µM TSA. 14D. ChIP analysis of H3 acetylation in the IL-6 promoter of macrophages isolated from Tet2−/− or +/+ mice (n=6/genotype) after 10 hours of LPS/IFNγ treatment.

FIGS. 15A-15B demonstrate effects of Tet2-deficiency on the expression of inflammasome components. Peritoneal macrophages were isolated from Tet2−/− or +/+ mice (n=3 mice/genotype) and treated with 10 ng/ml LPS and 2 ng/ml IFN-γ (15A) or 25 µg/ml oxLDL, 5 ng/ml TNF and 2 ng/ml IFN-γ (15B) for the indicated times. Gene expression was analyzed by qRT-PCR analysis.

Figure 16:
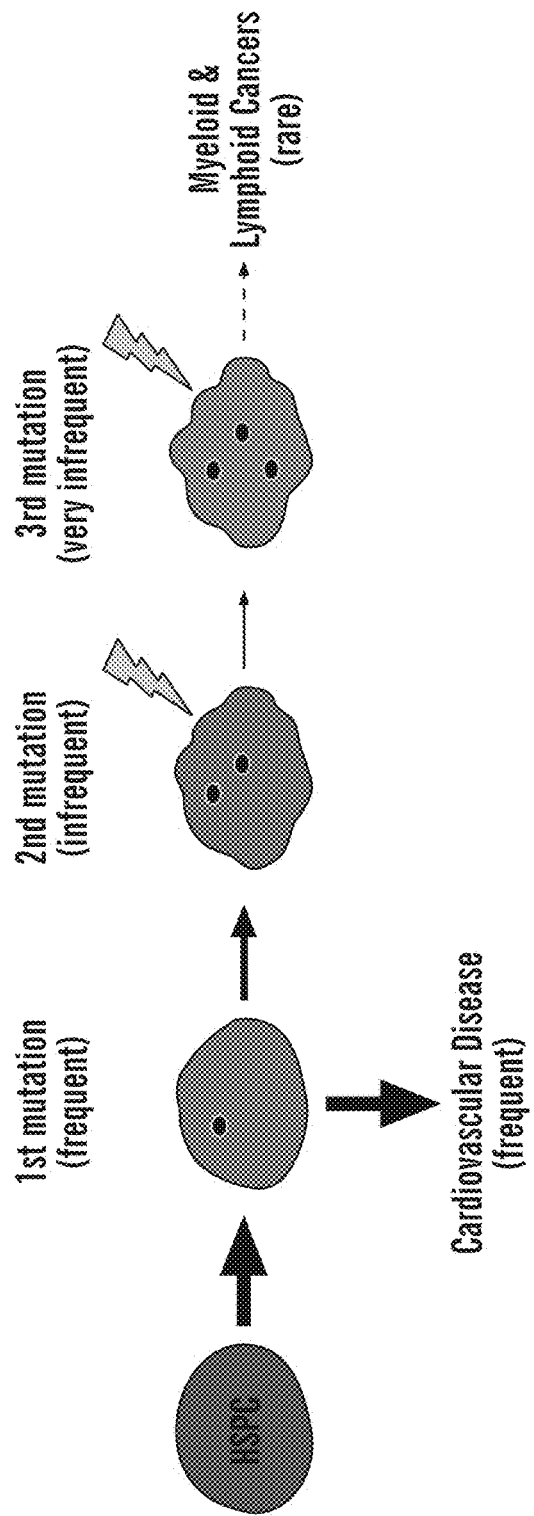
Figure 17A:
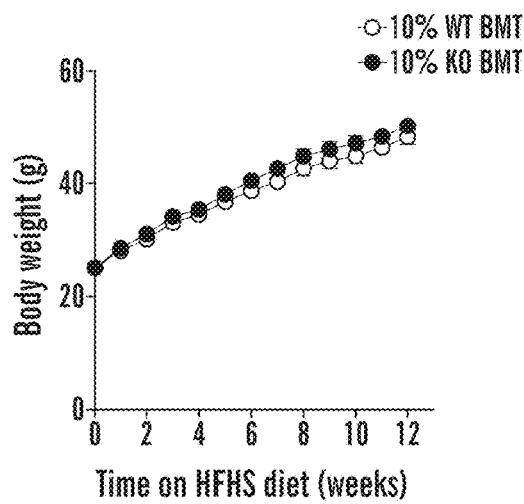
Figure 17B:
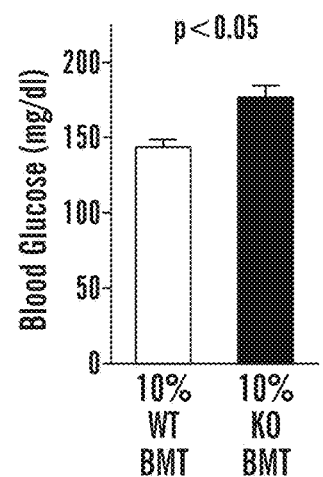
Figure 17C:
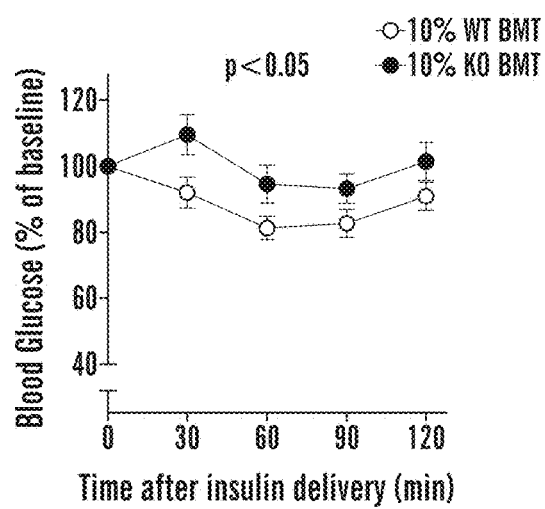
Figure 17D:
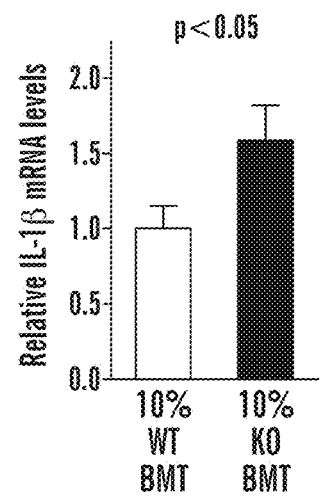

FIG. 16 depicts a schematic illustrating a common mechanistic basis between cancer and cardiometabolic disease, such as cardiovascular disease.

FIGS. 17A-17D demonstrate that clonal hematopoiesis associated with Tet2 deficiency promotes obesity-induced metabolic dysfunction. Mice were subjected to competitive bone marrow transplantation and fed a high fat/high sucrose (HFHS) diet for 12 weeks to induce obesity and associated metabolic dysfunction. 17A. Body weight. 17B. Fasting blood glucose levels. 17. Systemic insulin sensitivity assessed by an oral insulin tolerance test (ITT). 17D. IL-1β transcript expression in epididymal fat, assessed by quantitative PCR.

Figure 18:
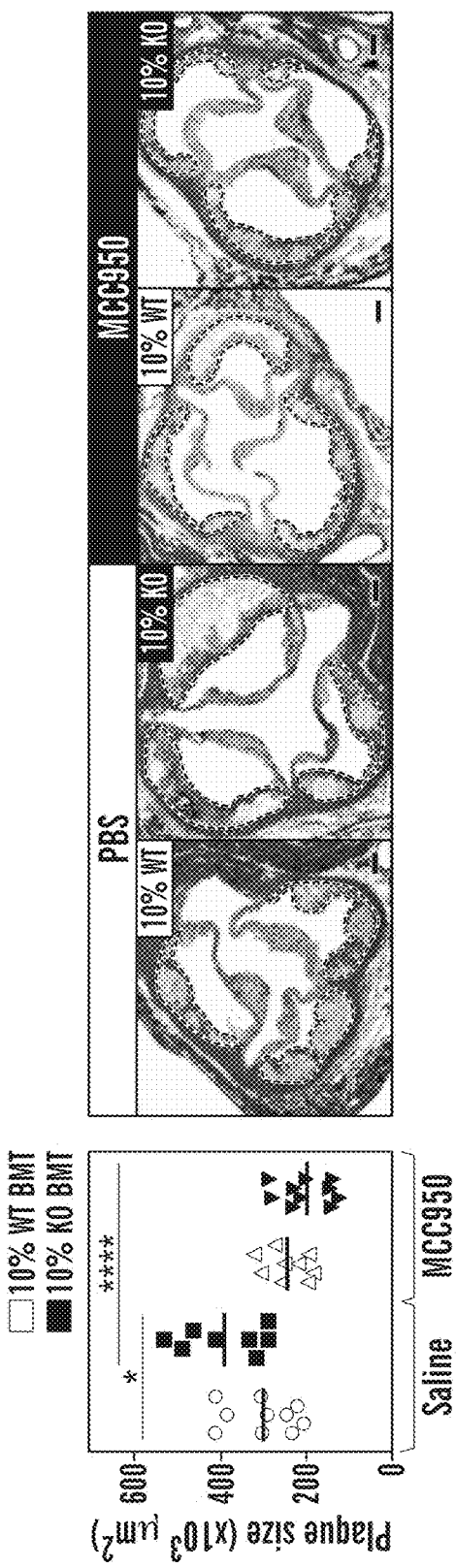
Figure 19A:
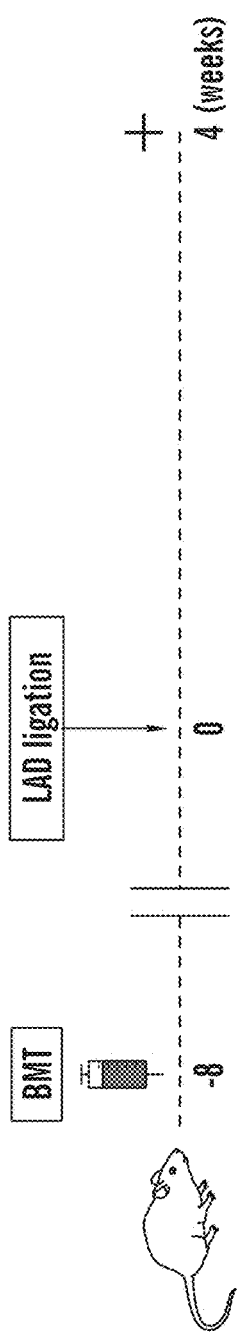
Figure 19B:
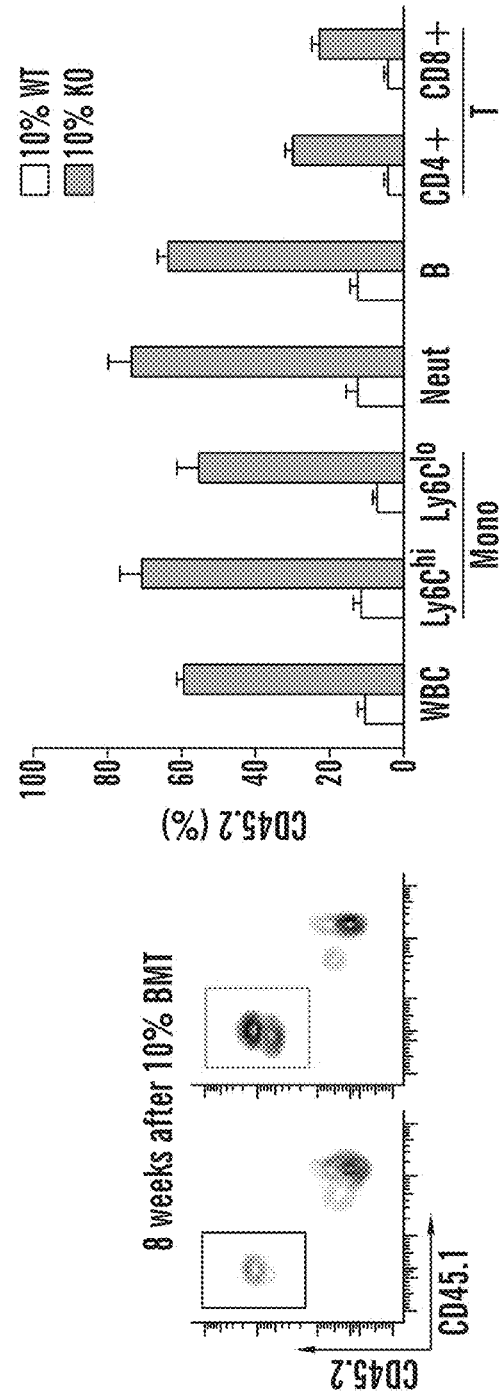
Figure 19C:
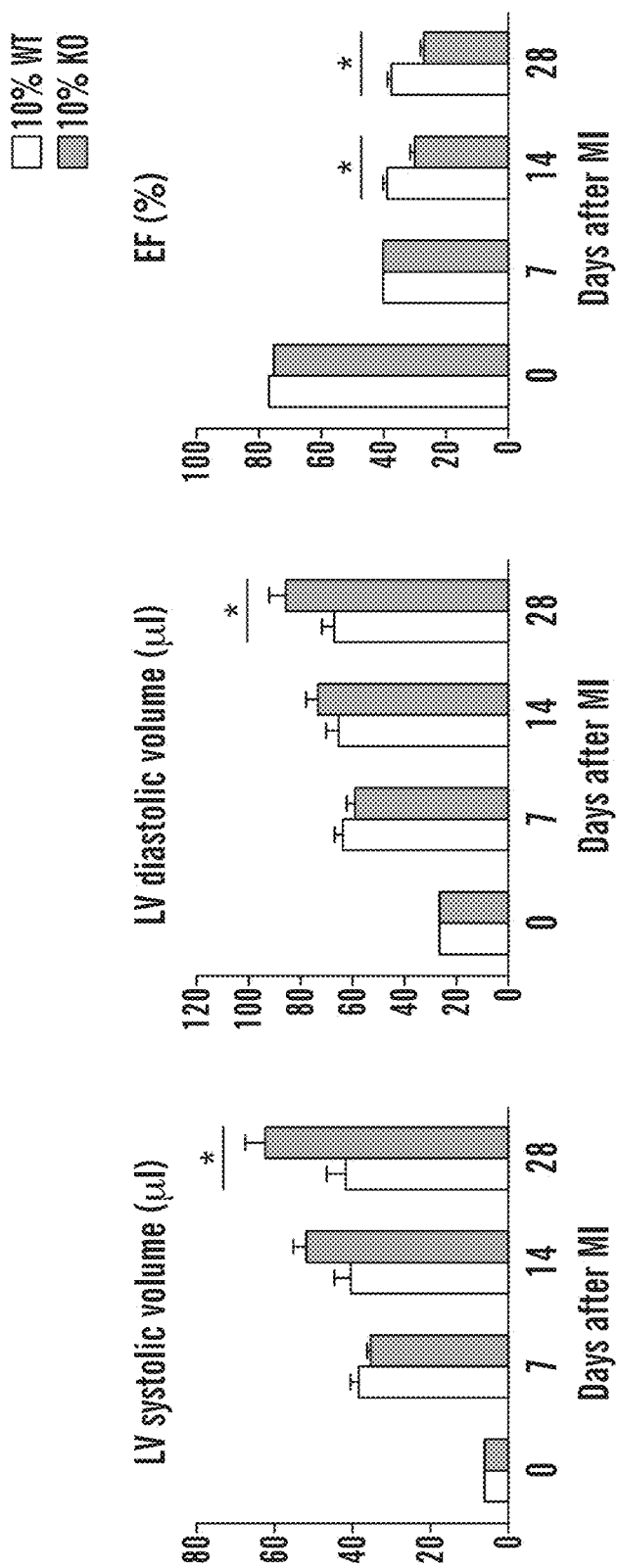
Figure 20A:
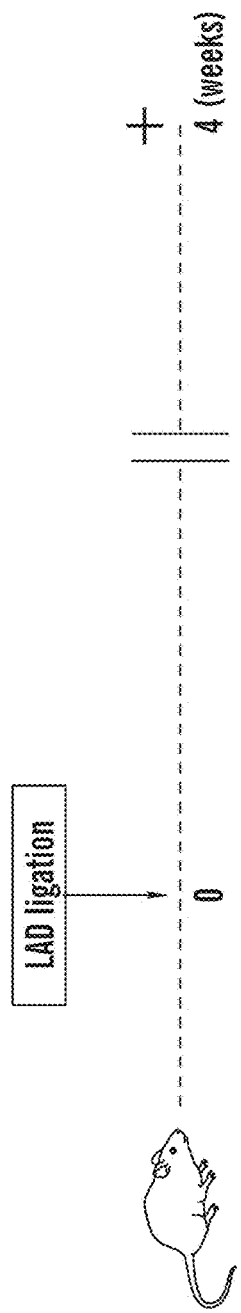
Figure 20B:
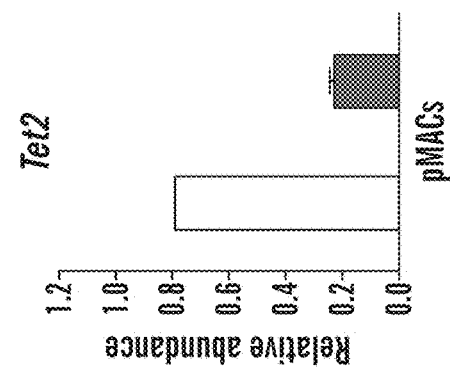
Figure 20C:
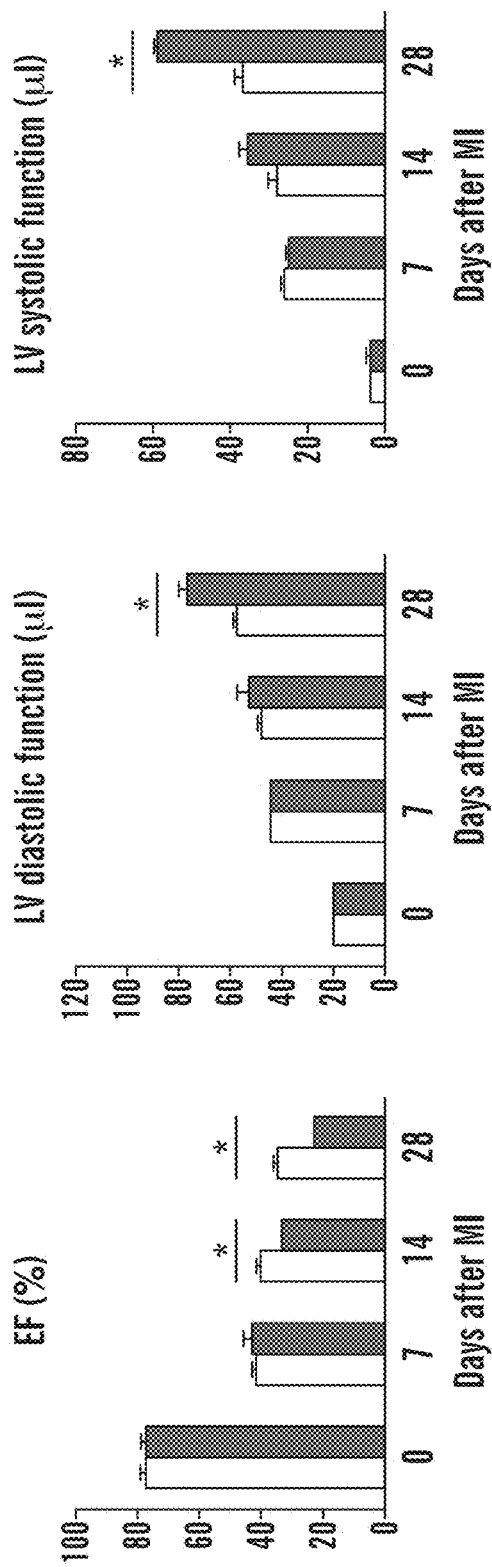

FIG. 18 shows that the NLRP3 inflammasome is essential for the accelerated atherosclerosis associated with clonal expansion of Tet2-deficient hematopoietic cells. Aortic root plaque size in high fat/high cholesterol diet-fed 10% KO-BMT mice and 10% WT-BMT. Mice received a continuous infusion of the inflammasome inhibitor MCC950 (5 mg/kg/day) or phosphate buffered saline vehicle via subcutaneous osmotic pumps. Representative images of hematoxylin/eosin-stained sections are shown; plaques are delineated by discontinuous lines (scale bar: 100 µm). Statistical significance was evaluated by 2-way ANOVA with Tukey multiple comparison test (*p<0.05, ****p<0.001).

FIGS. 19A-19F show that hematopoietic Tet2-KO mice display worse post-infarction remodeling. 19A. Scheme of the experimental study. Mice underwent partial (10%) bone marrow reconstitution with Tet2-deficient cells or WT cells following lethal irradiation. After 8 weeks of recovery, mice underwent permanent LAD ligation. 19B. Tet2-KO Bone marrow cells (CD45.2+) display a competitive advantage over wild type competitor cells (CD45.1+) in their ability to expand into multiple blood cell lineages in vivo. 19C. Echocardiographic evaluation shows that mice with partial reconstitution of Tet2-deficient cells display worsening cardiac remodeling after LAD ligation compared to mice receiving bone marrow from wild-type mice. 19D. Representative images of myocardial tissue sections stained with Masson-Trichrome dye at 4 weeks after ligation. Hearts were sliced sequentially from the ligation site to apex. 19E. Wheat germ agglutinin-staining of the heart sections from hearts isolated at 4 weeks after LAD ligation. Staining shows that the non-infarcted, remote area of the heart display greater hypertrophy of the cardiac myocytes. 19F. qPCR analysis of the remote area showing IL-1beta transcript is elevated in hearts from mice that received partial reconstitution with Tet2-deficient bone marrow at 4 weeks after LAD ligation. BMT=bone marrow transplantation, LAD=left anterior descending, WT=wild-type, EF=ejection fraction, LV=left ventricle, WBC=white blood cells.

FIGS. 20A-20F demonstrate that conditional myeloid Tet2-deficiency in mice leads to worse cardiac remodeling in hearts subjected to LAD ligation. 20A. Scheme of the study. Control and Tet2-knockout (KO) mice underwent LAD ligation. Conditional Tet2-KO mice were constructed by crossing Tet2flox/flox mice with transgenic mice expressing cre recombinase from the LysM myeloid cell-specific promoter. 20B. The efficiency of Tet2 ablation was analyzed in peritoneal macrophages (pMACs) from the conditional Tet2-KO mice. 20C. Echocardiographic evaluation shows that mice with conditional Tet2 ablation in myeloid cells display worsening cardiac remodeling after LAD ligation surgery compared to wild-type mice. 20D. Representative images of myocardial tissue sections stained with Masson-Trichrome dye at 4 weeks after LAD ligation surgery. Hearts were sliced sequentially from the ligation site to apex. e. qPCR analysis of IL-1beta transcript in the remote area of the myocardium showing greater IL-1beta up-regulation in conditional Tet2-KO mice relative to wild-type mice after LAD ligation surgery. 20F. qPCR analysis of bone marrow-derived macrophages showing that IL-1beta transcript is up-regulated in Tet2 knockout compared to wild-type cells under baseline conditions in vitro.

FIGS. 21A-21C show that inflammasome inhibition reverse the exacerbated post-infarction remodeling associated with hematopoietic Tet2-deficiency. 21A. Scheme of the experimental study. Mice underwent partial (10%) bone marrow reconstitution with Tet2-deficient cells or WT cells following lethal irradiation. After 8 weeks of recovery, mice underwent permanent LAD ligation. PBS or MCC-950 infusion by osmotic pump was initiated 1 week after LAD ligation for 4 weeks. 21B. Echocardiographic analysis of ejection fraction (EF) shows that treatment with the NLRP3 inflammasome inhibitor MCC950 protects against adverse cardiac remodeling in mice reconstituted with Tet2-KO and wild-type bone marrow, and eliminates the differences in cardiac parameters between Tet2-deficient and WT conditions at the 5 week time point post-LAD ligation. 21C. MCC950 inhibits the increase in cardiac myocyte hypertrophy after LAD ligation in mice reconstituted with Tet2-KO and wild-type bone marrow, and eliminates the differences in cell size between Tet2-deficient and WT conditions.

FIG. 22A-22E show the inflammasome inhibitor MCC950 inhibits adverse cardiac remodeling in pressure overloaded hearts and eliminates differences in cardiac parameters between mice that are partially reconstituted with wild-type and Tet2-deficient bone marrow. 22A. Scheme of the experimental study. Mice underwent partial (10%) bone marrow reconstitution with Tet2-deficient cells or WT cells following lethal irradiation. After 8 weeks of recovery, mice underwent permanent TAC surgery to produce pressure overload on the heart. 22B. Measurement of heart weight (HW) and wet lung weight (LW) adjusted by tibia length (TL), showing that MCC950 ameliorates the increase of cardiac and lung mass after pressure overload in both strains of mice and eliminates the differences in these parameters between the Tet2-deficient and WT conditions. 22C. Measurement of myocyte cross-sectional area (CSA) shows that MCC950 inhibits hypertrophy after pressure overload both in wild type and hematopoietic Tet2-KO mice and eliminates the difference in this parameters between the Tet2-deficient and WT conditions. 22D. Echocardiographic parameters show that mice reconstituted with Tet2-knockout bone marrow show greater deterioration of cardiac function after pressure overload that can be reversed by treatment with MCC950. Treatment with MCC950 eliminates the differences in the echocardiographic parameters between the Tet2-deficient and WT conditions. LVPWTd=left ventricle posterior wall thickness at diastole, FS=fractional shortening. 22E. Picro sirius staining shows that mice reconstituted with Tet2-knockout bone marrow exhibit greater cardiac fibrosis after pressure overload that can be reversed by treatment with MCC950. The MCC950 treatment eliminates the difference in this parameter between the Tet2-deficient and WT conditions.

Figure 23A:
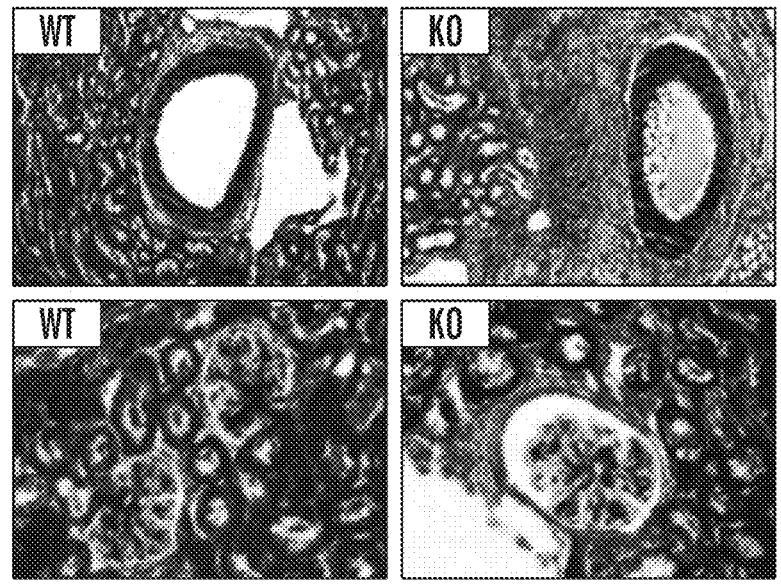
Figure 23B:
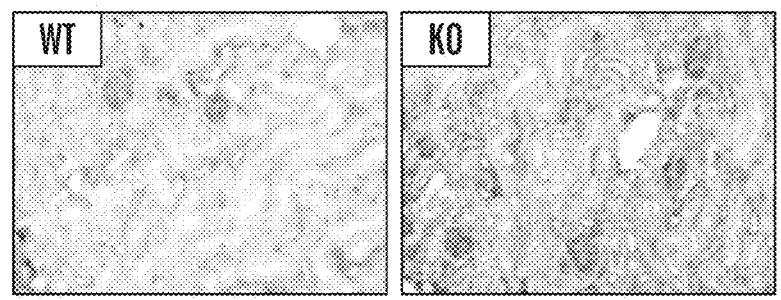
Figure 24A:
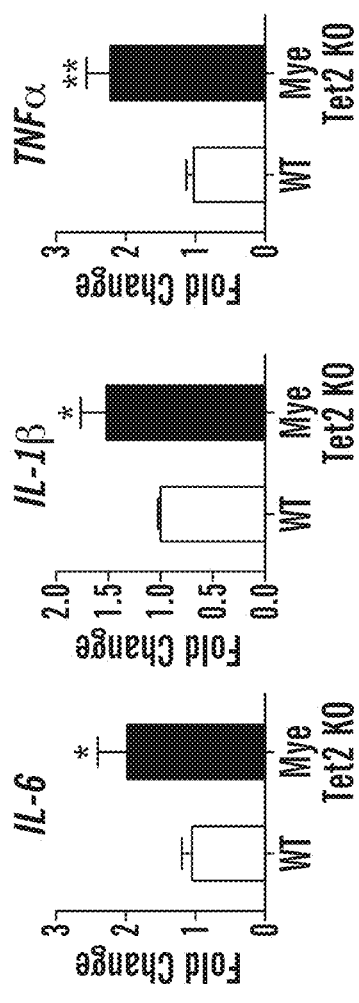
Figure 24B:
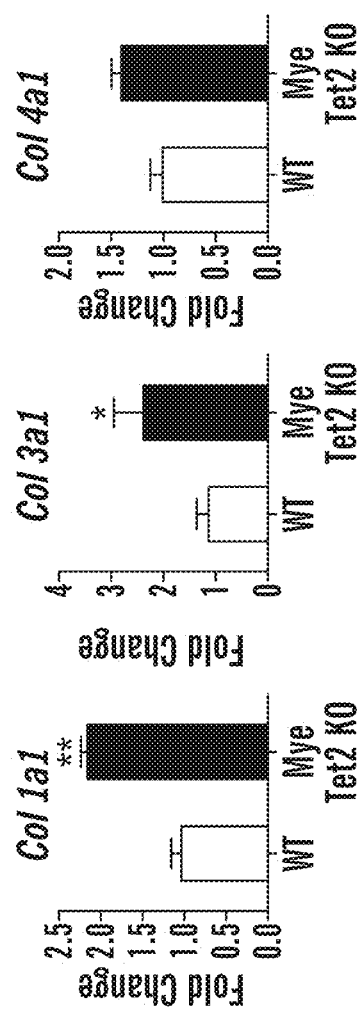
Figure 24C:
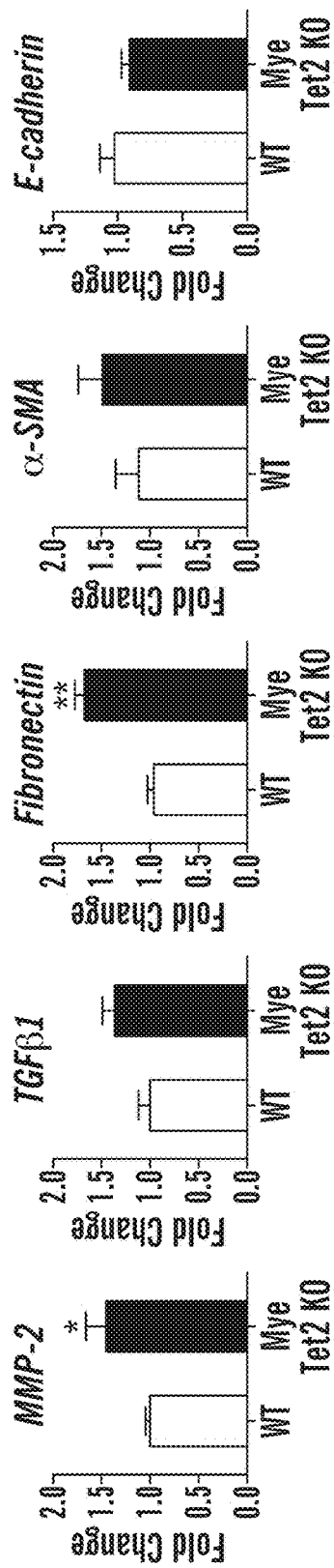
Figure 24D:
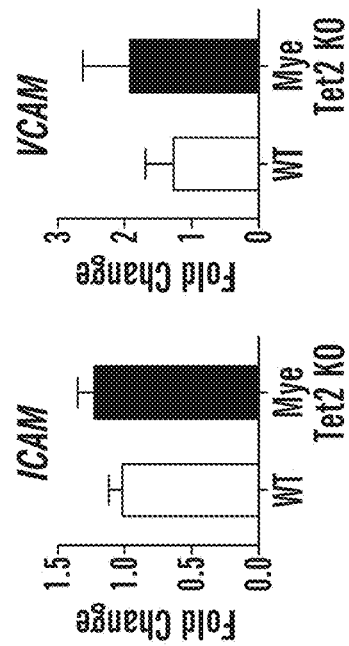

FIGS. 23A and 23B show that myeloid cell Tet2-deficiency promotes renal fibrosis and macrophage infiltration in kidneys of angiotensin II-treated mice. Both groups of mice were treated by infusion of angiotensin II (2 mg/kg/day) for 4 weeks prior to harvest. Perivascular and interstitial fibrosis was evaluated by collagen deposition using Masson's trichrome staining on paraffin sections 23A. Macrophage infiltration 23B in kidneys was detected by a rat anti-Mac3 monoclonal antibody, followed by ImmPRESS™ HRP Anti-Rat IgG and DAB Substrate (Vector Laboratories). Microscopy images were required on a Keyence BZ-9000 microscope and analyzed using Image J software. Representative images are shown.

FIGS. 24A-24D show that myeloid cell Tet2-deficiency promotes the expression of pro-inflammatory cytokines, fibrosis related cytokines and adhesion molecules in kidneys of angiotensin II-treated mice. 24A-24D. Gene expression patterns of pro-inflammatory cytokines 24A, collagen 24B, fibrosis-related genes 24C and adhesion molecules 24D were quantified by qRT-PCR in control in kidneys isolated from wild-type (WT) mice (n=5) and mice deficient in Tet2 in myeloid (mye Tet2-KO mice) (n=8). Both groups of mice were treated by infusion of angiotensin II (2 mg/kg/day) for 4 weeks prior to harvest. Data are shown as mean±SEM, statistical significance was evaluated by unpaired Student's t test (normally distributed continuous variables) or Mann-Whitney U test (non-normally distributed continuous variables) (*p<0.05, **P<0.01).

Figure 25:
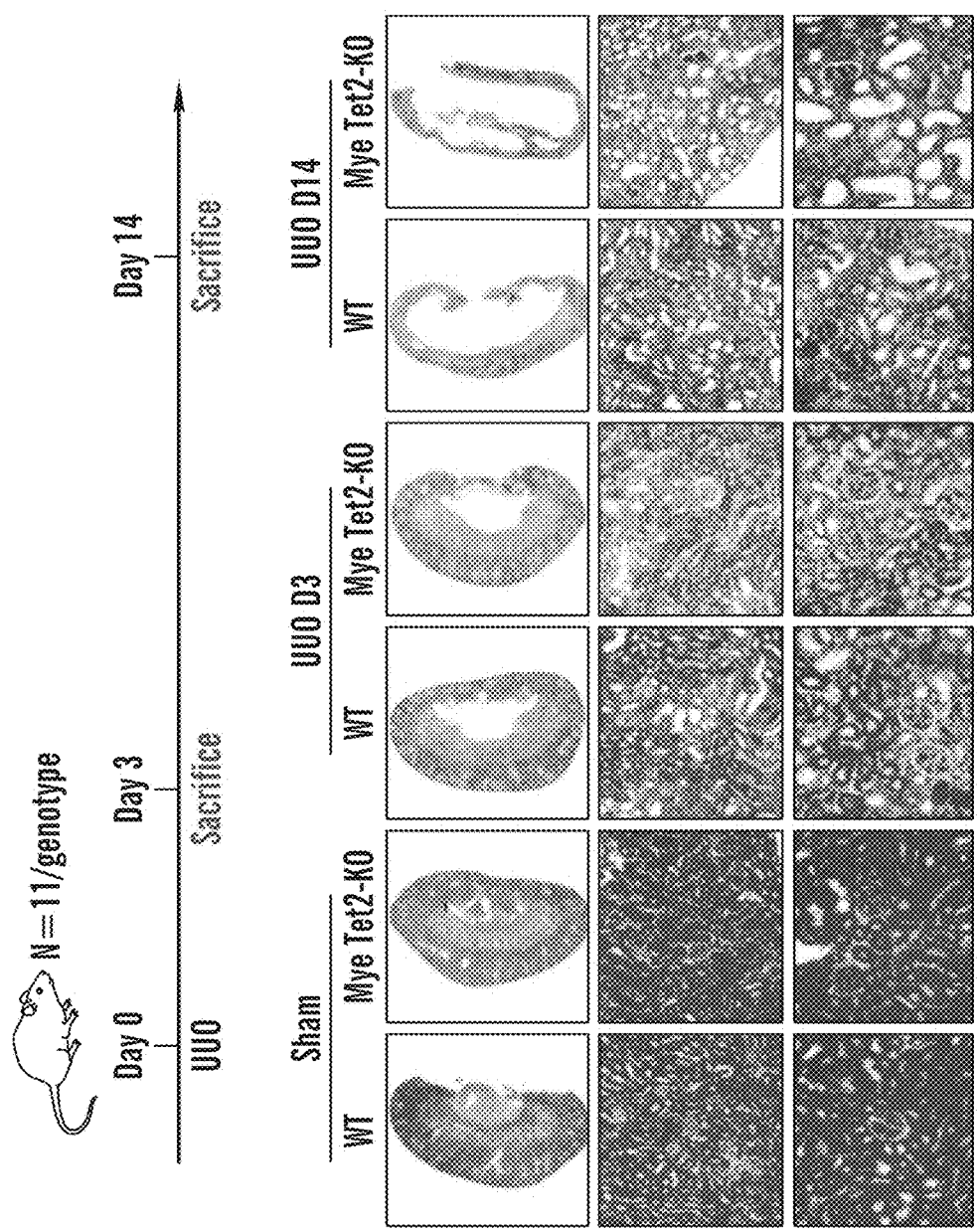

FIG. 25 shows the effects of Tet2 deficiency in myeloid cells on the structure and morphology of tubules in mice subjected to the unilateral ureteral obstruction (UUO) model of kidney failure. Tubular atrophy or dilation and inflammatory cells infiltration in kidneys of mice after UUO surgery were evaluated by H&E staining. Presentative images are shown. Microscopic images were acquired on a Keyence BZ-9000 microscope and analyzed using Image J software.

Figure 26:
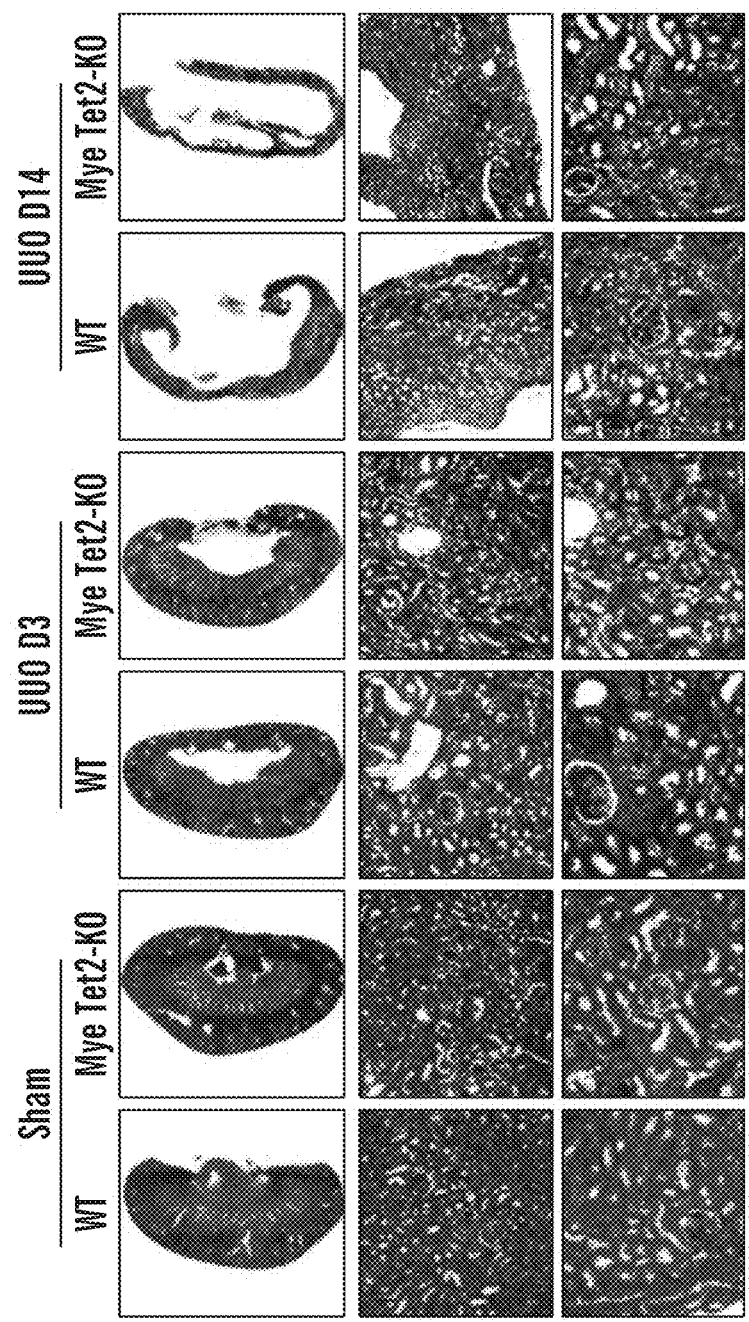

FIG. 26 demonstrates the effects of Tet2 deficiency in myeloid cells on renal tubular interstitial fibrosis in mice subjected to the unilateral ureteral obstruction (UUO) model of kidney failure. Fibrosis was evaluated by collagen deposition using Masson's trichrome staining of paraffin sections. Microscopic images were acquired on a Keyence BZ-9000 microscope and analyzed using Image J software.

DETAILED DESCRIPTION

Advances in DNA sequencing have revealed that aging is associated with an increased frequency of somatic mutations in proliferative tissues, particularly in the hematopoietic system. Recently, large exome sequencing studies in humans have shown that aging is associated with an increased frequency of somatic mutations in the hematopoietic system which provide a competitive growth advantage to the mutant cell and therefore allow its clonal expansion (i.e., clonal hematopoiesis) (Jaiswal et al, Genovese et al. NEJM 2014; Xi et al, Nat Med 2014). Furthermore, recent studies employing ultra-deep sequencing suggest that somatic mutations in blood cells are much more prevalent than previously recognized (McKerrell, Cell Reports 2015). However, while recent human studies suggest that somatic mutations can be associated with a broad spectrum of human disease, there is a lack of experimental evidence supporting their causal contribution to age-associated disorders other than cancer (Science special issues on "Mutation and Human Disease" (September 2015) and "Why We Age" (December 2015)). In contrast, herein, experimental evidence is provided that mechanistically links clinically relevant somatic mutations in hematopoietic cells to cardiovascular disease (CVD), metabolic, renal, and other chronic diseases that have a large inflammatory component. The experimental demonstrations described herein provide novel evidence of the causal contribution of a scenario of genome mosaicism in the hematopoietic system and subsequent clonal hematopoiesis to a non-hematological disorder.

Epidemiological studies show that HSPCs develop mutations that promote their clonal expansion at a relatively high frequency in the aging population. While very few of the HSCs acquire subsequent mutations in oncogenes that lead to blood cancers, the mechanistic findings of the studies described herein, using Tet2 as an example, show that a single mutation that occurs frequently can predispose an individual to CVD and stroke that are common in the elderly (>50% of individuals). As described herein, one of the most frequently mutated genes in human peripheral blood is TET2, an epigenetic regulator of gene transcription known to play pivotal roles in the modulation of hematopoiesis and myelopoiesis. The studies described herein demonstrate for the first time that (i) Progressive expansion of Tet2-deficient hematopoietic cells (i.e., clonal hematopoiesis), as occurs in human individuals carrying somatic mutations in this gene, is shown to promote atherogenesis in LDLR−/− mice; (ii) Tet2 functions as a novel inhibitor of vascular inflammation in the setting of atherosclerosis, which provides the first demonstration of the role of Tet2 in chronic sterile inflammation (distinct from pathogen-induced inflammation); and (iii) Tet2 inhibits pro-inflammatory IL-1β signaling at multiple levels, by modulating IL-1β transcription, NLRP3 inflammasome-mediated IL-1β secretion and IL-1-Receptor 1-mediated IL-1β signaling. Accordingly, the studies described herein support a new paradigm of causal risk for cardiovascular diseases and other inflammation-mediated diseases.

Hematopoietic stem cells (HSCs) and hematopoietic progenitor cells (HPCs) divide to produce blood cells by a continuous regeneration process. As the cells divide, they are prone to accumulating mutations, including deletions, insertions, and substitutions, that generally do not affect function. However, some mutations confer advantages in self-renewal, proliferation or both, resulting in clonal expansion of the cells comprising the mutations in question. The frequency of such somatic mutation events increases with age.

The studies described herein demonstrate that preferential and progressive expansion of a subset of hematopoietic cells bearing somatic mutations in TET2 lead to pro-inflammatory IL-1β signaling at multiple levels, including increased IL-1β transcription, increased NLRP3 inflammasome-mediated IL-1β secretion, and increased IL-1-Receptor 1-mediated IL-1β signaling. Accordingly, provided herein are compositions, methods, and assays for modulating TET2 mutation-mediated IL-1β (interleukin-1β) proinflammatory activity, particularly when caused by somatic mutations in TET2.

Compositions and Theranostic Methods for Treating IL-1β Proinflammatory Activity Accordingly, in some aspects, provided herein are pharmaceutical compositions comprising an inhibitor of TET2 mutation-mediated IL-1β (interleukin-1β) proinflammatory activity and a pharmaceutically acceptable carrier for use in a subject having one or more TET2 somatic mutations in a sub-population of hematopoietic cells.

Also provided herein, in some aspects, are methods for treating a subject having, or at risk for, a TET2 mutation-mediated IL-1β proinflammatory disease comprising administering a therapeutically effective amount of a pharmaceutical composition comprising an inhibitor of TET2 mutation-mediated IL-1β (interleukin-1β) proinflammatory activity and a pharmaceutically acceptable carrier to a subject having one or more TET2 somatic mutations in a sub-population of hematopoietic cells.

"Methylcytosine dioxygenase TET2" or "TET2" is a member of the family of TET proteins, which have been shown to be responsible for conversion of 5-methylcytosine (5mC) to 5-hydroxymethylcytosine (5hmC), as well as function in embryonic stem cell regulation, myelopoiesis, and zygote development (Dawlaty et al., 2011; Gu et al., 2011; Iqbal et al., 2011; Ito et al., 2010; Ko et al., 2010; Koh et al., 2011; Wossidlo et al., 2011). TET2 is a dioxygenase that catalyzes the conversion of the modified genomic base 5-methylcytosine (5mC) into 5-hydroxymethylcytosine (5hmC) and plays a key role in active DNA demethylation. TET2 has a preference for 5-hydroxymethylcytosine in CpG motifs, and has also been shown to mediate subsequent conversion of 5hmC into 5-formylcytosine (5fC), and conversion of 5fC to 5-carboxylcytosine (5caC). Methylation at the C5 position of cytosine bases is an epigenetic modification of the mammalian genome which plays an important role in transcriptional regulation. In addition to its role in DNA demethylation, TET2 has also been shown to be involved in the recruitment of the O-GlcNAc transferase OGT to CpG-rich transcription start sites of active genes, thereby promoting histone H2B GlcNAcylation by OGT. Similarly, TET2 has been reported to recruit histone deacetylases (HDACs) to specific gene promoters, contributing to histone deacetylation and gene repression (Zhang et al 2015).

Accordingly, the terms "TET2" or "TET-2," as used herein, refers to the genomic sequence of NG_028191.1 (SEQ ID NO: 1) encoding: the mRNA sequence of NM_001127208.2 (isoform 1, SEQ ID NO: 2), which encodes the 2002 amino acid polypeptide having the amino acid sequence of NP_001120680.1 (isoform 1, SEQ ID NO: 3); the mRNA sequence of NM_017628.4 (isoform 2, SEQ ID NO: 4) encoding the 1165 amino acid polypeptide having the amino acid sequence of NP_060098.3 (isoform 2, SEQ ID NO: 5); together with any additional naturally occurring allelic, splice variants, and processed forms thereof. Typically, TET2 refers to human TET2. Reference to specific sub-fragments or sub-sequences of TET2 can be identified in the application, e.g., by "nucleic acids 211-402 of TET2." Specific nucleic acid or amino acid residues of TET2 can be referred to as, for example, "S282 of TET2" or "S282 of SEQ ID NO: 3."

A "somatic mutation," as used herein, refers to a change in the genetic structure of a subject that is not inherited from a parent, and also not passed to offspring. Hence, a somatic mutation is a genetic change that occurs in any cell after the first cell division, wherein the mutation is replicated in all cells that descend from the mutated cell. The somatic cells that descend from the original mutated cell comprise a clonal variant within the body of the subject. Where these mutations are present in cells of somatic origin and not present in the germline, they are often called a somatic cell mutation or an acquired mutation. Somatic mutations will be present in only a subset of the cells contributing DNA to an analysis, since the mutant sequence will be present in fewer than 50% of the sequence reads arising from that genomic site. In other words, somatic mutations are identified as when a specific sequence is measured as occurring at a fraction of total sequences that deviates significantly from the frequency expected for the far-larger number of inherited variants—namely around 0%, around 50% or around 100%.

Somatic mutations can occur in a sub-population of cells for example, such as a sub-population of hematopoietic cells. Somatic mutations in TET2 relevant to the compositions and methods described herein include any nucleic acid or consequent amino acid somatic mutations in TET2, found in a subset of hematopoietic cells, leading to increased pro-inflammatory IL-1β signaling, including increased IL-1β transcription, increased NLRP3 inflammasome-mediated IL-1β secretion, and/or increased IL-1-Receptor 1-mediated IL-1β signaling. Such somatic mutations in the TET2 gene can be disruptive, in that they have an observed or predicted effect on protein function, or non-disruptive. As used herein, a "non-disruptive mutation" is typically a missense mutation, in which a codon is altered such that it codes for a different amino acid, but the encoded protein, i.e., TET2, is still expressed. Somatic mutations in TET2 include, for example, frameshift mutations, nonsense mutations, missense mutations or splice-site variant mutations, as those terms are known to those of ordinary skill in the art.

In some embodiments, one or more somatic mutations in TET2, in addition to leading to increased pro-inflammatory IL-1β signaling, also result in clonal hematopoiesis. As used herein, "clonal hematopoiesis" refers to clonal outgrowth of a sub-population of hematopoietic cells having one or more somatic mutations in TET2.

TET2 mutations relevant to the compositions and methods described herein include any nucleic acid mutations in the genomic sequence of TET2 of SEQ ID NO: 1 leading to: an S460F mutation in SEQ ID NO: 3; a D666G mutation in SEQ ID NO: 3; a P941S mutation in SEQ ID NO: 3; a C1135Y missense mutation in SEQ ID NO: 3, a R73 frameshift insertion mutation in SEQ ID NO: 3, a Y85 frameshift deletion mutation in SEQ ID NO: 3, a S123 frameshift deletion mutation in SEQ ID NO: 3, an E170 frameshift deletion mutation in SEQ ID NO: 3; a D162 frameshift deletion mutation in SEQ ID NO: 3; an I181 frameshift deletion mutation in SEQ ID NO: 3, a T221 frameshift insertion mutation in SEQ ID NO: 3; an L260 frameshift deletion mutation in SEQ ID NO: 3; an I274 frameshift deletion mutation in SEQ ID NO: 3; a L311 frameshift insertion mutation in SEQ ID NO: 3; a Q341 nonsense mutation in SEQ ID NO: 3; a Q383 nonsense mutation in SEQ ID NO: 3; a S423 nonsense mutation in SEQ ID NO: 3; a L427 frameshift insertion mutation in SEQ ID NO: 3, a S420 frameshift deletion mutation in SEQ ID NO: 3, a S424 frameshift deletion mutation in SEQ ID NO: 3, a S462 frameshift deletion mutation in SEQ ID NO: 3, an I472 frameshift deletion mutation in SEQ ID NO: 3; a Q481 nonsense mutation in SEQ ID NO: 3; a T518 frameshift insertion mutation in SEQ ID NO: 3; a S530 nonsense mutation in SEQ ID NO: 3, a S543 frameshift deletion mutation in SEQ ID NO: 3, a Q530 nonsense mutation in SEQ ID NO: 3; a L532 frameshift deletion mutation in SEQ ID NO: 3, a L532 nonsense mutation in SEQ ID NO: 3; a R544 nonsense mutation in SEQ ID NO: 3; a W585 nonsense mutation in SEQ ID NO: 3; a Q595 frameshift deletion mutation in SEQ ID NO: 3, a L579 frameshift insertion mutation in SEQ ID NO: 3; a S588 nonsense mutation in SEQ ID NO: 3, a G634 frameshift deletion mutation in SEQ ID NO: 3; a Q656 frameshift deletion mutation in SEQ ID NO: 3; a P690 frameshift deletion mutation in SEQ ID NO: 3; a R686 frameshift deletion mutation in SEQ ID NO: 3; an E692 frameshift insertion mutation in SEQ ID NO: 3; a Q705 nonsense mutation in SEQ ID NO: 3; a F713 frameshift deletion mutation in SEQ ID NO: 3; a Q734 nonsense mutation in SEQ ID NO: 3; a S757 nonsense mutation in SEQ ID NO: 3; a L759 frameshift deletion mutation in SEQ ID NO: 3; a Q764 frameshift deletion mutation in SEQ ID NO: 3; a I771 frameshift deletion mutation in SEQ ID NO: 3; a Q779 nonsense mutation in SEQ ID NO: 3; an H783 frameshift insertion mutation in SEQ ID NO: 3; a Q770 nonsense mutation in SEQ ID NO: 3; a E819 frameshift deletion mutation in SEQ ID NO: 3; a H839 frameshift deletion mutation in SEQ ID NO: 3; a K858 frameshift deletion mutation in SEQ ID NO: 3; a Q886 nonsense mutation in SEQ ID NO: 3; a L878 frameshift deletion mutation in SEQ ID NO: 3; an M906 frameshift insertion mutation in SEQ ID NO: 3; a Q909 nonsense mutation in SEQ ID NO: 3; a Q910 nonsense mutation in SEQ ID NO: 3; a Q912 frameshift deletion mutation in SEQ ID NO: 3; a Q937 nonsense mutation in SEQ ID NO: 3; a Q916 nonsense mutation in SEQ ID NO: 3; a P989 frameshift insertion mutation in SEQ ID NO: 3; an A1014 frameshift insertion mutation in SEQ ID NO: 3; a Q1042 nonsense mutation in SEQ ID NO: 3; a Q1030 nonsense mutation in SEQ ID NO: 3; an H1064 frameshift insertion mutation in SEQ ID NO: 3; a T1078 frameshift deletion mutation in SEQ ID NO: 3; a T1107 frameshift deletion mutation in SEQ ID NO: 3; a N1103 frameshift deletion mutation in SEQ ID NO: 3; a T1114 frameshift deletion mutation in SEQ ID NO: 3; a Q1127 frameshift insertion mutation in SEQ ID NO: 3; an S282F mutation in SEQ ID NO: 3; a N312S mutation in SEQ ID NO: 3; an L346P mutation in SEQ ID NO: 3; and an G to A splice site mutation at position 106158509 of SEQ ID NO: 1.

In some embodiments of the compositions and methods described herein, the one or more TET2 somatic mutations are selected from an S282F mutation in SEQ ID NO: 3, an N312S mutation in SEQ ID NO: 3, an L346P mutation in SEQ ID NO: 3, an S460F mutation in SEQ ID NO: 3, a D666G mutation in SEQ ID NO: 3, a P941S mutation in SEQ ID NO: 3, and a C1135Y mutation in SEQ ID NO: 3.

The compositions and methods described herein require, in some embodiments, sequencing of at least part of the genome in a sample comprising hematopoietic cells, including, for example, an enriched for population of myeloid cells, obtained from a subject. Sequencing can be carried out according to any suitable technique, many of which are generally known in the art. Many proprietary sequencing systems are available commercially and can be used in the context of the methods described herein, such as for example from Illumina, USA. Single-cell sequencing methods are known in the art, as noted for example by Eberwine et al., Nature Methods 11, 25-27 (2014) doi:10.1038/nmeth.2769 Published online 30 Dec. 2013; and single-cell sequencing in microfluidic droplets (Nature 510, 363-369 (2014) doi: 10.1038/nature13437).

Sequencing of DNA can be performed on tissues or cells. Sequencing of specific cell types (for example, hematopoietic cells obtained by flow sorting or myeloid lineage hematopoietic cells) can identify mutations in specific cell types that provide specific predictive value for use with the compositions and methods described herein. Sequencing can also be conducted in single cells, using appropriate single-cell sequencing strategies. Single-cell analyses can be used to identify high-risk combinations of mutations co-occurring in the same cells. Co-occurrence signifies that the mutations are occurring in the same cell clone and carry a greater risk, and therefore have a greater predictive value, than occurrence of the same mutations in different individual cells, for example. Certain sequences, such as those with high GC content, repetitive elements and/or low sequence complexity are prone to sequencing errors and false positive creation due to artifacts caused by enzyme slippage and other reading errors. Hence, care must be taken to ensure that any sequence changes observed in these regions are real and not artifact.

The inhibitors of TET2 mutation-mediated IL-1β proinflammatory activity are particularly useful for subjects having one or more somatic mutations in TET2 in a population of hematopoietic cells. As used herein, an "inhibitor of TET2 mutation-mediated IL-1β (interleukin-1β) proinflammatory activity" refers to any agent or molecule that significantly blocks, inhibits, reduces, or interferes with the downstream effects of somatic mutations in TET2 that lead to increased IL-1β proinflammatory activity or signaling in vitro, in situ, and/or in vivo, including increased IL-1β transcription, increased NLRP3 inflammasome-mediated IL-1β secretion, and/or increased IL-1-receptor I (IL-1R1)-mediated IL-1β signaling. Exemplary inhibitors of TET2 mutation-mediated IL-1β (interleukin-1β) proinflammatory activity contemplated for use in the various aspects and embodiments described herein include, but are not limited to, antibodies or antigen-binding fragments thereof that specifically bind to IL-1β and/or antibodies or antigen-binding fragments thereof that specifically bind to IL-1 receptors, such as IL1R1, thereby inhibiting/reducing/blocking IL-1β interaction(s) with its receptors; small molecule agents that target or specifically bind IL-1β, IL-1-receptors, and/or IL-1 signaling components, such as caspase-1, and inhibit/reduce/block IL-1-mediated proinflammatory activity; RNA or DNA aptamers that bind to IL-1β or IL-1-receptors and inhibit/reduce/block IL-1β-mediated proinflammatory activity; and/or IL-1 receptor fragments or fusion polypeptides thereof that block endogenous IL-1β interactions with endogenous IL-1 receptors.

In regard to NLRP3 inflammasome-mediated IL-1β secretion, and inhibitors thereof foe use as inhibitors of TET2 mutation-mediated IL-1β (interleukin-1β) proinflammatory activity, as described herein, as known to those of skill in the art, the NLRP3 inflammasome is present primarily in immune and inflammatory cells following activation by inflammatory stimuli; these cells include macrophages, monocytes, DCs, and splenic neutrophils. Activation of the NLRP3 inflammasome occurs in two steps. The first step involves a priming or initiating signal, in which many PAMPs or DAMPs are recognized by TLRs, leading to activation of nuclear factor kappa B (NF-κB)-mediated signaling, which in turn up-regulates transcription of inflammasome-related components, including inactive NLRP3, proIL-1β, and proIL-18 (Bauernfeind et al., 2009; Franchi et al., 2012, 2014). The second step of inflammasome activation is the oligomerization of NLRP3 and subsequent assembly of NLRP3, ASC, and procaspase-1 into a complex. This triggers the transformation of procaspase-1 to caspase-1, as well as the production and secretion of mature IL-1β and IL-18 (Kim et al., 2015; Ozaki et al., 2015; Rabeony et al., 2015). An inhibitor of TET2 mutation-mediated IL-1β (interleukin-1β) proinflammatory activity useful in the methods and compositions described herein can thus target any of the steps and/or components leading to NLRP3 inflammasome activation (see, for example, non-limiting examples in B-Z Shao et al., NLRP3 inflammasome and its inhibitors: a review; Front Pharmacol. 2015; 6: 262).

The inhibitors of TET2 mutation-mediated IL-1β proinflammatory activity described herein result in a significant inhibition or reduction or decrease in any of the pathways leading to IL-1β-mediated proinflammatory activity or signaling, such as IL-1β transcription, IL-1β translation, NLRP3 inflammasome-mediated IL-1β secretion, and/or IL-1β binding to IL-1 receptor and consequent IL-1-receptor I (IL-1R1)-mediated IL-1β signaling. As used herein, the terms reduce(s)/reduced/reducing/reduction, inhibit(s)/inhibiting/inhibited or decrease(s)/decreasing/decreased generally means either a reduction or inhibition of at least 5%, at least 10%, at least 25%, at least 50%, at least 60%, at least 70%, at least 80%, at least 90%, at least 95%, at least 98%, or more, compared to the level of IL-1β transcription, IL-1β translation, NLRP3 inflammasome-mediated IL-1β secretion, and/or IL-1β binding to IL-1 receptor and consequent IL-1-receptor I (IL-1R1)-mediated IL-1β signaling under the same conditions but without the presence of inhibitors of TET2 mutation-mediated IL-1β proinflammatory activity described herein. Assays for measuring such inhibition or reduced interactions are known in the art and are described herein in the Examples.

A disease or medical condition is considered to be mediated by "IL-1β (interleukin-1β) proinflammatory activity" if the spontaneous or experimental disease or medical condition is associated with, or mediated by, for example, elevated levels of IL-1β in bodily fluids or tissue, or if cells or tissues taken from the body produce elevated levels of IL-1 in culture. In many cases, such diseases mediated by IL-1β proinflammatory activity are also recognized by the following additional two conditions: (1) pathological findings associated with the disease or medical condition can be mimicked experimentally in animals by the administration of IL-1β; and (2) the pathology induced in experimental animal models of the disease or medical condition can be inhibited or abolished by treatment with agents which inhibit the action of IL-1β. A non-limiting list of disorders and diseases known to be mediated by or exacerbated by aberrant, elevated IL-1β activity include hereditary syndromes with mutations in inflammasome-associated genes, such as cryopyrin-associated periodic syndromes (CAPS), Familial Mediterranean fever, Pyogenic arthritis, pyoderma gangrenosum and acne (PAPA) syndrome, Deficiency of IL-1Ra (DIRA); Crystal-induced arthropathies, such as gout; systemic-onset juvenile arthritis or Still disease, adult-onset Still disease; rheumatoid arthritis; osteoarthritis; Schnitzler syndrome; Behçet disease; Crohn's disease; periodontal diseases; COPD (Chronic Obstructive Pulmonary Disease); and neutrophil-triggered skin diseases, such as pyoderma gangrenosum, psoriasis pustulosa, Sweet syndrome; and chronic kidney disorders.

In some embodiments of the compositions and methods described herein, a disease mediated by IL-1β (interleukin-1β) proinflammatory activity is a cardiometabolic disease. Cardiometabolic diseases include cardiovascular diseases, as well as those disorders that complicate the risk and clinical management of cardiovascular conditions by potentiating and/or exacerbating hypertension, hyperlipidemia, atherosclerosis and cardiomyopathy, and include insulin resistance, hyperglycemia, obesity, type 2 diabetes mellitus, metabolic syndrome, hyperlipidemia and oxidative stress.

As used herein, the phrase "cardiovascular condition, disease or disorder" is intended to include all disorders characterized by insufficient, undesired or abnormal blood vessel or cardiac function, e.g. hypertension, ischemic heart disease, hypertensive heart disease and pulmonary hypertensive heart disease, valvular disease, cardiac arrhythmia, vascular disease, myocardial infarction, congestive heart failure, myocarditis, atherosclerosis, restenosis, and any condition which leads to congestive heart failure in a subject, particularly a human subject. Insufficient or abnormal cardiac function can be the result of disease, injury and/or aging. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

In some embodiments of the compositions and methods described herein, a disease mediated by IL-1β (interleukin-1β) proinflammatory activity is a chronic kidney disease.

In regard to the methods of treating chronic kidney disease mediated by IL-1β (interleukin-10) proinflammatory activity, the term "chronic kidney disease" or CKD refers to renal diseases that slowly and progressively worsen over time due to the progressive loss of nephrons and consequent loss of renal function. In the early stages, there may be no symptoms. The loss of function usually takes months or years to occur. It may be so slow that symptoms do not appear until kidney function is less than one-tenth of normal. The final stage of chronic kidney disease is called end-stage renal disease (ESRD). At this stage, the kidneys are no longer able to remove enough wastes and excess fluids from the body. The patient needs dialysis or a kidney transplant. Diabetes, which leads to diabetic nephropathy, and high blood pressure are the two most common causes of chronic kidney disease and account for most cases. Other diseases and conditions that can damage the kidneys and lead to chronic kidney disease, include, but are not limited to: autoimmune disorders (such as systemic lupus erythematosus and scleroderma); birth defects of the kidneys (such as polycystic kidney disease); certain toxic chemicals; glomerulonephritis; injury or trauma; kidney stones and infection; problems with the arteries leading to or inside the kidneys; some pain medications and other drugs (such as cancer drugs); reflux nephropathy (in which the kidneys are damaged by the backward flow of urine into the kidneys); etc. As used herein, "proteinuria" refers to the presence of an excess of serum proteins in the urine. Proteinuria can, in some embodiments, be indicative of kidney disease, but, by itself, is not conclusive. In some embodiments of these aspects and all such aspects described herein, a subject having or at risk for a chronic kidney disease has diabetic nephropathy.

In some embodiments of the aspects descried herein, an inhibitor of TET2 mutation-mediated IL-1β (interleukin-1β) proinflammatory activity is an IL-1β inhibitory compound. As used herein, an "IL-1β inhibitory compound" or "IL-1β inhibitor" or "inhibitor of IL-1β" refers to a compound or agent capable of specifically inhibiting or specifically preventing activation of cellular receptors to IL-1β and consequent downstream effects of IL-1β signaling. Classes of interleukin-1β inhibitors include: interleukin-1 receptor antagonists such as IL-1ra; anti-IL-1 receptor antibodies (e.g., EP 623674), the contents of which is hereby incorporated by reference in its entirety; IL-1β binding proteins such as soluble IL-1 receptors (e.g., U.S. Pat. No. 5,492,888, U.S. Pat. No. 5,488,032, and U.S. Pat. No. 5,464,937, U.S. Pat. No. 5,319,071, and U.S. Pat. No. 5,180,812, the contents of which are hereby incorporated by reference in their entireties); anti-IL-1β monoclonal antibodies (e.g., WO 9501997, WO 9402627, WO 9006371, U.S. Pat. No. 4,935,343, EP 364778, EP 267611 and EP 220063, the contents of which are hereby incorporated by reference in their entireties); IL-1 receptor I accessory proteins (e.g., WO 96/23067, the disclosure of which is hereby incorporated by reference), and other compounds and proteins which block in vivo synthesis, including in vivo transcription, in vivo translation, and/or extracellular release of IL-1β.

In some embodiments of the aspects described herein, the IL-1β inhibitor is selected from any of the IL-1β or inflammasome inhibitors listed in Table 1.

TABLE 1

Exemplary List of IL-1β inhibitors for use as TET2 mutation-mediated IL-1β (interleukin-1β) proinflammatory activity.

| Product Name | Active Ingredient | Molecule Type | Target | Mode of Action | Route of Administration | Product Description |
|---|---|---|---|---|---|---|
| ABT981 | — | Large molecule-Antibody | Interleukin 1A (IL1A), Interleukin 1B (IL1B) | Interleukin-1alpha (IL-1alpha) Inhibitor, Interleukin-1beta (IL-1beta) Inhibitor | Subcutaneous | ABT981 is a dual variable immunoglobulin (DVD-Ig) consisting of interleukin 1, beta antibody and interleukin 1, alpha antibody. It binds and inhibits the interleukin-1 alpha, beta (IL-1 a/β). |
| AC201 Also known as AC 201, AC 203, AC203 | diacerein | Small molecule | Caspase, Apoptosis-Related Cysteine Peptidase 1 (CASP1), Interleukin 1B (IL1B) | Caspase-1 Inhibitor, Interleukin-1beta (IL-1beta) Inhibitor | Oral, Topical | AC201 contains diacerein as an active ingredient. Diacerein is a small molecule which inhibits the production and activity of caspase-1 and the cytokine interleukin-1beta (IL-1Beta), and |

TABLE 1-continued

Exemplary List of IL-1β inhibitors for use as TET2 mutation-mediated IL-1β (interleukin-1β) proinflammatory activity.

| Product Name | Active Ingredient | Molecule Type | Target | Mode of Action | Route of Administration | Product Description |
|---|---|---|---|---|---|---|
| | | | | | | down-regulate IL-1Beta receptors. AC201 reduces the HbA1c/blood sugar levels. |
| Anti-interleukin-1 Beta antibody by ABZYME | | Large molecule-Antibody | Interleukin 1B (IL1B) | Interleukin-1beta (IL-1beta) Inhibitor | | Anti-interleukin-1 Beta antibody is a targeted human monoclonal antibody. |
| APX002 Also known as APX 002, TK 002, TK002 | interleukin 1, beta monoclonal antibody (humanized) | Large molecule-Antibody | Interleukin 1B (IL1B) | Interleukin-1beta (IL-1beta) Inhibitor | | APX002 is a humanized monoclonal antibody which inhibits interleukin-1-beta. |
| Canakinumab/Ilaris Also known as IL 1 Beta Mab NOVARTIS, IL 1 Beta Monoclonal Antibody NOVARTIS, Interleukin 1 Beta Monoclonal Antibody NOVARTIS | canakinumab | Large molecule-Antibody | Interleukin 1B (IL1B) | Interleukin-1beta (IL-1beta) Inhibitor | Subcutaneous | Canakinumab is an interleukin 1 beta monoclonal antibody derived from a mouse monoclonal antibody (mAb) acting against IL-1 beta. |
| CDP48 Also known as CDP 484 | interleukin 1, beta antibody (pegylated) | Large molecule-Antibody | Interleukin 1 Receptor, Type II (IL1R2) | Interleukin-1 Beta (IL-1 Beta) Receptor Antagonist | | CDP484 is a PEGylated antibody fragment targeting pro-inflammatory cytokine interleukin 1-beta. |
| CP412245 Also known as CP 412,245, CP 412245, CP412,245 | | Small molecule | Interleukin 1 Receptor, Type II (IL1R2) | Interleukin-1 Beta (IL-1 Beta) Receptor Antagonist | | CP412245 is a potent inhibitor of stimulus-coupled IL-1beta post-translational processing. It is a diarylsulfonylurea compound that blocks formation of mature IL-1 without increasing the amount of procytokine that is released extracellularly. |
| CYT013 IL1bQb, interleukin 1 beta Also known as interleukin 1 receptor antagonist protein | | | Interleukin 1 Receptor, Type II (IL1R2) | Interleukin-1 Beta (IL-1 Beta) Receptor Antagonist | Subcutaneous | CYT013IL1bQb is a therapeutic vaccine consisting of modified interleukin-1 beta molecules coupled to the virus-like particle Qb. The vaccine induces antibodies production against IL-1 beta to decrease inflammation and reduce disease progression. |
| MCC 950 or MCC950/CRID3/CP-456773 | | Small molecule | | | | NLRP3 inflammasome inhibitor. Blocking apoptosis-associated speck-like protein (ASC) |

TABLE 1-continued

Exemplary List of IL-1β inhibitors for use as TET2 mutation-mediated IL-1β (interleukin-1β) proinflammatory activity.

| Product Name | Active Ingredient | Molecule Type | Target | Mode of Action | Route of Administration | Product Description |
|---|---|---|---|---|---|---|
| | | | | | | oligomerization, Inhibiting of canonical and non-canonical NLRP3 inflammasome. Targeted against interleukin-1 beta. |
| immunereszumab | interleukin 1, beta antibody | Large molecule-Antibody | Interleukin 1B (IL1B) | | | |
| Inflabion | diacerein | Small molecule | Interleukin 1 (IL1) | Interleukin-1 (IL-1) Inhibitor | Oral | Inflabion contains diacerein as an active ingredient. Diacerin (diacerein) is an anthraquinone derivative that acts via inhibition of interleukin-1beta. |
| Inflammasome modulator OPSONA | | Small molecule | Interleukin 1B (IL1B) | Interleukin-1beta (IL-1beta) Inhibitor | | Inflammasome modulator interferes with inflammasome mediated release of interleukin (IL)-1beta. It is a specific IL1-β inhibitor. |
| LY2189102 Also known as LY 2189102 | interleukin 1, beta monoclonal antibody (humanized) | Large molecule-Antibody | Interleukin 1 Receptor, Type II (IL1R2) | Interleukin-1 Beta (IL-1 Beta) Receptor Antagonist | Intravenous, Subcutaneous | LY2189102 contains interleukin 1, beta monoclonal antibody as an active ingredient. It is targeted against interleukin-1 beta. |
| MEDI8968 Also known as MEDI 8968 | interleukin 1 receptor monoclonal antibody (human) | Large molecule-Antibody | Interleukin 1A (IL1A), Interleukin 1B (IL1B) | Interleukin-1alpha (IL-1alpha) Inhibitor, Interleukin-1beta (IL-1beta) Inhibitor | Subcutaneous | MEDI8968 is a fully human IgG2 monoclonal antibody (mAb) that binds selectively to Interleukin-1 Receptor I (IL-1R1) to inhibit the binding of IL-1 alpha and IL-1 beta. |
| PGE3935199 Also known as PGE 3935199 | | | Caspase, Apoptosis-Related Cysteine Peptidase 1 (CASP1) | Caspase-1 Inhibitor | Oral | PGE3935199 is a caspase-1 inhibitor. Interleukin-1β converting enzyme (Caspase-1, ICE) is involved in the processing of Pro-IL-1β to the active cytokine IL-1β. |
| PGE527667 Also known as PGE 527667 | | | Caspase, Apoptosis-Related Cysteine Peptidase 1 (CASP1) | Caspase-1 Inhibitor | Oral | PGE527667 is a Caspase-1 inhibitor. Interleukin-1β converting enzyme (Caspase-1, ICE) is involved in the processing of Pro-IL-1β to the active cytokine IL-1β. |
| TRK530 Also known as TRK 530 | | | Interleukin 1B (IL1B) | Interleukin-1beta (IL-1beta) Inhibitor | Oral | TRK530 is an immunomodulatory bisphosphonate derivative that is directed against interleukin 1b. |
| XL 130 Also known as interleukin 1 receptor antagonist protein (pasylated) | | Large molecule | Interleukin 1 Receptor (IL1R) | Interleukin-1 (IL-1) Receptor Antagonist | | XL130 contains PASylated interleukin 1 receptor antagonist protein as an active ingredient. Interleukin 1 receptor antagonist |

TABLE 1-continued

Exemplary List of IL-1β inhibitors for use as TET2 mutation-mediated IL-1β (interleukin-1β) proinflammatory activity.

| Product Name | Active Ingredient | Molecule Type | Target | Mode of Action | Route of Administration | Product Description |
|---|---|---|---|---|---|---|
| XOMA052 Also known as S78989, S78989, XMA005.2, XOMA 052 | gevokizumab | Large molecule-Antibody | Interleukin 1B (IL1B) | Interleukin-1beta (IL-1beta) Inhibitor | Intravenous, Subcutaneous | protein acts by preventing the interaction of IL-1 with the receptor. XOMA052 contains gevokizumab as an active ingredient. Gevokizumab is a humanized monoclonal antibody directed against interleukin 1b. |
| AMG108 Also known as AMG 108 | interleukin 1 receptor monoclonal antibody (human) | Large molecule-Antibody | Interleukin 1 (IL1) | Interleukin-1 (IL-1) Inhibitor | Subcutaneous | AMG108 is a fully human interleukin 1 receptor monoclonal antibody that binds to and inhibits the action of interleukin-1 (IL-1). |
| HL 2351, IL1Ra hyFc | | | Interleukin 1 (IL1) | Interleukin-1 (IL-1) Inhibitor | Subcutaneous | HL2351 is a long acting fusion protein of IL-1Ra and hybrid fc fragment (hyFc) which inhibits interleukin-1. |
| IL1Hy1 Also known as IL 1F5, IL 1Hy1, interleukin 1 family, member 5, interleukin 1 HY1 | | | Interleukin 1 Receptor (IL1R) | Interleukin-1 (IL-1) Receptor Antagonist | | IL1Hy1 is an interleukin-1 receptor antagonist that acts by blocking the binding of interleukin-1 (IL-1) to cell receptors. |
| Interleukin 1 ra AXXO Also known as interleukin 1 receptor antagonist protein (recombinant, human) | | Large molecule | Interleukin 1 Receptor (IL1R) | Interleukin-1 (IL-1) Receptor Antagonist | | Recombinant human interleukin 1 receptor antagonist protein acts by preventing the interaction of IL-1 with the receptor. |
| Orthokine Also known as interleukin 1 receptor antagonist protein | | | Interleukin 1 Receptor (IL1R) | Interleukin-1 (IL-1) Receptor Antagonist | Intra-articular | Orthokine is an autologous serum solution derived from the patient's blood. It contains the interleukin-1 receptor antagonist (IL-1Ra) protein that prevents the interaction of IL-1 with the receptor. |
| PRT 1000 Also known as interleukin 1 receptor antagonist protein | | | Interleukin 1 Receptor (IL1R) | Interleukin-1 (IL-1) Receptor Antagonist | | PRT1000 contains MB-IL1RA which is an interleukin-1 receptor antagonist protein (IL1RA), fused with a matrix binding domain It is a potent cytokine inhibitor and prevents the interaction of IL1 with the receptor. |

TABLE 1-continued

Exemplary List of IL-1β inhibitors for use as TET2 mutation-mediated IL-1β (interleukin-1β) proinflammatory activity.

| Product Name | Active Ingredient | Molecule Type | Target | Mode of Action | Route of Administration | Product Description |
|---|---|---|---|---|---|---|
| Anakinra/Kineret | | Large molecule | Interleukin 1 Receptor (IL1R) | Interleukin-1 (IL-1) Receptor Antagonist | | interleukin 1 (IL1) receptor antagonist. |
| Rilonacept | | Large molecule | | | | Rilonacept has one extracellular domain of IL-1 receptor type 1 (IL-1R1) and one of IL-1 receptor accessory protein (IL-1RAcP) bound to the Fc portion of IgG |
| β-hydroxybutyrate (BHB) | | Small molecule NLRP3 inhibitor | | | | Blocking ASC oligomerization, Inhibiting K+/potassium efflux; |
| MicroRNA-223 | | Micro RNA | | | | Suppressing NLRP3 protein expression by binding to a conserved site in the 3' UTR of the NLRP3 transcript,. |

In some embodiments of the aspects described herein, the IL-1β inhibitor is an IL-1β inhibitor antibody or antigen-binding fragment thereof that binds to IL-1β and reduces/inhibits/prevents IL-1β binding to its receptor(s), thereby inhibiting IL-1β-mediated pro-inflammatory activity. As used herein, "antibodies" or "antigen-binding fragments" thereof include monoclonal, human, humanized or chimeric antibodies, single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

The terms "antibody fragment" or "antigen-binding fragment" include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$—$C_H1$-$V_H$-$C_H1$) which, together with complementary light chain polypeptides, form a pair of antigen binding regions (Zapata et al. Protein Eng. 8(10): 1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

Accordingly, in some embodiments of the aspects described herein, the IL-1β inhibitor antibody or antigen-binding fragment thereof is selected from ABT981, an anti-interleukin-1β inhibitor antibody by ABZYME, APX002, Canakinumab/Ilaris, CDP48, immunereszumab, LY2189102, MEDI8968, and XOMA052.

In some embodiments of the aspects described herein, the IL-1β inhibitor is an IL-1 receptor antagonist. As used herein, an "interleukin-1 receptor antagonist" ("IL-1ra") is any agent or molecule, including small molecules and antibody or antigen-binding fragments thereof, that binds to an interleukin-1 receptor thereby preventing binding of IL-1β to the receptor and thereby inhibiting IL-1β-mediated pro-inflammatory activity. Interleukin 1 receptor antagonists, as well as methods of making and using thereof, are described in, for example, U.S. Pat. No. 5,075,222; WO 91/08285; WO 91/17184; AU 9173636; WO 92/16221; WO93/21946; WO 94/06457; WO 94/21275; FR 2706772; WO 94/21235; DE 4219626, WO 94/20517; WO 96/22793 and WO 97/28828, the contents of which are incorporated herein by reference in their entireties. The proteins include glycosylated as well as non-glycosylated IL-1 receptor antagonists.

Accordingly, in some embodiments of the aspects described herein, the IL-1 receptor antagonist is selected from CDP484, CP412245, CYT013 IL1bQb, XL 130, AMG108, HL 2351, IL1Hy1, AXXO, orthokine, PRT 1000, anakinra, and rilonacept.

In some embodiments of the aspects described herein, the IL-1β inhibitor is a small molecule or microRNA inhibitor that inhibits IL-1β-mediated pro-inflammatory activity. Such small molecule inhibitors can target or specifically bind IL-1β, IL-1-receptors, and/or IL-1 signaling components, such as caspase-1, and/or the NLRP3 inflammasome, or components thereof, thereby inhibiting/reducing/blocking IL-1β-mediated proinflammatory activity. As used herein, "small molecule inhibitors" include, but are not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da.

Accordingly, in some embodiments of the aspects described herein, the small molecule or microRNA IL-1β inhibitor is selected from, AC201, MCC950 or CRID3, inflabion, inflammasome modulator OPSONA, PGE3935199, PGE527667, TRK530, p-hydroxybutyrate (BHB), and microRNA-223. In some embodiments of the aspects described herein, the small molecule IL-1p inhibitor is MCC950.

In some embodiments of the aspects descried herein, an inhibitor of TET2 mutation-mediated IL-1β (interleukin-1β) proinflammatory activity is a TET2 activating compound or TET2 potentiatior. As used herein, the terms "TET2 activating compound" or "TET2 potentiatior" or "TET2 activator" or "TET2 agonist" refer to a molecule or agent that mimics or up-regulates (e.g., increases, potentiates or supplements) the biological activity of TET2, thereby decreasing or inhibiting IL-1β (interleukin-1β) proinflammatory activity caused by deficient TET2 activity. A TET2 potentiator or agonist can be, in some embodiments, a TET2 protein fragment or derivative thereof having at least one bioactivity of the wild-type TET2. A TET2 activator can also be a compound which increases TET2 dioxygenase activity, TET2 mutation-mediated histone H2B GlcNAcylation, and/or TET2 mutation-mediated histone deacetylase recruitment to specific gene promoters, for example. Exemplary TET2 activating compounds or agonists contemplated for use in the various aspects and embodiments described herein include, but are not limited to, RNA or DNA aptamers; TET2 structural analogs or TET2 fragments, derivatives, or fusion polypeptides thereof, and small molecule agents that target or bind to TET2 and act as functional mimics of TET2.

A subject in need of the pharmaceutical compositions and methods comprising inhibitors of TET2 mutation-mediated IL-1β (interleukin-1β) proinflammatory activity and a pharmaceutically acceptable carrier described herein has or identified as having one or more TET2 somatic mutations in a sub-population of their hematopoietic cells. As used herein, a "sub-population" of hematopoietic cells comprising the one or more TET2 mutations in the subject refers to at least 1% of hematopoietic cells, at least 2% of hematopoietic cells, at least 3% of hematopoietic cells, at least 4% of hematopoietic cells, at least 5% of hematopoietic cells, at least 6% of hematopoietic cells, at least 7% of hematopoietic cells, at least 8% of hematopoietic cells, at least 9% of hematopoietic cells, at least 10% of hematopoietic cells, at least 11% of hematopoietic cells, at least 12% of hematopoietic cells, at least 13% of hematopoietic cells, at least 15% of hematopoietic cells, at least 15% of hematopoietic cells, at least 20% of hematopoietic cells, or more, or between 1-5% of hematopoietic cells, between 1-10% of hematopoietic cells, between 1-15% of hematopoietic cells, between 1-20% of hematopoietic cells, between 5-10% of hematopoietic cells, between 5-15% of hematopoietic cells, between 5-20% of hematopoietic cells, between 10-15% of hematopoietic cells, between 10-20% of hematopoietic cells, between 15-20% of hematopoietic cells, present in a sample obtained from the subject. In some embodiments, a sub-population of cells in a subject can refer to a specific cell type or lineage within the hematopoietic cells in the subject, such as myeloid lineage cells or macrophages. In such embodiments, the "sub-population" of cells comprising the one or more TET2 mutations in the subject refers to at least 1% of myeloid cells, at least 2% of myeloid cells, at least 3% of myeloid cells, at least 4% of myeloid cells, at least 5% of myeloid cells, at least 6% of myeloid cells, at least 7% of myeloid cells, at least 8% of myeloid cells, at least 9% of myeloid cells, at least 10% of myeloid cells, at least 11% of myeloid cells, at least 12% of myeloid cells, at least 13% of myeloid cells, at least 15% of myeloid cells, at least 15% of myeloid cells, at least 20% of myeloid cells, or more, or between 1-5% of myeloid cells, between 1-10% of myeloid cells, between 1-15% of myeloid cells, between 1-20% of myeloid cells, between 5-10% of myeloid cells, between 5-15% of myeloid cells, between 5-20% of myeloid cells, between 10-15% of myeloid cells, between 10-20% of myeloid cells, between 15-20% of myeloid cells, or greater than 20% of myeloid cells present in a sample obtained from the subject.

The terms "biological sample" or "sample" as used herein refers to a cell or population of cells or a quantity of tissue or fluid from a subject comprising one or more hematopoietic cells. Most often, the biological sample has been removed from a subject, but the term "biological sample" can also refer to cells or tissue analyzed in vivo, i.e., without removal from the subject. Thus, a "sample" of hematopoietic cells can be obtained from any tissue or organ in the subject comprising cells of hematopoietic origin, including blood, spleen, lymph nodes, cord blood, placenta, and bone marrow. Hematopoietic cells (HSCs) include myeloid cells (monocytes and macrophages, neutrophils, basophils, eosinophils, erythrocytes, megakaryocytes/platelets, dendritic cells), and lymphoid lineages (T-cells, B-cells, NKT-cells, NK-cells), as well as progenitor cell populations, including multipotent cells, such as hematopoietic stem cells. As used herein, the term "population of hematopoietic cells" encompasses a heterogeneous or homogeneous population of hematopoietic cells and/or hematopoietic progenitor cells. In other words, a population of hematopoietic cells comprising at least two different cell types is referred to herein as a "heterogeneous population."

In some aspects, provided herein are sensitive and specific companion diagnostic and treatment methods, also referred to herein as "theranostic methods," to detect and closely monitor TET2 somatic mutations associated with disease, particularly IL-1β mediated disorders, including cardiometabolic diseases. As used herein, a "companion diagnostic" refers to a diagnostic method and or reagent that are used to identify subjects susceptible to treatment with a particular treatment or to monitor treatment and/or to identify an effective dosage for a subject or sub-group or other group of subjects.

Accordingly, in some aspects, provided herein are theranostic methods for treating a subject having, or at risk for, a TET2 mutation-mediated IL-1β proinflammatory disease comprising: (a) sequencing a hematopoietic cell sample from the subject to identify one or more somatic mutations in TET2, and (b) administering a therapeutically effective amount of a pharmaceutical composition comprising an inhibitor of TET2 mutation-mediated IL-1β (interleukin-1β) proinflammatory activity and a pharmaceutically acceptable carrier if one or more somatic mutations in TET2 are identified in the hematopoietic cell sample.

A sample of hematopoietic cells for use in the methods and uses described herein can, in some embodiments, undergo further processing, such as via flow cytometric sorting and/or magnetic bead based sorting methods, to become an enriched population of hematopoietic cells for analysis of TET2 mutations, using any method known to one of skill in the art.

In some embodiments of the aspects described herein, a sample comprising hematopoietic cells isolated from a subject, such as a sample obtained from peripheral blood, is then further processed, for example, by cell sorting (e.g., magnetic sorting or FACS), to obtain a population of enriched or isolated hematopoietic cells or a sub-population thereof, for example, myeloid-derived cells.

The terms "isolate" and "methods of isolation," as used herein, refer to any process whereby a cell or population of cells, such as a population of hematopoietic cells, is removed from a subject or sample in which it was originally found, or a descendant of such a cell or cells. The term "isolated population," as used herein, refers to a population of cells that has been removed and separated from a biological sample, or a mixed or heterogeneous population of cells found in such a sample. Such a mixed population includes, for example, a population of hematopoietic cells obtained from peripheral blood. In some embodiments, an isolated population is a substantially pure population of cells as compared to the heterogeneous population from which the cells were isolated or enriched from. In some embodiments of this aspect and all such aspects described herein, the isolated population is an isolated population of myeloid cells. In other embodiments of this aspect and all aspects described herein, the isolated population comprises a substantially pure population of myeloid cells as compared to a heterogeneous population of hematopoietic cells comprising various other cells types.

The term "substantially pure," with respect to a particular cell population, refers to a population of cells that is at least about 75%, at least about 80%, at least about 85%, at least about 90%, at least about 95%, at least about 98%, or at least about 99% pure, with respect to the cells making up a total cell population.

The terms "enriching" or "enriched" are used interchangeably herein and mean that the yield (fraction) of cells of one type, such as hematopoietic cells for use in the methods and uses described herein, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

In some embodiments of the aspects described herein, markers specific for different hematopoietic cell types are used to isolate or enrich for these cells. A "marker," as used herein, describes the characteristics and/or phenotype of a cell. Markers can be used for selection of cells comprising characteristics of interest. Markers will vary with specific cells. Markers are characteristics, whether morphological, functional or biochemical (enzymatic), particular to a cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, appearance (e.g., smooth, translucent), and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art.

Accordingly, as used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to.

A cell can be designated "positive" or "negative" for any cell-surface marker, and both such designations are useful for the practice of the methods described herein. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell may express messenger RNA for a cell-surface marker, in order to be considered positive for the methods described herein, the cell must express it on its surface. Similarly, a cell is considered "negative" for a cell-surface marker if it does not express the marker on its cell-surface in amounts sufficient to be detected using methods known to those of skill in the art, such as contacting a cell with an antibody that binds specifically to that marker and subsequently performing flow cytometric analysis of such a contacted cell to determine whether the antibody is bound the cell. In some embodiments, where agents specific for cell-surface lineage markers used, the agents can all comprise the same label or tag, such as fluorescent tag, and thus all cells positive for that label or tag can be excluded or removed, to leave uncontacted hematopoietic stem or progenitor cells for use in the methods described herein. In some embodiments of the aspects described herein, an agent specific for a cell-surface molecule, such as an antibody or antigen-binding fragment, is labeled with a tag to facilitate the isolation of the hematopoietic stem cells. The terms "label" or "tag", as used herein, refer to a composition capable of producing a detectable signal indicative of the presence of a target, such as, the presence of a specific cell-surface marker in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods to isolate and enrich endothelial cell progenitor cells.

In some embodiments of the aspects described herein, a variety of methods to isolate a substantially pure or enriched population of cells, such as myeloid cells, are available to a skilled artisan, including immunoselection techniques, such as high-throughput cell sorting using flow cytometric methods, affinity methods with antibodies labeled to magnetic beads, biodegradable beads, non-biodegradable beads, and antibodies panned to surfaces including dishes, and any combination of such methods.

As defined herein, "positive selection" refers to techniques that result in the isolation or enrichment of cells expressing specific cell-surface markers, while "negative selection" refers techniques that result in the isolation or enrichment of cells not expressing specific cell-surface markers. In some embodiments, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select cells expressing one or more specific cell-surface markers.

As defined herein, "flow cytometry" refers to a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. Increasing the number of lasers and detectors allows for labeling by multiple antibodies, and can more precisely identify a target population by their phenotypic markers. Certain flow cytometric instruments can take digital images of individual cells, allowing for the analysis of fluorescent signal location within or on the surface of cells.

A common variation of flow cytometric techniques is to physically sort particles based on their properties, so as to purify populations of interest, using "fluorescence-activated cell sorting" As defined herein, "fluorescence-activated cell sorting" or "flow cytometric based sorting" methods refer to flow cytometric methods for sorting a heterogeneous mixture of cells from a single biological sample into one or more containers, one cell at a time, based upon the specific light scattering and fluorescent characteristics of each cell and provides fast, objective and quantitative recording of fluorescent signals from individual cells as well as physical separation of cells of particular interest. Accordingly, in some embodiments, fluorescence-activated cell sorting (FACS) can be used with the methods described herein to isolate and enrich for populations of cells, such as myeloid cells, from a sample of hematopoietic cells.

In some embodiments of the methods described herein, the methods further comprise monitoring clonality of TET2 somatic mutations in a subject. In other words, following the treatment, the size or percentage of the clone harboring a TET2 somatic mutation is determined to monitor the effectiveness of the treatment.

In some embodiments of the methods described herein, the methods further comprise decreasing the number or percentage of hematopoietic clones comprising the one or more TET2 mutation(s) in the subject by transfusing the subject with hematopoietic stem cells in which the mutations are absent or reduced, for example, by administering a bone marrow transplant.

In some such embodiments, the subject is transfused with autologous bone marrow. Alternatively, or additionally, in some embodiments, the subject is transfused with allogeneic bone marrow.

A bone marrow transplant is a procedure where healthy bone marrow stem cells, are infused into a subject to replace damaged or diseased bone marrow, or to replace damaged peripheral blood cells generated from bone marrow stem cells. Prior to the transplant, chemotherapy, radiation, or both can be given. In what is known as ablative (myeloablative) treatment, typically used for cancer treatments, high-dose chemotherapy, radiation, or both are given to kill peripheral cells, as well as all healthy bone marrow that remains, and allows new stem cells to grow in the bone marrow. Reduced intensity treatments, also called a mini transplant, can also be performed where lower doses of chemotherapy and radiation are received before a transplant. For the methods described herein, where the issues arise from somatic mutations in the periphery, total ablation of the bone marrow may not be required.

If an autologous stem cell transplant is used, apheresis can be used to collect blood stem cells. Briefly, blood is withdrawn from the subject's body and one or more blood components are removed, such as all leukocytes or all myeloid cells, and transfusion of the remaining cells are performed. Before apheresis, daily injections of growth factor can be administered to increase stem cell production and move stem cells into circulating blood so they can be collected. During apheresis, blood is drawn from a vein and circulated through a machine. The machine separates blood into different parts, including hematopoietic stem cells. These stem cells can be collected and frozen for future use in the bone marrow transplant.

In some embodiments of the methods described herein, the methods further comprise decreasing the number or percentage of hematopoietic cells or clones comprising the one or more TET2 mutations in the subject by performing therapeutic cytapheresis on the subject.

Therapeutic cytapheresis removes cellular components from blood, returning plasma. It is most often used to remove defective RBCs and substitute normal ones in patients with sickle cell anemia who have the following conditions: acute chest syndrome, stroke, pregnancy, or frequent, severe sickle cell crises. Other known uses of cytapheresis include collection of peripheral blood stem cells for autologous or allogeneic bone marrow reconstitution (an alternative to bone marrow transplantation) and collection of lymphocytes for use in immune modulation cancer therapy (adoptive immunotherapy).

In the methods described herein, a subject undergoing therapeutic cytapheresis can also be administered one or more agents to stimulate hematopoietic stem cell migration from the bone marrow to the blood, following removal of all cellular components from the blood using therapeutic cytapheresis.

In some embodiments, a subject undergoing therapeutic cytapheresis can further be transfused with autologous blood. Alternatively, or additionally, in some embodiments, the subject is further transfused with allogeneic blood.

In those embodiments where the subject is transfused with autologous blood, the blood can undergo processing steps prior to transfusion to remove and/or decrease the number of hematopoietic cells having the one or more TET2 mutations. Such processing steps can include flow cytometric or magnetic bead-based sorting and enrichment methods to remove hematopoietic cells having the one or more TET2 mutations In some embodiments of the methods described herein, the subject is administered or transfused with hematopoietic cells that have been modified to correct any somatic mutations in TET2, using any method known in the art to modify or incorporate target genes into the genome of a cell so as to facilitate the expression of such genes, also referred to herein as "gene targeting" or "gene therapy" methods.

One system for the integration or modification of target genes into the genome of a hematopoietic cell is the clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al. Nature Biotechnology 31:227 (2013) and can be used as an efficient means of site-specifically editing hematopoietic stem cell genomes in order to cleave DNA prior to the incorporation of a gene encoding a target gene, such as a TET2 gene lacking the somatic mutations described herein. The use of CRISPR/Cas to modulate gene expression has been described in, e.g., U.S. Pat. No. 8,697,359, the disclosure of which is incorporated herein by reference. Alternative methods for site-specifically cleaving genomic DNA prior to the incorporation of a gene of interest in a hematopoietic cell include the use of zinc finger nucleases (ZFNs) and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. The use of ZFNs and TALENs in genome editing applications is described, e.g., in Urnov et al. Nature Reviews Genetics 11:636 (2010); and in Joung et al. Nature Reviews Molecular Cell Biology 14:49 (2013), the disclosure of both of which are incorporated herein by reference.

Another method that can be used for incorporating polynucleotides encoding target genes into hematopoietic stem cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In certain cases, these excision sites may be terminal repeats or inverted terminal repeats. Once excised from the transposon, the gene of interest can be integrated into the genome of a mammalian cell by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene of interest to the DNA of the mammalian cell genome completes the incorporation process. In certain cases, the transposon may be a retrotransposon, such that the gene encoding the target gene is first transcribed to an RNA product and then reverse-transcribed to DNA before incorporation in the mammalian cell genome. Exemplary transposon systems include the piggybac transposon (described in detail in, e.g., WO 2010/085699) and the sleeping beauty transposon (described in detail in, e.g., US2005/0112764), the disclosures of each of which are incorporated herein by reference.

Additional genome editing techniques that can be used to incorporate polynucleotides encoding target genes into the genome of a hematopoietic cell include the use of ARCUS™ meganucleases that can be rationally designed so as to site-specifically cleave genomic DNA. The use of these enzymes for the incorporation of genes encoding target genes into the genome of a mammalian cell is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a target gene into the nuclear DNA of a hematopoietic stem cell. These single-chain nucleases have been described extensively in, e.g., U.S. Pat. No. 8,021,867 and U.S. Pat. No. 8,445,251, the disclosures of each of which are incorporated herein by reference.

Another example of a platform that can be used to facilitate the expression of a target gene in a hematopoietic cell is by the integration of the polynucleotide encoding a target gene into the nuclear genome of the cell. A variety of techniques have been developed for the introduction of exogenous genes into a eukaryotic genome. One such technique involves the insertion of a target gene into a vector, such as a viral vector. Vectors for use with the compositions and methods of the invention can be introduced into a cell by a variety of methods, including transformation, transfection, direct uptake, projectile bombardment, and by encapsulation of the vector in a liposome, and are well known in the art. Examples of suitable methods of transfecting or transforming cells include calcium phosphate precipitation, electroporation, microinjection, infection, lipofection and direct uptake. Such methods are described in more detail, for example, in Green, et al., *Molecular Cloning: A Laboratory Manual*, Fourth Edition, Cold Spring Harbor University Press, New York (2014); and Ausubel, et al, *Current Protocols in Molecular Biology*, John Wiley & Sons, New York (2015), the disclosures of each of which are incorporated herein by reference.

Examples of viral vectors useful in the methods described herein include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including herpes virus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996, the disclosure of which is incorporated herein by reference). Other examples of viral vectors include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described in, e.g., U.S. Pat. No. 5,801,030, the disclosure of which is incorporated herein by reference.

In some embodiments, the methods further comprise initiating a monitoring regimen following the administration of one or more treatments to the subject. For example, monitoring includes repeating the diagnostic steps of the method on the subject on a monthly, bi-monthly or quarterly basis to determine whether there is, for example, reduced IL-1β (interleukin-1β) proinflammatory activity or decreased percentages of hematopoietic cells in the blood having one or more TET2 mutations described herein.

In some embodiments of the methods described herein, the theranostic methods comprise further administering one or more additional therapeutic agents to the subject, in addition to the inhibitor of TET2 mutation-mediated IL-1β (interleukin-1) proinflammatory activity. Such an additional therapeutic agent can be co-administered with the inhibitor of TET2 mutation-mediated IL-1β (interleukin-1β) proinflammatory activity. As used herein, the phrase "co-administering" or to "co-administer" means the administration of an inhibitor described herein and another compound, e.g., a therapeutic agent, separately, simultaneously, and/or sequentially over a period of time as determined by a qualified care giver.

Non-limiting examples of additional therapeutic agents that can be administered to a subject having one or more TET2 somatic mutations include quinidine, procainamide, disopyramide, lidocaine, phenytoin, mexiletine, flecainide, propafenone, moricizine, propranolol, esmolol, timolol, metoprolol, atenolol, bisoprolol, amiodarone, sotalol, ibutilide, dofetilide, dronedarone, E-4031, verapamil, diltiazem, adenosine, digoxin, magnesium sulfate, warfarin, heparins, anti-platelet drugs (e.g., aspirin and clopidogrel), beta blockers (e.g., metoprolol and carvedilol), angiotensin-converting enzyme (ACE) inhibitors (e.g., captopril, zofenopril, enalapril, ramipril, quinapril, perindopril, lisinopril, benazepril, fosinopril, casokinins and lactokinins), statins (e.g., atorvastatin, cerivastatin, fluvastatin, lovastatin, pitavastatin, mevastatin, pravastatin, rosuvastatin, and simvastatin), aldosterone antagonist agents (e.g., eplerenone and spironolactone), digitalis, diuretics, digoxin, inotropes (e.g., Milrinone), vasodilators and omega-3 fatty acids and combinations thereof.

In some aspects and embodiments of the methods directed to treatment of chronic kidney diseases, the additional therapeutic agent is an angiotensin-converting enzyme (ACE) inhibitor, an angiotensin II receptor blocker (ARB), or a mineralocorticoid receptor (MR) antagonist.

ACE inhibitors for use with the compositions and methods described herein include, but are not limited to, benazepril (marketed in the U.S. as LOTENSIN™), captopril (marketed in the U.S. as CAPOTEN™), enalapril/enalaprilat (marketed in the U.S. as VASOTEC™ oral and injectable), fosinopril (marketed in the U.S. as MONOPRIL™), lisinopril (marketed in the U.S. as ZESTRIL™ and PRINIVIL™), moexipril (marketed in the U.S. as UNIVASC™), perindopril (marketed in the U.S. as ACEON™), quinapril (marketed in the U.S. as ACCUPRIL™), ramipril (marketed in the U.S. as ALTACE™), and trandolapril (marketed in the U.S. as MAVIK™). ARBs for use with the inhibitors described herein include candesartan (marketed in the U.S. as ATACAND™), irbesartan (marketed in the U.S. as AVAPRO™), olmesartan (marketed in the U.S. as BENICAR™), losartan (marketed in the U.S. as COZAAR™), valsartan (marketed in the U.S. as DIOVAN™), telmisartan (marketed in the U.S. as MICARDIS™), and eprosartan (marketed in the U.S. as TEVETEN™).

In some embodiments of these methods and all such methods described herein, the method further comprises administering to the subject an effective amount of a diuretic. Diuretics include, but are not limited to, torsemide (marketed in the U.S. as DEMADEX™), furosemide (marketed in the U.S. as LASIX™), bumetanide (marketed in the U.S. as BUMEX™), ethacrynic acid (marketed in the U.S. as EDECRIN™), torsemide (marketed in the U.S. as DEMADEX™), amiloride, (marketed in the U.S. as MIDAMOR™), acetazolamide (marketed in the U.S. as DIAMOX™), pamabrom (marketed in the U.S. as AQUABAN™), mannitol (marketed in the U.S. as ARIDOL™ or OSMITROL™), traimterene (marketed in the U.S. as DYRENIUM™), spironolactone (marketed in the U.S. as ALDACTONE), amiloride (marketed in the U.S. as MIDAMOR™), indapamide (marketed in the U.S. as LOZOL™), hydrochlorothiazide (marketed in the U.S. as HYDRODIURIL™), metolazone (marketed in the U.S. as ZAROXOLYN™ or MYKROX™), methylclothiazide (marketed in the U.S. as AQUATENSEN™ or ENDURON™), hydrocholorthiazide (marketed in the U.S. as AQUAZIDE H™ or ESIDRIX™ or MICROZIDE™), chlorothiazide (marketed in the U.S. as DIURIL™), bendroflumethiazide (marketed in the U.S. as NATURETIN™), polythiazide (marketed in the U.S. as RENESE™), hydroflumethiazide (marketed in the U.S. as SALURON™), and chlorthalidone (marketed in the U.S. as THALITONE™). For a complete listing also see, e.g., Physician's Desk Reference, 2017 Edition, PDR Network (2016).

As used herein, the terms "treat" or "treatment" or "treating" as used herein in reference to use of inhibitors of TET2 mutation-mediated IL-1β proinflammatory activity for the treatment of a cardiovascular disease or disorder refers to therapeutic treatment, wherein the object is to prevent or slow the development of the disease, such as slow down the development of a cardiac disorder, or reducing at least one adverse effect or symptom of a cardiovascular condition, disease or disorder, i.e., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In some embodiments, the term "treating" when used in reference to a treatment of a cardiovascular disease or disorder is used to refer to the reduction of a symptom and/or a biochemical marker of a cardiovascular disease or disorder, for example a reduction in at least one biochemical marker of a cardiovascular disease by at least about 10% would be considered an effective treatment. Examples of such biochemical markers of cardiovascular disease include a reduction of, for example, creatine phosphokinase (CPK), aspartate aminotransferase (AST), lactate dehydrogenase (LDH) in the blood, and/or a decrease in a symptom of cardiovascular disease, such as atherosclerosis, and/or an improvement in blood flow and cardiac function as determined by someone of ordinary skill in the art as measured by electrocardiogram (ECG or EKG), or echocardiogram (heart ultrasound), Doppler ultrasound and nuclear medicine imaging. A reduction in a symptom of a cardiovascular disease by at least about 10% would also be considered effective treatment by the methods as disclosed herein. As alternative examples, a reduction in a symptom of cardiovascular disease, for example a reduction of at least one of the following; dyspnea, chest pain, palpitations, dizziness, syncope, edema, cyanosis etc. by at least about 10% or a cessation of such systems, or a reduction in the size one such symptom of a cardiovascular disease by at least about 10% would also be considered as affective treatments by the methods as disclosed herein. In some embodiments, it is preferred, but not required that the therapeutic agent actually eliminate the cardiovascular disease or disorder, rather just reduce a symptom to a manageable extent.

The term "effective amount" as used herein refers to the amount of therapeutic agent of pharmaceutical composition to alleviate at least one or more symptom of the disease or disorder, and relates to a sufficient amount of pharmacological composition to provide the desired effect. With reference to the treatment of, for example, a cardiovascular condition or disease in a subject, the term "effective amount" refers to the amount that is safe and sufficient to prevent or delay the development or a cardiovascular disease or disorder. The amount can thus cure or cause the cardiovascular disease or disorder to go into remission, slow the course of cardiovascular disease progression, slow or inhibit a symptom of a cardiovascular disease or disorder, slow or inhibit the establishment of secondary symptoms of a cardiovascular disease or disorder or inhibit the development of a secondary symptom of a cardiovascular disease or disorder. The effective amount for the treatment of the cardiovascular disease or disorder depends on the type of cardiovascular disease to be treated, the severity of the symptoms, the subject being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of a cardiovascular disease or disorder as discussed herein, and any treatment or administration of the compositions or formulations that leads to a decrease of at least one symptom of the cardiovascular disease or disorder as disclosed herein, for example, decreased levels of atherosclerosis in the blood vessels, increased heart ejection fraction, decreased rate of heart failure, decreased infarct size, decreased associated morbidity (pulmonary edema, renal failure, arrhythmias) improved exercise tolerance or other quality of life measures, and decreased mortality indicates effective treatment.

By "reduce" or "inhibit" in terms of the methods of treatment of chronic kidney disease and proteinuria described herein is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter or symptom of a chronic kidney disease. Reduce or inhibit can refer to, for example, symptoms of the disorder being treated, for example, high blood pressure, protein in the urine, etc.

High blood pressure is almost always present during all stages of chronic kidney disease. A nervous system exam may show signs of nerve damage. The health care provider may hear abnormal heart or lung sounds when listening with a stethoscope. The early symptoms of chronic kidney disease are also symptoms of other illnesses. These symptoms can be the only signs of kidney disease until the condition is more advanced. Symptoms of chronic kidney disease can include: appetite loss; general ill feeling and fatigue; headaches; itching (pruritus) and dry skin; nausea; weight loss without trying to lose weight; etc. Other symptoms that can develop, especially when kidney function has gotten worse, include: abnormally dark or light skin; bone pain; brain and nervous system symptoms; drowsiness and confusion; problems concentrating or thinking; numbness in the hands, feet, or other areas; muscle twitching or cramps; breath odor; easy bruising, bleeding, or blood in the stool; excessive thirst; frequent hiccups; low level of sexual interest and impotence; stopping of menstrual periods (amenorrhea); shortness of breath; sleep problems, such as insomnia, restless leg syndrome, and obstructive sleep apnea; swelling of the feet and hands (edema); vomiting, typically in the morning.

Accordingly, in some embodiments of the methods described herein, an effective amount of a composition comprising an inhibitor of TET2 mutation-mediated IL-1β (interleukin-1β) proinflammatory activity described herein is administered to a subject in order to alleviate one or more symptoms of chronic kidney disease. As used herein, "alleviating a symptom chronic kidney disease" is ameliorating any condition or symptom associated with the chronic kidney disease. Alternatively, alleviating a symptom of a chronic kidney disease can involve reducing one or more symptoms of the chronic kidney disease in the subject relative to an untreated control suffering from chronic kidney disease or relative to the subject prior to the treatment. As compared with an equivalent untreated control, or the subject prior to the treatment with the inhibitor, such reduction or degree of prevention is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more, as measured by any standard technique. Desirably, the chronic kidney disease is significantly reduced or undetectable, as detected by any standard method known in the art, in which case the chronic kidney disease is considered to have been treated. A patient who is being treated for a chronic kidney disease is one who a medical practitioner has diagnosed as having such a condition. Diagnosis can be by any suitable means known to one of ordinary skill in the art. Diagnosis and monitoring can involve, for example, detecting the level of specific proteins or molecules in a urine, blood, or serum sample, such as, for example, albumin, calcium, cholesterol, complete blood count (CBC), electrolytes, magnesium, phosphorous, potassium, sodium, or any combination thereof, assays to detect, for example, creatinine clearance;

creatinine levels; BUN (blood urea nitrogen); through the use of specific techniques or procedures, such as an abdominal CT scan, abdominal MRI, abdominal ultrasound, kidney biopsy, kidney scan, kidney ultrasound; via detection of changes in results of assays or tests for erythropoietin, PTH; bone density test, or Vitamin D; or any combination of such detection methods and assays.

The compositions and methods described herein ideally result in a therapeutic significant reduction in one or more symptoms. A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, that the total daily usage of the compositions and formulations as disclosed herein will be decided by the attending physician within the scope of sound medical judgment. The exact amount required will vary depending on factors such as the type of disease being treated.

The inhibitors of TET2 mutation-mediated IL-1β proinflammatory activity described herein can be administered using any means or route known to those of ordinary skill in the art and known to provide desired effects. As used herein, the terms "administering," and "introducing" are used interchangeably herein and refer to the placement of the therapeutic agents as disclosed herein into a subject by a method or route which results in delivering of such agent(s) at a desired site. The compounds can be administered by any appropriate route which results in an effective treatment in the subject, including topical administration.

Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1

Recent human studies have shown that aging is paralleled by an increased frequency of somatic mutations in the hematopoietic system that allow the expansion of mutant hematopoietic cells (clonal hematopoiesis), and are associated with increased risk of atherosclerotic cardiovascular disease (ACVD). However, whether there is a direct causal connection between these mutations and CVD remains unknown. Mutations in the epigenetic modifier TET2 are frequent in the hematopoietic system of elderly individuals and have been associated with clonal hematopoiesis.

While CVD is the leading cause of death in the elderly, almost 60% of elderly patients with atherosclerotic CVD have either no or just one conventional CV risk factors (e.g. hypertension, hypercholesterolemia, etc.) (1). Furthermore, increasing evidence suggests that most middle-aged individuals at low CV risk, based on traditional risk factors, exhibit significant subclinical atherosclerosis (2, 3). These clinical data indicate the possibility of previously unidentified age-dependent factors that contribute to the development of CVD. The accumulation of somatic DNA mutations is a hallmark of aging, particularly in proliferating tissues, which over time can become a mosaic of cells with different genotypes due to the clonal expansion of single, de novo mutations (4). However, while human studies indicate that somatic mutations may be associated with a broad spectrum of human disease (5-7), there is very little information on the potential causal role of somatic mutations in age-associated disorders other than cancer.

Recent human studies have shown that normal aging is associated with an increased frequency of somatic mutations in the hematopoietic system, which provide a competitive growth advantage to the mutant cell and therefore allow its progressive clonal expansion (clonal hematopoiesis) (7-11). This acquired clonal mosaicism in the hematopoietic system of healthy individuals predicts an increased risk of subsequent hematologic cancer (7-9), but it has also recently been associated with higher prevalence of vascular complications of diabetes, greater incidence of atherosclerotic conditions (i.e. coronary heart disease, stroke) and increased frequency of CVD-related deaths (6, 7). While these human studies suggest a connection between somatic mutations in hematopoietic cells, clonal hematopoiesis and atherosclerosis, their descriptive nature does not allow cause-effect relationships, or even directionality, to be established. These associations could simply reflect shared consequences of the aging process or be secondary to confounding factors, especially given that they were uncovered in elderly populations with high proportions of diabetic individuals (6, 7).

Most of the reported somatic mutations associated with age-related clonal hematopoiesis occur in a small number of genes encoding epigenetic regulators (7-10). The present study focuses on one of these genes, TET2, the first gene reported to exhibit somatic mutations in blood cells in individuals with clonal hematopoiesis without hematological malignancies (10). More than 70 different mutations have been reported in the TET2 gene in blood cells (7-10), which are likely to result in loss of gene function given that most are small insertions/deletions or non-sense mutations. This gene encodes a multifaceted epigenetic regulator of gene transcription that modulates hematopoietic stem and progenitor cell (HSPC) self-renewal (12-15), but whose role in CVD remains largely unexplored. To mimic the human scenario of clonal hematopoiesis and test the hypothesis that clonal expansion of Tet2-deficient hematopoietic cells contributes to atherosclerosis, a competitive bone marrow transplantation (BMT) strategy was used to generate atherosclerosis-prone Ldlr−/− chimeric mice with a small proportion of Tet2-deficient hematopoietic stem and progenitor cells (HSPCs). Lethally irradiated Ldlr−/− recipients were transplanted with suspensions of BM cells containing 10% Tet2−/− cells and 90% Tet2+/+ cells (10% KO-BMT mice), and then fed a high fat diet (HFD) for 9 weeks to induce atherosclerosis development (FIGS. 5A-5B). To distinguish donor Tet2−/− and Tet2+/+ cells in this experimental setting, Tet2+/+ cells were obtained from mice carrying the CD45.1 variant of the CD45 hematopoietic antigen, whereas Tet2−/− cells were obtained from mice carrying the CD45.2 variant of this protein. Control mice (10% WT-BMT) were transplanted with 10% CD45.2+ Tet2+/+ cells and 90% CD45.1+ Tet2+/+ cells.

Flow cytometry analysis of CD45.2+ cells in the blood of transplanted mice established that this BMT strategy led to clonal expansion of Tet2−/− hematopoietic cells. Immediately prior to the start of HFD feeding (4 weeks after BMT), CD45.2+ cells already represented approximately 28% of blood cells in 10% KO-BMT mice, compared with the expected ~10% in WT controls (FIGS. 1A, 1B). CD45.2+ cells in 10% KO-BMT expanded further over time, reaching 42% of blood cells after 2 weeks of HFD (6 weeks after BMT) and 56% after 8 weeks of HFD (12 weeks after BMT), whereas the frequency of CD45.2+ cells remained constant in WT controls. This clonal expansion of Tet2-deficient HSPCs is similar to that observed when human cells carrying somatic TET2 mutations are transplanted into immune-deficient mice (16), showing that Tet2−/− murine cells and human TET2 mutant cells exhibit similar properties. The efficient ablation of Tet2 in CD45.2+ cells of 10% KO-BMT mice was confirmed by qRT-PCR analysis of magnetically-sorted white blood cell (WBC) fractions (FIG. 1C), which exhibited a ~92% purity of CD45.2+ cells (FIG. 6A). No changes were observed in the expression of Tet1 or Tet3, two related epigenetic modulators. Although the absolute number of HSPCs, defined as Lineage−, Sca1+, c-Kit+ (LSK) cells was comparable in the BM and spleen of 10% KO-BMT mice and WT controls (FIG. 6B), CD45.2+ cells represented 69% of LSK cells in the BM (FIG. 6C) and 61% in the spleen (FIG. 6D) of 10% KO-BMT mice at 13 weeks post-BMT. These data further support the idea that Tet2-deficient HSPCs exhibit a competitive growth advantage over WT counterparts, which allows their clonal expansion, consistent with previous studies reporting that Tet2 inactivation enhances HSPC self-renewal (12-15). The transplanted Tet2−/− BM cells expanded into all blood cell lineages, although with marked differences, with the highest CD45.2+ frequency in the myeloid lineage and the lowest in the T-lymphoid lineage in BM (FIG. 1D), spleen (FIG. 1E) and blood (FIGS. 1F, 1G) of 10% KO-BMT mice, in agreement with previous studies with Tet2-deficient mice (12-15) and TET2-mutant human cells (16). This expansion of Tet2−/− HSPCs, did not affect total blood cell counts as the numbers of T cells, B cells, neutrophils and monocytes were comparable in 10% KO-BMT mice and WT controls (FIG. 6E), consistent with human studies showing that cancer-free individuals carrying TET2 mutations do not exhibit significant changes in the absolute numbers of WBC subsets (7, 10).

Figure 2E:
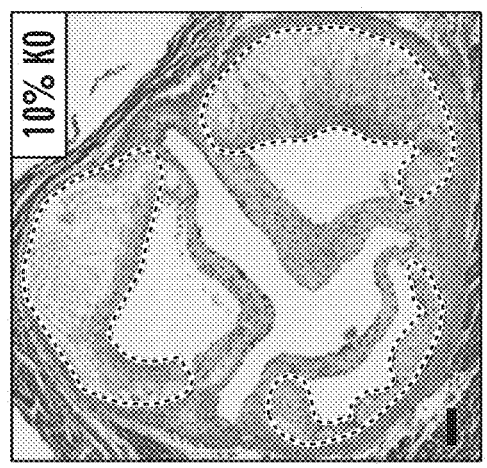
Figure 2E:
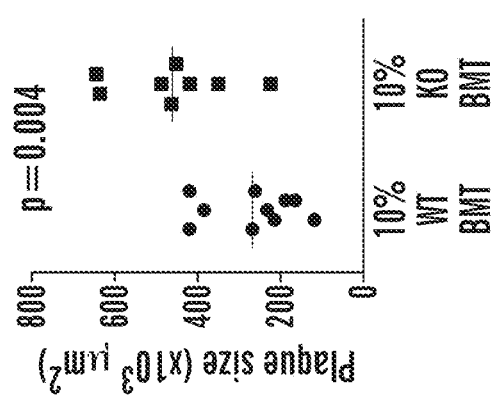
Figure 2E:
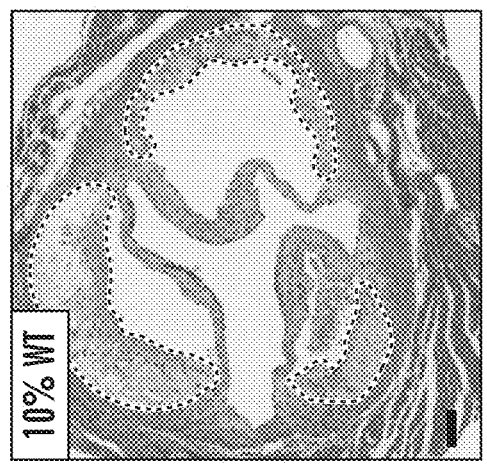
Figure 2F:
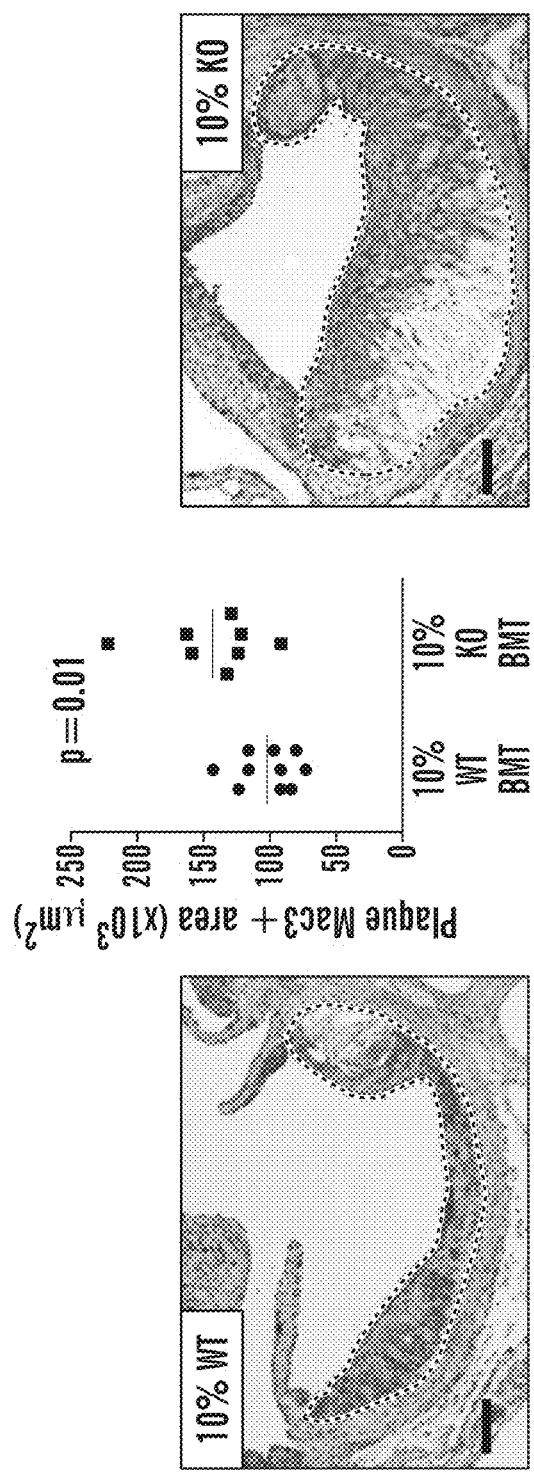

Having demonstrated that the BMT strategy led to the clonal expansion of Tet2-deficient HSPCs cells and therefore mimics the human scenario of clonal hematopoiesis associated with TET2 mutations, it was next evaluated whether this affects the development of atherosclerosis and related metabolic abnormalities. No significant differences between genotypes were observed in body weight (FIG. 2A), blood glucose levels (FIG. 2B) or systemic insulin sensitivity (FIG. 2C) after nine weeks of HFD-feeding. As expected, HFD-fed Ldlr−/− mice developed marked hypercholesterolemia, which was comparable in 10% WT-BMT mice and 10% KO-BMT mice (FIG. 2D). While BM genotype did not affect these metabolic parameters, it had a profound effect in atherosclerotic plaque size as 10% KO-BMT mice exhibited 73% larger plaques in the aortic root than WT controls (FIG. 2E). This was paralleled by an increase in macrophage numbers in the intima of the aortic wall in 10% KO-BMT mice (FIG. 2F), whereas no significant differences between genotypes were observed in lesional content of collagen or vascular smooth muscle cells (FIG. 8). No differences were observed either in plaque cell apoptosis measured by TUNEL (FIG. 9A). Similarly, proliferation rates of total plaque cells or lesional macrophages were comparable in 10% KO-BMT mice and WT controls, as evidenced by immunofluorescent co-staining of the macrophage marker CD68 and the proliferation antigen Ki-67 (FIG. 9B).

Figures 1F, 1G:
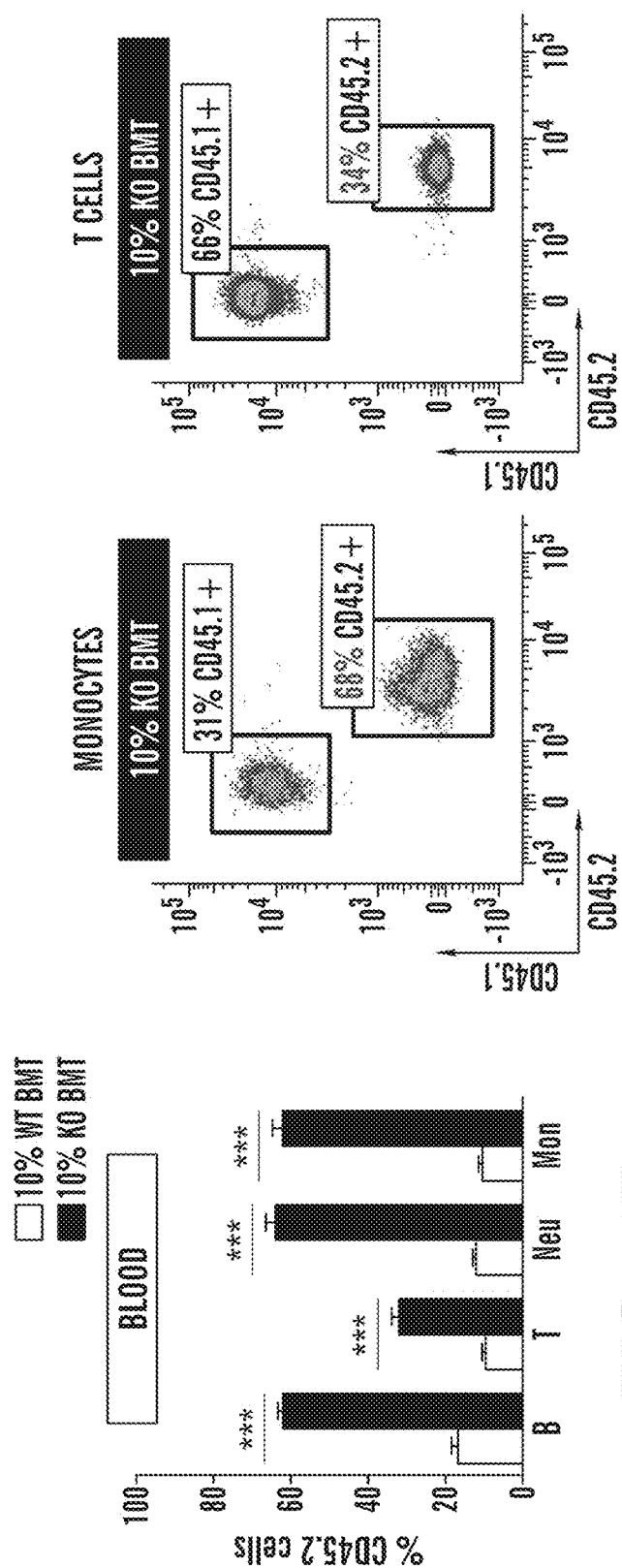

The above-described expansion of Tet2-deficient hematopoietic cells observed in BM, spleen and blood was reflected in the immune cell composition of the atherosclerotic vascular wall, as revealed by flow cytometry analysis of aortic arch samples from HFD-fed mice. CD45.2+ cells represented 59% of total immune cells, 63% of macrophages and 35% of T-cells present in the aortic wall of 10% KO-BMT (FIGS. 1G, 1H, and 7). The low number of neutrophils or B cells in the aortic arch at this early stage of atherosclerosis precluded their inclusion in this analysis. Overall, these data demonstrate that clonal expansion of Tet2-deficient hematopoietic cells accelerates atherosclerosis development in a manner independent of alterations in systemic metabolism or macrophage proliferation or apoptosis in the plaque.

Figure 10A:
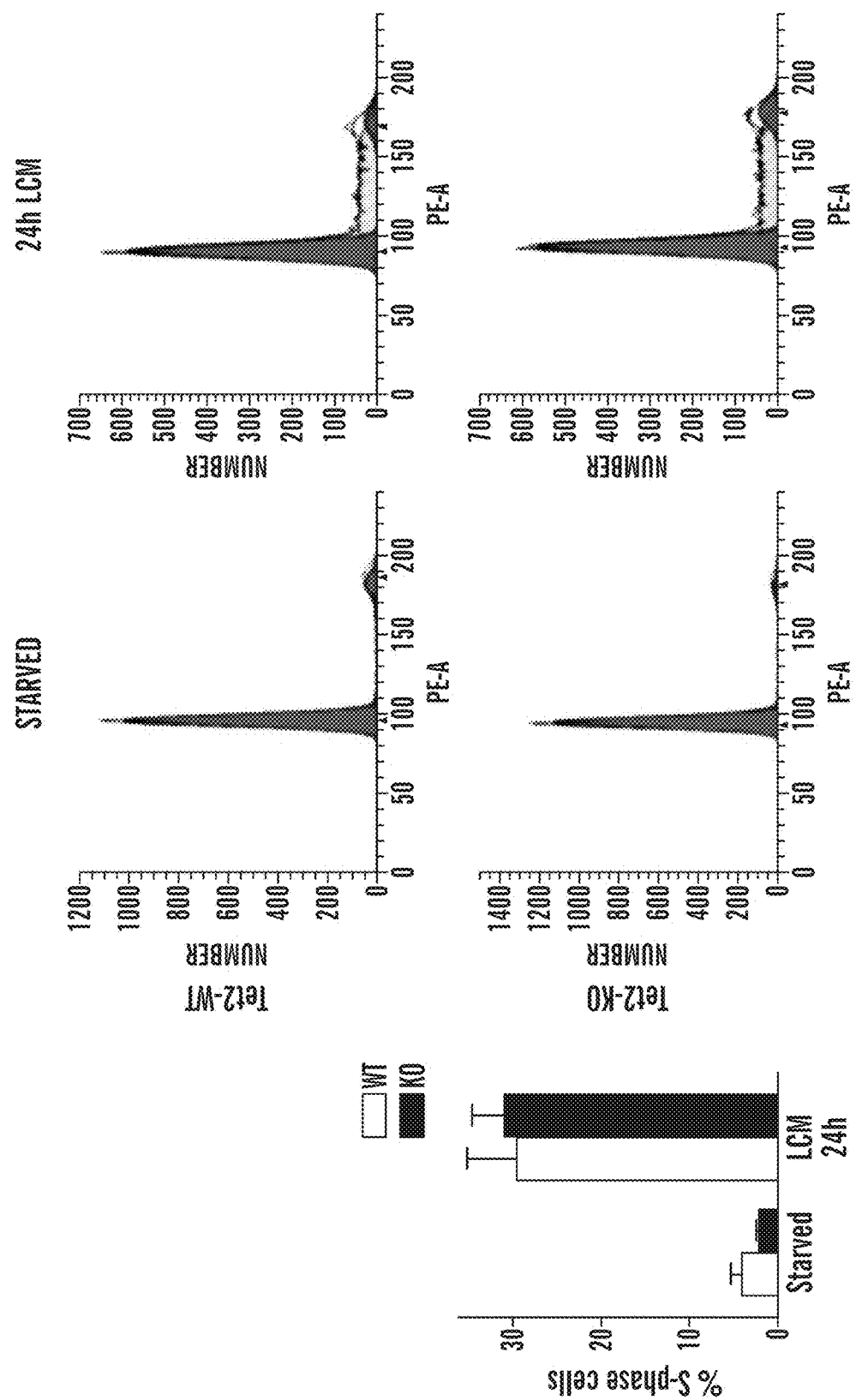
Figure 10B:
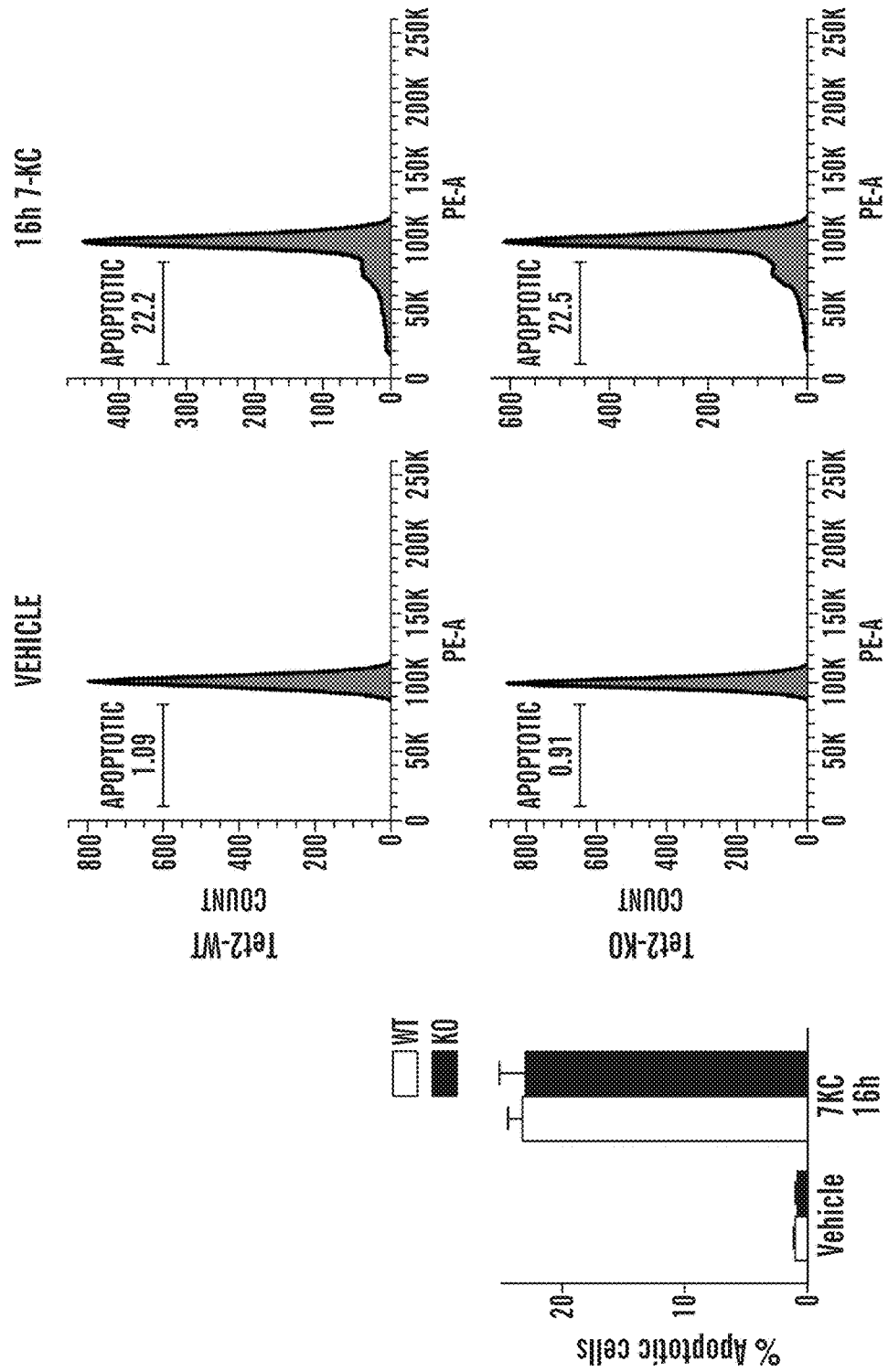

As described above, Tet2-deficient HSPCs expand preferentially into the myeloid lineage, mainly the macrophage population within the atherosclerotic plaque. Based on this observation, it was hypothesized that the expansion of Tet2-deficient hematopoietic cells accelerates atherosclerosis mainly by generating a pool of macrophages with enhanced pro-atherogenic activities. To test this possibility, it was evaluated whether Tet2 deficiency affects macrophage functions relevant to atherosclerosis development. Consistent with the in vivo data, Tet2 deficiency did not have a significant effect in MCSF-induced proliferation (FIG. 10A) or oxysterol-induced apoptosis (FIG. 10B) of cultured macrophages. Similarly, it did not affect oxidized LDL (oxLDL) uptake (FIG. 10C) or the expression of scavenger receptors SR-A and CD36 (FIG. 10D). To evaluate whether Tet2 deficiency affects pro-inflammatory macrophage activation, Affymetrix microarray was performed on Tet2-deficient macrophages treated with a combination of lipopolysaccharide (LPS, 10 ng/ml) and IFNγ (2 ng/ml). A widespread alteration in gene expression was found in Tet2−/− macrophages where 475 genes were significantly altered by a fold change greater than 1.5-fold compared to WT macrophages (q<0.05, FIG. 3A).

Figure 3A:
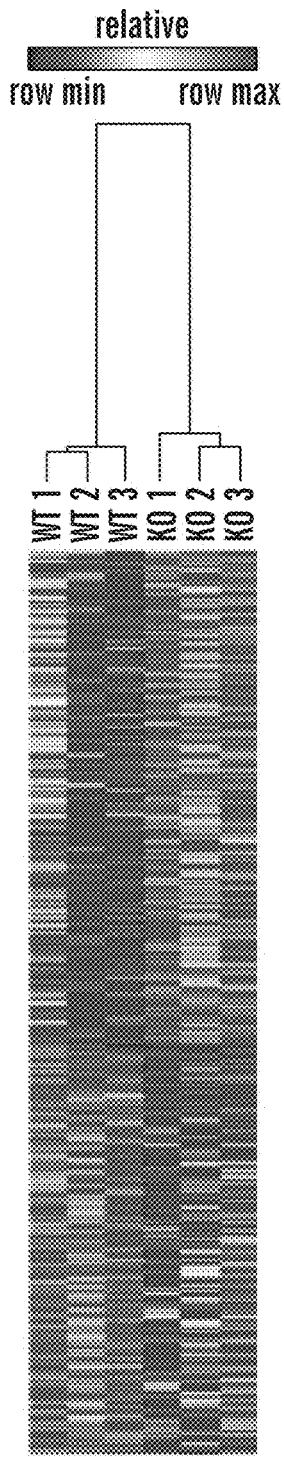
Figure 3B:
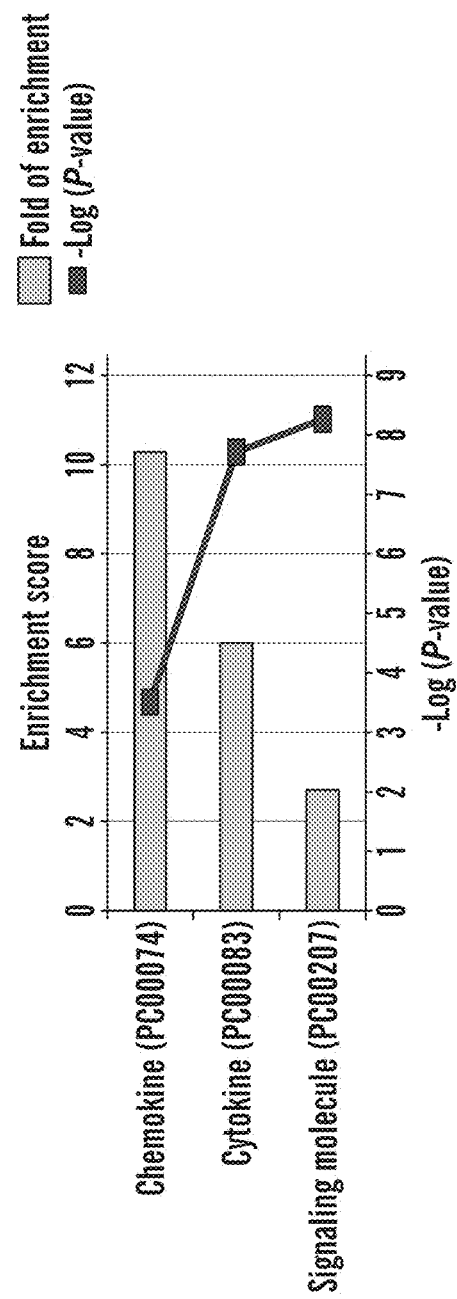
Figure 3C:
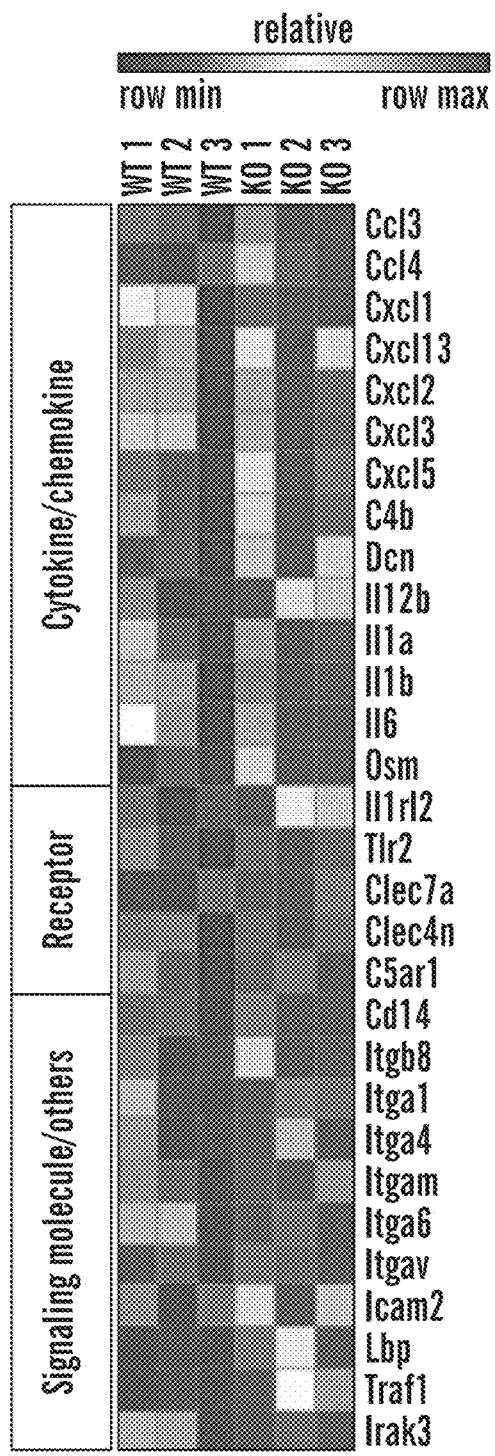
Figure 3D:
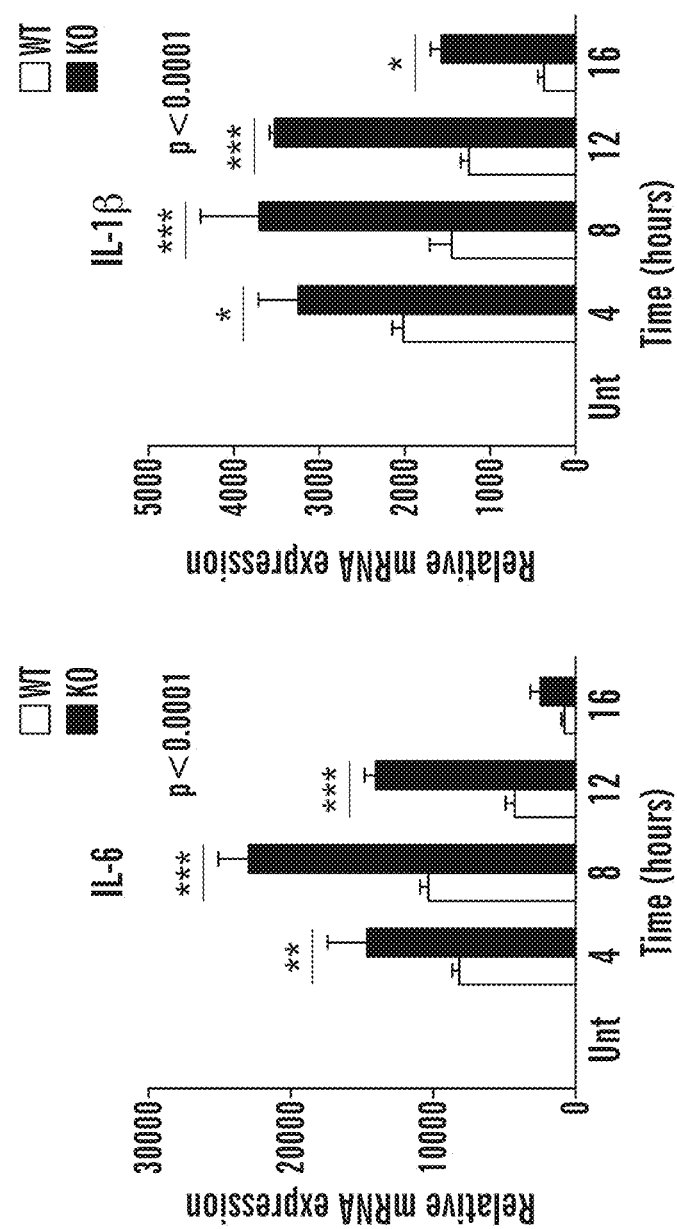
Figure 3E:
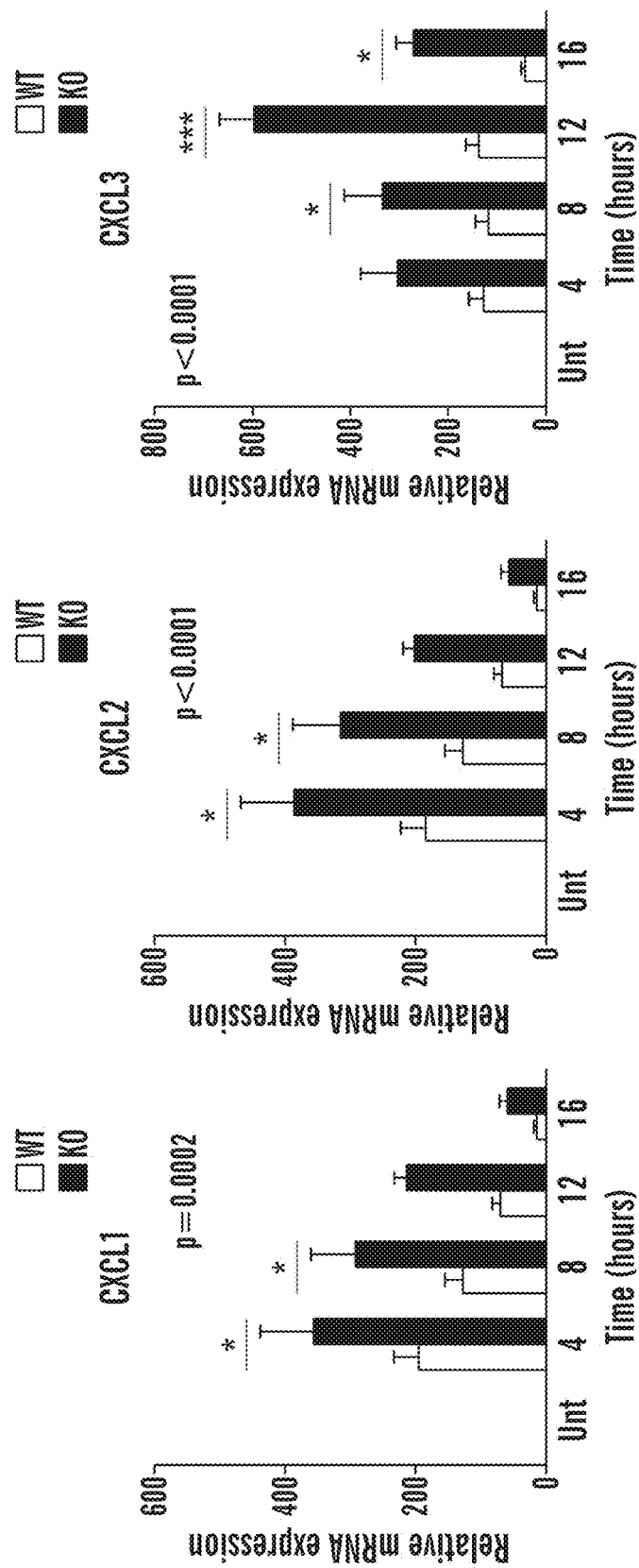
Figures 3F, 3G:
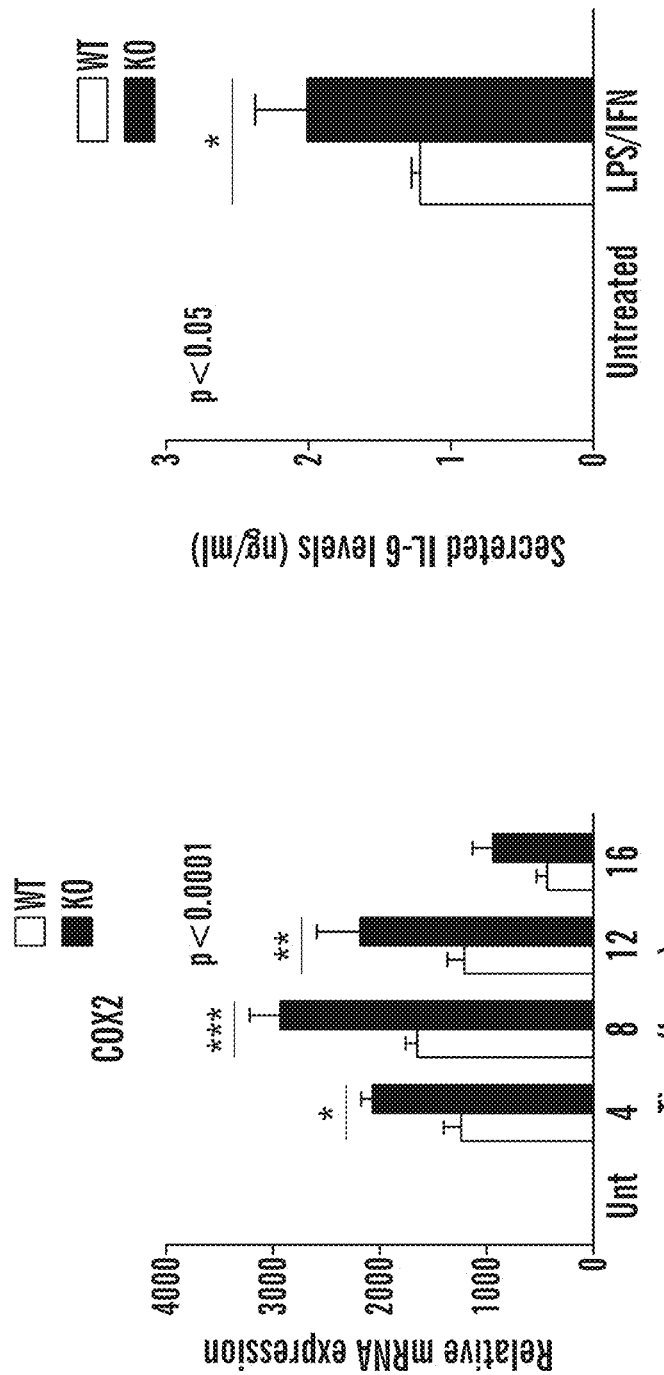

PANTHER functional annotation software revealed that transcripts encoding for cytokine, chemokine and signaling molecules were the top three over-represented protein classes altered in the transcriptome of Tet2-deficient macrophages (FIG. 3B). Genes in these protein classes encoding for proteins with known pro-inflammatory actions were mostly upregulated in Tet2-deficient macrophages (FIG. 3C), indicating that Tet2 inhibits pro-inflammatory activation of macrophages. Consistent with this observation, qRT-PCR analysis confirmed that Tet2-deficient macrophages exhibit markedly increased expression of pro-inflammatory cytokines, such as IL-6, IL-1β, IL-1α, or TNF (FIG. 3D, FIG. 11A.); chemokines, such as CXCL1,2,3, CCL3 or CCL5 (FIG. 3E, FIG. 11B); and enzymes, such as COX-2 (FIG. 3F). The increased expression of most of these pro-inflammatory genes was apparent at early time-points of stimulation and sustained over time. This pattern of gene expression was also evident in Tet2−/− macrophages stimulated with higher doses of LPS (100 ng/ml) and IFNγ (20 ng/ml, FIG. 11C). Consistent with its effects at the level of transcription, Tet2 deficiency resulted in increased secretion of IL-6 protein (FIG. 3G). These data indicate that Tet2 acts as a negative transcriptional regulator of pro-inflammatory responses, and are consistent with a previous study reporting that Tet2 represses IL-6 expression at late phase of LPS stimulation (17). The results described herein reveal that Tet2 has broader effects on pro-inflammatory cytokine/chemokine expression than previously reported, particularly when macrophages are co-stimulated with TH1 cytokines such as IFNγ.

However, the situation in vivo in the atherosclerotic plaque is particularly complex, as lesional macrophages are exposed to multiple signals simultaneously. Therefore, the anti-inflammatory actions of Tet2 in cultured macrophages were further evaluated by testing their effect on macrophage response to a cocktail of low doses of oxLDL (25 μg/ml), TNF (5 ng/ml) and IFNγ (2 ng/ml), three pro-inflammatory stimuli present in atherosclerotic plaques. Under these conditions, Tet2 ablation resulted in generally increased pro-inflammatory cytokine/chemokine expression in this context, although to a lesser extent than after LPS/IFNγ stimulation (FIGS. 12A-12B), with the exception of IL-1β, which was markedly upregulated in Tet2-deficient macrophages at all time-points of oxLDL/TNF/IFNγ stimulation (FIG. 4A). These data indicate a predominant role for IL-1β in the exacerbated atherosclerosis associated with Tet2-deficient HSPC expansion. Supporting this notion, gene expression analysis in the aortic arch of mice fed a HFD for 9 weeks revealed a significant >2-fold increase in transcript levels of IL-1β in 10% KO-BMT compared to control BMT mice (FIG. 4B). In contrast, no significant differences between genotypes were observed in the aortic expression of other cytokines/chemokines or other macrophage-enriched genes at this early time point, with the exception of the chemokine CXCL3, which was also significantly upregulated in the aortic arch of 10% KO-BMT mice (FIGS. 13A, 13B). Under the conditions of these assays atherosclerotic plaques in the aortic arch are small and in a nascent stage (18), indicating that the increased IL-1β expression is an early event driving the accelerated atherosclerosis development associated with Tet2-deficient HSPC expansion. Because endothelial cell activation is a key mechanism contributing to early atherogenesis, it was evaluated whether the increased IL-1β expression in 10% KO-BMT mice was paralleled by changes in the aortic expression of endothelial adhesion molecules. The expression of P-selectin, an adhesion molecule essential for monocyte/neutrophil recruitment to the arterial wall in early atherogenesis (19, 20), was significantly increased in 10% KO-BMT, and trends of increased expression were observed for other adhesion molecules, such as E-selectin and ICAM1 (FIG. 13A). There was a significant correlation between IL-1β and P-selectin expression in the aortic arch samples (FIG. 13B), further indicating the contribution of IL-1β to the aortic expression of P-selectin. Overall, these results support a central role for IL-1β in the increased atherosclerosis associated with clonal expansion of Tet2-deficient hematopoietic cells, which, without wishing to be limited or constrained by theory, may be mediated by exacerbated endothelial cell activation in the arterial wall.

Although many details of its role in regulating chromatin architecture remain unknown, Tet2 has emerged as a multifaceted epigenetic regulator that is able to facilitate both transcription activation and repression depending on the molecular and cellular context. Given that Tet2 loss-of-function is associated with increased IL-1β gene expression, experiments were focused on potential mechanisms of Tet2-mediated transcriptional repression in macrophages. Consistent with previous studies showing that Tet2 can inhibit gene transcription via Hdac1/2-mediated histone deacetylation (17), treatment with the Hdac inhibitor Trichostatin A (TSA) resulted in increased IL-1β expression in LPS/IFNγ-treated macrophages and abolished expression differences between Tet2-deficient and WT genotypes (FIG. 14A). Further supporting a role for Hdac-induced histone deacetylation in Tet2-mediated repression of IL-1β, CHIP-qPCR analysis revealed greater histone H3 acetylation at the IL-1β promoter in Tet2-deficient macrophages (FIG. 14B). In contrast, HDAC inhibition with TSA reduced transcript expression of other pro-inflammatory cytokines, such as IL-6 or TNF, in agreement with previous reports (21), and did not affect differences between genotypes (FIG. 14C). Consistent with these findings, H3 acetylation at the IL-6 promoter was comparable in Tet2-deficient and WT macrophages (FIG. 14D). Overall, these data indicate that reduced Hdac-mediated histone deacetylation can account for the effects of Tet2 loss-of-function on IL-1β expression in macrophages, while alternative mechanisms contribute to its effects on the expression of other genes.

Figure 4D:
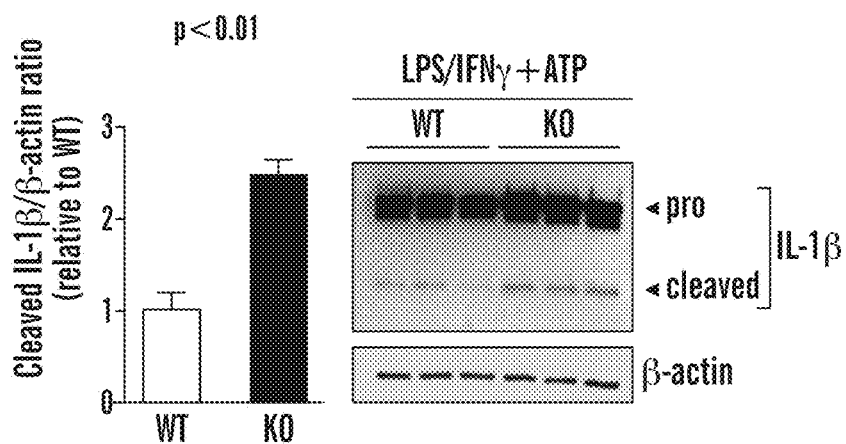
Figure 4E:
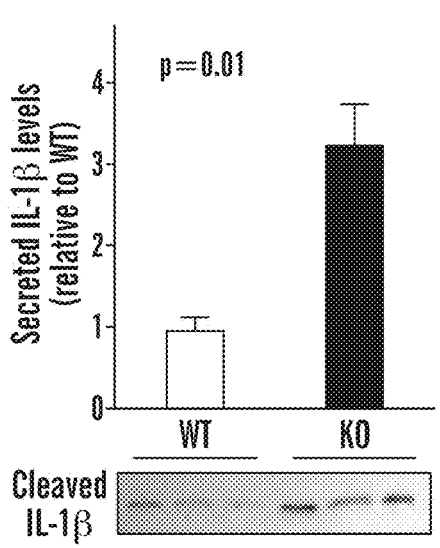
Figure 4F:
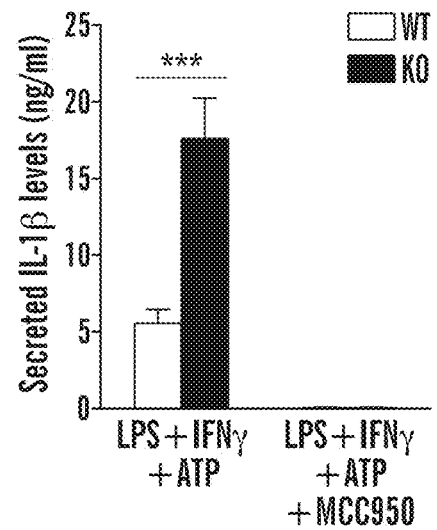
Figure 4G:
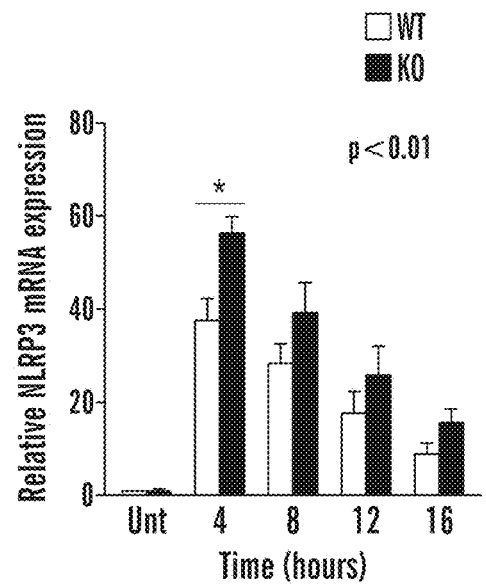
Figure 4H:
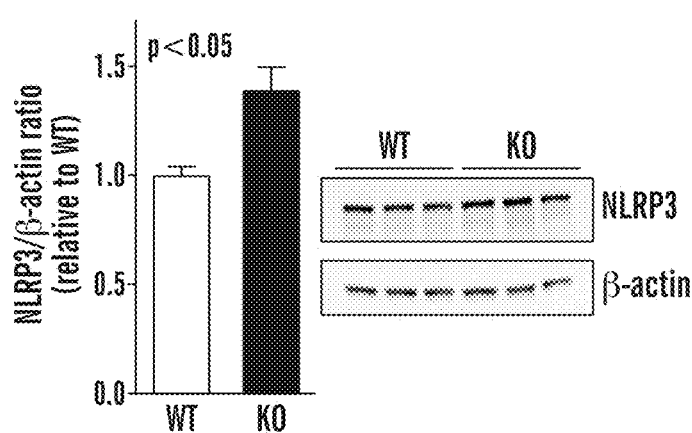
Figure 4I:
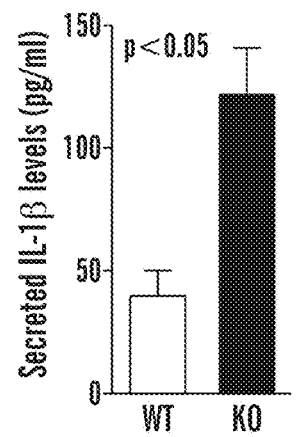
Figure 4J:
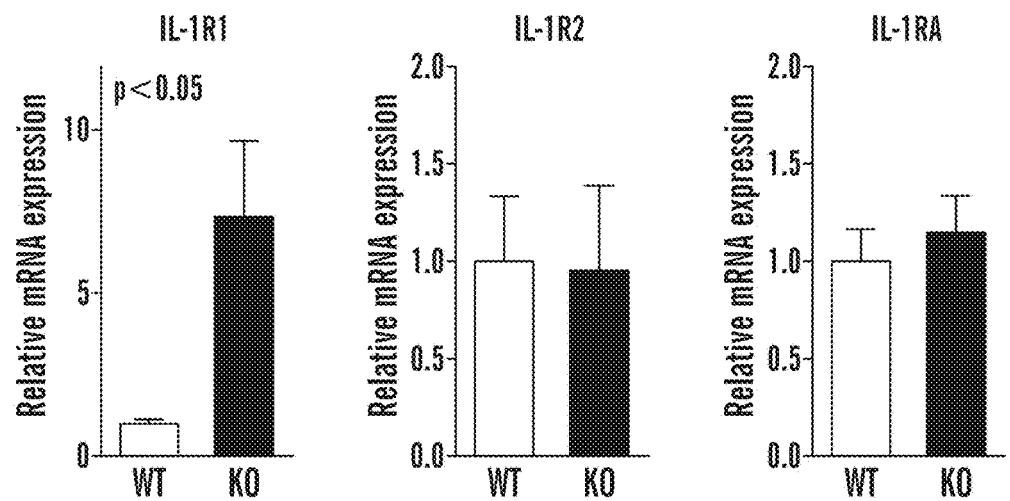
Figure 4K:
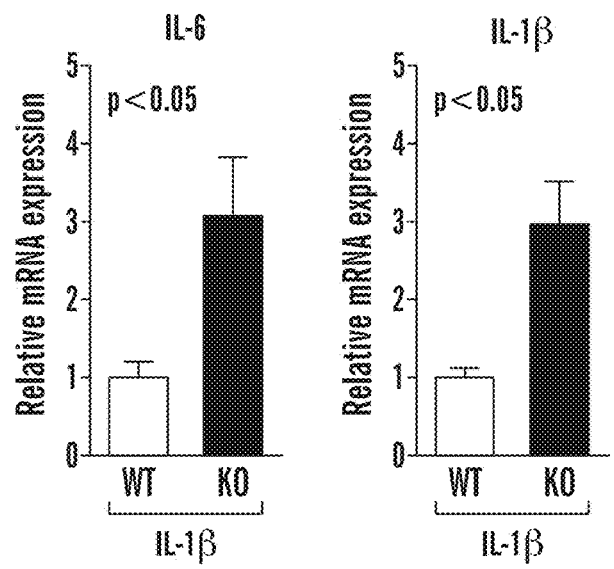

Given that IL-1β is synthesized as an inactive protein (pro-IL-1β), which requires proteolytic cleavage for its secretion, the effects of Tet2-deficiency on IL-1β post-translational processing were evaluated. IL-1β cleavage is frequently mediated by the NLRP3 inflammasome, a multiprotein complex that is activated by a variety of danger signals and plays key roles in multiple inflammatory conditions. NLRP3 inflammasome activation is a two-step process requiring a priming signal, that promotes pro-IL-1β and NLRP3 expression, and an activation signal, that promotes inflammasome assembly. To investigate whether Tet2 deficiency facilitates NLRP3-mediated IL-1β processing and secretion, IL-1β cleavage was evaluated by Western Blot analysis in LPS/IFNγ-primed macrophages treated with ATP for inflammasome activation. As shown in FIGS. 4C, 4D, Tet2-deficient macrophages exhibit significant increases in intracellular pro-IL-1β and cleaved IL-1β, consistent with the observed changes at the transcriptional level. However, the effect on cleaved IL-1β levels (2.5-fold. FIG. 4D) was substantially greater than that on pro-IL-1β levels (1.6-fold, FIG. 4C), indicating that Tet2 loss-of-function promotes IL-1β secretion by macrophages beyond its effects on IL-1β transcription and the production of pro-IL-1β protein. Consistent with these findings, a >3-fold increase was observed in secreted IL-1β levels in the supernatant of LPS/IFNγ/ATP-treated, Tet2-deficient macrophages compared to WT controls both by Western Blot (FIG. 4E) and ELISA analysis (FIG. 4F). IL-1β secretion was completely abrogated by co-treatment with MCC950 (FIG. 4F), a specific NLRP3 inhibitor (22), indicating that Tet2-deficiency affects NLRP3-mediated IL-1β secretion. To test this possibility, the effect of Tet2 on the expression of key inflammasome components was evaluated. NLRP3 transcript and protein levels were significantly increased in Tet2−/− macrophages compared to WT controls after LPS/IFNγ treatment (FIGS. 4G, 4H), whereas no change was observed in the expression of other NLRP3 inflammasome components (FIG. 15A). Consistent with these findings, Tet2 deficiency also enhanced NLRP3 expression in macrophages treated with low dose oxLDL/TNF/IFNγ (FIG. 15B), as well as IL-1β secretion induced by co-treatment with cholesterol crystals (FIG. 4I), a relevant inducer of inflammasome activation and IL-1β secretion in atherosclerotic plaques (23). Overall, these data demonstrate that Tet2 deficiency contributes to IL-1β production by enhancing NLRP3 priming in addition to promoting IL-1β gene transcription, and are consistent with a central role of enhanced IL-1β signaling in the increased atherosclerosis associated with expansion of Tet2-deficient hematopoietic cells. Supporting this notion, Tet2 deficiency also increased basal expression of the activating IL-1β receptor IL-1R1, without affecting the expression of the inhibitory IL-1β receptor IL-1R2 or the IL-1 receptor antagonist (IL-1RA) (FIG. 4J). Consistent with his observation, Tet2-deficient macrophages exhibited an enhanced response to treatment with recombinant IL-1β, as reflected by a ~3-fold increase in IL-6 and IL-1β transcript levels compared to WT macrophages (FIG. 4K).

The studies described herein provide mouse genetic evidence supporting a causal connection between exacerbated CVD in humans and clonal hematopoiesis associated with somatic TET2 mutations in HSPCs, and it represents the first report of a direct contribution of genome mosaicism in the hematopoietic system to the development of a non-hematological disease, specifically atherosclerosis. Furthermore, when considered in light of previous cancer studies (13, 14, 24), the results presented herein indicate that the expansion of TET2-mutant HSPCs represents a pathophysiological mechanism that is shared between blood cancers and CVD. These studies show that Tet2 loss-of-function accelerates atherosclerosis development by exacerbating pro-inflammatory IL-1β signaling in macrophages at multiple levels including elevated expression of pro-IL-1β, modulation of the NLRP3 inflammasome that mediates pro-IL-1β maturation, and activation of the IL-1β receptor IL-1R1. IL-1β is a potential therapeutic target in the setting of atherosclerosis, and neutralizing antibodies against this cytokine are being evaluated in human clinical trials for the treatment of CVD (25). In addition, pharmacological inhibitors of the NLRP3 inflammasome have displayed efficacy in preclinical models of inflammatory diseases (22). In this regard, the studies described herein are of particular clinical relevance, as it suggests that IL-1β blockade or NLRP3 inflammasome inhibition can be particularly effective for the prevention/treatment of CVD in individuals carrying somatic mutations in TET2 and other related genes in hematopoietic cells.

Materials and Methods

Mice.

C57Bl/6J Ldlr-deficient mice (Ldlr−/−), C57Bl/6J Tet2-deficient mice (Tet2−/−) (12) and C57Bl/6 Cd45.1 Pep Boy mice were obtained from Jackson Laboratories. Mice were maintained on a 12-h light/dark schedule in a specific pathogen-free animal facility and given food and water ad libitum. The number of mice included in each study is indicated in the legends of the figures.

Bone Marrow Transplantation and Atherosclerosis Induction.

Lethally irradiated Ldlr−/− recipients were transplanted with suspensions of BM cells containing 10% CD45.2+ Tet2−/− cells and 90% CD45.1+ Tet2+/+ cells (10% KO-BMT mice), or 10% CD45.2+ Tet2+/+ cells and 90% CD45.1+ Tet2+/+ cells (10% WT-BMT mice) (Fig. S1). BM cells were isolated from femurs and tibias of donor mice after euthanasia. Donor CD45.2+ cells were obtained from Tet2+/+ or −/− littermates; donor CD45.1+ cells were obtained from Pep Boy mice. Recipient Ldlr−/− mice were irradiated in a pie cage (Braintree Scientific) to limit mobility and ensure equal dose of irradiation and were exposed to two radiation doses of 550 rad three hours apart using an X-RAD 320 Biological Irradiator. After the second irradiation, each recipient mouse was injected with $10^7$ BM cells i.v. Sterilized caging, food and water were provided during the first 14 days post-transplant and water was supplemented with antibiotics (Sulfatrim). Mice that did not recover full pre-irradiation body weight 28 days after transplant were excluded from further analysis. Starting four weeks after BMT, mice were fed a high fat Western diet (Harlan-Teklad, Adjusted Calories Diet; 42% from fat, 0.2% cholesterol) for nine weeks to promote hyperlipidemia and the development of atherosclerosis.

Assessment of Systemic Metabolism.

Plasma cholesterol levels were determined using an enzymatic assay (Cholesterol E, WAKO Diagnostics), Blood glucose levels were measured with an ACCU-CHEK glucometer (Roche Diagnostics). Insulin tolerance tests (ITT) were performed on 5 h-fasted mice injected intraperitoneally with 0.6 U/Kg human insulin (Humulin R, Eli Lilly), and blood glucose levels were measured immediately before and 15, 30, 60, 90, and 120 minutes after glucose injection.

Quantification of Atherosclerosis Burden.

Mice were euthanized and aortas were removed after in situ perfusion with phosphate-buffered saline (PBS) injected through the left ventricle of the heart. Tissue fixation was achieved by immersion in 4% paraformaldehyde in PBS overnight at 4° C. Aortic tissue was then dehydrated and embedded in paraffin for sectioning. All histological sections comprising the aortic root as determined by the location of the aortic valve leaflets were cut at a thickness of 6 µm. An operator who was blinded to genotype quantified plaque size in aortic root sections by computer-assisted morphometric analysis of microscopy images acquired on a KEYENCE BZ-9000 microscope. For each mouse, atherosclerosis plaque size in aortic root cross-sections was calculated as the average of 5 independent sections separated by ~18 µm.

Immunohistochemical Analysis of Atherosclerotic Plaque Composition.

Plaque composition was examined by immunohistochemical techniques performed by a researcher blinded to genotype. Vascular smooth muscle cells (VSMCs) were identified with mouse anti-smooth muscle α-actin (SMA) monoclonal alkaline phosphatase-conjugated antibody (clone 1A4, SIGMA) and Vector Red Alkaline Phosphatase Substrate (Vector Laboratories). Macrophages were detected with a rat anti-Mac3 monoclonal antibody (clone M3/84, Santa Cruz Biotechnologies), followed by biotin-conjugated goat anti-rat secondary antibody (Santa Cruz Biotechnologies), streptavidcin-HRP (Vector Laboratories) and DAB substrate (Vector Laboratories). Specimens were counterstained with hematoxylin. Collagen content was determined by a modified Masson's trichrome staining with Fast Green as collagen stain. Microscopy images were acquired on a KEYENCE BZ-9000 microscope and analyzed using IMAGEJ software using the Color Deconvolution plugin.

Assessment of Plaque Cell Proliferation and Apoptosis.

Macrophage proliferation within atherosclerotic plaques was assessed by double immunofluorescent staining with monoclonal antibodies against Ki-67 (clone SP6, Vector Laboratories) and CD68 (Clone FA-11, AbD Serotec). After deparaffinization, antigen retrieval and blockade of non-specific interactions (5% horse serum in PBS, 45 min), histological sections were incubated for 2 h at 37° C. with primary antibodies. CD68 was visualized with Alexa Fluor 488-conjugated anti-rat IgG and Ki-67 with Alexa Fluor 635-conjugated anti-rabbit IgG (both from Life Technologies). Nuclei were stained with DAPI and slides were mounted in SLOWFADE GOLD ANTIFADE Reagent (Life Technologies) to acquire images on a LEICA SP5 confocal microscope fitted with a 40× oil-immersion objective. Settings were adjusted to maximize the signal-to-noise ratio. The sequential mode was used for image acquisition in order to avoid any interference from overlapping fluorescence. Images were analyzed with ImageJ software by a researcher who was blinded to genotype. Plaque apoptosis was determined using the terminal deoxynucleotidyl transferase dUTP nick-end labelling (TUNEL) method, following the manufacturer's recommendations (In Situ Cell Death Detection Kit Fluorescein, Roche). Images were acquired on a KEYENCE BZ-9000 microscope.

Flow Cytometry Analyses of Blood and Tissue Samples.

Peripheral blood was obtained from the facial vein. Bone marrow cells were flushed out of two femurs and two tibias per mouse. Spleen was gently pressed through a 70 µm cell strainer in PBS containing 10% fetal bovine serum (FBS) to prepare single cell suspensions. Aortic arches were digested for 45 minutes at 37° C. in RPMI containing 10% FBS and 0.25 mg/ml LIBERASE™ (Roche Life Science). The following fluorescent antibodies were used for staining and flow cytometry analysis: eFluor450-conjugated anti-CD45.2, FITC-conjugated anti-CD45.2, Pe-Cy7-conjugated anti-CD45.1, FITC-conjugated anti-CD11b, eFluor450-conjugated anti-CD11B, PE-conjugated anti-CD115, APC-conjugated anti-CD3, FITC-conjugated anti-Lineage cocktail (from eBioscience); APC-Cy7-conjugated anti-B220, PerCP-Cy5.5-conjugated anti-Ly6G, PE-Cy7-conjugated anti-c-Kit, AlexaFluor647-conjugated anti-Sca-1 (from BD Biosciences); APC-conjugated anti-mouse F4/80 (from R&D Systems); PerCP-Cy5.5 anti-CD45.1 (from BioLegend). HPSCs were identified as Lineage-, c-Kit+, Sca1+; monocytes, as CD45+, CD11b+, CD115Hi; neutrophils, as CD45+, CD11b+, $CD115^{Lo}$, Ly6g+, T lymphocytes as CD45+, CD11B+, B220-, CD3+; B lymphocytes as CD45+, CD11b−, CD3-, B220+; and aortic macrophages as CD45+, CD11B+, $F4/80^{Hi}$. Dead cells were excluded from analysis with DAPI staining. 123 count EBEADS (eBioscience) were used to quantify absolute cell numbers. A BD LSR II Flow Cytometer (BD Bioscience) was used for data acquisition. Data were analyzed with FLOWJO Software.

Cell Culture Studies.

Thioglycollate-elicited macrophages were obtained from the peritoneal cavity of mice 4 days after intraperitoneal injection of 1 ml of aged 4% Brewer's thioglycollate broth (BD Difco). Macrophages were allowed to adhere for 4 hours and cultured in RPMI medium supplemented with antibiotics and 10% FBS (PERFORMANCE PLUS FBS, Gibco). Bone marrow-derived macrophages were obtained from suspensions of femoral BM that were differentiated for 7 days in the presence of RPMI medium supplemented with antibiotics, 10% fetal bovine serum and 15% L929-cell conditioned medium as a source of macrophage colony-stimulating factor (MCSF). Cell cycle progression and apoptosis of cultured macrophages was evaluated by flow cytometry analysis of DNA content. After fixation in 80% ethanol for 1 h at −20° C., cells were incubated for 30 min with 50 µg/mL propidium iodide containing 0.25 mg/mL RNAse A (both from SIGMA). For cell cycle analysis, DNA histograms were fitted into cell cycle distributions using the MODFIT 3.0 software (Verity Software House). For analysis of apoptosis induced by treatment with 7-ketocholesterol (Sigma), hypodiploid (SubG1) cells were quantified using with FLOWJO Software. Uptake of fluorescent dil-conjugated oxidized LDL (Alfa Aesar) was evaluated by flow cytometry analysis. Pro-inflammatory activation of macrophages was achieved by treatment with various combinations of multiple stimuli as described in main text and figure legends. The following stimuli were used: LPS (Invivogen), recombinant IFNγ protein (Peprotech), oxLDL (Alfa Aesar) and recombinant TNF protein (Peprotech). For NLRP3 inflammasome activation, LPS/IFNγ-primed macrophages were treated with 5 mM ATP (SIGMA) for 15 or 30 minutes. Alternatively, macrophages were treated for 8 hours with a combination of oxLDL, TNF, IFNγ and cholesterol crystals. For cholesterol crystal preparation, Cholesterol (Sigma) was dissolved in 95% Ethanol, heated to 600 and cooled down at room temperature to allow crystallization.

Gene Expression Analysis by qRT-PCR.

Total RNA from tissues and cultured cells was isolated using QIAZOL reagent and RNEASY kits (QIAGEN). RNA (0.3-1.5 µg) was reverse transcribed with ISCRIPT™ Advanced cDNA Synthesis Kit kits (Bio-Rad). qRT-PCR was performed with Power SYBR® Green reagent (ThermoFisher Scientific) in a VIIA7 PCR system. Primers for mouse gene expression studies are shown in Table 2. TAQMAN® assays for human gene expression studies were from Life Technologies. Results were analyzed with the ΔΔCt method. 36B4, β-actin or the combination of both were used as reference genes for normalization. The following primers were used:

TABLE 2

SEQ ID NOs: 8-57

| Gene | Forward Primer (SEQ ID NOs: 8-32) | Reverse Primer (SEQ ID NOs: 33-57) |
|---|---|---|
| 36B4 | GCTCCAAGCAGATGCAGCA | CCGGATGTGAGGCAGCAG |
| β-actin | GGCTGTATTCCCCTCCATCG | CCAGTTGGTAACAATGCCATGT |
| IL-1β | TGACAGTGATGAGAATGACCTGTTC | TTGGAAGCAGCCCTTCATCT |
| IL-6 | GCTACCAAACTGGATATAATCAGGA | CCAGGTAGCTATGGTACTCCAGAA |
| IL-1α | GCACCTTACACCTACCAGAGT | AAACTTCTGCCTGACGAGCTT |
| TNF | CGGAGTCCGGGCAGG | GCTGGGTAGAGAATGGATGAA |
| CCL2/MCP1 | CAGCCAGATGCAGTTAACGC | GCCTACTCATTGGGATCATCTTG |
| CXCL1 | CCGAAGTCATAGCCACACTCAA | CAAGGGAGCTTCAGGGTCAA |
| CXCL2 | TGACTTCAAGAACATCCAGAGCTT | CTTGAGAGTGGCTATGACTTCTGTCT |
| CXCL3 | TTTGAGACCATCCAGAGCTTGA | CCTTGAGAGTGGCTATGACTTCTGT |
| CCL3 | GCGCCATATGGAGCTGACA | CGTGGAATCTTCCGGCTGTA |
| CCL5 | CAGCAGCAAGTGCTCCAATC | CACACACTTGGCGGTTCCTT |
| COX2 | TGGTGCCTGGTCTGATGA | GTGGTAACCGCTCAGGTGTTG |
| SR-A | TCAGACTGAAGGACTGGGAACA | GGAGGCCCTTGAATGAAGGT |
| CD36 | TGCCCATGCCGAGAGTCT | CAGAGGCGCACCAAACCT |
| SELP | CATCTGGTTCAGTGCTTTGATCT | ACCCGTGAGTTATTCCATGAGT |
| SELE | ATGCCTCGCGCTTTCTCTC | GTAGTCCCGCTGACAGTATGC |
| ICAM1 | GTGATGCTCAGGTATCCATCCA | CACAGTTCTCAAAGCACAGCG |
| VCAM | TAGAGTGCAAGGAGTTCGGG | CCGGCATATACGAGTGTGAA |
| IL-1R1 | GTGCTACTGGGGCTCATTTGT | GGAGTAAGAGGACACTTGCGAAT |
| IL-1R2 | GTTTCTGCTTTCACCACTCCA | GAGTCCAATTTACTCCAGGTCAG |
| IL1RA | TCCCAGATTCTGAAGGCTTG | GTGAGACGTTGGAAGGCAGT |
| NLRP3 | ATTACCCGCCCGAGAAAGG | TCGCAGCAAAGATCCACACAG |
| PYCARD | GACAGTGCAACTGCGAGAAG | CGACTCCAGATAGTAGCTGACAA |
| CASP1 | ACAAGGCACGGGACCTATG | TCCCAGTCAGTCCTGGAAATG |

Gene Expression Analysis by Microarrays.

Total RNA from Tet2−/− and +/+ macrophages was isolated using an ALLPREP DNA/RNA Mini Kit (Qiagen), and checked for quality prior to submission to the Boston University Medical Campus Microarray Core Facility. The samples were amplified, labeled and hybridized on 6 Mouse Gene 2.0 ST arrays (Affymetrix, Santa Clara, Calif.) per the manufacturer's instructions. Gene level signal values were normalized together using the Robust Multiarray Average (RMA) algorithm, and annotated to BrainArray Cdf files (26) using affyPLM package (version 1.34.0) included in the Bioconductor software suite (v. 2.12). Differential expression was assessed using the moderated pairwise t test implemented in the limma package (version 3.14.4). Both .cel files and expression values were deposited into MIAME compliant NCBI Gene Expression Omnibus with accession number: GSE81398. Multiple hypothesis testing was performed by calculating the Benjamini-Hochberg false discovery rate and an additional filtered FDR q-value was calculated after removing genes that were expressed below array-wise median value to reduce the probability of producing false positive results. In this study, genes with a fold change ≥1.5 or ≤−1.5 fold with a filtered q-value<0.05 were considered as statistically significant differentially expressed genes (DEG). The list of DEG was uploaded to PANTHER Classification System for statistical overrepresentation test using default settings (27). Heap map was generated by using GENE-E software from Broad Institute, found on the worldwide web at broadinstitute.org/cancer/software/GENE-E/index.html.

Analysis of Cytokine Secretion.

IL-6 and IL-1β were analyzed in macrophage culture supernatants using commercial enzyme-linked immunoabsorbent assays (ELISA) according to manufacturer's instructions (R&D Systems).

SDS-PAGE and Western Blot.

Protein extracts from cultured macrophages were obtained using ice-cold lysis buffer (Cell Signaling Technologies) supplemented with protease and phosphatase inhibitors (Roche Applied Science). Equal amounts of protein lysates were resolved by SDS-PAGE. The following antibodies were used for immunoblotting: rabbit polyclonal anti-IL-1β (GeneTex), mouse monoclonal anti-NLRP3 (Clone Cryo-2, AdipoGen Life Sciences) and rabbit monoclonal anti-β-actin (Cell Signaling Technologies).

Analysis of Histone Acetylation.

Histone H3 acetylation was evaluated by chromatin immunoprecipitation combined with qRT-PCR (ChIP-qPCR) using the SimpleChIP Plus Enzymatic Chromatin Immunoprecipitation Kit (Cell Signaling Technologies) and anti-acetyl-Histone H3 antibody (EMD Millipore). qRT-PCR was performed on a CFX96 thermal cycler (Bio-Rad) using SsoAdvanced Universal SYBR Green Master Mix (Bio-Rad). ChIP-qPCR data was analyzed using the percent input method. Acetylated H3 percent input was normalized to histone H3 ChIP percent input and presented as the ratio H3Ac:H3. The following primers were used:

Statistical Analysis

Data are shown as mean±SEM unless otherwise stated. Statistical significance of differences in experiments with two groups and only one variable was assessed by unpaired Student's t tests (with Welch correction for unequal variance when appropriate) or Mann-Whitney U Tests. Differences in experiments with more than one independent variable were evaluated by two-way analysis of variance (ANOVA) with post-hoc Sidak's multiple comparison tests. Results of ITT experiments were evaluated by two-way repeated measures ANOVA. All statistical tests were performed using GRAPH-PAD PRISM software (GraphPad Software Inc.).

Example 2

An NLRP3 Inhibitor Showed Greater Atheroprotective Activity in Chimeric Mice Reconstituted with TET2-Deficient Cells than in Nonchimeric Mice.

The data described herein demonstrate a central role of enhanced IL-1β signaling in the increased atherosclerosis associated with expansion of TET2-deficient hematopoietic cells. In support of this idea, when 10% KO-BMT mice were continuously infused with the NLRP3 inhibitor MCC950, the difference in aortic plaque size between these chimeric mice and nonchimeric control mice was eliminated (FIG. 18). These studies revealed that MCC950 exerts greater atheroprotective actions in conditions of clonal hematopoiesis associated with TET2 deficiency, as it decreased atherosclerotic plaque size by ~50% in 10% KO-BMT mice, whereas it led to a nonstatistically significant 20% reduction in 10% WT-BMT controls. Overall, these studies demonstrate that NLRP3-mediated IL-1β overproduction is essential for the atherogenic consequences of clonal expansion of TET2-deficient cells.

Example 3

Tet2-Mediated Clonal Hematopoiesis Accelerates Experimental Heart Failure

Recent studies have shown that cells of the hematopoietic system undergo clonal expansion due in part to the occurrence of somatic mutations in oncogenes. This condition is common in the elderly, and associated with an increased incidence of coronary heart disease. As shown herein, in part, the epigenetic regulator TET2 is frequently mutated in individuals exhibiting clonal hematopoiesis, and experimental studies have shown that inactivating mutations at this locus can promote atherosclerotic cardiovascular disease. Here, it was investigated whether hematopoietic mutations in Tet2 can contribute to heart failure independent of atherosclerotic disease in two models of murine heart failure.

TABLE 3

SEQ ID NOs: 58-61

| Gene Promoter | Position relative to TSS* | Forward Primer (SEQ ID NOs: 58-59) | Reverse Primer (SEQ ID NOs: 60-61) |
|---|---|---|---|
| IL-1β | −181 | AAGTGTGTCATCGTGGTGGAA | GTGCATCTACGTGCCTACCTT |
| IL-6 (Ref.17) | −166 | CCTGCGTTTAAATAACATCAGCTTTAGCTT | GCACAATGTGACGTCGTTTAGCATCGAA |

*With respect to the 5' end of the downstream primers. Based on GRCm38.p3 C57BL/6J Methods and Results Heart failure was induced in C57/B16 mice by pressure overload, achieved by transverse aortic constriction (TAC), or by chronic ischemia, induced by the permanent ligation of the left anterior descending (LAD) artery (FIGS. 19, 20). In both models, Tet2-deficient hematopoietic cells were used to partially reconstitute the bone marrow of lethally irradiated mice, leading to their clonal expansion. Alternatively, Tet2 was specifically ablated in myeloid cells using Cre recombinase expressed from the LysM promoter. In mice, undergoing LAD ligation, Tet2-deficiency led to worsened cardiac remodeling and function regardless of the means of Tet2 ablation. In mice undergoing TAC, Tet2-deficiency led to greater hypertrophy and systolic dysfunction regardless of the means of Tet2 ablation. In both models, Tet2 deficiency was associated with a failure to resolve inflammation at late time points, and this was associated with increased IL-1β expression. Treatment with the NLRP3 inflammasome inhibitor MCC950 protected against the development of heart failure and eliminated differences in cardiac parameters between Tet2-deficient and wild-type (WT) mice (FIGS. 21, 22).

Conclusions

The deficiency in Tet2 in hematopoietic cells is associated with greater cardiac dysfunction and inflammation in murine models of myocardial ischemia and hypertrophy. These effects were eliminated by inhibiting the NLRP3 inflammasome. These data indicate that individuals with TET2-mediated clonal hematopoiesis are at greater risk of developing heart failure independent of atherosclerotic burden, and that these individuals exhibit a greater benefit from therapies that target the NLRP3 inflammasome.

Example 4

Tet2-Deficiency Accelerates Kidney Disease

Background

Kidney failure is estimated to afflict 5 to 10% of the world population. Risk factors for kidney disease include hypertension and diabetes. It is increasingly appreciated that there is crosstalk between the heart and kidneys, and that renal function is a strong predictor of outcome in ischemic CVD and heart failure.

Results

Using the angiotensin II-infusion model it was shown that ablation of Tet2 (using Cre recombinase expressed from the LysM promoter) leads to kidney dysfunction, inflammation and fibrosis. Myeloid deficiency of Tet2 led to increased: 1) inflammation (both macrophage infiltration and IL-6 and IL-1β gene expression); 2) vascular and interstitial fibrosis/collagen accumulation, 3) dilated tubules/renal tubular cell hypertrophy; 4) glomerular hypertrophy/Bowman's capsule expansion; and 5) glomerular basement membrane thickening/glomerulosclerosis (FIGS. 23, 24). Similar results have been obtained in mice subjected to the unilateral ureteral obstruction (UUO) model of kidney failure (FIG. 25).

Conclusions

The deficiency in Tet2 in myeloid hematopoietic cells is associated with greater kidney pathology in two models of murine renal failure. These data indicate that individuals with TET2-mediated clonal hematopoiesis are at greater risk of kidney failure. Because Tet2-deficiency is associated with elevated IL-1β signaling, therapies that target the NLRP3 inflammasome are useful for individuals with kidney failure.

We claim:

1. A method for treating a subject having a TET2 mutation-mediated cardiometabolic disease or disorder comprising administering a therapeutically effective amount of a pharmaceutical composition comprising a blocking IL-1β inhibitor antibody or antigen-binding fragment thereof and a pharmaceutically acceptable carrier to a subject having one or more inactivating TET2 mutations in a sub-population of peripheral blood hematopoietic cells.

2. The method of claim 1, wherein at least 2% of the peripheral blood hematopoietic cells have the one or more inactivating TET2 mutations.

3. The method of claim 1, wherein the one or more inactivating TET2 mutations are selected from an S282F mutation in SEQ ID NO: 3, an N312S mutation in SEQ ID NO: 3, an L346P mutation in SEQ ID NO: 3, an S460F mutation in SEQ ID NO: 3, a D666G mutation in SEQ ID NO: 3, a P941S mutation in SEQ ID NO: 3, and a C1135Y mutation in SEQ ID NO: 3.

4. The method of claim 1, wherein the blocking IL-1β inhibitor antibody or antigen-binding fragment thereof is selected from ABT981, APX002, Canakinumab, CDP48, immunereszumab, LY2189102, MEDI8968, and gevokizumab.

5. The method of claim 1, further comprising monitoring hematopoietic cell clonality, IL-1β proinflammatory activity, or a combination thereof following the administration of the inhibitor of TET2 mutation-mediated IL-1β proinflammatory activity.

6. The method of claim 1, further comprising decreasing the number or percentage of hematopoietic cells comprising the one or more TET2 mutations in the subject by performing therapeutic cytapheresis on the subject.

7. The method of claim 1, wherein the subject has a cardiovascular disease or disorder.

8. The method of claim 7, wherein said cardiovascular disease or disorder is selected from the group consisting of: atherosclerosis, hypertension, ischemic heart disease, hypertensive heart disease and pulmonary hypertensive heart disease, valvular disease, cardiac arrhythmia, vascular disease, myocardial infarction, congestive heart failure, myocarditis, and restenosis.

9. A method for treating a subject for cardiometabolic disease, comprising:
  (a) identifying a subject as having one or more TET2 inactivating mutations in a sub-population of peripheral blood hematopoietic cells, and
  (b) administering to said subject a therapeutically effective amount of a blocking IL-1β inhibitor antibody or antigen-binding fragment thereof.

10. The method of claim 9, wherein at least 2% of the peripheral blood hematopoietic cells have the one or more inactivating TET2 mutations.

11. The method of claim 9, wherein the one or more inactivating TET2 mutations are selected from an S282F mutation in SEQ ID NO: 3, an N312S mutation in SEQ ID NO: 3, an L346P mutation in SEQ ID NO: 3, an S460F mutation in SEQ ID NO: 3, a D666G mutation in SEQ ID NO: 3, a P941S mutation in SEQ ID NO: 3, and a C1135Y mutation in SEQ ID NO: 3.

12. The method of claim 9, wherein the blocking IL-1β inhibitor antibody or antigen-binding fragment thereof is selected from ABT981, APX002, Canakinumab, CDP48, immunereszumab, LY2189102, MEDI8968, and gevokizumab.

13. The method of claim 9, further comprising monitoring hematopoietic cell clonality, IL-1β proinflammatory activity, or a combination thereof following the administration of the inhibitor of TET2 mutation-mediated IL-1β proinflammatory activity.

14. The method of claim 9, further comprising decreasing the number or percentage of hematopoietic cells comprising the one or more TET2 mutations in the subject by performing therapeutic cytapheresis on the subject.

15. The method of claim 9, wherein the subject has a cardiovascular disease or disorder.

16. The method of claim 9, wherein said cardiovascular disease or disorder is selected from the group consisting of;

atherosclerosis, hypertension, ischemic heart disease, hypertensive heart disease and pulmonary hypertensive heart disease, valvular disease, cardiac arrhythmia, vascular disease, myocardial infarction, congestive heart failure, myocarditis, and restenosis.

* * * * *